US009862952B2

(12) United States Patent
Khvorova et al.

(10) Patent No.: US 9,862,952 B2
(45) Date of Patent: Jan. 9, 2018

(54) OLIGONUCLEOTIDE COMPOUNDS FOR TREATMENT OF PREECLAMPSIA AND OTHER ANGIOGENIC DISORDERS

(71) Applicants: University of Massachusetts, Boston, MA (US); BETH ISRAEL DEACONESS MEDICAL CENTER, INC., Boston, MA (US)

(72) Inventors: Anastasia Khvorova, Westborough, MA (US); Melissa Moore, Chestnut Hill, MA (US); Anton A. Turanov, Boston, MA (US); Ananth Karumanchi, Chestnut Hill, MA (US)

(73) Assignees: UNIVERSITY OF MASSACHUSETTS, Boston, MA (US); BETH ISRAEL DEACONESS MEDICAL CENTER, Boston, MA (US)

( * ) Notice: Subject to any disclaimer, the term of this patent is extended or adjusted under 35 U.S.C. 154(b) by 0 days.

(21) Appl. No.: 15/089,437

(22) Filed: Apr. 1, 2016

(65) Prior Publication Data

US 2016/0355826 A1 Dec. 8, 2016

Related U.S. Application Data

(60) Provisional application No. 62/291,961, filed on Feb. 5, 2016, provisional application No. 62/291,678, filed on Feb. 5, 2016, provisional application No. 62/142,745, filed on Apr. 3, 2015.

(51) Int. Cl.
*A61K 31/713* (2006.01)
*C12N 15/113* (2010.01)

(52) U.S. Cl.
CPC ........ *C12N 15/1138* (2013.01); *A61K 31/713* (2013.01); *C12N 15/1137* (2013.01); *C12N 2310/14* (2013.01); *C12N 2310/315* (2013.01); *C12N 2310/321* (2013.01); *C12N 2310/322* (2013.01); *C12N 2310/344* (2013.01); *C12N 2310/346* (2013.01); *C12N 2310/351* (2013.01); *C12N 2310/50* (2013.01)

(58) Field of Classification Search
None
See application file for complete search history.

(56) References Cited

U.S. PATENT DOCUMENTS

| 4,522,811 | A | 6/1985 | Eppstein et al. |
| 5,328,470 | A | 7/1994 | Nabel et al. |
| 5,684,143 | A | 11/1997 | Gryaznov et al. |
| 5,814,014 | A | 9/1998 | Elsberry et al. |
| 5,858,988 | A | 1/1999 | Wang |
| 6,093,180 | A | 7/2000 | Elsberry |
| 6,107,094 | A | 8/2000 | Crooke |
| 6,168,587 | B1 | 1/2001 | Bellhouse et al. |
| 6,177,403 | B1 | 1/2001 | Stedman |
| 6,194,389 | B1 | 2/2001 | Johnston et al. |
| 6,291,438 | B1 | 9/2001 | Wang |
| 6,471,996 | B1 | 10/2002 | Sokoll et al. |
| 6,472,375 | B1 | 10/2002 | Hoon et al. |
| 7,250,496 | B2 | 7/2007 | Bentwich |
| 7,459,547 | B2 | 12/2008 | Zamore et al. |
| 7,732,593 | B2 | 6/2010 | Zamore et al. |
| 7,750,144 | B2 | 7/2010 | Zamore et al. |
| 7,772,203 | B2 | 8/2010 | Zamore et al. |
| 8,304,530 | B2 | 11/2012 | Zamore et al. |
| 8,309,704 | B2 | 11/2012 | Zamore et al. |
| 8,309,705 | B2 | 11/2012 | Zamore et al. |
| 8,329,892 | B2 | 12/2012 | Zamore et al. |
| 8,431,544 | B1 | 4/2013 | Agrawal et al. |
| 2003/0143732 | A1 | 7/2003 | Fosnaugh et al. |
| 2004/0198640 | A1* | 10/2004 | Leake ................... C12N 15/111 514/44 R |
| 2005/0220766 | A1 | 10/2005 | Amalfitano et al. |
| 2006/0078542 | A1 | 4/2006 | Mah et al. |
| 2006/0094032 | A1* | 5/2006 | Fougerolles ......... A61K 31/712 435/6.16 |
| 2007/0135372 | A1* | 6/2007 | MacLachlan ........ C12N 15/113 514/44 A |
| 2007/0191273 | A1 | 8/2007 | Ambati et al. |
| 2007/0259827 | A1 | 11/2007 | Aronin et al. |
| 2008/0039415 | A1 | 2/2008 | Stewart et al. |
| 2008/0119427 | A1 | 5/2008 | Bhat et al. |
| 2008/0269149 | A1 | 10/2008 | Bowles et al. |
| 2009/0143322 | A1 | 6/2009 | Burkoth et al. |
| 2010/0186103 | A1 | 7/2010 | Gao et al. |

(Continued)

FOREIGN PATENT DOCUMENTS

CN 101199858 A 6/2008
WO 03/029459 A2 4/2003

(Continued)

OTHER PUBLICATIONS

Yu et al. (Aug. 31, 2012) "Single-stranded RNAs use RNAi to potently and allele-selectively inhibit mutant huntingtin expression," Cell. 150(5):895-908.
Zeng et al. (2002) "Both natural and designed micro RNAs can inhibit the expression of cognate mRNAs when expressed in human cells," Mol. Cell. 9(6):1327-1333.
Zeng et al. (2003) "Sequence requirements for micro RNA processing and function in human cells," RNA. 9 (1):112-123.
International Search Report with Written Opinion corresponding to International Patent Application No. PCT/US2016/025722, dated Aug. 12, 2016.
International Search Report with Written Opinion corresponding to International Patent Application No. PCT/US2016/025731, dated Sep. 9, 2016.
International Search Report with Written Opinion corresponding to International Patent Application No. PCT/US2016/025753, dated Sep. 14, 2016.

(Continued)

*Primary Examiner* — Tracy Vivlemore
(74) *Attorney, Agent, or Firm* — Lathrop Gage LLP; James H. Velema, Esq.

(57) ABSTRACT

This disclosure relates to novel targets for angiogenic disorders. Novel oligonucleotides are also provided. Methods of using the novel oligonucleotides for the treatment of angiogenic disorders (e.g., preeclampsia) are also provided.

40 Claims, 59 Drawing Sheets

(56) References Cited

U.S. PATENT DOCUMENTS

| | | | |
|---|---|---|---|
| 2013/0131141 | A1 | 5/2013 | Khvorova et al. |
| 2014/0296486 | A1 | 10/2014 | Gao et al. |

FOREIGN PATENT DOCUMENTS

| | | |
|---|---|---|
| WO | 2004/008946 A2 | 1/2004 |
| WO | 2004/044136 A2 | 5/2004 |
| WO | 2006/019430 A2 | 2/2006 |
| WO | 2007/051045 A2 | 5/2007 |
| WO | 2008/154482 A2 | 12/2008 |
| WO | 2009/099991 A2 | 8/2009 |
| WO | 2010/033247 A2 | 3/2010 |
| WO | 2012/005898 A2 | 1/2012 |
| WO | 2012/118911 A1 | 9/2012 |
| WO | 2013/165816 A2 | 11/2013 |
| WO | 2014/076195 A1 | 5/2014 |
| WO | 2015/161184 A1 | 10/2015 |

OTHER PUBLICATIONS

Alexopoulou et al. (2001) "Recognition of double-stranded RNA and activation of NF-κb by Toll-like receptor 3," Nature. 413:732-738.

Allerson et al. (2005) "Fully 2'-Modified Oligonucleotide Duplexes with Improved in Vitro Potency and Stability compared to Unmodified Small Interfering RNA," J. Med. Chem. 48(4):901-904.

Alterman et al. (Dec. 12, 2015) "Hydrophobically Modified siRNAs Silence Huntingtin mRNA in Primary Neurons and Mouse Brain," Mol. Ther.: Nucleic Acids. 4(12):e266. pp. 1-12.

Altschul et al. (1997) "Gapped Blast and PSI-Blast: a new generation of protein database search programs," Nucleic Acids Res. 25(17):3389-3402.

Ameres et al. (2007) "Molecular basis for target RNA recognition and cleavage by human RISC," Cell. 130:101-112.

Anderson et al. (2008) "Experimental validation of the importance of seed complement frequency to siRNA specificity," RNA. 14:853-861.

Anderson et al. (2008) "Identifying siRNA-induced off-targets by microarray analysis," Ch.4 In; Methods in Molecular Biology. 442:45-63.

Bagella et al. (1998) "Cloning of murine CDK9/PITALRE and its tissue-specific expression in development," J. Cell. Physiol. 177:206-213.

Bartlett (2006) "Insights into the kinetics of siRNA-mediated gene silencing from live-cell and live-animal bioluminescent imaging," Nucleic Acids Research. 34:322-333.

Behlke et al. (2008) "Chemical modification of siRNAs for in vivo use," Oligonucleotides. 18:305-320.

Billy et al. (2001) "Specific interference with gene expression induced by long, double-stranded RNA in mouse embryonal teratocarcinoma cell lines," Proc Natl Acad Sci USA. 98(25)14428-14433.

Birmingham et al. (2006) "3' UTR seed matches, but not overall identity, are associated with RNAi off-targets," Nat. Methods. 3:199-204.

Birmingham et al. (2007) "A protocol for designing siRNAs with high functionality and specificity," Nature Protocols. 2:2068-2078.

Braasch et al. (2003) "RNA Interference in Mammalian Cells by Chemically-Modified RNA," Biochemistry 12:7967-7975.

Brennecke et al. (2003) "Towards a complete description of the microRNA complement of animal genomes," Genome Biol. 4(9):228.

Brummelkamp et al. (2002) "A system for stable expression of short interfering RNAs in mammalian cells," Science. 296:550-553.

Burchard et al. (2009) "MicroRNA-like off-target transcript regulation by siRNAs is species specific," RNA. 15:308-315.

Byrne et al. (Nov. 1, 2013) "Novel hydrophobically modified asymmetric RNAi compounds (sd-rxRNA) demonstrate robust efficacy in the eye," Journal of Ocular Pharmacology and Therapeutics. 29:855-864.

Calegari et al. (2002) "Tissue-specific RNA interference in postimplantation mouse embryos with endoribonuclease-prepared short interfering RNA," Proc. Natl. Acad. Sci. USA. 99(22):14236-14240.

Charrier et al. (May 3, 2012) "Inhibition of SRGAP2 function by its human-specific paralogs induces neoteny during spine maturation," Cell. 149(4):923-935.

Cho et al. (Feb. 13, 2012) "Vascular endothelial growth factor receptor 1 morpholino decreases angiogenesis in a murine corneal suture model," Invest. Opthamol. Visual Sci. 53(2):685-692.

Shoe et al. (2005) "Crystal structure of human toll-like receptor 3 (TLR3) ectodomain," Science. 309:581-585.

Coelho et al. (Aug. 29, 2013) "Safety and efficacy of RNAi therapy for transthyretin amyloidosis," The New England Journal of Medicine. 369:819-829.

Deleavey et al. (Jan. 5, 2013) "The 5' binding MID domain of human Argonaute2 tolerates chemically modified nucleotide analogues" Nucleic Acid Therapeutics. 23:81-87.

Difiglia et al. (2007) "Therapeutic silencing of mutant huntingtin with siRNA attenuates striatal and cortical neuropathology and behavioral deficits," Proc. Natl. Acad. Sci. USA. 104(43):17204-17209.

Doench et al. (2003) "siRNAs can function as miRNAs," Genes Dev. 17(4):438-442.

Eckstein (2000) "Phosphorothioate Oligodeoxynucleotides: What Is Their Origin and What Is Unique About Them?" Antisense Nucleic Acid Drug Dev. 10(2):117-121.

Elmen et al. (2005) "Locked nucleic acid (LNA) mediated improvements in siRNA stability and functionality," Nucleic Acids Res. 33(11:439-447.

Fan et al. (Oct. 20, 2014) "Endometrial VEGF induces placental sFLT1 and leads to pregnancy complications," J. Clin. Inves. 124(11):4941-4952.

Federov et al. (2006) "Off-target effects by siRNA can induce toxic phenotype," RNA. 12:1188-1196.

Frazier (Nov. 9, 2015) "Antisense Oligonucleotide Therapies: The Promise and the Challenges from a Toxicologic Pathologist's Perspective," Toxicologic Pathology. 43:78-89.

Gaglione et al. (2010) "Recent progress in chemically modified siRNAs," Mini Rev. Med. Chem. 10(7):578-595.

Godard et al. (1995) "Antisense Effects of Cholesterol-Oligodeoxynucleotide Conjugates Associated with Poly (alkylcyanoacrylate) Nanoparticles," Eur. J. Biochem. 232(2):404-410.

Grad et al. (2003) "Computational and experimental identification of C. elegans microRNAs," Mol. Cell. 11 :5):1253-1263.

Griffiths-Jones (2004) "The microRNA Registry," Nuc. Acids Res. 32(Database Issue):D109-D111.

Grimm et al. (2006) "Fatality in mice due to oversaturation of cellular microRNA/short hairpin RNA pathways," Nature. 441:537-541.

Herdewijn (2000) "Heterocyclic modifications of oligonucleotides and antisense technology," Antisense Nucleic Acid Drug Dev. 10(4):297-310.

Heydarian et al. (2009) "Novel splice variants of sFlt1 are upregulated in preeclampsia," Placenta. 30:250-255.

Heyer et al. (Dec. 12, 2014) "An optimized kit-free method for making strand-specific deep sequencing libraries from RNA fragments," Nucleic Acids Res. 43(1):e2. pp. 1-14.

Hutvagner et al. (2002) "A microRNA in a multiple-turnover RNAi enzyme complex," Science. 297 (5589):2056-2060.

Jackson et al. (2006) "Position-specific chemical modification of siRNAs reduces 'off-target' transcript silencing," RNA. 12:1197-1205.

Jackson et al. (2010) "Recognizing and avoiding siRNA off-target effects for target identification and therapeutic application," Nature Reviews in Drug Discovery. 9:57-67.

Jacque et al. (2002) "Modulation of HIV-1 replication by RNA interference," Nature. 418:435-438.

Judge et al. (2006) "Design of Noninflammatory Synthetic siRNA Mediating Potent Gene Silencing in Vivo," Molecular Therapy. 13:494-505.

(56) References Cited

OTHER PUBLICATIONS

Karlin et al. (1990) "Methods for assessing the statistical significance of molecular sequence features by using general scoring schemes," Proc. Natl. Acad. Sci. USA. 87:2264-2268.
Karlin et al. (1993) "Applications and statistics for multiple high-scoring segments in molecular sequences," Proc. Natl. Acad. Sci. USA 90:5873-5877.
Kenski et al. (2012) "siRNA-optimized Modifications for Enhanced In Vivo Activity," Mol. Ther. Nucleic Acids. 1:e5. pp. 1-8.
Khvorova et al. (2003) "Functional siRNAs and miRNAs Exhibit Strand Bias," Cell. 115:209-216.
Khvorova et al. (Mar. 15, 2016) "Abstract IA27: Advances in oligonucleotide chemistry for the treatment of neurodegenerative disorders and brain tumors," Cancer Res. 76(6) Abstract No. IA27.
Lagos-Quintana et al. (2001) "Identification of novel genes coding for small expressed RNAs," Science. 294 (5543):853-858.
Lai et al. (2003) "Computational identification of *Drosophila* microRNA genes," Genome Biol. 4(7):R42. pp. 1-20.
Lau et al. (2001) "An abundant class of tiny RNAs with probable regulatory roles in Caenorhabditis elegans," Science. 294(5543):858-862.
Lau et al. (2006) "Characterization of the piRNA complex from rat testes," Science. 313(5785):363-367.
Lee et al. (2001) "An extensive class of small RNAs in Caenorhabditis elegans," Science. 294(5543):862-864.
Lee et al. (2002) "Expression of small interfering RNAs targeted against HIV-1 rev transcripts in human cells," Nal Biotechnol. 20:500-505.
Lim et al. (2003) "The microRNAs of Caenorhabditis elegans," Genes Dev. 17(8):991-1008.
Lim et al. (2003) "Vertebrate microRNA genes," Science. 299(5612):1540.
Lima et al. (Aug. 31, 2012) "Single-stranded siRNAs activate RNAi in animals," Cell. 150:883-894.
Lorenz et al. (2004) "Steroid and lipid conjugates of siRNAs to enhance cellular uptake and gene silencing in liver cells," Bioorg. Med. Chem. Lett. 14:4975-4977.
Luo et al. (Jun. 18, 2013) "Photoreceptor avascular privilege is shielded by soluble VEGF receptor-1," eLife. 6: e19456. pp. 1-22.
McCaffrey et al. (2002) "RNA interference in adult mice," Nature. 418(6893):38-39.
McManus et al. (2002) "Gene silencing using micro-RNA designed hairpins," RNA. 8:842-850.
Miyagishi et al. (2002) "U6 promoter-driven siRNAs with four uridine 3' overhangs efficiently suppress targeted gene expression in mammalian cells," Nat. Biotechnol. 20:497-500.
Molitoris et al. (2009) "siRNA Targeted to p53 Attenuates Ischemic and Cisplatin-Induced Acute Kidney Injury," Journal of the American Society of Nephrology. 20:1754-1764.
Myers et al. (1988) "Optimal alignments in linear space," Comput. Appl. Biosci. 4(1):11-17.
Nair et al. (Dec. 10, 2014) "Multivalent N-Acetylgalactosamine-Conjugated siRNA Localizes in Hepatocytes and Elicits Robust RNAi-Mediated Gene Silencing," J. Am. Chem. Soc. 136(49):16958-16961.
Nielsen et al. (2001) "Sequence-selective recognition of DNA by strand displacement with a thymine-substituted polyamide," Science. 254:1497-1500.
Nikan et al. (Aug. 9, 2016) "Docosahexaenoic Acid Conjugation Enhances Distribution and Safety of siRNA upon Local Administration in Mouse Brain," Mol. Ther. Nucleic Acids. 5(8):e344. pp. 1-11.
Owen et al. (Mar. 15, 2012) "Morpholino-mediated increase in soluble Flt-1 expression results in decreased ocular and tumor neovascularization," PloS One. 7(3):e33576. pp. 1-9.
Paddison et al. (2002) "Short hairpin RNAs (shRNAs) induce sequence-specific silencing in mammalian cells," Gene Dev. 16:948-958.

Pasquinelli et al. (2000) "Conservation of the sequence and temporal expression of let-7 heterochronic regulatory RNA," Nature. 408(6808):86-89.
Paul et al. (2002) "Effective expression of small interfering RNA in human cells," Nature Biotechnol. 20:505-508.
Peel et al. (Feb. 12, 2015) "Conjugation and Evaluation of Small Hydrophobic Molecules to Triazole-Linked siRNAs," ACS Med. Chem. Lett. 6(2):117-122.
Petersen et al. (2003) "LNA: a versatile tool for therapeutics and genomics," Trends Biotechnol 21:74-81.
Putnam (1996) "Antisense strategies and therapeutic applications," Am. J. Health Syst. Pharm. 53(2):151-160.
Reinhart et al. (2002) "Small RNAs correspond to centromere heterochromatic repeats," Science. 297(5588):1831.
Rigo et al. (Apr. 20, 2014) "Pharmacology of a central nervous system delivered 2'-O-methoxyethyl-modified survival of motor neuron splicing oligonucleotide in mice and nonhuman primates," The Journal of Pharmacology and Experimental Therapeutics. 350:46-55.
Rodriguez-Lebron et al. (2005) "Intrastriatal rAAV-mediated delivery of anti-huntingtin shRNAs induces partial reversal of disease progression in R6/1 Huntington's disease transgenic mice," Mol. Ther. 12(4):618-633.
Rusckowski et al. (2000) "Biodistribution and metabolism of a mixed backbone oligonucleotide (GEM 231) following single and multiple dose administration in mice," Antisense Nucleic Acid Drug Dev. 10(5):333-345.
Schirle et al. (Oct. 31, 2014) "Gene Regulation. Structural basis for microRNA targeting," Science. 346:608-613.
Schwab et al. (1994) "An approach for new anticancer drugs: oncogene-targeted antisense DNA," Ann. Oncol. 5 (Suppl 4):55-58.
Schwarz et al. (2003) Asymmetry in the Assembly of the RNAi Enzyme Complex. Cell 115:199-208.
Song et al. (2003) "Sustained Small Interfering RNA-Mediated Human Immunodeficiency Virus Type 1 Inhibition in Primary Macrophages," Journal of Virology. 77:7174-7181.
Soutschek et al. (2004) "Therapeutic silencing of an endogenous gene by systemic administration of modified siRNAs," Nature. 432:173-178.
Stalder et al. (Mar. 19, 2013) "The rough endoplasmatic reticulum is a central nucleation site of siRNA-mediated RNA silencing," EMBO J. 32:1115-1127.
Stein (2001) "Inhibition of Vesivirus infections in mammalian tissue culture with antisense morpholino oligomers," Antisense Nucleic Acid Drug Dev. 11(5):317-25.
Stokman et al. (2010) "Application of siRNA in targeting protein expression in kidney disease," Advanced Drug Delivery Reviews. 62:1378-1389.
Sui et al. (2002) "A DNA vector-based RNAi technology to suppress gene expression in mammalian cells," Proc Natl Acad Sci USA. 99:5515-5520.
Tabernero et al. (Apr. 2013) "First-in-humans trial of an RNA interference therapeutic targeting VEGF and KSP in cancer patients with liver involvement," Cancer Discovery. 3:406-417.
Thomas et al. (2009) "A recently evolved novel trophoblast-enriched secreted form of fms-like tyrosine kinase-1 variant is up-regulated in hypoxia and preeclampsia," J. Clin. Endocrinol. Metabol. 94:2524-2530.
Tuschl (2002) "Expanding small RNA interference," Nat. Biotechnol. 20(5):446-448.
Tuschl et al. (May 6, 2004) "The siRNA User Guide," Accessible on the Internet at URL: http://diyhpl.us/~bryan/irc/protocol-online/protocol-cache/sima.html. [Last Accessed Aug. 11, 2016].
Vaught et al. (2004) "T7 RNA Polymerase Transcription with 5-Position Modified UTP Derivatives," J. Am. Chem. Soc. 126:11231-11237.
Vorobjev et al. (2001) "Nuclease resistance and RNase H sensitivity of oligonucleotides bridged by oligomethylenediol and oligoethylene glycol linkers," Antisense Nucleic Acid Drug Dev. 11(2):77-85.
Watanabe et al. (2008) "Endogenous siRNAs from naturally formed dsRNAs regulate transcripts in mouse oocytes," Nature. 453(7194):539-543.

(56) References Cited

OTHER PUBLICATIONS

Wooddell et al. (Feb. 26, 2013) "Hepatocyte-targeted RNAi Therapeutics for the Treatment of Chronic Hepatitis B Virus Infection," Molecular Therapy. 21:973-985.
Xia et al. (2002) "siRNA-mediated gene silencing in vitro and in vivo," Nature Biotechnol. 20(10):1006-1010.
Young et al. (2010) "Pathogenesis of preeclampsia," Annual Review of Pathology. 5:173-192.
Younis et al. (2013) "Overview of the Nonclinical Development Strategies and Class-Effects of Oligonucleotide-Based Therapeutics," Ch. 26 In; A Comprehensive Guide to Toxicology in Preclinical Drug Development. Ed.: Faqi. Academic Press. pp. 647-664.
Yu et al. (2002) "RNA interference by expression of short-interfering RNAs and hairpin RNAs in mammalian cells," Proc Natl Acad Sci USA. 99:6047-6052.
Felber et al. (Sep. 2012) "The interactions of amphiphilic antisense oligonucleotides with serum proteins and their effects on in vitro silencing activity," Biomaterials. 33(25):5955-5965.
International Search Report with Written Opinion corresponding to International Patent Application No. PCT/US2016/046810, dated Nov. 29, 2016.

\* cited by examiner

- Cholesterol
- TEG linker
- Phosphorothioate
- 5'-Phosphate
- Sense strand
- Antisense strand sFLT1 i13

Exon 13 Intron 13

GAAGAAAGAAATTACAATCAGAG|GTGAGCACTGCAACAAAAAGGCTGTTTTCTCTCGGATCTCCAAATTAAAAGCA

2283

CAAGGAATGATTGTGTACCACACAAAGTAATGTAAAAACATTAAAAAGTAAGGACTCATTAAAAAGTAACAGTTGTCTCATATCAT

← 3' end of i13-short

CTTGATTTATTGTCACTGTTGCTAACTTTCAGGCTCGGAGGAGATGCTCCCCAAAATGAGTTCGGAGATGATAGC
AGTAATAATGAGAGACCCCCGGGCTCCAGCTCTCGGGGAGGCCCATTCAGGCCGGGGGTGCTGCTCCGGGGGCCGACTTG
GTGCACGTTTGGATTTGGAGGATCCCTGCCACTGCCCTTTGTCTGTGTTTGTTGCTGTGTTTTCTCCTGCCTGATA
AACAACAACTTGGATGATCCCAATTTTGATGCCAACCCTCTTTTATTTTTAAGCGGGCGCCCCTATAGT sFLT1 i14

Exon 14 Exon e15

ACAAACAAGAGCCTG|AACTGTATACATCAAGTCTCACCATTGTCTCATCATCATCATCAT

2519

CGTCATCATCATCATCATCATAGCTATCATCATCATAGCTACCATTTATTGAA

AAGTATTATGTGTCAACTTCAAACAACTTATCCTTTAGTTGGAGAGAGCCAAGAGACAATCATAACAAATAACAAATGGCCG
GGCATGGTGGCTCACGCCTGTAATCCCAGCACTTTGGGAGGCCACTTTGAGGTCAGGAGTTCAAGACCAGCCTGG
GACCAGCCTGACCAAGATGGTGAAATGCTGTCTCTATTAAAAATACAAAAATTAGCCAGGCATGGTGGTGGCTCATGCCTG
TAATGCCAGCTACTCGGGAGGCTGAGACAGGAG....

*Fig. 6B*

| | hsiRNA | Accession number | Targeting region | Oligonucleotide sequence (sense/antisense) | IC50, nM (Hela) | IC50, nM (CTB) |
|---|---|---|---|---|---|---|
| Lead Compound | sFLT1_i13_2283 | NM_001159920 | CTCTCGGATCTCCAAATTTA | fG#mC#fA.mU.fC.mU.fC.mA.fA.mA.fA.mU.fU#mU.#fA-tegChol PmU#fA#mA.mU.fU.mU.fG.mG.fA.mG.fA.mU.fC#mC#fG.#mA#fG.#mA#fG | 35.5 | 40 |
| | sFLT1_e15a_2519 | NM_001160030 | CATCATAGCTACCATTTATT | fU#mA#fG.mU.fU.mA.fC.mU.fA.mU.fG.mA.fU.mG#mU.#fA-tegChol PmU#fA#mU.fU.mA.fU.mU.fA.mG.fU.mA.fC.fU#fA.#mU#fG.#mA#fG | 81 | 58 |
| Back up Compound | sFLT1_i13_2318 | NM_001159920 | ATTGTACCACACAAAGTAAT | fA#mC#fC.mA.fC.mA.fC.mU.fU.mU.fG.mU.mG#mU.#fA-tegChol PmU#fA#mU.fU.mA.fC.mU.fU.mU.fG.mU.fG.fU.#mG#fU.#mA#fU | 54 | 130 |
| | sFLT1_e15a_2585 | NM_001160030 | GAGCCAAGACAATCATAACA | fA#mA#fG.mA.fC.mA.fA.mU.fC.mA.fU.mA.fA#mC#fA-tegChol PmU#fG#mU.fU.mU.fG.mU.mC.fU.mU.fG.mG#mC#fC | 49 | 172 |

*Fig. 6C*

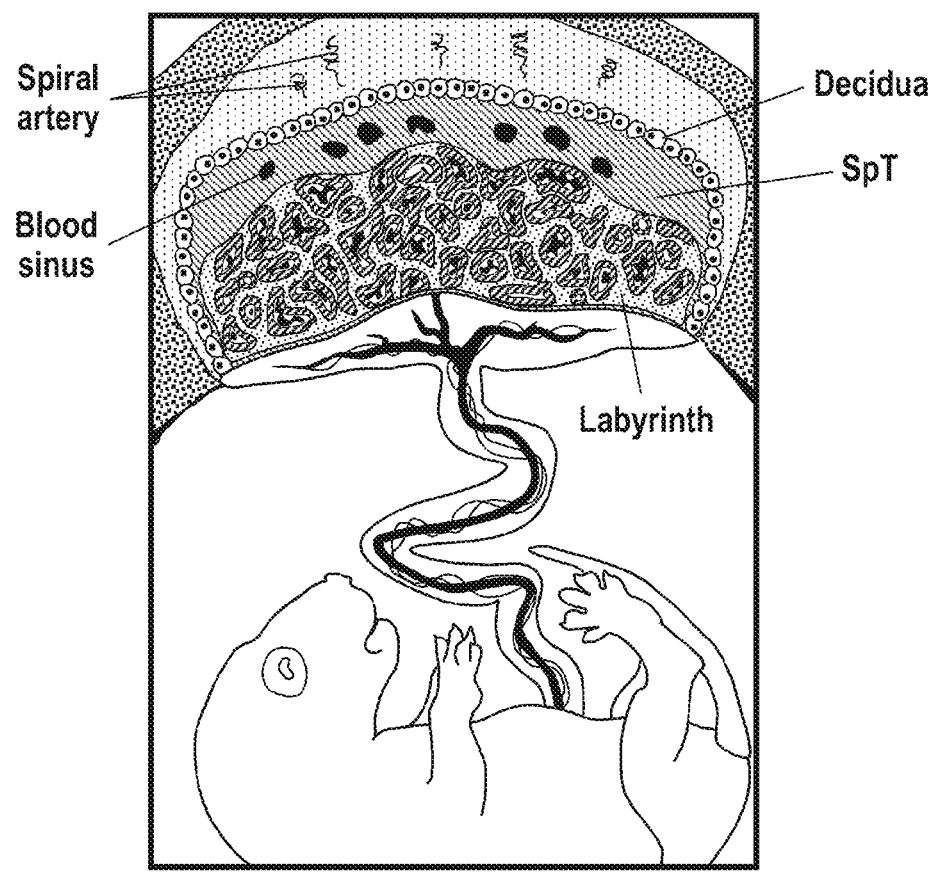
*Fig. 12A*
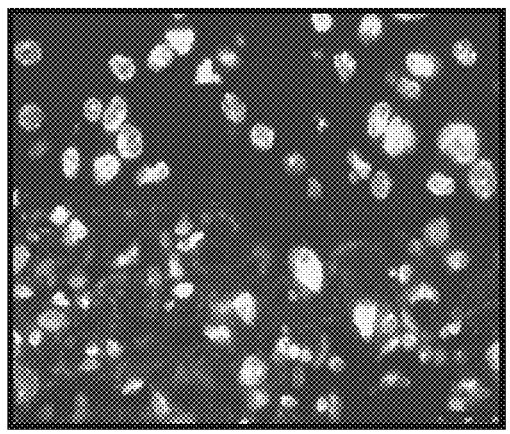   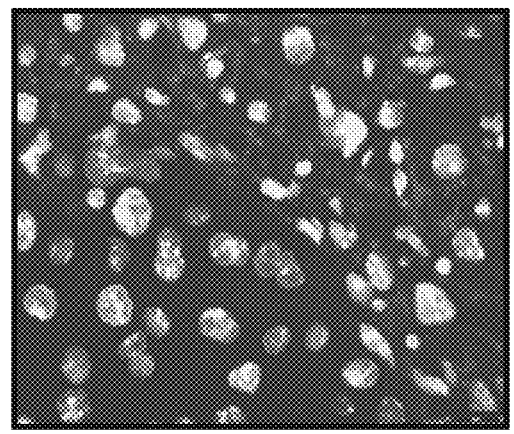
*Fig. 12B*     *Fig. 12C*

| AUCGA GGUCC GCG | Accession Number | Pos | Targeting Region (20 mer) | Targeting Region (30 mer) | Sense Naked | Guide 20 mer |
|---|---|---|---|---|---|---|
| sFLT1-i13 | NM_001159920.1 | 2247 | AAUCAGAGGUGAGCACUGCA | AUUACAAUCAGAGGUGAGCACUGCAACAAA | AAUCAGAGGUGAGCACUGCA | UGCAGUGCUCACCUCUGAUU |
| sFLT1-i13 | NM_001159920.1 | 2252 | GAGGUGAGCACUGCAACAAA | AAUCAGAGGUGAGCACUGCAACAAAAGGC | GAGGUGAGCACUGCAACAAA | UUUGUUGCAGUGCUCACCUC |
| sFLT1-i13 | NM_001159920.1 | 2253 | AGGUGAGCACUGCAACAAAA | AUCAGAGGUGAGCACUGCAACAAAAGGCU | AGGUGAGCACUGCAACAAAA | UUUUGUUGCAGUGCUCACCU |
| sFLT1-i13 | NM_001159920.1 | 2256 | UGAGCACUGCAACAAAAGG | AGAGGUGAGCACUGCAACAAAAGGCUGUU | UGAGCACUGCAACAAAAGG | CCUUUUGUUGCAGUGCUCA |
| sFLT1-i13 | NM_001159920.1 | 2279 | UUUUCUCUCGGAUCUCCAAA | GCCUGUUUUCUCUCGGAUCUCCAAAUUUAA | UUUUCUCUCGGAUCUCCAAA | UUUGGAGAUCCGAGAGAAAA |
| sFLT1-i13 | NM_001159920.1 | 2280 | UUUCUCUCGGAUCUCCAAAU | GCUGUUUUCUCUCGGAUCUCCAAAUUUAAA | UUUCUCUCGGAUCUCCAAAU | AUUGGAGAUCCGAGAGAAA |
| sFLT1-i14 | NM_001159920.2 | 2283 | CUCUCGGAUCUCCAAAUUUA | GUUUUCUCUCGGAUCUCCAAAUUUAAAAGC | CUCUCGGAUCUCCAAAUUUA | UAAAUUUGGAGAUCCGAGAG |
| sFLT1-i13 | NM_001159920.1 | 2284 | UCUCGGAUCUCCAAAUUUAA | UUUUCUCUCGGAUCUCCAAAUUUAAAAGCA | UCUCGGAUCUCCAAAUUUAA | UUAAAUUUGGAGAUCCGAGA |
| sFLT1-i13 | NM_001159920.1 | 2286 | UCGGAUCUCCAAAUUUAAAA | UUCUCUCGGAUCUCCAAAUUUAAAAGCACA | UCGGAUCUCCAAAUUUAAAA | UUUUAAAUUUGGAGAUCCGA |
| sFLT1-i13 | NM_001159920.1 | 2293 | UCCAAAUUUAAAAGCACAAG | GGAUCUCCAAAUUUAAAAGCACAAGGAAUG | UCCAAAUUUAAAAGCACAAG | CUUGUGCUUUUAAAUUUGGA |
| sFLT1-i13 | NM_001159920.1 | 2294 | CCAAAUUUAAAAGCACAAGG | GAUCUCCAAAUUUAAAAGCACAAGGAAUGA | CCAAAUUUAAAAGCACAAGG | CCUUGUGCUUUUAAAUUUGG |
| sFLT1-i13 | NM_001159920.1 | 2295 | CAAAUUUAAAAGCACAAGGA | AUCUCCAAAUUUAAAAGCACAAGGAAUGAU | CAAAUUUAAAAGCACAAGGA | UCCUUGUGCUUUUAAAUUUG |
| sFLT1-i13 | NM_001159920.1 | 2304 | AGCACAAGGAAUGUACCACA | UUUAAAAGCACAAGGAAUGUACCACAAAGU | AAGCACAAGGAAUGUACCACA | UACAAUCAUCCUUGUGCUU |
| sFLT1-i13 | NM_001159920.1 | 2313 | GAAUGUACCACAAAGUAAU | ACAAGGAAUGUACCACAAAGUAAUGUAAA | GAAUGAUUACCACAAAGUA | UUUGUGGUACAAUUCAUUC |
| sFLT1-i13 | NM_001159920.1 | 2318 | AUUGUACCACAAAGUAAUGU | GAAUGAUUGUACCACAAAGUAAUGUAAA | AUUGUACCACAAAGUAAUGU | AUUACUUUGUGGUACAAU |
| sFLT1-i13 | NM_001159920.1 | 2321 | GUACCACAAAGUAAUGUA | UGAUUGUACCACAAAGUAAUGUAAAACA | GUACCACAAAGUAAUGUA | UACAUUACUUUGUGGUAC |
| sFLT1-i13 | NM_001159920.1 | 2322 | UACCACAAAGUAAUGUAAA | GAUUGUACCACAAAGUAAUGUAAAACAU | UACCACAAAGUAAUGUAAA | UUACAUUACUUUGUGGUA |
| sFLT1-i13 | NM_001159920.1 | 2324 | CCACACAAAGUAAUGUAAAA | UUGUACCACAAAGUAAUGUAAAACAUUA | CCACAAAGUAAUGUAAAA | UUUUACAUUACUUUGUGG |
| sFLT1-i13 | NM_001159920.1 | 2326 | ACACAAAGUAAUGUAAAACA | GUACCACAAAGUAAUGUAAAACACUG | ACACAAAGUAAUGUAAAACA | UGUUUUACAUUACUUUGUGU |
| sFLT1-i13 | NM_001159920.1 | 2332 | AGUAAUGUAAAACAUUAAAG | CACAAAGUAAUGUAAAACAUUAAAGGACUG | AGUAAUGUAAAACAUUAAAG | CUUUAAUGUUUUACAUUACU |
| sFLT1-i13 | NM_001159920.1 | 2333 | GUAAAUGUAAAACAUUAAAGG | ACAAAGUAAUGUAAAACAUUAAAGGACUCA | GUAAAUGUAAAACAUUAAAGG | CCUUUAAUGUUUUACAUUAC |
| sFLT1-i13 | NM_001159920.1 | 2339 | UAAAACAUUAAAGGACUCUA | UAAUGUAAAACAUUAAAGGACUCAUUAAA | UAAAACAUUAAAGGACUCUA | AUGAGUCCUUUAAUGUUUU |
| sFLT1-i13 | NM_001159920.1 | 2343 | ACAUUAAAGGACUCAUUAAA | GUAAAACAUUAAAGGACUCAUUAAAAAGUA | ACAUUAAAGGACUCAUUAAA | UUUAAUGAGUCCUUUAAUGU |
| sFLT1-i13 | NM_001159920.1 | 2351 | GGACUCAUUAAAAAGUAACA | UUUAAAGGACUCAUUAAAAAGUAACAGUUGU | GGACUCAUUAAAAAGUAACA | UGUUACUUUUUAAUGAGUCC |
| sFLT1-i13 | NM_001159920.1 | 2353 | ACUCAUUAAAAAGUAACAGU | AAGGACUCAUUAAAAAGUAACAGUGUCU | ACUCAUUAAAAAGUAACAGU | ACUGUUACUUUUUAAUGAGU |
| sFLT1-i13 | NM_001159920.1 | 2362 | AAAGUAACAGUUGUCUCUA | AUUAAAAAGUAACAGUUGUCUCUAUCAUC | AAAGUAACAGUUGUCUCUA | UAUGAGACAACUGUUACUUU |

| | | | | | |
|---|---|---|---|---|---|
| sFLT1-i15a | NM_001160030.1 | 2471 | CAUCAUCAUCAUCAUAGCUA | GUCAUCAUCAUCAUCAUAGCUAUCAUCAUC | CAUCAUCAUCAUCAUAGCUA | UAGCUAUGAUGAUGAUGAUG |
| sFLT1-i15a | NM_001160030.1 | 2474 | CAUCAUCAUCAUAGCUAUCA | AUCAUCAUCAUCAUAGCUAUCAUCAUAUU | CAUCAUCAUCAUAGCUAUCA | UGAUAGCUAUGAUGAUGAUC |
| sFLT1-i15a | NM_001160030.1 | 2477 | CAUCAUCAUAGCUAUCAUCA | AUCAUCAUCAUAGCUAUCAUCAUAUUAUC | CAUCAUCAUAGCUAUCAUCA | UGAUGAUAGCUAUGAUGAUG |
| sFLT1-i15a | NM_001160030.1 | 2508 | AUCAUCAUCAUCAUAGC | UCAUCAUCAUCAUCAUAGCUACCA | AUCAUCAUCAUCAUAGC | GCUAUGAUGAUGAUGAUGAU |
| sFLT1-i15a | NM_001160030.1 | 2510 | CAUCAUCAUCAUAGCUA | AUCAUCAUCAUCAUAGCUACCAUU | CAUCAUCAUCAUAGCUA | UAGCUAUGAUGAUGAUGAUG |
| sFLT1-i15a | NM_001160030.1 | 2513 | CAUCAUCAUAGCUACCA | CAUCAUCAUCAUAGCUACCAUUUAU | CAUCAUCAUAGCUACCA | UGGUAGCUAUGAUGAUGAUG |
| sFLT1-i15a | NM_001160030.1 | 2518 | UCAUCAUAGCUACCAUUUAU | CAUCAUAGCUACCAUUUAUUGAAA | UCAUAGCUACCAUUUAU | AUAAAUGGUAGCUAUGAUGA |
| sFLT1-i15a | NM_001160030.1 | 2519 | CAUCAUAGCUACCAUUUAUU | AUCAUAGCUACCAUUUAUUGAAAA | CAUCAUAGCUACCAUUUAUU | AAUAAAUGGUAGCUAUGAUG |
| sFLT1-i15a | NM_001160030.1 | 2525 | AGCUACCAUUUAUUGAAA | AUCAGCUACCAUUUAUUGAAAACUAUUA | AGCUACCAUUUAUUGAAA | GUUUCAAUAAAUGGUAGCU |
| sFLT1-i15a | NM_001160030.1 | 2528 | UACCAUUUAUUGAAAACUAU | AUAGCUACCAUUUAUUGAAAACUAUUA | UACCAUUUAUUGAAAACUAU | AUAGUUUUCAAUAAAUGGUA |
| sFLT1-i15a | NM_001160030.1 | 2556 | AACUUCAAGAACUAUCCU | GUGUCAACUUCAAGAACUAUCCUUUAGU | AACUUCAAGAACUAUCCU | AGGAUAAGUUCUUUGAGAUU |
| sFLT1-i15a | NM_001160030.1 | 2561 | CAAGAACUAUCCUUUAGU | AACUUCAAGAACUAUCCUUUAGUUGGAG | CAAAGAACUAUCCUUUAGU | ACUAAAGGAUAAGUUCUUUG |
| sFLT1-i15a | NM_001160030.1 | 2572 | UCCUUUAGUUGGAGAGCCAA | ACUUUAGUUGGAGAGCCAAGACAA | UCCUUUAGUUGGAGAGCCAA | UUGGCUCUCCAACUAAAGGA |
| sFLT1-i15a | NM_001160030.1 | 2574 | CUUUAGUUGGAGAGCCAAGA | UUAUCCUUUAGUUGGAGAGCCAAGACAA | CUUUAGUUGGAGAGCCAAGA | UCUUGGCUCUCCAACUAAAG |
| sFLT1-i15a | NM_001160030.1 | 2576 | UUAGUUGGAGAGCCAAGACA | AUCCUUUAGUUGGAGAGCCAAGACAAUCAU | UUAGUUGGAGAGCCAAGACA | UGUCUUGGCUCUCCAACUA |
| sFLT1-i15a | NM_001160030.1 | 2577 | UAGUUGGAGAGCCAAGACAA | UCCUUUAGUUGGAGAGCCAAGACAAUCAUA | UAGUUGGAGAGCCAAGACAA | UGUCUUGGCUCUCCAACUA |
| sFLT1-i15a | NM_001160030.1 | 2580 | UUGGAGAGCCAAGACAAUCA | UUUAGUUGGAGAGCCAAGACAAUCAAUACA | UUGGAGAGCCAAGACAAUCA | UGAUUGUCUUGGCUCUCCAA |
| sFLT1-i15a | NM_001160030.1 | 2582 | GGAGAGCCAAGACAAUCAUA | UAGGUUGGAGAGCCAAGACAAUCAUAACA | GGAGAGCCAAGACAAUCAUA | UAUGAUUGUCUUGGCUCUCC |
| sFLT1-i15a | NM_001160030.1 | 2585 | GAGCCAAGACAAUCAUAACA | UUGGAGAGCCAAGACAAUCAUAACAAUAAC | GAGCCAAGACAAUCAUAACA | UGUUAUGAUUGUCUUGGCUC |
| sFLT1-i15a | NM_001160030.1 | 2588 | CCAAGACAAUCAUAACAAUA | GAGAGCCAAGACAAUCAUAACAAUAACAAA | CCAAGACAAUCAUAACAAUA | UAUUGUUAUGAUUGUCUUGG |
| sFLT1-i15a | NM_001160030.1 | 2590 | AAGACAAUCAUAACAAUAAC | GAGCCAAGACAAUCAUAACAAUAACAAUAAC | AAGACAAUCAUAACAAUAAC | GUUAUUGUUAUGAUUGUCUU |
| FLT1 | NM_002019.4 | 331 | AGCUCUGAACUGCUUCUCACAGG | UGCUCUCAGCUGCUGAACUGCUUCUCACAGGAUCUA | AGCUCUGAACUGCUUCUCACAGG | CCUGUGAGAAUCAGACAGCU |
| FLT1 | NM_002019.4 | 376 | GAUCCUGAACUGAGUUUAAA | UAAAAGAUCCUGAACUGAGUUUAAAAGGCA | GAUCCUGAACUGAGUUUAAA | UUUAAACUCAGUUCAGGAUC |
| FLT1 | NM_002019.4 | 377 | AUCCUGAACUGAGUUUAAAA | AAAAGAUCCUGAACUGAGUUUAAAAGGCAC | AUCCUGAACUGAGUUUAAAA | UUUUAAACUCAGUUCAGGAU |
| FLT1 | NM_002019.4 | 381 | UGAACUGAGUUUAAAAGGCA | GAUCCUGAACUGAGUUUAAAAGGCACCCAG | UGAACUGAGUUUAAAAGGCA | UGCCUUUUAAACUCAGUUCA |
| FLT1 | NM_002019.4 | 389 | GUUUAAAAGGCACCCAGCAC | ACUGAGUUUAAAAGGCACCCAGCACGUACAC | GUUUAAAAGGCACCCAGCAC | GUGCUGGGUGCCUUUUAAAC |
| FLT1 | NM_002019.4 | 867 | AUCAAAUGCAACGUACAAAG | AUCAUAUCAAAUGCAACGUACAAAGA | AUCAAAUGCAACGUACAAAG | CUUUGUACGUUGCAUUUGAU |
| FLT1 | NM_002019.4 | 868 | UCAAAUGCAACGUACAAAGA | UCAUAUCAAAUGCAACGUACAAAGAA | UCAAAUGCAACGUACAAAGA | UCUUUGUACGUUGCAUUUGA |
| FLT1 | NM_002019.4 | 1384 | GUUGUAUGGUUAAAAGAUGG | CGGAAGUUGUAUGGUUAAAAGAUGGUUAC | GUUGUAUGGUUAAAAGAUGG | CCAUCUUUUAACCAUACAAC |
| FLT1 | NM_002019.4 | 1528 | UUUAAAAACCUCACUGCCAC | AUGUGUUUAAAAACCUCACUGCCACUCUAA | UUUAAAAACCUCACUGCCAC | GUGGCAGUGAGGUUUUUAAA |
| FLT1 | NM_002019.4 | 1530 | UAAAAACCUCACUGCCACUC | GUGUUUAAAAACCUCACUGCCACUCUAAUU | UAAAAACCUCACUGCCACUC | GAGUGGCAGUGAGGUUUUUA |
| FLT1 | NM_002019.4 | 1532 | AAAACCUCACUGCCACUCUA | GUUUAAAAACCUCACUGCCACUCUAAUUGU | AAAACCUCACUGCCACUCUA | UAGAGUGGCAGUGAGGUUUU |
| FLT1 | NM_002019.4 | 1781 | GAAACAGAAUUGAGAGCAUC | CAUGGGAACAGAAUUGAGAGCAUCACUCA | GAAACAGAAUUGAGAGCAUC | GAUGCUCUCAAUUCUGUUUC |

| Sense P2 | Guide P2 | H. sapien | M. musculus | Papio hamadryas | Target mRNA Expression (% control) |
|---|---|---|---|---|---|
| fA#mA#fUmC#AmG#AmG#UmUfCmAfCmC#fU#fA-tegChol | P-mU#fG#mC#AmG#UmG#CmU#CmA#CmC#fU#mG#fA#mU#fU | yes | | yes | 85.1 |
| fC#mA#fGmC#AmG#fCmU#fUmG#CmA#fCmA#fC#fA-tegChol | P-mU#fU#mU#fGmU#fUmA#fCmA#fGmU#fC#fA#mC#fA#mU#fC | yes | | yes | 101.7 |
| fA#mG#fGmU#fGmC#AmC#CmA#fCmC#U#fU#fA-tegChol | P-mU#fG#mU#fU#mG#fUmG#fCmA#fCmU#fC#mA#fC#mU#fC | yes | | yes | 55.2 |
| fU#mG#fAmG#fCmA#fCmC#AmA#CmA#fCm A#fA-tegChol | P-mU#fU#mU#fU#mU#fGmU#fUmG#fCmA#fGmC#fA#mA#fC#fU | yes | | yes | 58.8 |
| fU#mU#fUmU#fUmC#mU#fCmU#fCmG#AmU#fUmC#fA#fA-tegChol | P-mU#fU#mU#fU#mU#fCmU#fCmG#mA#fGmA#fGmA#fC#fA#mA#fA | yes | | yes | 71.5 |
| fU#mU#fUmC#fUmC#GmA#fAmU#fCmC#fAmA#fC#fA-tegChol | P-mU#fU#mU#fU#mC#fGmA#fGmA#fUmC#fC#mA#fA#mA#fA | yes | | yes | 105.2 |
| fC#mU#fCmU#fCmG#AmU#fUmC#fUmC#fAmA#fG#fA-tegChol | P-mU#fA#fAmA#fAmU#fUmG#fAmG#fAmG#UmC#fC#mG#mA#fG | yes | yes | yes | 8.0 |
| fU#mU#fCmU#fCmG#AmU#fUmC#fUmC#fAmU#fA#mU#fA-tegChol | P-mU#fU#mA#fAmA#fAmU#fUmG#fAmG#fAmU#fA#mC#fA#mA#fG | yes | | yes | 94.4 |
| fU#mC#fGmG#fAmU#fCmC#AmU#fCmC#fAmA#fC#fA-tegChol | P-mU#fU#mU#fU#mU#fAmA#fAmU#fUmG#fGmA#fA#mC#fC#fA#mG#fA | yes | | yes | 98.2 |
| fU#mC#fCmA#fAmA#fUmA#fAmA#fAmU#fA#mU#fA-tegChol | P-mU#fU#mU#fU#mU#fGmU#fUmA#fAmA#fC#mG#fA#fA | yes | | yes | 106.2 |
| fC#mC#fAmA#fAmU#fAmA#fAmA#mC#fA#fA-tegChol | P-mU#fU#mU#fA#mU#fU#fU#mU#fGmU#fUmA#fA#mU#fA#fA | yes | | yes | 92.7 |
| fC#mA#fAmA#fAmU#fUmC#mU#fAmU#mA#fA-tegChol | P-mU#fU#fC#mC#fU#mU#fA#fA#mU#fGmU#fU#mA#fA#fC | yes | | yes | 87.2 |
| fC#mA#fAmA#fUmU#fCmC#mA#fAmA#mU#fA-tegChol | P-mU#fU#fC#mC#fU#mU#fU#fU#mA#fA#mU#fGmU#fU#mA#fG | yes | | yes | 73.9 |
| fA#mA#fGmC#fAmC#fAmG#fAmG#fA#mG#fA-tegChol | P-mU#fA#fAmA#fAmU#fCmC#mU#fCmU#fU#mC#fA#mU#fU#mC | yes | | yes | 111.4 |
| fC#mA#fGmA#fAmU#fGmU#fAmC#fCmU#fA#mA#fA-tegChol | P-mU#fU#fC#mU#fU

| | | | |
|---|---|---|---|
| fA#mG#mC#CmUfCmU#CmUfGmC#UmU#C#A##A-tegChol | P-mU#fC#mU#Gmu#GmAfGmAfAmGfCmA#fG#mA#G#mC#U | yes | yes | 24.9 |
| fG#mA#fUmC#ICmUfGmAfAmC#UmGfA#mG#fA#mG#fA-tegChol | P-mU#mUfAmAfAmCfUmCfAmGfUmA#fG#mU##A#mU##C | yes | yes | 32.2 |
| fA#mU#fCmCfUmGfAmA#CmA#G#mU#fA##A-tegChol | P-mU#U#mUfUmAfAmA#CmU#CmA#GmU##U#mC#A#mG#mA#U | yes | yes | 26.9 |
| fU#mG##AmAfCmA#GmUfA#mA#mA##A#A-tegChol | P-mU#G#mC#CmUfU#mU#AfAmA#CmU#CmA#G#mU#mC##A | yes | yes | 10.7 |
| fG#mU#UmUfAmA#GmCfCmA#C#mC#A-tegChol | P-mU#U#fCmU#GmU#GmAfCmGfUm#Gmu#mC#A#mA#A#C | yes | yes | 60.8 |
| fA#mU#fCmAfAmU#mUfGmCfAmAfCfG#mnA##A-tegChol | P-mU#C#fmU#UmUfUmfAmCfGmU#UfGmCfA

|  | Acceptable TPP | Ideal TPP | Comments |
|---|---|---|---|
| Indications and Usage | Severe preterm preeclampsia, gestational age between 28 to 34 weeks | Severe preterm preeclampsia, gestational age between 24 to 34 weeks | Preliminary studies show no compound transfer to the fetus. It is essential to validate this claim, which should support expansion of gestational window to ages where full organ development has not yet been achieved. |
| Efficacy | 30-50% reduction in sFLT1 | 30-40% reduction in sFLT1 | 30% reduction in circulating sFLT1 was shown to be sufficient to treat PE. More extensive down-regulation might not be desired. We will explore if the desired level of silencing can be achieved with dose reduction or alternatively target only one of the three major contributing isoforms |
| Dosage and Administration | IV or SC, daily | SC, once | Current pilot PK studies indicate that single SC administration results in drug accumulation in placental labyrinth at concentrations exceeding therapeutically efficacious doses. The drug persists in placenta with only half being cleared after 5 days. In combination with biological mechanism of function, where single loading of the RISC complex results in weeks of silencing, data support potential for month-long duration of effect upon single administration |
| Dosage Forms and Strengths | IV solution | SC, dried | So far have seen equal levels of placental delivery via IV and SC administration, so we will favor SC in future studies. The oligonucleotides are chemically synthesized and their half-life in dry form is expected to exceed decades. Compounds are easily soluble in saline at the point of care. |
| Contra-indications | PE with severe fetal growth restriction | None | Upon severe fetal growth restriction, PE might be essential to provide sufficient blood flow to the fetus. Thus PE associated with severe fetal growth restriction is not a candidate for this treatment option. |
| Adverse Reactions | Small degree of hypotension, minor, reversible increase in transaminases, injection site reaction, minimal transfer to fetus with no functional consequences | None, injection site reaction, no transfer to fetus | No adverse effects observed at doses used to date. Oligonucleotides in general are known to cause injection site reaction and some elevation in liver enzymes as class specific adverse events, although the extent varies with different chemical variants. While injection site reaction (usually mild if any) is not problematic, PE women already have poor liver function and any additional negative modulation might be problematic. This issue will be studied in detail. |
| Clinical Pharmacology | Liver/kidney/placenta | Preferential placental delivery, drug persists in target tissue | Pilot data indicate that the drug persists in target tissues for extended time periods (less than 50% cleared in 5 days). This will be studied in detail and addressed in this proposal. Current chemical variant delivers to kidney and liver endothelium, skin around administration site and placental labyrinth. Additional chemical optimization will be performed to increase percentage of drug delivered to placenta |
| Nonclinical Toxicology |  |  | Will be studied later as part of standard IND enabling toxicology package |

*Fig. 14*

| | | Mother weight | | | Baby information | | |
|---|---|---|---|---|---|---|---|
| animal ID | Injection | e10 | e19 | weight gain | no. born | no. death | weight |
| M81 | sFLT1-2283 | 40 | 60 | 20 | 13 | 0 | 1.475+/-0.083 |
| M82 | sFLT1-2283 | 38 | 59 | 21 | 13 | 0 | 1.569+/-0.063 |
| M83 | sFLT1-2283 | 35 | 64 | 29 | 18 | 0 | 1.345+/-0.086 |
| M84 | sFLT1-2283 | 34 | 52 | 18 | 10 | 1 | 1.628+/-0.048 |
| M85 | sFLT1-2283 | 41 | 68 | 27 | 16 | 0 | 1.580+/-0.082 |
| M86 | sFLT1-2283 | 35 | 58 | 23 | 16 | 0 | 1.248+/-0.072 |
| M87 | sFLT1-2283 | 40 | 64 | 24 | 14 | 0 | 1.486+/-0.080 |
| M88 | sFLT1-2283 | 38 | 63 | 25 | 15 | 0 | 1.439+/-0.060 |
| M89 | sFLT1-2283 | 37 | 64 | 27 | 17 | 0 | 1.340+/-0.278 |
| M90 | PBS | 38 | 53 | 15 | 10 | 0 | 1.654+/-0.067 |
| M91 | PBS | 38 | 56 | 18 | 10 | 0 | 1.666+/-0.083 |
| M92 | PBS | 37 | 59 | 22 | 15 | 0 | 1.419+/-0.116 |
| M93 | PBS | 33 | 56 | 23 | 15 | 0 | 1.489+/-0.065 |
| M94 | PBS | 35 | 58 | 22 | 13 | 0 | 1.602+/- 0.053 |
| M95 | PBS | 39 | 63 | 24 | 15 | 0 | 1.383+/-0.108 |
| M96 | PBS | 32 | 55 | 23 | 14 | 0 | 1.409+/- 0.072 |
| M97 | PBS | 36 | 59 | 23 | 13 | 0 | 1.451+/-0.045 |
| M98 | PBS | 43 | 64 | 21 | 13 | 0 | 1.479+/-0.128 |

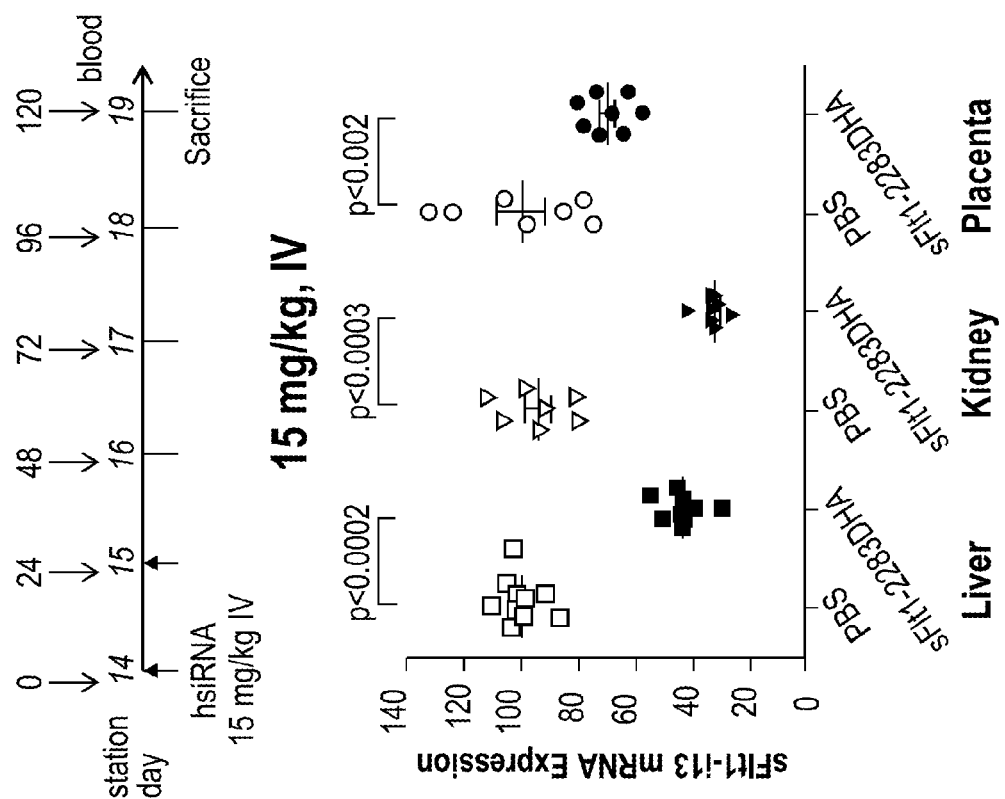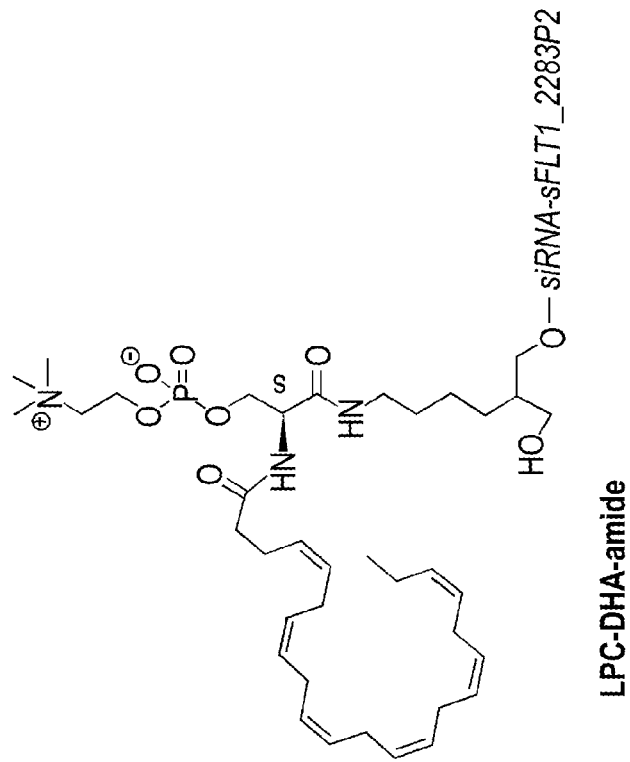
Fig. 26

(5'-3')   R¹R³A̱=A-A̱-U-U̱-U-G̱-G-A̱-G-A̱-U-C̱=C=G̱=A=G̱=AR³G̱

(3'-5')   R²-A̱R³U=U̱-U-A̱-A-A̱-C-C̱-U-C̱-U-A̱=GR³G̱

(5'-3')   R¹R³A̱=U-A̱-A-A̱-U-G̱-G-U̱-A-G̱-C-U̱=A=U̱=G=A̱=UR³G (3'-5')   R²-A̱R³U=A̱-U-U̱-U-A̱-C-C̱-A-U̱-C-G̱=AR³U̱

Legend

X̱ - 2'-deoxy-2'-fluoro
X - 2'-O-methyl (5'-3')  R¹=A̲=A-A̲-U-U̲-U-G̲-G-A̲-G-A̲-U-C̲=C=G̲=A=G̲=A=G̲

. . . . . . . . . . . . .

(3'-5')  R²-A̲=U=U̲-U-A̲-A-A̲-C-C̲-U-C̲-U-A̲=G=G̲

(5'-3')  R¹=A̲=U-A̲-A-A̲-U-G̲-G-U̲-A-G̲-C-U̲=A=U̲=G=A̲=U=G̲

. . . . . . . . . . . . .

(3'-5')  R²-A̲=U=A̲-U-U̲-U-A̲-C-C̲-A-U̲-C-G̲=A=U̲

Legend

X̲- 2'-deoxy-2'-fluoro
X- 2'-O-methyl

SEQUENCE LISTING

<160> NUMBER OF SEQ ID NOS: 713

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctctcggatc tccaaattta                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
catcatagct accatttatt                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
attgtaccac acaaagtaat                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gagccaagac aatcataaca                                              20

<210> SEQ ID NO 5
<211> LENGTH: 114
<212> TYPE: DNA
<213> ORGANISM: Homo sapiens

<400> SEQUENCE: 5
gtgagcactg caacaaaaag gctgttttct ctcggatctc caaatttaaa agcacaagga    60
atgattgtac cacacaaagt aatgtaaaac attaaaggac tcattaaaaa gtaa         114

<210> SEQ ID NO 6
<211> LENGTH: 456
<212> TYPE: DNA
<213> ORGANISM: Homo sapiens

<400> SEQUENCE: 6

```
gaagaaagaa attacaatca gaggtgagca ctgcaacaaa aaggctgttt tctctcggat      60
ctccaaattt aaaagcacaa ggaatgattg taccacacaa agtaatgtaa aacattaaag     120
gactcattaa aaagtaacag ttgtctcata tcatcttgat ttattgtcac tgttgctaac    180
tttcaggctc ggaggagatg ctcctcccaa aatgagttcg gagatgatag cagtaataat    240
gagaccccg ggctccagct ctgggccccc cattcaggcc gaggggctg ctccgggggg      300
ccgacttggt gcacgtttgg atttggagga tccctgcact gccttctctg tgtttgttgc    360
tcttgctgtt ttctcctgcc tgataaacaa caacttggga tgatcctttc cattttgatg    420
ccaacctctt tttatttta agcggcgccc tatagt                                456
```

<210> SEQ ID NO 7
<211> LENGTH: 570
<212> TYPE: DNA
<213> ORGANISM: Homo sapiens

<400> SEQUENCE: 7

```
aactgtatac atcaacgtca ccatcgtcat cgtcatcatc accattgtca tcatcatcat     60
catcgtcatc atcatcatca tcatagctat catcattatc atcatcatca tcatcatcat    120
catagctacc atttattgaa aactattatg tgtcaacttc aaagaactta tcctttagtt    180
ggagagccaa gacaatcata acaataacaa atggccgggc atggtggctc acgcctgtaa    240
tcccagcact ttgggaggcc aaggcaggtg gatcatttga ggtcaggagt ccaagaccag    300
cctgaccaag atggtgaaat gctgtctcta ttaaaaatac aaaattagcc aggcatggtg    360
gctcatgcct gtaatgccag ctactcggga ggctgagaca ggagaatcac ttgaacccag    420
gaggcagagg ttgcagggag ccgagatcgt gtactgcact ccagcctggg caacaagagc    480
gaaactccgt ctcaaaaaac aaataaataa ataaataaat aaacagacaa aattcacttt    540
ttattctatt aaacttaaca tacatgctaa                                      570
```

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8

```
uaaauuugga gauccgagag                                                  20
```

<210> SEQ ID NO 9
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9

```
ggaucuccaa auuua                                                       15
```

<210> SEQ ID NO 10
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 10
uauaaauggu agcuaugaug                                                   20

<210> SEQ ID NO 11
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uagcuaccau uuaua                                                        15

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uaaauuugga gauccgagag                                                   20

<210> SEQ ID NO 13
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ggaucuccaa auuua                                                        15

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uauaaauggu agcuaugaug                                                   20

<210> SEQ ID NO 15
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uagcuaccau uuaua                                                        15

<210> SEQ ID NO 16
<211> LENGTH: 13
<212> TYPE: RNA
<213> ORGANISM: Homo sapiens

<400> SEQUENCE: 16
```

-continued aucgaggucc gcg                                                          13

<210> SEQ ID NO 17
<211> LENGTH: 20
<212> TYPE: RNA
<213> ORGANISM: Homo sapiens

<400> SEQUENCE: 17
aaucagaggu gagcacugca                                                   20

<210> SEQ ID NO 18
<211> LENGTH: 20
<212> TYPE: RNA
<213> ORGANISM: Homo sapiens

<400> SEQUENCE: 18
gaggugagca cugcaacaaa                                                   20

<210> SEQ ID NO 19
<211> LENGTH: 20
<212> TYPE: RNA
<213> ORGANISM: Homo sapiens

<400> SEQUENCE: 19
aggugagcac ugcaacaaaa                                                   20

<210> SEQ ID NO 20
<211> LENGTH: 20
<212> TYPE: RNA
<213> ORGANISM: Homo sapiens

<400> SEQUENCE: 20
ugagcacugc aacaaaaagg                                                   20

<210> SEQ ID NO 21
<211> LENGTH: 20
<212> TYPE: RNA
<213> ORGANISM: Homo sapiens

<400> SEQUENCE: 21
uuuucucucg gaucuccaaa                                                   20

<210> SEQ ID NO 22
<211> LENGTH: 20
<212> TYPE: RNA
<213> ORGANISM: Homo sapiens

<400> SEQUENCE: 22
uuucucucgg aucuccaaau                                                   20

<210> SEQ ID NO 23
<211> LENGTH: 20
<212> TYPE: RNA
<213> ORGANISM: Homo sapiens

<400> SEQUENCE: 23
cucucggauc uccaaauuua                                                   20

<210> SEQ ID NO 24
<211> LENGTH: 20
<212> TYPE: RNA
<213> ORGANISM: Homo sapiens

```
<400> SEQUENCE: 24
ucucggaucu ccaaauuuaa                                          20

<210> SEQ ID NO 25
<211> LENGTH: 20
<212> TYPE: RNA
<213> ORGANISM: Homo sapiens

<400> SEQUENCE: 25
ucggaucucc aaauuuaaaa                                          20

<210> SEQ ID NO 26
<211> LENGTH: 20
<212> TYPE: RNA
<213> ORGANISM: Homo sapiens

<400> SEQUENCE: 26
uccaaauuua aaagcacaag                                          20

<210> SEQ ID NO 27
<211> LENGTH: 20
<212> TYPE: RNA
<213> ORGANISM: Homo sapiens

<400> SEQUENCE: 27
ccaaauuuaa aagcacaagg                                          20

<210> SEQ ID NO 28
<211> LENGTH: 20
<212> TYPE: RNA
<213> ORGANISM: Homo sapiens

<400> SEQUENCE: 28
caaauuuaaa agcacaagga                                          20

<210> SEQ ID NO 29
<211> LENGTH: 20
<212> TYPE: RNA
<213> ORGANISM: Homo sapiens

<400> SEQUENCE: 29
aagcacaagg aaugauugua                                          20

<210> SEQ ID NO 30
<211> LENGTH: 20
<212> TYPE: RNA
<213> ORGANISM: Homo sapiens

<400> SEQUENCE: 30
gaaugauugu accacacaaa                                          20

<210> SEQ ID NO 31
<211> LENGTH: 20
<212> TYPE: RNA
<213> ORGANISM: Homo sapiens

<400> SEQUENCE: 31
auuguaccac acaaaguaau                                          20

<210> SEQ ID NO 32
<211> LENGTH: 20
<212> TYPE: RNA
<213> ORGANISM: Homo sapiens
```

```
<400> SEQUENCE: 32
guaccacaca aaguaaugua                                              20

<210> SEQ ID NO 33
<211> LENGTH: 20
<212> TYPE: RNA
<213> ORGANISM: Homo sapiens

<400> SEQUENCE: 33
uaccacacaa aguaauguaa                                              20

<210> SEQ ID NO 34
<211> LENGTH: 20
<212> TYPE: RNA
<213> ORGANISM: Homo sapiens

<400> SEQUENCE: 34
ccacacaaag uaauguaaaa                                              20

<210> SEQ ID NO 35
<211> LENGTH: 20
<212> TYPE: RNA
<213> ORGANISM: Homo sapiens

<400> SEQUENCE: 35
acacaaagua auguaaaaca                                              20

<210> SEQ ID NO 36
<211> LENGTH: 20
<212> TYPE: RNA
<213> ORGANISM: Homo sapiens

<400> SEQUENCE: 36
aguaauguaa aacauuaaag                                              20

<210> SEQ ID NO 37
<211> LENGTH: 20
<212> TYPE: RNA
<213> ORGANISM: Homo sapiens

<400> SEQUENCE: 37
guaauguaaa acauuaaagg                                              20

<210> SEQ ID NO 38
<211> LENGTH: 20
<212> TYPE: RNA
<213> ORGANISM: Homo sapiens

<400> SEQUENCE: 38
uaaaacauua aaggacucau                                              20

<210> SEQ ID NO 39
<211> LENGTH: 20
<212> TYPE: RNA
<213> ORGANISM: Homo sapiens

<400> SEQUENCE: 39
acauuaaagg acucauuaaa                                              20

<210> SEQ ID NO 40
<211> LENGTH: 20
<212> TYPE: RNA
```

```
<213> ORGANISM: Homo sapiens

<400> SEQUENCE: 40
ggacucauua aaaaguaaca                                              20

<210> SEQ ID NO 41
<211> LENGTH: 20
<212> TYPE: RNA
<213> ORGANISM: Homo sapiens

<400> SEQUENCE: 41
acucauuaaa aaguaacagu                                              20

<210> SEQ ID NO 42
<211> LENGTH: 20
<212> TYPE: RNA
<213> ORGANISM: Homo sapiens

<400> SEQUENCE: 42
aaaguaacag uugucucaua                                              20

<210> SEQ ID NO 43
<211> LENGTH: 20
<212> TYPE: RNA
<213> ORGANISM: Homo sapiens

<400> SEQUENCE: 43
caucaucauc aucauagcua                                              20

<210> SEQ ID NO 44
<211> LENGTH: 20
<212> TYPE: RNA
<213> ORGANISM: Homo sapiens

<400> SEQUENCE: 44
caucaucauc auagcuauca                                              20

<210> SEQ ID NO 45
<211> LENGTH: 20
<212> TYPE: RNA
<213> ORGANISM: Homo sapiens

<400> SEQUENCE: 45
caucaucaua gcuaucauca                                              20

<210> SEQ ID NO 46
<211> LENGTH: 20
<212> TYPE: RNA
<213> ORGANISM: Homo sapiens

<400> SEQUENCE: 46
aucaucauca ucaucauagc                                              20

<210> SEQ ID NO 47
<211> LENGTH: 20
<212> TYPE: RNA
<213> ORGANISM: Homo sapiens

<400> SEQUENCE: 47
caucaucauc aucauagcua                                              20

<210> SEQ ID NO 48
<211> LENGTH: 20
```

```
<212> TYPE: RNA
<213> ORGANISM: Homo sapiens

<400> SEQUENCE: 48
caucaucauc auagcuacca                                                20

<210> SEQ ID NO 49
<211> LENGTH: 20
<212> TYPE: RNA
<213> ORGANISM: Homo sapiens

<400> SEQUENCE: 49
ucaucauagc uaccauuuau                                                20

<210> SEQ ID NO 50
<211> LENGTH: 20
<212> TYPE: RNA
<213> ORGANISM: Homo sapiens

<400> SEQUENCE: 50
caucauagcu accauuuauu                                                20

<210> SEQ ID NO 51
<211> LENGTH: 20
<212> TYPE: RNA
<213> ORGANISM: Homo sapiens

<400> SEQUENCE: 51
agcuaccauu uauugaaaac                                                20

<210> SEQ ID NO 52
<211> LENGTH: 20
<212> TYPE: RNA
<213> ORGANISM: Homo sapiens

<400> SEQUENCE: 52
uaccauuuau ugaaaacuau                                                20

<210> SEQ ID NO 53
<211> LENGTH: 20
<212> TYPE: RNA
<213> ORGANISM: Homo sapiens

<400> SEQUENCE: 53
aacuucaaag aacuuauccu                                                20

<210> SEQ ID NO 54
<211> LENGTH: 20
<212> TYPE: RNA
<213> ORGANISM: Homo sapiens

<400> SEQUENCE: 54
caaagaacuu auccuuuagu                                                20

<210> SEQ ID NO 55
<211> LENGTH: 20
<212> TYPE: RNA
<213> ORGANISM: Homo sapiens

<400> SEQUENCE: 55
uccuuuaguu ggagagccaa                                                20

<210> SEQ ID NO 56
```

```
<211> LENGTH: 20
<212> TYPE: RNA
<213> ORGANISM: Homo sapiens

<400> SEQUENCE: 56
cuuuaguugg agagccaaga                                              20

<210> SEQ ID NO 57
<211> LENGTH: 20
<212> TYPE: RNA
<213> ORGANISM: Homo sapiens

<400> SEQUENCE: 57
uuaguuggag agccaagaca                                              20

<210> SEQ ID NO 58
<211> LENGTH: 20
<212> TYPE: RNA
<213> ORGANISM: Homo sapiens

<400> SEQUENCE: 58
uaguuggaga gccaagacaa                                              20

<210> SEQ ID NO 59
<211> LENGTH: 20
<212> TYPE: RNA
<213> ORGANISM: Homo sapiens

<400> SEQUENCE: 59
uuggagagcc aagacaauca                                              20

<210> SEQ ID NO 60
<211> LENGTH: 20
<212> TYPE: RNA
<213> ORGANISM: Homo sapiens

<400> SEQUENCE: 60
ggagagccaa gacaaucaua                                              20

<210> SEQ ID NO 61
<211> LENGTH: 20
<212> TYPE: RNA
<213> ORGANISM: Homo sapiens

<400> SEQUENCE: 61
gagccaagac aaucauaaca                                              20

<210> SEQ ID NO 62
<211> LENGTH: 20
<212> TYPE: RNA
<213> ORGANISM: Homo sapiens

<400> SEQUENCE: 62
ccaagacaau cauaacaaua                                              20

<210> SEQ ID NO 63
<211> LENGTH: 20
<212> TYPE: RNA
<213> ORGANISM: Homo sapiens

<400> SEQUENCE: 63
aagacaauca uaacaauaac                                              20
```

```
<210> SEQ ID NO 64
<211> LENGTH: 30
<212> TYPE: RNA
<213> ORGANISM: Homo sapiens

<400> SEQUENCE: 64
auuacaauca gaggugagca cugcaacaaa                                     30

<210> SEQ ID NO 65
<211> LENGTH: 30
<212> TYPE: RNA
<213> ORGANISM: Homo sapiens

<400> SEQUENCE: 65
aaucagaggu gagcacugca acaaaaaggc                                     30

<210> SEQ ID NO 66
<211> LENGTH: 30
<212> TYPE: RNA
<213> ORGANISM: Homo sapiens

<400> SEQUENCE: 66
aucagaggug agcacugcaa caaaaaggcu                                     30

<210> SEQ ID NO 67
<211> LENGTH: 30
<212> TYPE: RNA
<213> ORGANISM: Homo sapiens

<400> SEQUENCE: 67
agaggugagc acugcaacaa aaaggcuguu                                     30

<210> SEQ ID NO 68
<211> LENGTH: 30
<212> TYPE: RNA
<213> ORGANISM: Homo sapiens

<400> SEQUENCE: 68
ggcuguuuuc ucucggaucu ccaaauuuaa                                     30

<210> SEQ ID NO 69
<211> LENGTH: 30
<212> TYPE: RNA
<213> ORGANISM: Homo sapiens

<400> SEQUENCE: 69
gcuguuuucu cucggaucuc caaauuuaaa                                     30

<210> SEQ ID NO 70
<211> LENGTH: 30
<212> TYPE: RNA
<213> ORGANISM: Homo sapiens

<400> SEQUENCE: 70
guuuucucuc ggaucuccaa auuuaaaagc                                     30

<210> SEQ ID NO 71
<211> LENGTH: 30
<212> TYPE: RNA
<213> ORGANISM: Homo sapiens

<400> SEQUENCE: 71
uuuucucucg gaucuccaaa uuuaaaagca                                     30
```

<210> SEQ ID NO 72
<211> LENGTH: 30
<212> TYPE: RNA
<213> ORGANISM: Homo sapiens

<400> SEQUENCE: 72
uucucucgga ucuccaaauu uaaaagcaca                                    30

<210> SEQ ID NO 73
<211> LENGTH: 30
<212> TYPE: RNA
<213> ORGANISM: Homo sapiens

<400> SEQUENCE: 73
ggaucuccaa auuuaaaagc acaaggaaug                                    30

<210> SEQ ID NO 74
<211> LENGTH: 30
<212> TYPE: RNA
<213> ORGANISM: Homo sapiens

<400> SEQUENCE: 74
gaucuccaaa uuuaaaagca caaggaauga                                    30

<210> SEQ ID NO 75
<211> LENGTH: 30
<212> TYPE: RNA
<213> ORGANISM: Homo sapiens

<400> SEQUENCE: 75
aucuccaaau uuaaaagcac aaggaaugau                                    30

<210> SEQ ID NO 76
<211> LENGTH: 30
<212> TYPE: RNA
<213> ORGANISM: Homo sapiens

<400> SEQUENCE: 76
uuuaaaagca caaggaauga uuguaccaca                                    30

<210> SEQ ID NO 77
<211> LENGTH: 30
<212> TYPE: RNA
<213> ORGANISM: Homo sapiens

<400> SEQUENCE: 77
acaaggaaug auuguaccac acaaaguaau                                    30

<210> SEQ ID NO 78
<211> LENGTH: 30
<212> TYPE: RNA
<213> ORGANISM: Homo sapiens

<400> SEQUENCE: 78
gaaugauugu accacacaaa guaauguaaa                                    30

<210> SEQ ID NO 79
<211> LENGTH: 30
<212> TYPE: RNA
<213> ORGANISM: Homo sapiens

<400> SEQUENCE: 79
ugauuguacc acacaaagua auguaaaaca                                    30

<210> SEQ ID NO 80
<211> LENGTH: 30
<212> TYPE: RNA
<213> ORGANISM: Homo sapiens

<400> SEQUENCE: 80
gauuguacca cacaaaguaa uguaaaacau                             30

<210> SEQ ID NO 81
<211> LENGTH: 30
<212> TYPE: RNA
<213> ORGANISM: Homo sapiens

<400> SEQUENCE: 81
uuguaccaca caaaguaaug uaaaacauua                             30

<210> SEQ ID NO 82
<211> LENGTH: 30
<212> TYPE: RNA
<213> ORGANISM: Homo sapiens

<400> SEQUENCE: 82
guaccacaca aaguaaugua aaacauuaaa                             30

<210> SEQ ID NO 83
<211> LENGTH: 30
<212> TYPE: RNA
<213> ORGANISM: Homo sapiens

<400> SEQUENCE: 83
cacaaaguaa uguaaaacau uaaaggacuc                             30

<210> SEQ ID NO 84
<211> LENGTH: 30
<212> TYPE: RNA
<213> ORGANISM: Homo sapiens

<400> SEQUENCE: 84
acaaaguaau guaaaacauu aaaggacuca                             30

<210> SEQ ID NO 85
<211> LENGTH: 30
<212> TYPE: RNA
<213> ORGANISM: Homo sapiens

<400> SEQUENCE: 85
uaauguaaaa cauuaaagga cucauuaaaa                             30

<210> SEQ ID NO 86
<211> LENGTH: 30
<212> TYPE: RNA
<213> ORGANISM: Homo sapiens

<400> SEQUENCE: 86
guaaaacauu aaaggacuca uuaaaaagua                             30

<210> SEQ ID NO 87
<211> LENGTH: 30
<212> TYPE: RNA
<213> ORGANISM: Homo sapiens

<400> SEQUENCE: 87
uuaaaggacu cauuaaaaag uaacaguugu                                              30

<210> SEQ ID NO 88
<211> LENGTH: 30
<212> TYPE: RNA
<213> ORGANISM: Homo sapiens

<400> SEQUENCE: 88
aaaggacuca uuaaaaagua acaguugucu                                              30

<210> SEQ ID NO 89
<211> LENGTH: 30
<212> TYPE: RNA
<213> ORGANISM: Homo sapiens

<400> SEQUENCE: 89
auuaaaaagu aacaguuguc ucauaucauc                                              30

<210> SEQ ID NO 90
<211> LENGTH: 30
<212> TYPE: RNA
<213> ORGANISM: Homo sapiens

<400> SEQUENCE: 90
gucaucauca ucaucaucau agcuaucauc                                              30

<210> SEQ ID NO 91
<211> LENGTH: 30
<212> TYPE: RNA
<213> ORGANISM: Homo sapiens

<400> SEQUENCE: 91
aucaucauca ucaucauagc uaucaucauu                                              30

<210> SEQ ID NO 92
<211> LENGTH: 30
<212> TYPE: RNA
<213> ORGANISM: Homo sapiens

<400> SEQUENCE: 92
aucaucauca ucauagcuau caucauuauc                                              30

<210> SEQ ID NO 93
<211> LENGTH: 30
<212> TYPE: RNA
<213> ORGANISM: Homo sapiens

<400> SEQUENCE: 93
ucaucaucau caucaucauc auagcuacca                                              30

<210> SEQ ID NO 94
<211> LENGTH: 30
<212> TYPE: RNA
<213> ORGANISM: Homo sapiens

<400> SEQUENCE: 94
aucaucauca ucaucaucau agcuaccauu                                              30

<210> SEQ ID NO 95
<211> LENGTH: 30
<212> TYPE: RNA
<213> ORGANISM: Homo sapiens

<400> SEQUENCE: 95
aucaucauca ucaucauagc uaccauuuau					30

<210> SEQ ID NO 96
<211> LENGTH: 30
<212> TYPE: RNA
<213> ORGANISM: Homo sapiens

<400> SEQUENCE: 96
caucaucauc auagcuacca uuuauugaaa					30

<210> SEQ ID NO 97
<211> LENGTH: 30
<212> TYPE: RNA
<213> ORGANISM: Homo sapiens

<400> SEQUENCE: 97
aucaucauca uagcuaccau uuauugaaaa					30

<210> SEQ ID NO 98
<211> LENGTH: 30
<212> TYPE: RNA
<213> ORGANISM: Homo sapiens

<400> SEQUENCE: 98
aucauagcua ccauuuauug aaaacuauua					30

<210> SEQ ID NO 99
<211> LENGTH: 30
<212> TYPE: RNA
<213> ORGANISM: Homo sapiens

<400> SEQUENCE: 99
auagcuacca uuuauugaaa acuauuaugu					30

<210> SEQ ID NO 100
<211> LENGTH: 30
<212> TYPE: RNA
<213> ORGANISM: Homo sapiens

<400> SEQUENCE: 100
gugucaacuu caaagaacuu auccuuuagu					30

<210> SEQ ID NO 101
<211> LENGTH: 30
<212> TYPE: RNA
<213> ORGANISM: Homo sapiens

<400> SEQUENCE: 101
aacuucaaag aacuuauccu uuaguuggag					30

<210> SEQ ID NO 102
<211> LENGTH: 30
<212> TYPE: RNA
<213> ORGANISM: Homo sapiens

<400> SEQUENCE: 102
acuuauccuu uaguuggaga gccaagacaa					30

<210> SEQ ID NO 103
<211> LENGTH: 30
<212> TYPE: RNA
<213> ORGANISM: Homo sapiens

<400> SEQUENCE: 103
uuauccuuua guuggagagc caagacaauc					30

<210> SEQ ID NO 104
<211> LENGTH: 30
<212> TYPE: RNA
<213> ORGANISM: Homo sapiens

<400> SEQUENCE: 104
auccuuuagu uggagagcca agacaaucau					30

<210> SEQ ID NO 105
<211> LENGTH: 30
<212> TYPE: RNA
<213> ORGANISM: Homo sapiens

<400> SEQUENCE: 105
uccuuuaguu ggagagccaa gacaaucaua					30

<210> SEQ ID NO 106
<211> LENGTH: 30
<212> TYPE: RNA
<213> ORGANISM: Homo sapiens

<400> SEQUENCE: 106
uuuaguugga gagccaagac aaucauaaca					30

<210> SEQ ID NO 107
<211> LENGTH: 30
<212> TYPE: RNA
<213> ORGANISM: Homo sapiens

<400> SEQUENCE: 107
uaguuggaga gccaagacaa ucauaacaau					30

<210> SEQ ID NO 108
<211> LENGTH: 30
<212> TYPE: RNA
<213> ORGANISM: Homo sapiens

<400> SEQUENCE: 108
uuggagagcc aagacaauca uaacaauaac					30

<210> SEQ ID NO 109
<211> LENGTH: 30
<212> TYPE: RNA
<213> ORGANISM: Homo sapiens

<400> SEQUENCE: 109
gagagccaag acaaucauaa caauaacaaa					30

<210> SEQ ID NO 110
<211> LENGTH: 30
<212> TYPE: RNA
<213> ORGANISM: Homo sapiens

<400> SEQUENCE: 110
gagccaagac aaucauaaca auaacaaaug					30

<210> SEQ ID NO 111
<211> LENGTH: 418
<212> TYPE: DNA
<213> ORGANISM: Homo sapiens -continued

<400> SEQUENCE: 111

| acaacaagag | cctgaactgt | atacatcaac | gtcaccatcg | tcatcgtcat | catcaccatt | 60 |
| gtcatcatca | tcatcatcgt | catcatcatc | atcatcatag | ctatcatcat | tatcatcatc | 120 |
| atcatcatca | tcatcatagc | taccatttat | tgaaaactat | tatgtgtcaa | cttcaaagaa | 180 |
| cttatccttt | agttggagag | ccaagacaat | cataacaata | acaaatggcc | gggcatggtg | 240 |
| gctcacgcct | gtaatcccag | cactttggga | ggccaaggca | ggtggatcat | ttgaggtcag | 300 |
| gagtccaaga | ccagcctgac | caagatggtg | aaatgctgtc | tctattaaaa | atacaaaatt | 360 |
| agccaggcat | ggtggctcat | gcctgtaatg | ccagctactc | gggaggctga | gacaggag | 418 |

<210> SEQ ID NO 112
<211> LENGTH: 20
<212> TYPE: DNA
<213> ORGANISM: Homo sapiens

<400> SEQUENCE: 112
ctctcggatc tccaaattta                                               20

<210> SEQ ID NO 113
<211> LENGTH: 20
<212> TYPE: DNA
<213> ORGANISM: Homo sapiens

<400> SEQUENCE: 113
catcatagct accatttatt                                               20

<210> SEQ ID NO 114
<211> LENGTH: 20
<212> TYPE: DNA
<213> ORGANISM: Homo sapiens

<400> SEQUENCE: 114
attgtaccac acaaagtaat                                               20

<210> SEQ ID NO 115
<211> LENGTH: 20
<212> TYPE: DNA
<213> ORGANISM: Homo sapiens

<400> SEQUENCE: 115
gagccaagac aatcataaca                                               20

<210> SEQ ID NO 116
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ggaucuccaa auuua                                                    15

<210> SEQ ID NO 117
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 117
uaaauuugga gauccgagag                                              20

<210> SEQ ID NO 118
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
uagcuaccau uuaua                                                   15

<210> SEQ ID NO 119
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uauaaauggu agcuaugaug                                              20

<210> SEQ ID NO 120
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
accacacaaa guaaa                                                   15

<210> SEQ ID NO 121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uuuacuuugu gugguacaau                                              20

<210> SEQ ID NO 122
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
aagacaauca uaaca                                                   15

<210> SEQ ID NO 123
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
```
uguuaugauu gcuuggcuc                                          20

<210> SEQ ID NO 124
<211> LENGTH: 20
<212> TYPE: RNA
<213> ORGANISM: Homo sapiens

<400> SEQUENCE: 124
aaucagaggu gagcacugca                                          20

<210> SEQ ID NO 125
<211> LENGTH: 20
<212> TYPE: RNA
<213> ORGANISM: Homo sapiens

<400> SEQUENCE: 125
gaggugagca cugcaacaaa                                          20

<210> SEQ ID NO 126
<211> LENGTH: 20
<212> TYPE: RNA
<213> ORGANISM: Homo sapiens

<400> SEQUENCE: 126
aggugagcac ugcaacaaaa                                          20

<210> SEQ ID NO 127
<211> LENGTH: 20
<212> TYPE: RNA
<213> ORGANISM: Homo sapiens

<400> SEQUENCE: 127
ugagcacugc aacaaaaagg                                          20

<210> SEQ ID NO 128
<211> LENGTH: 20
<212> TYPE: RNA
<213> ORGANISM: Homo sapiens

<400> SEQUENCE: 128
uuuucucucg gaucuccaaa                                          20

<210> SEQ ID NO 129
<211> LENGTH: 20
<212> TYPE: RNA
<213> ORGANISM: Homo sapiens

<400> SEQUENCE: 129
uuucucucgg aucuccaaau                                          20

<210> SEQ ID NO 130
<211> LENGTH: 20
<212> TYPE: RNA
<213> ORGANISM: Homo sapiens

<400> SEQUENCE: 130
cucucggauc uccaaauuua                                          20

<210> SEQ ID NO 131
<211> LENGTH: 20
<212> TYPE: RNA
<213> ORGANISM: Homo sapiens

<400> SEQUENCE: 131
ucucggaucu ccaaauuuaa                                              20

<210> SEQ ID NO 132
<211> LENGTH: 20
<212> TYPE: RNA
<213> ORGANISM: Homo sapiens

<400> SEQUENCE: 132
ucggaucucc aaauuuaaaa                                              20

<210> SEQ ID NO 133
<211> LENGTH: 20
<212> TYPE: RNA
<213> ORGANISM: Homo sapiens

<400> SEQUENCE: 133
uccaaauuua aaagcacaag                                              20

<210> SEQ ID NO 134
<211> LENGTH: 20
<212> TYPE: RNA
<213> ORGANISM: Homo sapiens

<400> SEQUENCE: 134
ccaaauuuaa aagcacaagg                                              20

<210> SEQ ID NO 135
<211> LENGTH: 20
<212> TYPE: RNA
<213> ORGANISM: Homo sapiens

<400> SEQUENCE: 135
caaauuuaaa agcacaagga                                              20

<210> SEQ ID NO 136
<211> LENGTH: 20
<212> TYPE: RNA
<213> ORGANISM: Homo sapiens

<400> SEQUENCE: 136
aagcacaagg aaugauugua                                              20

<210> SEQ ID NO 137
<211> LENGTH: 20
<212> TYPE: RNA
<213> ORGANISM: Homo sapiens

<400> SEQUENCE: 137
gaaugauugu accacacaaa                                              20

<210> SEQ ID NO 138
<211> LENGTH: 20
<212> TYPE: RNA
<213> ORGANISM: Homo sapiens

<400> SEQUENCE: 138
auuguaccac acaaaguaau                                              20

<210> SEQ ID NO 139
<211> LENGTH: 20
<212> TYPE: RNA
<213> ORGANISM: Homo sapiens

<400> SEQUENCE: 139
guaccacaca aaguaaugua				20

<210> SEQ ID NO 140
<211> LENGTH: 20
<212> TYPE: RNA
<213> ORGANISM: Homo sapiens

<400> SEQUENCE: 140
uaccacacaa aguaauguaa				20

<210> SEQ ID NO 141
<211> LENGTH: 20
<212> TYPE: RNA
<213> ORGANISM: Homo sapiens

<400> SEQUENCE: 141
ccacacaaag uaauguaaaa				20

<210> SEQ ID NO 142
<211> LENGTH: 20
<212> TYPE: RNA
<213> ORGANISM: Homo sapiens

<400> SEQUENCE: 142
acacaaagua auguaaaaca				20

<210> SEQ ID NO 143
<211> LENGTH: 20
<212> TYPE: RNA
<213> ORGANISM: Homo sapiens

<400> SEQUENCE: 143
aguaauguaa aacauuaaag				20

<210> SEQ ID NO 144
<211> LENGTH: 20
<212> TYPE: RNA
<213> ORGANISM: Homo sapiens

<400> SEQUENCE: 144
guaauguaaa acauuaaagg				20

<210> SEQ ID NO 145
<211> LENGTH: 20
<212> TYPE: RNA
<213> ORGANISM: Homo sapiens

<400> SEQUENCE: 145
uaaaacauua aaggacucau				20

<210> SEQ ID NO 146
<211> LENGTH: 20
<212> TYPE: RNA
<213> ORGANISM: Homo sapiens

<400> SEQUENCE: 146
acauuaaagg acucauuaaa				20

<210> SEQ ID NO 147
<211> LENGTH: 20
<212> TYPE: RNA

```
<213> ORGANISM: Homo sapiens

<400> SEQUENCE: 147
ggacucauua aaaguaaca                                          20

<210> SEQ ID NO 148
<211> LENGTH: 20
<212> TYPE: RNA
<213> ORGANISM: Homo sapiens

<400> SEQUENCE: 148
acucauuaaa aaguaacagu                                         20

<210> SEQ ID NO 149
<211> LENGTH: 20
<212> TYPE: RNA
<213> ORGANISM: Homo sapiens

<400> SEQUENCE: 149
aaaguaacag uugucucaua                                         20

<210> SEQ ID NO 150
<211> LENGTH: 20
<212> TYPE: RNA
<213> ORGANISM: Homo sapiens

<400> SEQUENCE: 150
caucaucauc aucauagcua                                         20

<210> SEQ ID NO 151
<211> LENGTH: 20
<212> TYPE: RNA
<213> ORGANISM: Homo sapiens

<400> SEQUENCE: 151
caucaucauc auagcuauca                                         20

<210> SEQ ID NO 152
<211> LENGTH: 20
<212> TYPE: RNA
<213> ORGANISM: Homo sapiens

<400> SEQUENCE: 152
caucaucaua gcuaucauca                                         20

<210> SEQ ID NO 153
<211> LENGTH: 20
<212> TYPE: RNA
<213> ORGANISM: Homo sapiens

<400> SEQUENCE: 153
aucaucauca ucaucauagc                                         20

<210> SEQ ID NO 154
<211> LENGTH: 20
<212> TYPE: RNA
<213> ORGANISM: Homo sapiens

<400> SEQUENCE: 154
caucaucauc aucauagcua                                         20

<210> SEQ ID NO 155
<211> LENGTH: 20
```

```
<212> TYPE: RNA
<213> ORGANISM: Homo sapiens

<400> SEQUENCE: 155
caucaucauc auagcuacca                                          20

<210> SEQ ID NO 156
<211> LENGTH: 20
<212> TYPE: RNA
<213> ORGANISM: Homo sapiens

<400> SEQUENCE: 156
ucaucauagc uaccauuuau                                          20

<210> SEQ ID NO 157
<211> LENGTH: 20
<212> TYPE: RNA
<213> ORGANISM: Homo sapiens

<400> SEQUENCE: 157
caucauagcu accauuuauu                                          20

<210> SEQ ID NO 158
<211> LENGTH: 20
<212> TYPE: RNA
<213> ORGANISM: Homo sapiens

<400> SEQUENCE: 158
agcuaccauu uauugaaaac                                          20

<210> SEQ ID NO 159
<211> LENGTH: 20
<212> TYPE: RNA
<213> ORGANISM: Homo sapiens

<400> SEQUENCE: 159
uaccauuuau ugaaaacuau                                          20

<210> SEQ ID NO 160
<211> LENGTH: 20
<212> TYPE: RNA
<213> ORGANISM: Homo sapiens

<400> SEQUENCE: 160
aacuucaaag aacuuauccu                                          20

<210> SEQ ID NO 161
<211> LENGTH: 20
<212> TYPE: RNA
<213> ORGANISM: Homo sapiens

<400> SEQUENCE: 161
caaagaacuu auccuuuagu                                          20

<210> SEQ ID NO 162
<211> LENGTH: 20
<212> TYPE: RNA
<213> ORGANISM: Homo sapiens

<400> SEQUENCE: 162
uccuuuaguu ggagagccaa                                          20

<210> SEQ ID NO 163
```

```
<211> LENGTH: 20
<212> TYPE: RNA
<213> ORGANISM: Homo sapiens

<400> SEQUENCE: 163
cuuuaguugg agagccaaga                                              20

<210> SEQ ID NO 164
<211> LENGTH: 20
<212> TYPE: RNA
<213> ORGANISM: Homo sapiens

<400> SEQUENCE: 164
uuaguuggag agccaagaca                                              20

<210> SEQ ID NO 165
<211> LENGTH: 20
<212> TYPE: RNA
<213> ORGANISM: Homo sapiens

<400> SEQUENCE: 165
uaguuggaga gccaagacaa                                              20

<210> SEQ ID NO 166
<211> LENGTH: 20
<212> TYPE: RNA
<213> ORGANISM: Homo sapiens

<400> SEQUENCE: 166
uuggagagcc aagacaauca                                              20

<210> SEQ ID NO 167
<211> LENGTH: 20
<212> TYPE: RNA
<213> ORGANISM: Homo sapiens

<400> SEQUENCE: 167
ggagagccaa gacaaucaua                                              20

<210> SEQ ID NO 168
<211> LENGTH: 20
<212> TYPE: RNA
<213> ORGANISM: Homo sapiens

<400> SEQUENCE: 168
gagccaagac aaucauaaca                                              20

<210> SEQ ID NO 169
<211> LENGTH: 20
<212> TYPE: RNA
<213> ORGANISM: Homo sapiens

<400> SEQUENCE: 169
ccaagacaau cauaacaaua                                              20

<210> SEQ ID NO 170
<211> LENGTH: 20
<212> TYPE: RNA
<213> ORGANISM: Homo sapiens

<400> SEQUENCE: 170
aagacaauca uaacaauaac                                              20
```

```
<210> SEQ ID NO 171
<211> LENGTH: 20
<212> TYPE: RNA
<213> ORGANISM: Homo sapiens

<400> SEQUENCE: 171
agcugucugc uucucacagg                                           20

<210> SEQ ID NO 172
<211> LENGTH: 20
<212> TYPE: RNA
<213> ORGANISM: Homo sapiens

<400> SEQUENCE: 172
gauccugaac ugaguuuaaa                                           20

<210> SEQ ID NO 173
<211> LENGTH: 20
<212> TYPE: RNA
<213> ORGANISM: Homo sapiens

<400> SEQUENCE: 173
auccugaacu gaguuuaaaa                                           20

<210> SEQ ID NO 174
<211> LENGTH: 20
<212> TYPE: RNA
<213> ORGANISM: Homo sapiens

<400> SEQUENCE: 174
ugaacugagu uuaaaaggca                                           20

<210> SEQ ID NO 175
<211> LENGTH: 20
<212> TYPE: RNA
<213> ORGANISM: Homo sapiens

<400> SEQUENCE: 175
guuuaaaagg cacccagcac                                           20

<210> SEQ ID NO 176
<211> LENGTH: 20
<212> TYPE: RNA
<213> ORGANISM: Homo sapiens

<400> SEQUENCE: 176
aucaaaugca acguacaaag                                           20

<210> SEQ ID NO 177
<211> LENGTH: 20
<212> TYPE: RNA
<213> ORGANISM: Homo sapiens

<400> SEQUENCE: 177
ucaaaugcaa cguacaaaga                                           20

<210> SEQ ID NO 178
<211> LENGTH: 20
<212> TYPE: RNA
<213> ORGANISM: Homo sapiens

<400> SEQUENCE: 178
guuguauggu uaaaagaugg                                           20
```

```
<210> SEQ ID NO 179
<211> LENGTH: 20
<212> TYPE: RNA
<213> ORGANISM: Homo sapiens

<400> SEQUENCE: 179
uuuaaaaacc ucacugccac                                              20

<210> SEQ ID NO 180
<211> LENGTH: 20
<212> TYPE: RNA
<213> ORGANISM: Homo sapiens

<400> SEQUENCE: 180
uaaaaaccuc acugccacuc                                              20

<210> SEQ ID NO 181
<211> LENGTH: 20
<212> TYPE: RNA
<213> ORGANISM: Homo sapiens

<400> SEQUENCE: 181
aaaaccucac ugccacucua                                              20

<210> SEQ ID NO 182
<211> LENGTH: 20
<212> TYPE: RNA
<213> ORGANISM: Homo sapiens

<400> SEQUENCE: 182
gaaacagaau ugagagcauc                                              20

<210> SEQ ID NO 183
<211> LENGTH: 30
<212> TYPE: RNA
<213> ORGANISM: Homo sapiens

<400> SEQUENCE: 183
auuacaauca gaggugagca cugcaacaaa                                   30

<210> SEQ ID NO 184
<211> LENGTH: 30
<212> TYPE: RNA
<213> ORGANISM: Homo sapiens

<400> SEQUENCE: 184
aaucagaggu gagcacugca acaaaaaggc                                   30

<210> SEQ ID NO 185
<211> LENGTH: 30
<212> TYPE: RNA
<213> ORGANISM: Homo sapiens

<400> SEQUENCE: 185
aucagaggug agcacugcaa caaaaaggcu                                   30

<210> SEQ ID NO 186
<211> LENGTH: 30
<212> TYPE: RNA
<213> ORGANISM: Homo sapiens

<400> SEQUENCE: 186
agaggugagc acugcaacaa aaaggcuguu                                   30
```

```
<210> SEQ ID NO 187
<211> LENGTH: 30
<212> TYPE: RNA
<213> ORGANISM: Homo sapiens

<400> SEQUENCE: 187
ggcuguuuuc ucucggaucu ccaaauuuaa                                      30

<210> SEQ ID NO 188
<211> LENGTH: 30
<212> TYPE: RNA
<213> ORGANISM: Homo sapiens

<400> SEQUENCE: 188
gcuguuuucu cucggaucuc caaauuuaaa                                      30

<210> SEQ ID NO 189
<211> LENGTH: 30
<212> TYPE: RNA
<213> ORGANISM: Homo sapiens

<400> SEQUENCE: 189 guuucucuc ggaucuccaa auuuaaaagc                                       30

<210> SEQ ID NO 190
<211> LENGTH: 30
<212> TYPE: RNA
<213> ORGANISM: Homo sapiens

<400> SEQUENCE: 190
uuuucucucg gaucuccaaa uuuaaaagca                                      30

<210> SEQ ID NO 191
<211> LENGTH: 30
<212> TYPE: RNA
<213> ORGANISM: Homo sapiens

<400> SEQUENCE: 191
uucucucgga ucuccaaauu uaaaagcaca                                      30

<210> SEQ ID NO 192
<211> LENGTH: 30
<212> TYPE: RNA
<213> ORGANISM: Homo sapiens

<400> SEQUENCE: 192
ggaucuccaa auuuaaaagc acaaggaaug                                      30

<210> SEQ ID NO 193
<211> LENGTH: 30
<212> TYPE: RNA
<213> ORGANISM: Homo sapiens

<400> SEQUENCE: 193
gaucuccaaa uuuaaaagca caaggaauga                                      30

<210> SEQ ID NO 194
<211> LENGTH: 30
<212> TYPE: RNA
<213> ORGANISM: Homo sapiens

<400> SEQUENCE: 194
```
aucuccaaau uuaaaagcac aaggaaugau                                30

<210> SEQ ID NO 195
<211> LENGTH: 30
<212> TYPE: RNA
<213> ORGANISM: Homo sapiens

<400> SEQUENCE: 195
uuuaaaagca caaggaauga uuguaccaca                                30

<210> SEQ ID NO 196
<211> LENGTH: 30
<212> TYPE: RNA
<213> ORGANISM: Homo sapiens

<400> SEQUENCE: 196
acaaggaaug auuguaccac acaaaguaau                                30

<210> SEQ ID NO 197
<211> LENGTH: 30
<212> TYPE: RNA
<213> ORGANISM: Homo sapiens

<400> SEQUENCE: 197
gaaugauugu accacacaaa guaauguaaa                                30

<210> SEQ ID NO 198
<211> LENGTH: 30
<212> TYPE: RNA
<213> ORGANISM: Homo sapiens

<400> SEQUENCE: 198
ugauuguacc acacaaagua auguaaaaca                                30

<210> SEQ ID NO 199
<211> LENGTH: 30
<212> TYPE: RNA
<213> ORGANISM: Homo sapiens

<400> SEQUENCE: 199
gauuguacca cacaaaguaa uguaaaacau                                30

<210> SEQ ID NO 200
<211> LENGTH: 30
<212> TYPE: RNA
<213> ORGANISM: Homo sapiens

<400> SEQUENCE: 200
uuguaccaca caaaguaaug uaaaacauua                                30

<210> SEQ ID NO 201
<211> LENGTH: 30
<212> TYPE: RNA
<213> ORGANISM: Homo sapiens

<400> SEQUENCE: 201
guaccacaca aaguaaugua aaacauuaaa                                30

<210> SEQ ID NO 202
<211> LENGTH: 30
<212> TYPE: RNA
<213> ORGANISM: Homo sapiens

<400> SEQUENCE: 202

```
cacaaaguaa uguaaaacau uaaaggacuc                                          30

<210> SEQ ID NO 203
<211> LENGTH: 30
<212> TYPE: RNA
<213> ORGANISM: Homo sapiens

<400> SEQUENCE: 203
acaaaguaau guaaaacauu aaaggacuca                                          30

<210> SEQ ID NO 204
<211> LENGTH: 30
<212> TYPE: RNA
<213> ORGANISM: Homo sapiens

<400> SEQUENCE: 204
uaauguaaaa cauuaaagga cucauuaaaa                                          30

<210> SEQ ID NO 205
<211> LENGTH: 30
<212> TYPE: RNA
<213> ORGANISM: Homo sapiens

<400> SEQUENCE: 205
guaaaacauu aaaggacuca uuaaaaagua                                          30

<210> SEQ ID NO 206
<211> LENGTH: 30
<212> TYPE: RNA
<213> ORGANISM: Homo sapiens

<400> SEQUENCE: 206
uuaaaggacu cauuaaaaag uaacaguugu                                          30

<210> SEQ ID NO 207
<211> LENGTH: 30
<212> TYPE: RNA
<213> ORGANISM: Homo sapiens

<400> SEQUENCE: 207
aaaggacuca uuaaaaagua acaguugucu                                          30

<210> SEQ ID NO 208
<211> LENGTH: 30
<212> TYPE: RNA
<213> ORGANISM: Homo sapiens

<400> SEQUENCE: 208
auuaaaaagu aacaguuguc ucauaucauc                                          30

<210> SEQ ID NO 209
<211> LENGTH: 30
<212> TYPE: RNA
<213> ORGANISM: Homo sapiens

<400> SEQUENCE: 209
gucaucauca ucaucaucau agcuaucauc                                          30

<210> SEQ ID NO 210
<211> LENGTH: 30
<212> TYPE: RNA
<213> ORGANISM: Homo sapiens
```

```
<400> SEQUENCE: 210
aucaucauca ucaucauagc uaucaucauu                                      30

<210> SEQ ID NO 211
<211> LENGTH: 30
<212> TYPE: RNA
<213> ORGANISM: Homo sapiens

<400> SEQUENCE: 211
aucaucauca ucauagcuau caucauuauc                                      30

<210> SEQ ID NO 212
<211> LENGTH: 30
<212> TYPE: RNA
<213> ORGANISM: Homo sapiens

<400> SEQUENCE: 212
ucaucaucau caucaucauc auagcuacca                                      30

<210> SEQ ID NO 213
<211> LENGTH: 30
<212> TYPE: RNA
<213> ORGANISM: Homo sapiens

<400> SEQUENCE: 213
aucaucauca ucaucaucau agcuaccauu                                      30

<210> SEQ ID NO 214
<211> LENGTH: 30
<212> TYPE: RNA
<213> ORGANISM: Homo sapiens

<400> SEQUENCE: 214
aucaucauca ucaucauagc uaccauuuau                                      30

<210> SEQ ID NO 215
<211> LENGTH: 30
<212> TYPE: RNA
<213> ORGANISM: Homo sapiens

<400> SEQUENCE: 215
caucaucauc auagcuacca uuuauugaaa                                      30

<210> SEQ ID NO 216
<211> LENGTH: 30
<212> TYPE: RNA
<213> ORGANISM: Homo sapiens

<400> SEQUENCE: 216
aucaucauca uagcuaccau uuauugaaaa                                      30

<210> SEQ ID NO 217
<211> LENGTH: 30
<212> TYPE: RNA
<213> ORGANISM: Homo sapiens

<400> SEQUENCE: 217
aucauagcua ccauuuauug aaaacuauua                                      30

<210> SEQ ID NO 218
<211> LENGTH: 30
<212> TYPE: RNA
<213> ORGANISM: Homo sapiens
```

-continued

```
<400> SEQUENCE: 218
auagcuacca uuuauugaaa acuauuaugu                                  30

<210> SEQ ID NO 219
<211> LENGTH: 30
<212> TYPE: RNA
<213> ORGANISM: Homo sapiens

<400> SEQUENCE: 219
gugucaacuu caaagaacuu auccuuuagu                                  30

<210> SEQ ID NO 220
<211> LENGTH: 30
<212> TYPE: RNA
<213> ORGANISM: Homo sapiens

<400> SEQUENCE: 220
aacuucaaag aacuuauccu uuaguuggag                                  30

<210> SEQ ID NO 221
<211> LENGTH: 30
<212> TYPE: RNA
<213> ORGANISM: Homo sapiens

<400> SEQUENCE: 221
acuuauccuu uaguuggaga gccaagacaa                                  30

<210> SEQ ID NO 222
<211> LENGTH: 30
<212> TYPE: RNA
<213> ORGANISM: Homo sapiens

<400> SEQUENCE: 222
uuauccuuua guuggagagc caagacaauc                                  30

<210> SEQ ID NO 223
<211> LENGTH: 30
<212> TYPE: RNA
<213> ORGANISM: Homo sapiens

<400> SEQUENCE: 223
auccuuuagu uggagagcca agacaaucau                                  30

<210> SEQ ID NO 224
<211> LENGTH: 30
<212> TYPE: RNA
<213> ORGANISM: Homo sapiens

<400> SEQUENCE: 224
uccuuuaguu ggagagccaa gacaaucaua                                  30

<210> SEQ ID NO 225
<211> LENGTH: 30
<212> TYPE: RNA
<213> ORGANISM: Homo sapiens

<400> SEQUENCE: 225
uuuaguugga gagccaagac aaucauaaca                                  30

<210> SEQ ID NO 226
<211> LENGTH: 30
<212> TYPE: RNA
```

```
<213> ORGANISM: Homo sapiens

<400> SEQUENCE: 226
uaguuggaga gccaagacaa ucauaacaau                                        30

<210> SEQ ID NO 227
<211> LENGTH: 30
<212> TYPE: RNA
<213> ORGANISM: Homo sapiens

<400> SEQUENCE: 227
uuggagagcc aagacaauca uaacauaac                                         30

<210> SEQ ID NO 228
<211> LENGTH: 30
<212> TYPE: RNA
<213> ORGANISM: Homo sapiens

<400> SEQUENCE: 228
gagagccaag acaaucauaa caauaacaaa                                        30

<210> SEQ ID NO 229
<211> LENGTH: 30
<212> TYPE: RNA
<213> ORGANISM: Homo sapiens

<400> SEQUENCE: 229
gagccaagac aaucauaaca auaacaaaug                                        30

<210> SEQ ID NO 230
<211> LENGTH: 30
<212> TYPE: RNA
<213> ORGANISM: Homo sapiens

<400> SEQUENCE: 230
ugcucagcug ucugcuucuc acaggaucua                                        30

<210> SEQ ID NO 231
<211> LENGTH: 30
<212> TYPE: RNA
<213> ORGANISM: Homo sapiens

<400> SEQUENCE: 231
uaaaagaucc ugaacugagu uuaaaaggca                                        30

<210> SEQ ID NO 232
<211> LENGTH: 30
<212> TYPE: RNA
<213> ORGANISM: Homo sapiens

<400> SEQUENCE: 232
aaaagauccu gaacugaguu uaaaaggcac                                        30

<210> SEQ ID NO 233
<211> LENGTH: 30
<212> TYPE: RNA
<213> ORGANISM: Homo sapiens

<400> SEQUENCE: 233
gauccugaac ugaguuuaaa aggcacccag                                        30

<210> SEQ ID NO 234
<211> LENGTH: 30
```

```
<212> TYPE: RNA
<213> ORGANISM: Homo sapiens

<400> SEQUENCE: 234
acugaguuua aaaggcaccc agcacaucau                                           30

<210> SEQ ID NO 235
<211> LENGTH: 30
<212> TYPE: RNA
<213> ORGANISM: Homo sapiens

<400> SEQUENCE: 235
aucauaucaa augcaacgua caaagaaaua                                           30

<210> SEQ ID NO 236
<211> LENGTH: 30
<212> TYPE: RNA
<213> ORGANISM: Homo sapiens

<400> SEQUENCE: 236
ucauaucaaa ugcaacguac aaagaaauag                                           30

<210> SEQ ID NO 237
<211> LENGTH: 30
<212> TYPE: RNA
<213> ORGANISM: Homo sapiens

<400> SEQUENCE: 237
cggaaguugu augguuaaaa gauggguuac                                           30

<210> SEQ ID NO 238
<211> LENGTH: 30
<212> TYPE: RNA
<213> ORGANISM: Homo sapiens

<400> SEQUENCE: 238
auguguuuaa aaaccucacu gccacucuaa                                           30

<210> SEQ ID NO 239
<211> LENGTH: 30
<212> TYPE: RNA
<213> ORGANISM: Homo sapiens

<400> SEQUENCE: 239
guguuuaaaa accucacugc cacucuaauu                                           30

<210> SEQ ID NO 240
<211> LENGTH: 30
<212> TYPE: RNA
<213> ORGANISM: Homo sapiens

<400> SEQUENCE: 240
guuuaaaaac cucacugcca cucuaauugu                                           30

<210> SEQ ID NO 241
<211> LENGTH: 30
<212> TYPE: RNA
<213> ORGANISM: Homo sapiens

<400> SEQUENCE: 241
caugggaaac agaauugaga gcaucacuca                                           30

<210> SEQ ID NO 242
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
aaucagaggu gagcacugca                                                    20

<210> SEQ ID NO 243
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
gaggugagca cugcaacaaa                                                    20

<210> SEQ ID NO 244
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
aggugagcac ugcaacaaaa                                                    20

<210> SEQ ID NO 245
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
ugagcacugc aacaaaaagg                                                    20

<210> SEQ ID NO 246
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
uuuucucucg gaucuccaaa                                                    20

<210> SEQ ID NO 247
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
uuucucucgg aucuccaaau                                                    20

<210> SEQ ID NO 248
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
cucucggauc uccaaauuua                                                      20

<210> SEQ ID NO 249
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
ucucggaucu ccaaauuuaa                                                      20

<210> SEQ ID NO 250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
ucggaucucc aaauuuaaaa                                                      20

<210> SEQ ID NO 251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
uccaaauuua aaagcacaag                                                      20

<210> SEQ ID NO 252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ccaaauuuaa aagcacaagg                                                      20

<210> SEQ ID NO 253
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
caaauuuaaa agcacaagga                                                      20

<210> SEQ ID NO 254
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 254
aagcacaagg aaugauugua                                                   20

<210> SEQ ID NO 255
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gaaugauugu accacacaaa                                                   20

<210> SEQ ID NO 256
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
auuguaccac acaaaguaau                                                   20

<210> SEQ ID NO 257
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
guaccacaca aaguaaugua                                                   20

<210> SEQ ID NO 258
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
uaccacacaa aguaauguaa                                                   20

<210> SEQ ID NO 259
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
ccacacaaag uaauguaaaa                                                   20

<210> SEQ ID NO 260
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 260
acacaaagua auguaaaaca                                                    20

<210> SEQ ID NO 261
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
aguaauguaa aacauuaaag                                                    20

<210> SEQ ID NO 262
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
guaauguaaa acauuaaagg                                                    20

<210> SEQ ID NO 263
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
uaaaacauua aaggacucau                                                    20

<210> SEQ ID NO 264
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
acauuaaagg acucauuaaa                                                    20

<210> SEQ ID NO 265
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
ggacucauua aaaguaaca                                                     20

<210> SEQ ID NO 266
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 266
acucauuaaa aaguaacagu                                                 20

<210> SEQ ID NO 267
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
aaaguaacag uugucucaua                                                 20

<210> SEQ ID NO 268
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
caucaucauc aucauagcua                                                 20

<210> SEQ ID NO 269
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
caucaucauc auagcuauca                                                 20

<210> SEQ ID NO 270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
caucaucaua gcuaucauca                                                 20

<210> SEQ ID NO 271
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
aucaucauca ucaucauagc                                                 20

<210> SEQ ID NO 272
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 272
caucaucauc aucauagcua                                          20

<210> SEQ ID NO 273
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
caucaucauc auagcuacca                                          20

<210> SEQ ID NO 274
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ucaucauagc uaccauuuau                                          20

<210> SEQ ID NO 275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
caucauagcu accauuuauu                                          20

<210> SEQ ID NO 276
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
agcuaccauu uauugaaaac                                          20

<210> SEQ ID NO 277
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
uaccauuuau ugaaaacuau                                          20

<210> SEQ ID NO 278
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 278
aacuucaaag aacuuauccu                                               20

<210> SEQ ID NO 279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
caaagaacuu auccuuuagu                                               20

<210> SEQ ID NO 280
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
uccuuuaguu ggagagccaa                                               20

<210> SEQ ID NO 281
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
cuuuaguugg agagccaaga                                               20

<210> SEQ ID NO 282
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
uuaguuggag agccaagaca                                               20

<210> SEQ ID NO 283
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
uaguuggaga gccaagacaa                                               20

<210> SEQ ID NO 284
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 284
uuggagagcc aagacaauca                                                  20

<210> SEQ ID NO 285
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
ggagagccaa gacaaucaua                                                  20

<210> SEQ ID NO 286
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
gagccaagac aaucauaaca                                                  20

<210> SEQ ID NO 287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
ccaagacaau cauaacaaua                                                  20

<210> SEQ ID NO 288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
aagacaauca uaacaauaac                                                  20

<210> SEQ ID NO 289
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
agcugucugc uucucacagg                                                  20

<210> SEQ ID NO 290
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
```
gauccugaac ugaguuuaaa                                          20

<210> SEQ ID NO 291
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
auccugaacu gaguuuaaaa                                          20

<210> SEQ ID NO 292
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
ugaacugagu uuaaaaggca                                          20

<210> SEQ ID NO 293
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
guuuaaaagg cacccagcac                                          20

<210> SEQ ID NO 294
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
aucaaaugca acguacaaag                                          20

<210> SEQ ID NO 295
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
ucaaaugcaa cguacaaaga                                          20

<210> SEQ ID NO 296
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296

```
guuguauggu uaaaagaugg                                          20

<210> SEQ ID NO 297
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
uuuaaaaacc ucacugccac                                          20

<210> SEQ ID NO 298
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
uaaaaaccuc acugccacuc                                          20

<210> SEQ ID NO 299
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
aaaaccucac ugccacucua                                          20

<210> SEQ ID NO 300
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
gaaacagaau ugagagcauc                                          20

<210> SEQ ID NO 301
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ugcagugcuc accucugauu                                          20

<210> SEQ ID NO 302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
uuuguugcag ugcucaccuc                                          20
```

<210> SEQ ID NO 303
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
uuuuguugca gugcucaccu                                               20

<210> SEQ ID NO 304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ccuuuuuguu gcagugcuca                                               20

<210> SEQ ID NO 305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
uuuggagauc cgagagaaaa                                               20

<210> SEQ ID NO 306
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
auuuggagau ccgagagaaa                                               20

<210> SEQ ID NO 307
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
uaaauuugga gauccgagag                                               20

<210> SEQ ID NO 308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
uuaaauuugg agauccgaga                                               20

<210> SEQ ID NO 309
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
uuuuaaauuu ggagauccga                                                  20

<210> SEQ ID NO 310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
cuugugcuuu uaaauuugga                                                  20

<210> SEQ ID NO 311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
ccuugugcuu uuaaauuugg                                                  20

<210> SEQ ID NO 312
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uccuugugcu uuuaaauuug                                                  20

<210> SEQ ID NO 313
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
uacaaucauu ccuugugcuu                                                  20

<210> SEQ ID NO 314
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
uuuguguggu acaaucauuc                                                  20

<210> SEQ ID NO 315
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
auuacuuugu gugguacaau                                                      20

<210> SEQ ID NO 316
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uacauuacuu uguguggguac                                                     20

<210> SEQ ID NO 317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
uuacauuacu uuguguggua                                                      20

<210> SEQ ID NO 318
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uuuuacauua cuuugugugg                                                      20

<210> SEQ ID NO 319
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
uguuuuacau uacuuugugu                                                      20

<210> SEQ ID NO 320
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
cuuuaauguu uuacauuacu                                                      20

<210> SEQ ID NO 321

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
ccuuuaaugu uuuacauuac                                               20

<210> SEQ ID NO 322
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
augaguccuu uaauguuuua                                               20

<210> SEQ ID NO 323
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
uuuaaugagu ccuuuaaugu                                               20

<210> SEQ ID NO 324
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uguuacuuuu uaaugagucc                                               20

<210> SEQ ID NO 325
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
acuguuacuu uuuaaugagu                                               20

<210> SEQ ID NO 326
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
uaugagacaa cuguuacuuu                                               20

<210> SEQ ID NO 327
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
uagcuaugau gaugaugaug                                              20

<210> SEQ ID NO 328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
ugauagcuau gaugaugaug                                              20

<210> SEQ ID NO 329
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
ugaugauagc uaugaugaug                                              20

<210> SEQ ID NO 330
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
gcuaugauga ugaugaugau                                              20

<210> SEQ ID NO 331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
uagcuaugau gaugaugaug                                              20

<210> SEQ ID NO 332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
ugguagcuau gaugaugaug                                              20

<210> SEQ ID NO 333
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 333
auaaauggua gcuaugauga                                               20

<210> SEQ ID NO 334
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
aauaaauggu agcuaugaug                                               20

<210> SEQ ID NO 335
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
guuuucaaua aaugguagcu                                               20

<210> SEQ ID NO 336
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
auaguuuuca auaaauggua                                               20

<210> SEQ ID NO 337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
aggauaaguu cuuugaaguu                                               20

<210> SEQ ID NO 338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
acuaaaggau aaguucuuug                                               20

<210> SEQ ID NO 339
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 339
uuggcucucc aacuaaagga                                              20

<210> SEQ ID NO 340
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
ucuuggcucu ccaacuaaag                                              20

<210> SEQ ID NO 341
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
ugucuuggcu cuccaacuaa                                              20

<210> SEQ ID NO 342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
uugucuuggc ucuccaacua                                              20

<210> SEQ ID NO 343
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
ugauugucuu ggcucuccaa                                              20

<210> SEQ ID NO 344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
uaugauuguc uuggcucucc                                              20

<210> SEQ ID NO 345
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 345
uguuaugauu gucuuggcuc                                               20

<210> SEQ ID NO 346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
uauuguuaug auugucuugg                                               20

<210> SEQ ID NO 347
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
guuauuguua ugauugucuu                                               20

<210> SEQ ID NO 348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
ccugugagaa gcagacagcu                                               20

<210> SEQ ID NO 349
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
uuuaaacuca guucaggauc                                               20

<210> SEQ ID NO 350
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
uuuuaaacuc aguucaggau                                               20

<210> SEQ ID NO 351
<211> LENGTH: 20
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 351
ugccuuuuaa acucaguuca					20

<210> SEQ ID NO 352
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
gugcugggug ccuuuuaaac					20

<210> SEQ ID NO 353
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
cuuuguacgu ugcauuugau					20

<210> SEQ ID NO 354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
ucuuuguacg uugcauuuga					20

<210> SEQ ID NO 355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
ccaucuuuua accauacaac					20

<210> SEQ ID NO 356
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
guggcaguga gguuuuuaaa					20

<210> SEQ ID NO 357
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 357
gaguggcagu gagguuuuua                                          20

<210> SEQ ID NO 358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
uagaguggca gugagguuuu                                          20

<210> SEQ ID NO 359
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
gaugcucuca auucuguuuc                                          20

<210> SEQ ID NO 360
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
aaucagaggu gagca                                               15

<210> SEQ ID NO 361
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
gaggugagca cugca                                               15

<210> SEQ ID NO 362
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
aggugagcac ugcaa                                               15

<210> SEQ ID NO 363
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 363
ugagcacugc aacaa                                                    15

<210> SEQ ID NO 364
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
uuuucucucg gaucu                                                    15

<210> SEQ ID NO 365
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uuucucucgg aucuc                                                    15

<210> SEQ ID NO 366
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
cucucggauc uccaa                                                    15

<210> SEQ ID NO 367
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
ucucggaucu ccaaa                                                    15

<210> SEQ ID NO 368
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
ucggaucucc aaauu                                                    15

<210> SEQ ID NO 369
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
uccaaauuua aaagc                                                          15

<210> SEQ ID NO 370
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
ccaaauuuaa aagca                                                          15

<210> SEQ ID NO 371
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
caaauuuaaa agcac                                                          15

<210> SEQ ID NO 372
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
aagcacaagg aauga                                                          15

<210> SEQ ID NO 373
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
gaaugauugu accac                                                          15

<210> SEQ ID NO 374
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
auuguaccac acaaa                                                          15

<210> SEQ ID NO 375
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
guaccacaca aagua                                                        15

<210> SEQ ID NO 376
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uaccacacaa aguaa                                                        15

<210> SEQ ID NO 377
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
ccacacaaag uaaug                                                        15

<210> SEQ ID NO 378
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
acacaaagua augua                                                        15

<210> SEQ ID NO 379
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
aguaauguaa aacau                                                        15

<210> SEQ ID NO 380
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
guaauguaaa acauu                                                        15

<210> SEQ ID NO 381
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
uaaaacauua aagga                                                        15

<210> SEQ ID NO 382
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
acauuaaagg acuca                                                   15

<210> SEQ ID NO 383
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ggacucauua aaaag                                                   15

<210> SEQ ID NO 384
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
acucauuaaa aagua                                                   15

<210> SEQ ID NO 385
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
aaaguaacag uuguc                                                   15

<210> SEQ ID NO 386
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
caucaucauc aucau                                                   15

<210> SEQ ID NO 387
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
caucaucauc auagc                                                   15

<210> SEQ ID NO 388
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
caucaucaua gcuau                                                          15

<210> SEQ ID NO 389
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
aucaucauca ucauc                                                          15

<210> SEQ ID NO 390
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
caucaucauc aucau                                                          15

<210> SEQ ID NO 391
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
caucaucauc auagc                                                          15

<210> SEQ ID NO 392
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ucaucauagc uacca                                                          15

<210> SEQ ID NO 393
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
caucauagcu accau                                                          15

```
<210> SEQ ID NO 394
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
agcuaccauu uauug                                                          15

<210> SEQ ID NO 395
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
uaccauuuau ugaaa                                                          15

<210> SEQ ID NO 396
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
aacuucaaag aacuu                                                          15

<210> SEQ ID NO 397
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
caaagaacuu auccu                                                          15

<210> SEQ ID NO 398
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
uccuuuaguu ggaga                                                          15

<210> SEQ ID NO 399
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
cuuuaguugg agagc                                                          15

<210> SEQ ID NO 400
```

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
uuaguuggag agcca                                                          15

<210> SEQ ID NO 401
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
uaguuggaga gccaa                                                          15

<210> SEQ ID NO 402
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
uuggagagcc aagac                                                          15

<210> SEQ ID NO 403
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
ggagagccaa gacaa                                                          15

<210> SEQ ID NO 404
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
gagccaagac aauca                                                          15

<210> SEQ ID NO 405
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
ccaagacaau cauaa                                                          15

<210> SEQ ID NO 406
<211> LENGTH: 15
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
aagacaauca uaaca                                                          15

<210> SEQ ID NO 407
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
agcugucugc uucuc                                                          15

<210> SEQ ID NO 408
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
gauccugaac ugagu                                                          15

<210> SEQ ID NO 409
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
auccugaacu gaguu                                                          15

<210> SEQ ID NO 410
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
ugaacugagu uuaaa                                                          15

<210> SEQ ID NO 411
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
guuuaaaagg caccc                                                          15

<210> SEQ ID NO 412
<211> LENGTH: 15
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 412
aucaaaugca acgua                                                          15

<210> SEQ ID NO 413
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
ucaaaugcaa cguac                                                          15

<210> SEQ ID NO 414
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
guuguauggu uaaaa                                                          15

<210> SEQ ID NO 415
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
uuuaaaaacc ucacu                                                          15

<210> SEQ ID NO 416
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
uaaaaaccuc acugc                                                          15

<210> SEQ ID NO 417
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
aaaaccucac ugcca                                                          15

<210> SEQ ID NO 418
<211> LENGTH: 15
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 418
gaaacagaau ugaga                                                    15

<210> SEQ ID NO 419
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
ucagugcuca ccucugauu                                                19

<210> SEQ ID NO 420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
uuguugcagu gcucaccuc                                                19

<210> SEQ ID NO 421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
uuuguugcag ugcucaccu                                                19

<210> SEQ ID NO 422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
uuuuuuguug cagugcuca                                                19

<210> SEQ ID NO 423
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
uuggagaucc gagagaaaa                                                19

<210> SEQ ID NO 424
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 424
uuuggagauc cgagagaaa                                               19

<210> SEQ ID NO 425
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
uaauuuggag auccgagag                                               19

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
uaaauuugga gauccgaga                                               19

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
uuuaaauuug gagauccga                                               19

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
uugugcuuuu aaauuugga                                               19

<210> SEQ ID NO 429
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
uuugugcuuu uaaauuugg                                               19

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
             oligonucleotide

<400> SEQUENCE: 430
ucuugugcuu uuaaauuug                                               19

<210> SEQ ID NO 431
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
ucaaucauuc cuugugcuu                                               19

<210> SEQ ID NO 432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
uuguguggua caaucauuc                                               19

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
uuacuuugug ugguacaau                                               19

<210> SEQ ID NO 434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
ucauuacuuu guguggauc                                               19

<210> SEQ ID NO 435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
uacauuacuu uguguggua                                               19

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 436
uuuacauuac uuugugugg                                                    19

<210> SEQ ID NO 437
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
uuuuuacauu acuuugugu                                                    19

<210> SEQ ID NO 438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
uuuaauguuu uacauuacu                                                    19

<210> SEQ ID NO 439
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
uuuuaauguu uuacauuac                                                    19

<210> SEQ ID NO 440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440 ugagccuuu aauguuuua                                                     19

<210> SEQ ID NO 441
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
uuaaugaguc cuuuaaugu                                                    19

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 442
uuuacuuuuu aaugagucc                                                19

<210> SEQ ID NO 443
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
uuguuacuuu uuaaugagu                                                19

<210> SEQ ID NO 444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
uugagacaac uguuacuuu                                                19

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
ugcuaugaug augaugaug                                                19

<210> SEQ ID NO 446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
uauagcuaug augaugaug                                                19

<210> SEQ ID NO 447
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
uaugauagcu augaugaug                                                19

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
```
uuaugaugau gaugaugau 19

<210> SEQ ID NO 449
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ugcuaugaug augaugaug 19

<210> SEQ ID NO 450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
uguagcuaug augaugaug 19

<210> SEQ ID NO 451
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
uaaaugguag cuaugauga 19

<210> SEQ ID NO 452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
uuaaauggua gcuaugaug 19

<210> SEQ ID NO 453
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
uuuucaauaa augguagcu 19

<210> SEQ ID NO 454
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uaguuuucaa uaaauggua                    19

<210> SEQ ID NO 455
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
ugauaaguuc uuugaaguu                    19

<210> SEQ ID NO 456
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
uuaaaggaua aguucuuug                    19

<210> SEQ ID NO 457
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
uggcucucca acuaaagga                    19

<210> SEQ ID NO 458
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
uuuggcucuc caacuaaag                    19

<210> SEQ ID NO 459
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
uucuuggcuc uccaacuaa                    19

<210> SEQ ID NO 460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
ugucuuggcu cuccaacua                    19

<210> SEQ ID NO 461
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 461
uauugucuug gcucuccaa                                              19

<210> SEQ ID NO 462
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 462
uugauugucu uggcucucc                                              19

<210> SEQ ID NO 463
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 463
uuuaugauug ucuuggcuc                                              19

<210> SEQ ID NO 464
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 464
uuuguuauga uugucuugg                                              19

<210> SEQ ID NO 465
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 465
uuauuguuau gauugucuu                                              19

<210> SEQ ID NO 466
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 466
uugugagaag cagacagcu                                              19

<210> SEQ ID NO 467
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
uuaaacucag uucaggauc                                                19

<210> SEQ ID NO 468
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
uuuaaacuca guucaggau                                                19

<210> SEQ ID NO 469
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
uccuuuuaaa cucaguuca                                                19

<210> SEQ ID NO 470
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
ugcugggugc cuuuuaaac                                                19

<210> SEQ ID NO 471
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
uuuguacguu gcauuugau                                                19

<210> SEQ ID NO 472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
uuuuguacgu ugcauuuga                                                19

```
<210> SEQ ID NO 473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473 uaucuuuaa ccauacaac                                                19

<210> SEQ ID NO 474
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
uggcagugag guuuuuaaa                                               19

<210> SEQ ID NO 475
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
uguggcagug agguuuuua                                               19

<210> SEQ ID NO 476
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
ugaguggcag ugagguuuu                                               19

<210> SEQ ID NO 477
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
uugcucucaa uucuguuuc                                               19

<210> SEQ ID NO 478
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
aaucagaggu gagca                                                   15

<210> SEQ ID NO 479
```

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
gaggugagca cugca                                                        15

<210> SEQ ID NO 480
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
aggugagcac ugcaa                                                        15

<210> SEQ ID NO 481
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
ugagcacugc aacaa                                                        15

<210> SEQ ID NO 482
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
uuuucucucg gauca                                                        15

<210> SEQ ID NO 483
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
uuucucucgg aucua                                                        15

<210> SEQ ID NO 484
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
cucucggauc uccaa                                                        15

<210> SEQ ID NO 485
<211> LENGTH: 15
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
ucucggaucu ccaaa                                                          15

<210> SEQ ID NO 486
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
ucggaucucc aaaua                                                          15

<210> SEQ ID NO 487
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
uccaaauuua aaaga                                                          15

<210> SEQ ID NO 488
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
ccaaauuuaa aagca                                                          15

<210> SEQ ID NO 489
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
caaauuuaaa agcaa                                                          15

<210> SEQ ID NO 490
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
aagcacaagg aauga                                                          15

<210> SEQ ID NO 491
<211> LENGTH: 15
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 491
gaaugauugu accaa                                                         15

<210> SEQ ID NO 492
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
auuguaccac acaaa                                                         15

<210> SEQ ID NO 493
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
guaccacaca aagua                                                         15

<210> SEQ ID NO 494
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
uaccacacaa aguaa                                                         15

<210> SEQ ID NO 495
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
ccacacaaag uaaua                                                         15

<210> SEQ ID NO 496
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
acacaaagua augua                                                         15

<210> SEQ ID NO 497
<211> LENGTH: 15
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 497
aguaauguaa aacaa                                                          15

<210> SEQ ID NO 498
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
guaauguaaa acaua                                                          15

<210> SEQ ID NO 499
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
uaaaacauua aagga                                                          15

<210> SEQ ID NO 500
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
acauuaaagg acuca                                                          15

<210> SEQ ID NO 501
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
ggacucauua aaaaa                                                          15

<210> SEQ ID NO 502
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
acucauuaaa aagua                                                          15

<210> SEQ ID NO 503
<211> LENGTH: 15
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 503
aaaguaacag uugua                                                          15

<210> SEQ ID NO 504
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
caucaucauc aucaa                                                          15

<210> SEQ ID NO 505
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
caucaucauc auaga                                                          15

<210> SEQ ID NO 506
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
caucaucaua gcuaa                                                          15

<210> SEQ ID NO 507
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
aucaucauca ucaua                                                          15

<210> SEQ ID NO 508
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
caucaucauc aucaa                                                          15

<210> SEQ ID NO 509
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 509
caucaucauc auaga                                                       15

<210> SEQ ID NO 510
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
ucaucauagc uacca                                                       15

<210> SEQ ID NO 511
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
caucauagcu accaa                                                       15

<210> SEQ ID NO 512
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
agcuaccauu uauua                                                       15

<210> SEQ ID NO 513
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
uaccauuuau ugaaa                                                       15

<210> SEQ ID NO 514
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
aacuucaaag aacua                                                       15

<210> SEQ ID NO 515
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 515
caaagaacuu aucca                                                  15

<210> SEQ ID NO 516
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
uccuuuaguu ggaga                                                  15

<210> SEQ ID NO 517
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
cuuuaguugg agaga                                                  15

<210> SEQ ID NO 518
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
uuaguuggag agcca                                                  15

<210> SEQ ID NO 519
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
uaguuggaga gccaa                                                  15

<210> SEQ ID NO 520
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
uuggagagcc aagaa                                                  15

<210> SEQ ID NO 521
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 521
ggagagccaa gacaa                                                          15

<210> SEQ ID NO 522
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
gagccaagac aauca                                                          15

<210> SEQ ID NO 523
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
ccaagacaau cauaa                                                          15

<210> SEQ ID NO 524
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
aagacaauca uaaca                                                          15

<210> SEQ ID NO 525
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
agcugucugc uucua                                                          15

<210> SEQ ID NO 526
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
gauccugaac ugaga                                                          15

<210> SEQ ID NO 527
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
```
auccugaacu gagua                    15

<210> SEQ ID NO 528
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
ugaacugagu uuaaa                    15

<210> SEQ ID NO 529
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
guuuaaaagg cacca                    15

<210> SEQ ID NO 530
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
aucaaaugca acgua                    15

<210> SEQ ID NO 531
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
ucaaaugcaa cguaa                    15

<210> SEQ ID NO 532
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
guuguauggu uaaaa                    15

<210> SEQ ID NO 533
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
uuuaaaaacc ucaca         15

<210> SEQ ID NO 534
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
uaaaaaccuc acuga         15

<210> SEQ ID NO 535
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
aaaaccucac ugcca         15

<210> SEQ ID NO 536
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
gaaacagaau ugaga         15

<210> SEQ ID NO 537
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
ugcagugcuc accucugauu         20

<210> SEQ ID NO 538
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
uuuguugcag ugcucaccuc         20

<210> SEQ ID NO 539
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
uuuuguugca gugcucaccu         20

<210> SEQ ID NO 540
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
ucuuuuuguu gcagugcuca                                                    20

<210> SEQ ID NO 541
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
uuuggagauc cgagagaaaa                                                    20

<210> SEQ ID NO 542
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
uuuuggagau ccgagagaaa                                                    20

<210> SEQ ID NO 543
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
uaaauuugga gauccgagag                                                    20

<210> SEQ ID NO 544
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
uuaaauuugg agauccgaga                                                    20

<210> SEQ ID NO 545
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
uuuuaaauuu ggagauccga                                                    20

```
<210> SEQ ID NO 546
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
uuugugcuuu uaaauuugga                                              20

<210> SEQ ID NO 547
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
ucuugugcuu uuaaauuugg                                              20

<210> SEQ ID NO 548
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
uccuugugcu uuuaaauuug                                              20

<210> SEQ ID NO 549
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
uacaaucauu ccuugugcuu                                              20

<210> SEQ ID NO 550
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
uuuguguggu acaaucauuc                                              20

<210> SEQ ID NO 551
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
uuuacuuugu gugguacaau                                              20
```

```
<210> SEQ ID NO 552
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
uacauuacuu uguguggugac                                              20

<210> SEQ ID NO 553
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
uuacauuacu uuguguggua                                               20

<210> SEQ ID NO 554
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
uuuuacauua cuuugugugg                                               20

<210> SEQ ID NO 555
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
uguuuuacau uacuuugugu                                               20

<210> SEQ ID NO 556
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
uuuuaauguu uuacauuacu                                               20

<210> SEQ ID NO 557
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
ucuuuaaugu uuuacauuac                                               20

<210> SEQ ID NO 558
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
uugaguccuu uaauguuuua                                                    20

<210> SEQ ID NO 559
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
uuuaaugagu ccuuuaaugu                                                    20

<210> SEQ ID NO 560
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
uguuacuuuu uaaugagucc                                                    20

<210> SEQ ID NO 561
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
ucuguuacuu uuuaaugagu                                                    20

<210> SEQ ID NO 562
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
uaugagacaa cuguuacuuu                                                    20

<210> SEQ ID NO 563
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
uagcuaugau gaugaugaug                                                    20

<210> SEQ ID NO 564
<211> LENGTH: 20
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
ugauagcuau gaugaugaug                                               20

<210> SEQ ID NO 565
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
ugaugauagc uaugaugaug                                               20

<210> SEQ ID NO 566
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
ucuaugauga ugaugaugau                                               20

<210> SEQ ID NO 567
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
uagcuaugau gaugaugaug                                               20

<210> SEQ ID NO 568
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
ugguagcuau gaugaugaug                                               20

<210> SEQ ID NO 569
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
uuaaauggua gcuaugauga                                               20

<210> SEQ ID NO 570
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 570
uauaaauggu agcuaugaug                                              20

<210> SEQ ID NO 571
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
uuuuucaaua aaugguagcu                                              20

<210> SEQ ID NO 572
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
uuaguuuuca auaaauggua                                              20

<210> SEQ ID NO 573
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
uggauaaguu cuuugaaguu                                              20

<210> SEQ ID NO 574
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
ucuaaaggau aaguucuuug                                              20

<210> SEQ ID NO 575
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
uuggcucucc aacuaaagga                                              20

<210> SEQ ID NO 576
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 576
ucuuggcucu ccaacuaaag                                                    20

<210> SEQ ID NO 577
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
ugucuuggcu cuccaacuaa                                                    20

<210> SEQ ID NO 578
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
uugucuuggc ucuccaacua                                                    20

<210> SEQ ID NO 579
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
ugauugucuu ggcucuccaa                                                    20

<210> SEQ ID NO 580
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
uaugauuguc uuggcucucc                                                    20

<210> SEQ ID NO 581
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
uguuaugauu gucuuggcuc                                                    20

<210> SEQ ID NO 582
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 582
uauuguuaug auugucuugg                                               20

<210> SEQ ID NO 583
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
uuuauuguua ugauugucuu                                               20

<210> SEQ ID NO 584
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
ucugugagaa gcagacagcu                                               20

<210> SEQ ID NO 585
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
uuuaaacuca guucaggauc                                               20

<210> SEQ ID NO 586
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
uuuuaaacuc aguucaggau                                               20

<210> SEQ ID NO 587
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
ugccuuuuaa acucaguuca                                               20

<210> SEQ ID NO 588
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 588
uugcugggug ccuuuuaaac                                          20

<210> SEQ ID NO 589
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
uuuuguacgu ugcauuugau                                          20

<210> SEQ ID NO 590
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
ucuuuguacg uugcauuuga                                          20

<210> SEQ ID NO 591
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
ucaucuuuua accauacaac                                          20

<210> SEQ ID NO 592
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
uuggcaguga gguuuuuaaa                                          20

<210> SEQ ID NO 593
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
uaguggcagu gagguuuuua                                          20

<210> SEQ ID NO 594
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
uagaguggca gugagguuuu                                       20

<210> SEQ ID NO 595
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
uaugcucuca auucuguuuc                                       20

<210> SEQ ID NO 596
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
aaucagaggu gagca                                            15

<210> SEQ ID NO 597
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
gaggugagca cugca                                            15

<210> SEQ ID NO 598
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
aggugagcac ugcaa                                            15

<210> SEQ ID NO 599
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
ugagcacugc aacaa                                            15

<210> SEQ ID NO 600
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 600
uuuucucucg gauca                                               15

<210> SEQ ID NO 601
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
uuucucucgg aucua                                               15

<210> SEQ ID NO 602
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
cucucggauc uccaa                                               15

<210> SEQ ID NO 603
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
ucucggaucu ccaaa                                               15

<210> SEQ ID NO 604
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
ucggaucucc aaaua                                               15

<210> SEQ ID NO 605
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
uccaaauuua aaaga                                               15

<210> SEQ ID NO 606
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
```
ccaaauuuaa aagca                                          15

<210> SEQ ID NO 607
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
caaauuuaaa agcaa                                          15

<210> SEQ ID NO 608
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
aagcacaagg aauga                                          15

<210> SEQ ID NO 609
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
gaaugauugu accaa                                          15

<210> SEQ ID NO 610
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
auuguaccac acaaa                                          15

<210> SEQ ID NO 611
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611
guaccacaca aagua                                          15

<210> SEQ ID NO 612
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
uaccacacaa aguaa								15

<210> SEQ ID NO 613
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
ccacacaaag uaaua								15

<210> SEQ ID NO 614
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
acacaaagua augua								15

<210> SEQ ID NO 615
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
aguaauguaa aacaa								15

<210> SEQ ID NO 616
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
guaauguaaa acaua								15

<210> SEQ ID NO 617
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
uaaaacauua aagga								15

<210> SEQ ID NO 618
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
acauuaaagg acuca								15

<210> SEQ ID NO 619
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
ggacucauua aaaaa                                                    15

<210> SEQ ID NO 620
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
acucauuaaa aagua                                                    15

<210> SEQ ID NO 621
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
aaaguaacag uugua                                                    15

<210> SEQ ID NO 622
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
caucaucauc aucaa                                                    15

<210> SEQ ID NO 623
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
caucaucauc auaga                                                    15

<210> SEQ ID NO 624
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
caucaucaua gcuaa                                                    15

```
<210> SEQ ID NO 625
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
aucaucauca ucaua                                                         15

<210> SEQ ID NO 626
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
caucaucauc aucaa                                                         15

<210> SEQ ID NO 627
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
caucaucauc auaga                                                         15

<210> SEQ ID NO 628
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
ucaucauagc uacca                                                         15

<210> SEQ ID NO 629
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
caucauagcu accaa                                                         15

<210> SEQ ID NO 630
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
agcuaccauu uauua                                                         15
```

-continued

```
<210> SEQ ID NO 631
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
uaccauuuau ugaaa                                                          15

<210> SEQ ID NO 632
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
aacuucaaag aacua                                                          15

<210> SEQ ID NO 633
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
caaagaacuu aucca                                                          15

<210> SEQ ID NO 634
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
uccuuuaguu ggaga                                                          15

<210> SEQ ID NO 635
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
cuuuaguugg agaga                                                          15

<210> SEQ ID NO 636
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
uuaguuggag agcca                                                          15

<210> SEQ ID NO 637
```

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
uaguuggaga gccaa                                                          15

<210> SEQ ID NO 638
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
uuggagagcc aagaa                                                          15

<210> SEQ ID NO 639
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
ggagagccaa gacaa                                                          15

<210> SEQ ID NO 640
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
gagccaagac aauca                                                          15

<210> SEQ ID NO 641
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
ccaagacaau cauaa                                                          15

<210> SEQ ID NO 642
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
aagacaauca uaaca                                                          15

<210> SEQ ID NO 643
<211> LENGTH: 15
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
agcugucugc uucua                                                         15

<210> SEQ ID NO 644
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
gauccugaac ugaga                                                         15

<210> SEQ ID NO 645
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
auccugaacu gagua                                                         15

<210> SEQ ID NO 646
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
ugaacugagu uuaaa                                                         15

<210> SEQ ID NO 647
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
guuuaaaagg cacca                                                         15

<210> SEQ ID NO 648
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
aucaaaugca acgua                                                         15

<210> SEQ ID NO 649
<211> LENGTH: 15
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 649
ucaaaugcaa cguaa                                                    15

<210> SEQ ID NO 650
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
guuguauggu uaaaa                                                    15

<210> SEQ ID NO 651
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
uuuaaaaacc ucaca                                                    15

<210> SEQ ID NO 652
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
uaaaaaccuc acuga                                                    15

<210> SEQ ID NO 653
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
aaaaccucac ugcca                                                    15

<210> SEQ ID NO 654
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
gaaacagaau ugaga                                                    15

<210> SEQ ID NO 655
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 655
ugcagugcuc accucugauu                                                      20

<210> SEQ ID NO 656
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
uuuguugcag ugcucaccuc                                                      20

<210> SEQ ID NO 657
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
uuuuguugca gugcucaccu                                                      20

<210> SEQ ID NO 658
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
ucuuuuuguu gcagugcuca                                                      20

<210> SEQ ID NO 659
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
uuuggagauc cgagagaaaa                                                      20

<210> SEQ ID NO 660
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
uuuuggagau ccgagagaaa                                                      20

<210> SEQ ID NO 661
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 661
uaaauuugga gauccgagag                                              20

<210> SEQ ID NO 662
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
uuaaauuugg agauccgaga                                              20

<210> SEQ ID NO 663
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
uuuuaaauuu ggagauccga                                              20

<210> SEQ ID NO 664
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
uuugugcuuu uaaauuugga                                              20

<210> SEQ ID NO 665
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 665
ucuugugcuu uaaauuuugg                                              20

<210> SEQ ID NO 666
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
uccuugugcu uuuaaauuug                                              20

<210> SEQ ID NO 667
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 667
uacaaucauu ccuugugcuu                                               20

<210> SEQ ID NO 668
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
uuuguguggu acaaucauuc                                               20

<210> SEQ ID NO 669
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
uuuacuuugu gugguacaau                                               20

<210> SEQ ID NO 670
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
uacauuacuu uguguggua c                                              20

<210> SEQ ID NO 671
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 671
uuacauuacu uuguguggua                                               20

<210> SEQ ID NO 672
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
uuuuacauua cuuugugugg                                               20

<210> SEQ ID NO 673
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
uguuuuacau uacuuugugu					20

<210> SEQ ID NO 674
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
uuuuaauguu uuacauuacu					20

<210> SEQ ID NO 675
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
ucuuuaaugu uuuacauuac					20

<210> SEQ ID NO 676
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 676
uugagaccuu uaauguuuua					20

<210> SEQ ID NO 677
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 677
uuuaaugagu ccuuuaaugu					20

<210> SEQ ID NO 678
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
uguuacuuuu uaaugagucc					20

<210> SEQ ID NO 679
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 679
ucuguuacuu uuuaaugagu                                               20

<210> SEQ ID NO 680
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
uaugagacaa cuguuacuuu                                               20

<210> SEQ ID NO 681
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
uagcuaugau gaugaugaug                                               20

<210> SEQ ID NO 682
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 682
ugauagcuau gaugaugaug                                               20

<210> SEQ ID NO 683
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 683
ugaugauagc uaugaugaug                                               20

<210> SEQ ID NO 684
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
ucuaugauga ugaugaugau                                               20

<210> SEQ ID NO 685
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
```
uagcuaugau gaugaugaug                                          20

<210> SEQ ID NO 686
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
ugguagcuau gaugaugaug                                          20

<210> SEQ ID NO 687
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
uuaaauggua gcuaugauga                                          20

<210> SEQ ID NO 688
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 688
uauaaauggu agcuaugaug                                          20

<210> SEQ ID NO 689
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 689
uuuuucaaua aaugguagcu                                          20

<210> SEQ ID NO 690
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
uuaguuuuca auaaauggua                                          20

<210> SEQ ID NO 691
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
uggauaaguu cuuugaaguu 20

<210> SEQ ID NO 692
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 692
ucuaaaggau aaguucuuug 20

<210> SEQ ID NO 693
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 693
uuggcucucc aacuaaagga 20

<210> SEQ ID NO 694
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 694
ucuuggcucu ccaacuaaag 20

<210> SEQ ID NO 695
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 695
ugucuuggcu cuccaacuaa 20

<210> SEQ ID NO 696
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 696
uugucuuggc ucuccaacua 20

<210> SEQ ID NO 697
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 697
ugauugucuu ggcucuccaa 20

<210> SEQ ID NO 698
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
uaugauuguc uuggcucucc                                              20

<210> SEQ ID NO 699
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
uguuaugauu gucuuggcuc                                              20

<210> SEQ ID NO 700
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
uauuguuaug auugucuugg                                              20

<210> SEQ ID NO 701
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
uuuauuguua ugauugucuu                                              20

<210> SEQ ID NO 702
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
ucugugagaa gcagacagcu                                              20

<210> SEQ ID NO 703
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
uuuaaacuca guucaggauc                                              20

-continued

<210> SEQ ID NO 704
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
uuuuaaacuc aguucaggau                                                   20

<210> SEQ ID NO 705
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
ugccuuuuaa acucaguuca                                                   20

<210> SEQ ID NO 706
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
uugcugggug ccuuuuaaac                                                   20

<210> SEQ ID NO 707
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
uuuuguacgu ugcauuugau                                                   20

<210> SEQ ID NO 708
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
ucuuuguacg uugcauuuga                                                   20

<210> SEQ ID NO 709
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
ucaucuuuua accauacaac                                                   20

```
<210> SEQ ID NO 710
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
uuggcaguga gguuuuuaaa                                              20

<210> SEQ ID NO 711
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
uaguggcagu gagguuuuua                                              20

<210> SEQ ID NO 712
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
uagaguggca gugagguuuu                                              20

<210> SEQ ID NO 713
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
uaugcucuca auucuguuuc                                              20
```

OLIGONUCLEOTIDE COMPOUNDS FOR TREATMENT OF PREECLAMPSIA AND OTHER ANGIOGENIC DISORDERS

RELATED APPLICATIONS

This application claims priority to U.S. Provisional Patent Application No. 62/291,961, filed Feb. 5, 2016, U.S. Provisional Patent Application No. 62/291,678, filed Feb. 5, 2016, and U.S. Provisional Patent Application No. 62/142,745, filed Apr. 3, 2015. The entire contents of these applications are herein incorporated by reference.

STATEMENT OF GOVERNMENT INTERESTS

This invention was made with government support under grant number OPP1086170 awarded by the National Science Foundation. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 9, 2016, is named 575952UM9-208PC_SL.txt and is 161,529 bytes in size.

FIELD OF THE INVENTION

This disclosure relates to novel angiogenic targets and novel oligonucleotide compounds for the treatment of angiogenic disorders (e.g., preeclampsia).

BACKGROUND

Complicating 5-8% of all pregnancies, preeclampsia (PE) is one of the three main causes of premature birth. The most notable characteristics of PE are hypertension, edema and excess protein in the urine (proteinuria) after the 20th week of pregnancy. Consequences for the fetus can be grave, ranging from small-for-gestational-age infancy to hypoxia-induced neurologic injury (e.g., cerebral palsy) to death. Maternal complications include renal failure, HELLP syndrome (Hemolysis, Elevated Liver enzymes, and Low Platelets), seizures, stroke, and death. PE and related hypertensive disorders are conservatively estimated to cause 76,000 maternal and 500,000 infant deaths globally each year. (See preeclampsia [dot] org.) In the United States, PE is responsible for 100,000 premature births and 10,500 infant deaths each year at a cost of roughly seven billion dollars (three billion dollars for maternal disabilities and four billion dollars related to infant morbidity) every year to the health care system. Across the globe, PE and subsequent eclampsia are major contributors to maternal, fetal and neonatal morbidity and mortality. Thus, PE represents a highly significant unmet public health need.

Although the root causes of PE have yet to be fully understood, it is now well established that the maternal signs and symptoms of hypertension, edema and proteinuria are caused by an excess of anti-angiogenic proteins in the mother's bloodstream. Chief among these are soluble fins-like tyrosine kinase 1 (sFLT1s) proteins. sFLT1s are truncated forms of the membrane-bound vascular endothelial growth factor (VEGF) receptor FLT1 (also known as VEGFR1). They normally function to buffer VEGF signaling. However, when sFLT1s are abnormally high in the mother's circulatory system, they can interfere with her body's own ability to respond to VEGF. Among other functions, VEGF is required for maintenance of the hepatic sinusoidal vasculature and other fenestrated vascular beds in the body (Kamba, T. et al. VEGF-dependent plasticity of fenestrated capillaries in the normal adult microvasculature. *American journal of physiology. Heart and circulatory physiology* 290, H560-576 (2006)). Breakdown of these structures impairs maternal kidney function, leading to hypertension, proteinuria and cerebral edema which are classic features of PE and eclampsia (Young, B. C., Levine, R. J. & Karumanchi, S. A. Pathogenesis of preeclampsia. *Annual review of pathology* 5, 173-192 (2010); Eremina, V. et al. Glomerular-specific alterations of VEGF-A expression lead to distinct congenital and acquired renal diseases. *The Journal of clinical investigation* 111, 707-716 (2003); Eremina, V. et al. VEGF inhibition and renal thrombotic microangiopathy. *The New England journal of medicine* 358, 1129-1136 (2008)).

Pilot studies using an extracorporeal device to remove sFLT1 from the bloodstream of severely preeclamptic women has demonstrated that lowering sFLT1 protein by just 30-40% in the maternal plasma can prolong PE pregnancies by 2 weeks without adverse consequences to the baby (Thadhani, R. et al. Pilot study of extracorporeal removal of soluble fins-like tyrosine kinase 1 in preeclampsia. *Circulation* 124, 940-950 (2011)). Moreover, animal studies support the hypothesis that targeting sFLT1 in PE may also lower the risk of neonatal respiratory problems and bronchopulmonary dysplasia, major complications of prematurity (Tang, J. R., Karumanchi, S. A., Seedorf, G., Markham, N. & Abman, S. H. Excess soluble vascular endothelial growth factor receptor-1 in amniotic fluid impairs lung growth in rats: linking preeclampsia with bronchopulmonary dysplasia. *American journal of physiology. Lung cellular and molecular physiology* 302, L36-46 (2012)). Yet, while apheresis (blood washing) is highly promising, it is unlikely to be applicable to all patients in all situations. Especially in low resource settings, a more cost effective approach with lower medical and general infrastructure requirements is desperately needed. RNA silencing via RNAi is one such approach.

A broad range of human diseases, including cancer, infection and neurodegeneration, can be treated via the silencing of specific genes using small oligonucleotides. ONTs (OligoNucleotide Therapeutics) are a new class of drugs, distinguished by targeting RNA or DNA directly, thus interfering with a disease-causing gene at its root, before it can produce the protein responsible for the disease phenotype. Advantages of ONTs over conventional drugs include ease of drug design based solely on base-pairing rules, an ability to access targets previously considered "undruggable" and their promise of unprecedented specificity, potency, and duration of effect. In addition, pharmacokinetics, pharmacodynamics and safety of ONTs is mostly defined by chemical modifications/formulation and is very similar between compound targeting different genes, enabling multi-gene silencing and simple development drugs targeting the same tissue (Videira, M., Arranja, A., Rafael, D. & Gaspar, R. Preclinical development of siRNA therapeutics: towards the match between fundamental science and engineered systems. *Nanomedicine: nanotechnology, biology, and medicine* 10, 689-702 (2014); H. Youths et al. in A Comprehensive Guide to Toxicology in Preclinical Drug Development. (ed. A. S. Faqi) 647-664 (Academic Press, 2013)). Significant effort in the last decade resulted in development of several types of both chemically-modified and formulated oligonucleotides with clear clinical efficacy (Whitehead, K. A., Langer, R. & Anderson, D. G. Knocking down barriers: advances in siRNA delivery. *Nature reviews. Drug discovery* 8, 129-138 (2009)). Thus, ONTs represent a new and potentially transformative therapeutic paradigm. Nonetheless, their clinical utility has been hampered by limited tissue distribution. Systemic administration has been generally limited to liver hepatocytes to date, with other tissues requiring local administration (de Fougerolles, A., Vornlocher, H. P., Maraganore, J. & Lieberman, J. Interfering with disease: a progress report on siRNA-based therapeutics. *Nature reviews. Drug discovery* 6, 443-453 (2007)).

One class of ONTs is siRNAs, small double-stranded oligonucleotides consisting of passenger (sense) and guide (antisense) strands. Upon cellular uptake, the guide strand is loaded into an RNA Induced Silencing Complex (RISC) capable of cleaving its complementary target RNA. The numbers of loaded RISCs per cell sufficient to induce efficient and long-term gene silencing or RNA interference (RNAi) are estimated at approximately 25-100 in vitro (Stalder, L. et al. The rough endoplasmatic reticulum is a central nucleation site of siRNA-mediated RNA silencing. *The EMBO journal* 32, 1115-1127 (2013)) and approximately 400 in vivo (Pei, Y. et al. Quantitative evaluation of siRNA delivery in vivo. *Rna* 16, 2553-2563 (2010)). Typically, 10-100 ng/gram of oligonucleotide delivered to a targeted tissue (Overhoff, M., Wunsche, W. & Sczakiel, G. Quantitative detection of siRNA and single-stranded oligonucleotides: relationship between uptake and biological activity of siRNA. Nucleic acids research 32, e170 (2004)) is adequate to generate a sufficient number of active RISC complexes and induce silencing. Loaded RISCs have weeks long stability, resulting in prolonged gene silencing (3-6 weeks) from a single administration (Whitehead, K. A., Langer, R. & Anderson, D. G. Knocking down barriers: advances in siRNA delivery. Nature reviews. Drug discovery 8, 129-138 (2009)).

SUMMARY

The present invention in based in part on the discovery that mRNA isoforms encoding sFLT1 proteins contain sequences not found in mRNA encoding full length FLT1 (fl-FLT1) protein that can be targeted for degradation, e.g., to treat PE, postpartum PE, eclampsia and/or HELLP syndrome. Provided herein are novel oligonucleotide sequences (e.g., small interfering RNAs (siRNAs)) that have been engineered to selectively decrease sFLT1 levels without affecting fl-FLT1 by binding to one or more of the sequences that are not present in fl-FLT1, e.g., one or more intronic regions of mRNA encoding one or more sFLT1 proteins. It was discovered that the novel siRNAs described herein were preferentially delivered to the placental trophoblasts (the cell type responsible for excess sFLT1 production) using systemic (i.e., intravenous or subcutaneous) delivery to the mother without delivery to the fetus. Therapeutic compounds and methods for treating one or more symptoms of PE and/or postpartum PE and/or eclampsia and/or HELLP syndrome are also provided.

In one aspect, a compound that binds to an intronic region of an mRNA encoding an sFLT1 protein, wherein the compound selectively inhibits expression of the sFLT1 protein in a cell or organism is provided.

In one embodiment, the compound comprises a single stranded (ss) RNA molecule or a double stranded (ds) RNA molecule that is between 15 and 35 bases in length. In one embodiment, the dsRNA molecule mediates degradation of the mRNA.

In one embodiment, the compound comprises a dsRNA having a sense strand and an antisense strand, wherein the antisense strand comprises a region of complementarity which is substantially complementary to 5' CTCTCGGATCTCCAAATTTA 3' (SEQ ID NO:1), 5' CATCATAGCTACCATTTATT 3' (SEQ ID NO:2), 5' ATTGTACCACACAAAGTAAT 3' (SEQ ID NO:3) or 5' GAGCCAAGACAATCATAACA 3' (SEQ ID NO:4). In one embodiment, the region of complementarity is complementary to at least 15, 16, 17 or 18 contiguous nucleotides of SEQ ID NO:1, SEQ ID NO:2, SEQ ID NO:3 or SEQ ID NO:4. In one embodiment, the region of complementarity contains no more than 3 mismatches with SEQ ID NO:1, SEQ ID NO:2, SEQ ID NO:3 or SEQ ID NO:4. In one embodiment, the region of complementarity is fully complementary to SEQ ID NO:1, SEQ ID NO:2, SEQ ID NO:3 or SEQ ID NO:4.

In one embodiment, the dsRNA is blunt-ended. In one embodiment, the dsRNA comprises at least one single stranded nucleotide overhang. In one embodiment, the dsRNA comprises naturally occurring nucleotides.

In one embodiment, the dsRNA comprises at least one modified nucleotide. In one embodiment, the modified nucleotide is chosen from the group of: a 2'-O-methyl modified nucleotide, a 2'-fluoro modified nucleotide, a nucleotide comprising a 5'-phosphorothioate group, and a terminal nucleotide linked to a cholesteryl derivative. In one embodiment, the modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. In one embodiment, the dsRNA comprises at least one 2'-O-methyl modified nucleotide, at least one 2'-fluoro modified nucleotide, at least one nucleotide comprising a 5' phosphorothioate group and a terminal nucleotide linked to a cholesteryl derivative.

In one embodiment, the dsRNA has a 5' end, a 3' end and complementarity to a target, and comprises a first oligonucleotide and a second oligonucleotide, wherein: (1) the first oligonucleotide comprises a sequence selected from the group consisting of SEQ ID NO:1, SEQ ID No:2, SEQ ID No:3 and SEQ ID NO:4; (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In one embodiment, the second oligonucleotide is linked to a hydrophobic molecule at the 3' end of the second oligonucleotide, e.g., an omega-3 fatty acid. In another embodiment, the hydrophobic molecule is docosanoic acid (DCA), docosahexaenoic acid (DHA), lysophosphatidylcholine esterified DHA (g2-DHA, also known as PC-DHA) or eicosapentaenoic acid (EPA).

In one embodiment, the linkage between the second oligonucleotide and the hydrophobic molecule comprises polyethylene glycol or triethylene glycol.

In one embodiment, the nucleotides at positions 1 and 2 from the 3' end of second oligonucleotide are connected to adjacent nucleotides via phosphorothioate linkages.

In one embodiment, the nucleotides at positions 1 and 2 from the 3' end of second oligonucleotide, and the nucleotides at positions 1 and 2 from the 5' end of second oligonucleotide, are connected to adjacent ribonucleotides via phosphorothioate linkages.

In one embodiment, expression of the sFLT1 protein in the cell or organism is reduced from about 30% to about 50%. In one embodiment, expression of the sFLT1 protein in the cell or organism is reduced from about 30% to about 40%.

In one aspect, a method for inhibiting expression of one or more sFLT1 proteins in a cell is provided. The method includes the steps of (a) introducing into the cell one or more compounds that bind to an intronic region of one or more mRNAs encoding one or more sFLT1 proteins, and (b) maintaining the cell produced in step (a) for a time sufficient to inhibit expression of the one or more sFLT1s proteins in the cell.

In one embodiment, the one or more compounds are one or more dsRNAs that mediate degradation of the one or more mRNAs. In one embodiment, a compound is a dsRNA having a sense strand and an antisense strand, wherein the antisense strand comprises a region of complementarity which is substantially complementary to SEQ ID NO:1, SEQ ID NO:2, SEQ ID NO:3, and/or SEQ ID NO:4. In one embodiment, one or more dsRNAs are each between 15 and 30 base pairs in length.

In one embodiment, expression of one or more sFLT1 proteins is reduced from about 30% to about 50%. In one embodiment, expression of one or more sFLT1 proteins is reduced from about 30% to about 40%.

In one aspect, an RNA molecule that is between 15 and 30 bases in length comprising a region of complementarity which is substantially complementary to SEQ ID NO:1, wherein the RNA molecule targets one or both of an intronic region of sFLT-i13 short and an intronic region of sFLT-i13 long is provided.

In one embodiment, the RNA is dsRNA having a sense strand and an antisense strand, wherein the antisense strand comprises the region of complementarity.

In one aspect, an RNA molecule that is between 15 and 30 bases in length comprising a region of complementarity which is substantially complementary to SEQ ID NO:2, wherein the RNA molecule targets one or both of an intronic region of sFLT-i15a (also known as sFLT-e15a) is provided.

In one embodiment, the RNA is dsRNA having a sense strand and an antisense strand, wherein the antisense strand comprises the region of complementarity.

In one aspect, a therapeutic compound is provided that binds to an intronic region of one or more mRNAs encoding one or more sFLT1 proteins, wherein the therapeutic compound selectively reduces expression of the one or more sFLT1 proteins, and wherein the therapeutic compound reduces one or more symptoms of PE, postpartum PE, eclampsia or HELLP syndrome when administered to a subject in need thereof.

In one embodiment, the one or more sFLT1 proteins are selected from the group consisting of sFLT1-i13 short, sFLT1-i13 long and sFlt1-i15a.

In one embodiment, the therapeutic compound comprises a first and a second oligonucleotide sequence, wherein the first oligonucleotide sequence binds an intronic region of one or both of sFLT1-i13 short and sFLT1-i13 long, and the second oligonucleotide sequence binds an intronic region of sFlt1-i15a. In one embodiment, the first and second oligonucleotide sequences are single stranded RNA (ssRNA) or double stranded RNA (dsRNA).

In one embodiment, a therapeutic compound is provided comprising a first dsRNA comprising a first sense strand and a first antisense strand and a second dsRNA comprising a second sense strand and a second antisense strand, wherein the first antisense strand comprises a first region of complementarity which is substantially complementary to SEQ ID NO:1 and the second antisense strand comprises a second region of complementarity which is substantially complementary to SEQ ID NO:2. In one embodiment, each dsRNA is between 15 and 30 base pairs in length. In one embodiment, the first region of complementarity is complementary to at least 15 contiguous nucleotides of SEQ ID NO:1, and the second region of complementarity is complementary to at least 15 contiguous nucleotides of SEQ ID NO:2. In one embodiment, the first region of complementarity contains no more than 3 mismatches with SEQ ID NO:1, and the second region of complementarity contains no more than 3 mismatches with SEQ ID NO:2. In one embodiment, the first region of complementarity is fully complementary to SEQ ID NO:1, and the second region of complementarity is fully complementary to SEQ ID NO:2.

In one embodiment, each dsRNA comprises at least one single stranded nucleotide overhang.

In one embodiment, each dsRNA comprises at least one modified nucleotide. In one embodiment, the modified nucleotide is chosen from the group of: a 2'-O-methyl modified nucleotide, a 2'-fluoro modified nucleotide, a nucleotide comprising a 5'-phosphorothioate group, and a terminal nucleotide linked to a cholesteryl derivative. In one embodiment, a modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. In one embodiment, a dsRNA comprises at least one 2'-O-methyl modified nucleotide, at least one 2'-fluoro modified nucleotide, at least one nucleotide comprising a 5' phosphorothioate group and a terminal nucleotide linked to a cholesteryl derivative.

In one embodiment, each dsRNA comprises a 5' end, a 3' end and complementarity to a target, wherein (1) the oligonucleotide comprises alternating 2'-methoxy-ribonucleotides and 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In one aspect, a pharmaceutical composition is provided. The composition includes a first dsRNA comprising a first sense strand and a first antisense strand, wherein the first antisense strand comprises a region of complementarity which is substantially complementary to SEQ ID NO:1, and wherein the first antisense strand selectively targets one or both of an intronic region of sFLT-i13 short and an intronic region of sFLT-i13 long; a second dsRNA comprising a second sense strand and a second antisense strand, wherein the second antisense strand comprises a region of complementarity which is substantially complementary to SEQ ID No:2, and wherein the second antisense strand selectively targets an intronic region of sFLT-i15a; and a pharmaceutically acceptable carrier.

In one embodiment, a method of treating or managing PE, eclampsia or HELLP syndrome comprising administering to a subject in need of such treatment or management a therapeutically effective amount of a pharmaceutical composition described herein is provided. In one embodiment, the pharmaceutical composition is administered intravenously or subcutaneously. In one embodiment, sFLT1 protein expression is reduced in the subject by about 30% to about 50%. In one embodiment, sFLT1 protein expression is reduced in the subject by about 30% to about 40%.

In one aspect, a method of treating one or more symptoms of PE, eclampsia or HELLP syndrome in a subject in need thereof is provided. The method includes administering to the subject a therapeutic compound that binds to an intronic region of one or more mRNAs encoding one or more sFLT1 proteins, wherein the therapeutic compound reduces expression of the one or more sFLT1 proteins.

In one embodiment, the one or more sFLT1 proteins are selected from the group consisting of sFLT1-i13 short, sFLT1-i13 long and sFlt1-i15a.

In one embodiment, the therapeutic compound comprises a first and a second oligonucleotide sequence, wherein the first oligonucleotide sequence binds an intronic region of one or both of sFLT1-i13 short and sFLT1-i13 long, and the second oligonucleotide sequence binds an intronic region of sFlt1-i15a. In one embodiment, the first and second oligonucleotide sequences are ssRNA or dsRNA.

In one embodiment, a therapeutic compound is provided comprising a first dsRNA comprising a first sense strand and a first antisense strand and a second dsRNA comprising a second sense strand and a second antisense strand, wherein the first antisense strand comprises a first region of complementarity which is substantially complementary to SEQ ID NO:1 and the second antisense strand comprises a second region of complementarity which is substantially complementary to SEQ ID NO:2. In one embodiment, each dsRNA is between 15 and 30 base pairs in length. In one embodiment, the first region of complementarity is complementary to at least 15 contiguous nucleotides of SEQ ID NO:1, and the second region of complementarity is complementary to at least 15 contiguous nucleotides of SEQ ID NO:2. In one embodiment, the first region of complementarity contains no more than 3 mismatches with SEQ ID NO:1, and the second region of complementarity contains no more than 3 mismatches with SEQ ID NO:2. In one embodiment, the first region of complementarity is fully complementary to SEQ ID NO:1, and the second region of complementarity is fully complementary to SEQ ID NO:2.

In one embodiment, each dsRNA comprises at least one single stranded nucleotide overhang.

In one embodiment, each dsRNA comprises at least one modified nucleotide. In one embodiment, the modified nucleotide is chosen from the group of: a 2'-O-methyl modified nucleotide, a 2'-fluoro modified nucleotide, a nucleotide comprising a 5'-phosphorothioate group, and a terminal nucleotide linked to a cholesteryl derivative. In one embodiment, a modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. In one embodiment, a dsRNA comprises at least one 2'-O-methyl modified nucleotide, at least one 2'-fluoro modified nucleotide, at least one nucleotide comprising a 5' phosphorothioate group and a terminal nucleotide linked to a cholesteryl derivative.

In one aspect, a pharmaceutical composition is provided. The pharmaceutical composition includes a first dsRNA comprising a first sense strand and a first antisense strand, wherein the first antisense strand comprises a region of complementarity which is substantially complementary to SEQ ID NO:1, and wherein the first antisense strand targets one or both of an intronic region of sFLT-i13 short and an intronic region of sFLT-i13 long, a second dsRNA comprising a second sense strand and a second antisense strand, wherein the second antisense strand comprises a region of complementarity which is substantially complementary to SEQ ID No:2, and wherein the second antisense strand targets an intronic region of sFLT-i15a, and a pharmaceutically acceptable carrier.

In one embodiment, a method of treating or managing PE, eclampsia or HELLP syndrome comprising administering to a subject in need of such treatment or management a therapeutically effective amount of the pharmaceutical composition described herein is provided.

In one embodiment, the pharmaceutical composition is administered intravenously or subcutaneously.

In one embodiment, sFLT1 protein expression is reduced in the subject by about 30% to about 50%. In one embodiment, sFLT1 protein expression is reduced in the subject by about 30% to about 40%.

In one aspect, a method of treating one or more symptoms of an angiogenic disorder in a subject in need thereof is provided, comprising administering to the subject any compound described herein.

In one aspect, a method of treating one or more symptoms of PE, eclampsia or HELLP syndrome in a subject in need thereof is provided, comprising administering to the subject any compound described herein.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIGS. 1A-1C depict a PolyAdenylation Site Sequencing (PAS-Seq) analysis of sFLT1 isoform expression in preeclamptic and normal placentas. (A) Schematically depicts Receptor Tyrosine Kinase (RTK) signaling modulation by soluble decoys, which can be generated by polyadenylation in an intron upstream of the TransMembrane™ and kinase domains. (Adapted from Vorlova, S. et al. Induction of antagonistic soluble decoy receptor tyrosine kinases by intronic polyA activation. *Molecular cell* 43, 927-939 (2011).) (B) PAS-Seq identifies alternative FLT1 polyadenylation sites. (C) Both i13 and i15 isoforms are overexpressed in preeclampsia. Total RNA was purified and analyzed by PAS-Seq (Heyer, E. E., Ozadam, H., Ricci, E. P., Cenik, C. & Moore, M. J. An optimized kit-free method for making strand-specific deep sequencing libraries from RNA fragments. *Nucleic Acids Res* 43, e2 (2015)) from five normal and six preeclamptic human placentas. Note that sFLT1-i14 refers to sFLT1415a.

FIGS. 6A-6C depict the identification and validation of functional hsiRNA compounds targeting i13 and i15 sFlt1 isoforms. (A) Schematically represents the exon-intron structure of sFLT1 i13 and i15 isoforms. (B) Depicts sFLT1 i13 and i15 mRNA sequences (SEQ ID NOS 6 and 111, respectively, in order of appearance). Locations of leading hsiRNAs hits are indicated (red lines). Stop codons are shown in red. (C) depicts hsiRNA targeting of sFLT1-i13 and sFlt1-i15a. FIG. 6(C) discloses the "Targeting region" sequences as SEQ ID NOS 112-115 and the "Oligonucleotide" sequences as SEQ ID NOS 116-123, all respectively, in order of appearance. Chemical modifications are as follows: P—5'-phosphate; f—2' fluoro; m—2'O-methyl; #—phosphorothioate. Note that sFLT1-i14 refers to sFLT1-i15a.

FIGS. 8A-8C depict the impact of hsiRNA chemistry and route of administration on placental accumulation and distribution. (A) A wild-type pregnant mouse (E15) was injected with Cy3-sFLT1-2283 (red) (10 mg/kg; IV via tail vein). Placentas were fixed after 24 hours, processed, and imaged on a Leica tiling fluorescent microscope; nuclei stained with DAPI (blue). (B) Depicts accumulation of sFLT1-i13-2283 (10 mg/kg) after 24 hours, and analyzed by PNA assay (n=3, mean+SEM). (C) Schematically represents different modification patterns of sFLT1-i13-2283 hsiRNA. P—5'-phosphate; Chol-teg—Cholesterol-teg linker; white spheres—RNA; black spheres—2'-O-methyl; grey spheres—2'-Fluoro; red spheres—phosphorothioate. Note that sFLT1-i14 refers to sFLT1-i15a.

FIGS. 12A-12C depict selective delivery of hsiRNA to the syncytial trophoblast layer of the mouse placenta labyrinth. (A) Depicts a schematic from Maltepe et al. (*J Clin Invest.* (2010) 120(4):1016-1025. doi:10.1172/JCI41211). (B) Depicts trophoblast distribution after intravenous administration of hsiRNA (63× magnification). (C) Depicts trophoblast distribution after subcutaneous administration of hsiRNA (63× magnification).

FIG. 13 depicts a list of all hits with efficacy in different chemical scaffolds and unique sequences of I13 short, I13 long and I15a isoforms, which were targeted as described further herein. FIG. 13 discloses "AUCGAGGUCCGCG" as SEQ ID NO: 16, "Targeting Region (20 mer)" sequences disclosed as SEQ ID NOS 124-182, "Targeting Region (30 mer)" sequences disclosed as SEQ ID NOS 183-241, "Sense Naked" sequences disclosed as SEQ ID NOS 242-300 and "Guide 20mer" sequences disclosed as SEQ ID NOS 301-359, "Sense P0" sequences disclosed as SEQ ID NOS 360-418, "Guide P0" sequences disclosed as SEQ ID NOS 419-477, "Sense P1" sequences disclosed as SEQ ID NOS 478-536, "Guide P1" sequences disclosed as SEQ ID NOS 537-595, "Sense P2" sequences disclosed as SEQ ID NOS 596-654 and "Guide P2" sequences disclosed as SEQ ID NOS 655-713, all respectively, in order of appearance.

FIG. 14 summarizes acceptable and ideal target product profiles and comments on the potential for addressing these needs according to certain exemplary embodiments.

FIG. 26 depicts sFLT1 silencing mediated by DHA-hsiRNA in pregnant mice (CD1) as detected in liver, kidney and placental tissues. sFLT1_2283P2-g2DHA (150813).

DETAILED DESCRIPTION

Figure 1A:
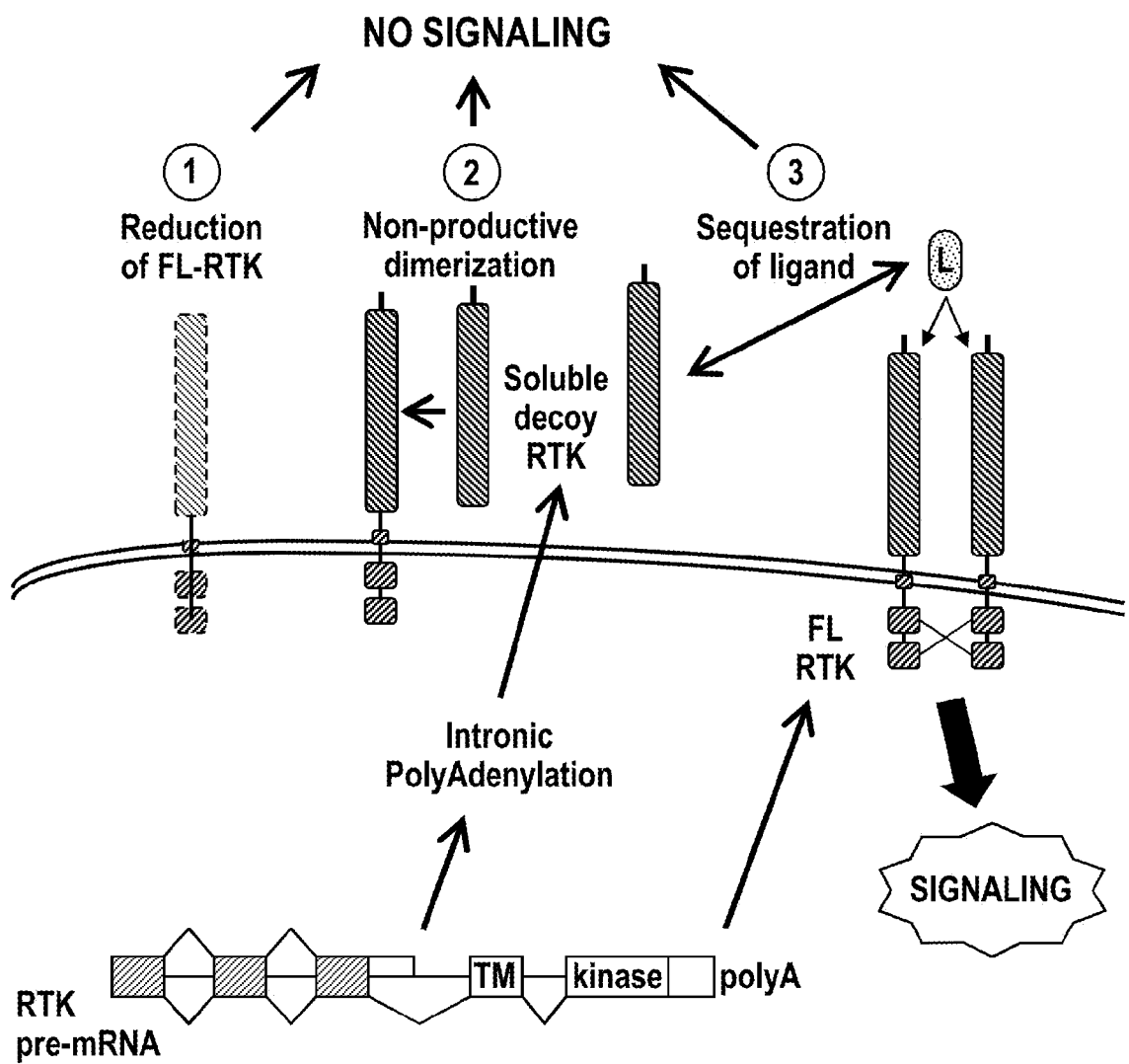

Novel angiogenic targets (e.g., PE target sequences, e.g., intron sequences of sFLT1 mRNAs) are provided. Also provided are novel siRNAs that selectively target intronic regions of mRNAs encoding angiogenic targets (e.g., sFLT1 proteins). Methods of treating angiogenic disorders, e.g., PE, postpartum PE, eclampsia and/or HELLP, are also provided.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

By "alteration" is meant a change (increase or decrease) in the expression levels of a gene, mRNA or polypeptide as detected by standard art known methods such as those described herein. As used herein, an increase or decrease includes a 10% change in expression levels, a 25% change, a 40% change, or a 50% or greater change in expression levels. In certain embodiments, an increase or decrease is a change in expression levels of between about 30% and about 50% or between about 30% and about 40%. "Alteration" can also indicate a change (increase or decrease) in the biological activity of any of the mRNAs or polypeptides of the invention (e.g., sFlt1 (e.g., sFlt1-i13 short, sFlt1-i13 long and/or sFlt1-i15a (also known as sFlt1-e15a)). Examples of biological activity for sFlt-1 include one or more clinical symptoms of PE or eclampsia. As used herein, an increase or decrease includes a 10% change in biological activity, preferably a 25% change, more preferably a 40% change, and most preferably a 50% or greater change in biological activity. In certain preferred embodiments, an increase or decrease is a change in expression levels of between about 30% and about 50% or between about 30% and about 40%.

Certain embodiments of the invention are directed to the treatment of one or more angiogenic disorders. By "treatment of an angiogenic disorder" is meant use of an oligonucleotide (e.g., an siRNA) of the invention in a pharmaceutical composition for the treatment of diseases involving the physiological and pathological processes of neovascularization, vasculogenesis and/or angiogenesis. As such, these pharmaceutical compositions are useful for treating diseases, conditions and disorders that require inhibition of neovascularization, vasculogenesis or angiogenesis, including but not limited to cancer tumor growth and metastasis, neoplasm, ocular neovascularization (including macular degeneration, diabetic retinopathy, ischemic retinopathy, retinopathy of prematurity, choroidal neovascularization), rheumatoid arthritis, osteoarthritis, chronic asthma, septic shock, inflammatory diseases, synovitis, bone and cartilage destruction, pannus growth, osteophyte formation, osteomyelitis, psoriasis, obesity, haemangioma, Kaposi's sarcoma, atherosclerosis (including atherosclerotic plaque rupture), endometriosis, warts, excess hair growth, scar keloids, allergic edema, dysfunctional uterine bleeding, follicular cysts, ovarian hyperstimulation, endometriosis, osteomyelitis, inflammatory and infectious processes (hepatitis, pneumonia, glumerulonephtritis), asthma, nasal polyps, transplantation, liver regeneration, leukomalacia, thyroiditis, thyroid enlargement, lymphoproliferative disorders, haematologic malignancies, vascular malformations, pre-eclampsia, eclampsia and/or HELLP syndrome.

By "preeclampsia" ("PE") is meant the multi-system disorder that is characterized by hypertension with proteinuria or edema, or both, and one or more of glomerular dysfunction, brain edema, liver edema, or coagulation abnormalities due to pregnancy or the influence of a recent pregnancy. PE generally occurs after the 20th week of gestation. PE is generally defined as some combination of the following symptoms: (1) a systolic blood pressure (BP)>140 mmHg and a diastolic BP>90 mmHg after 20 weeks gestation (generally measured on two occasions, 4-168 hours apart), (2) new onset proteinuria (1+ by dipstick on urinalysis, >300 mg of protein in a 24-hour urine collection, or a single random urine sample having a protein/creatinine ratio>v0.3), and (3) resolution of hypertension and proteinuria by 12 weeks postpartum.

Severe PE is generally defined as (1) a diastolic BP>110 mmHg (generally measured on two occasions, 4-168 hours apart) or (2) proteinuria characterized by a measurement of 3.5 g or more protein in a 24-hour urine collection or two random urine specimens with at least 3+ protein by dipstick. In PE, hypertension and proteinuria generally occur within seven days of each other. In severe PE, severe hypertension, severe proteinuria and HELLP syndrome (Hemolysis, Elevated Liver enzymes, Low Platelets) or eclampsia can occur simultaneously or only one symptom at a time.

Occasionally, severe PE can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "HELLP" syndrome is meant a group of symptoms that occur in pregnant woman characterized by hemolysis, elevated liver enzymes, and low platelet count. HELLP syndrome is thought to be a variant of PE, but it may be an entity of its own.

In certain aspects, PE includes postpartum PE. Postpartum PE is a rare condition that occurs when a woman has high blood pressure and excess protein in her urine soon after childbirth. Postpartum PE typically develops within 48 hours of childbirth. However, postpartum PE sometimes develops up to six weeks after childbirth, which is known as late postpartum PE. Signs and symptoms of postpartum PE and late postpartum PE are typically similar to those of PE that occurs during pregnancy and may include one or any combination of the following: high blood pressure (i.e., 140/90 mm Hg or greater; proteinuria; severe headaches; changes in vision, including temporary loss of vision, blurred vision or light sensitivity; swelling of the face and limbs; upper abdominal pain, usually under the ribs on the right side; nausea or vomiting; and decreased urination; sudden weight gain, typically more than 2 pounds (0.9 kilogram) a week.

By "intrauterine growth retardation (IUGR)" is meant a syndrome resulting in a birth weight which is less that 10 percent of the predicted fetal weight for the gestational age of the fetus. The current World Health Organization criterion for low birth weight is a weight less than 2,500 grams (5 lbs. 8 oz.) or below the 10th percentile for gestational age according to U.S. tables of birth weight for gestational age by race, parity, and infant sex (Zhang and Bowes, Obstet. Gynecol. 86:200-208, 1995). These low birth weight babies are also referred to as "small for gestational age (SGA)." PE is a condition known to be associated with IUGR or SGA.

Certain embodiments of the invention are directed to the treatment of one or more kidney disorders. By "treatment of a kidney disorder" is meant use of an oligonucleotide (e.g., an siRNA) of the invention in a pharmaceutical composition for the treatment of diseases, conditions or disorders associated with the kidney. Diseases, conditions or disorders associated with the kidney include, but are not limited to, Chronic Kidney Disease (CKD) (stages 1-5 with stage 1 being the mildest and usually causing few symptoms and stage 5 being a severe illness with poor life expectancy if untreated (stage 5 CKD is often called end stage renal disease, end stage renal failure, or end-stage kidney disease, chronic kidney failure or chronic renal failure), and Acute Renal Failure (ARF) (caused by traumatic injury with blood loss, sudden reduction of blood flow to the kidneys, damage to the kidneys from sepsis, obstruction of urine flow, damage from certain drugs or toxins, pregnancy complications (e.g., eclampsia, PE and/or HELLP syndrome) and the like).

Certain embodiments of the invention are directed to the treatment of one or more liver disorders. By "treatment of a liver disorder" is meant use of an oligonucleotide (e.g., an siRNA) of the invention in a pharmaceutical composition for the treatment of diseases, conditions or disorders associated with the liver. Diseases, conditions or disorders associated with the liver include, but are not limited to, fascioliasis, hepatitis (e.g., viral hepatitis, alcoholic hepatitis autoimmune hepatitis, hereditary hepatitis and the like), alcoholic liver disease (including alcoholic fatty liver disease, alcoholic hepatitis, and alcoholic cirrhosis), non-alcoholic fatty liver disease, steatohepatitis, non-alcoholic cirrhosis, primary liver cancer (e.g., hepatocellular carcinoma, cholangiocarcinoma, angiosarcoma, hemangiosarcoma and the like), primary biliary cirrhosis, primary sclerosing, centrilobular necrosis, Budd-Chiari syndrome, hemochromatosis, Wilson's disease, alpha 1-antitrypsin deficiency, glycogen storage disease type II, transthyretin-related hereditary amyloidosis, Gilbert's syndrome, biliary atresia, alpha-1 antitrypsin deficiency, Alagille syndrome, progressive familial intrahepatic cholestasis, and the like.

By "therapeutic amount" is meant an amount that when administered to a patient suffering from PE or eclampsia is sufficient to cause a qualitative or quantitative reduction in the symptoms of PE or eclampsia as described herein. A "therapeutic amount" can also mean an amount that when administered to a patient or subject suffering from PE or eclampsia is sufficient to cause a reduction in the expression levels of one or more sFLT1 proteins (e.g., one or more of FLT1-i13 short, sFLT1-i13 long and sFlt1-i15a) as measured by one or more of the assays described herein.

By "subject" is meant a mammal, including, but not limited to, a human or non-human mammal, such as non-human primates or other animals such as, e.g., bovine, equine, canine, ovine, feline, murine and the like. Included in this definition are pregnant, post-partum and non-pregnant mammals.

By "soluble FLT1 (sFLT1)" (also known as sVEGF-R1) is meant a soluble form of the FLT1 receptor that has sFLT1 biological activity (e.g., e.g., sFlt1-i13 short, sFlt1-i13 long and/or sFlt1-i15a (also known as sFlt1-e15a)). The biological activity of an sFLT1 polypeptide may be assayed using any standard method, for example, by assaying for one or more clinical symptoms of PE, postpartum PE, eclampsia and/or HELLP, by assaying sFLT1 mRNA and/or protein levels, by assaying sFLT1 binding to VEGF and the like. sFLT1 proteins lack the transmembrane domain and the cytoplasmic tyrosine kinase domain of the FLT1 receptor. sFLT1 proteins can bind to VEGF and PlGF bind with high affinity, but cannot induce proliferation or angiogenesis and are therefore functionally different from the Flt-1 and KDR receptors. sFLT1 was initially purified from human umbilical endothelial cells and later shown to be produced by trophoblast cells in vivo. As used herein, sFlt-1 includes any sFlt-1 family member or isoform, e.g., sFLT1-i13 (e.g., FLT1-i13 short and/or sFLT1-i13 long (sFLT1_v1), sFlt1-i15a (sFLT1_v2), sFLT1-e15a, sFLT1_v3, sFLT1_v4 and the like.

The sequence of the sFLT1-i13 short isoform is:

(SEQ ID NO: 5)
GTGAGCACTGCAACAAAAAGGCTGTTTTCTCTCGGATCTCCAAATTTAAA

AGCACAAGGAATGATTGTACCACACAAAGTAATGTAAAACATTAAAGGAC

TCATTAAAAAGTAA.

The sequence of the sFLT1-i13 long isoform is:

(SEQ ID NO: 6)
GAAGAAAGAAATTACAATCAGAGGTGAGCACTGCAACAAAAAGGCTGTTT

TCTCTCGGATCTCCAAATTTAAAAGCACAAGGAATGATTGTACCACACAA

AGTAATGTAAAACATTAAAGGACTCATTAAAAAGTAACAGTTGTCTCATA

TCATCTTGATTTATTGTCACTGTTGCTAACTTTCAGGCTCGGAGGAGATG

CTCCTCCCAAAATGAGTTCGGAGATGATAGCAGTAATAATGAGACCCCCG

GGCTCCAGCTCTGGGCCCCCCATTCAGGCCGAGGGGCTGCTCCGGGGGG

CCGACTTGGTGCACGTTTGGATTTGGAGGATCCCTGCACTGCCTTCTCTG

TGTTTGTTGCTCTTGCTGTTTTCTCCTGCCTGATAAACAACAACTTGGGA

TGATCCTTTCCATTTTGATGCCAACCTCTTTTTATTTTTAAGCGGCGCCC

TATAGT.

The sequence of the sFLT1415a (also known as sFlt1-e15a) isoform is:

(SEQ ID NO: 7)
AACTGTATACATCAACGTCACCATCGTCATCGTCATCATCACCATTGTCA

TCATCATCATCATCGTCATCATCATCATCATCATAGCTATCATCATTATC

```
                        -continued
ATCATCATCATCATCATCATAGCTACCATTTATTGAAAACTATTATG

TGTCAACTTCAAAGAACTTATCCTTTAGTTGGAGAGCCAAGACAATCATA

ACAATAACAAATGGCCGGGCATGGTGGCTCACGCCTGTAATCCCAGCACT

TTGGGAGGCCAAGGCAGGTGGATCATTTGAGGTCAGGAGTCCAAGACCAG

CCTGACCAAGATGGTGAAATGCTGTCTCTATTAAAAATACAAAATTAGCC

AGGCATGGTGGCTCATGCCTGTAATGCCAGCTACTCGGGAGGCTGAGACA

GGAGAATCACTTGAACCCAGGAGGCAGAGGTTGCAGGGAGCCGAGATCGT

GTACTGCACTCCAGCCTGGGCAACAAGAGCGAAACTCCGTCTCAAAAAAC

AAATAAATAAATAAATAAATAAACAGACAAAATTCACTTTTTATTCTATT

AAACTTAACATACATGCTAA.
``` sFLT1 protein levels can be measured by measuring the amount of free, bound (i.e., bound to growth factor), or total sFLT1 (bound+free). VEGF or PlGF levels are determined by measuring the amount of free PlGF or free VEGF (i.e., not bound to sFLT1). One exemplary metric is [sFLT1/(VEGF+PlGF)], also referred to as the PE anti-angiogenic index (PAAI).

By "pre-eclampsia anti-angiogenesis index (PAAI)" is meant the ratio of sFLT1/VEGF+PlGF used as an indicator of anti-angiogenic activity. A PAAI greater than 20 is considered to be indicative of PE or risk of PE.

By "vascular endothelial growth factor (VEGF)" is meant a mammalian growth factor that is homologous to the growth factor defined in U.S. Pat. Nos. 5,332,671; 5,240,848; 5,194,596; and Charnock-Jones et al. (Biol. Reproduction, 48: 1120-1128, 1993), and has VEGF biological activity. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g. VEGF-A, VEGF-B, VEGF-C, VEGF-D, VEGF-E, VEGF189, VEGF165, or VEGF 121). In certain embodiments, VEGF is the VEGF121 or VEGF 165 isoform (Tischer et al., J. Biol. Chem. 266, 11947-11954, 1991; Neufed et al. Cancer Metastasis 15:153-158, 1996), which is described in U.S. Pat. Nos. 6,447,768; 5,219,739; and 5,194,596, hereby incorporated by reference. Also included are mutant forms of VEGF such as the KDR-selective VEGF and Flt-selective VEGF described in Gille et al. (J. Biol. Chem. 276:3222-3230, 2001). VEGF includes human forms and can include other animal forms of VEGF (e.g. mouse, rat, dog, chicken or the like).

By "placental growth factor (PlGF)" is meant a mammalian growth factor that is homologous to the protein defined by GenBank accession number P49763 and that has PlGF biological activity. PlGF is a glycosylated homodimer belonging to the VEGF family and can be found in two distinct isoforms through alternative splicing mechanisms. PlGF is expressed by cyto- and syncytiotrophoblasts in the placenta and PlGF biological activities include induction of proliferation, migration, and activation of endothelial cells, particularly trophoblast cells.

By "trophoblast" is meant the mesectodermal cell layer covering the blastocyst that erodes the uterine mucosa and through which the embryo receives nourishment from the mother. Trophoblast cells contribute to the formation of the placenta.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein (e.g., causes production of one or more sFLT1 proteins) or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target (sFLT1) and non-target (flFLT1) genes) can differ by one or more nucleotides, e.g., at an intronic region. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is a allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The phrase "examining the function of a gene in a cell or organism" refers to examining or studying the expression, activity, function or phenotype arising therefrom.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, $^2$N-methylguanosine and $^{2,2}$N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-μ, wherein T is an mRNA targeting moiety, L is a linking moiety, and μ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portions of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant invention include step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

In some embodiments, the RNA silencing agents of the invention are designed to target intronic regions in mRNA molecules encoding one or more sFLT1 proteins.

The present invention targets one or more sFLT1 mRNAs and their corresponding proteins. One strand of double-stranded RNA (siRNA) complements a target sequence within the sFLT1 mRNA. After introduction of siRNA into a subject or cell, the siRNA partially unwinds, binds to an intronic target region within the sFLT1 mRNA in a site-specific manner, and activates an mRNA nuclease. This nuclease cleaves the sFLT1 mRNA, thereby halting translation of the sFLT1 protein. Cells rid themselves of partially digested mRNA, thus precluding translation, or cells digest partially translated proteins. In certain embodiments, sFLT1 protein expression is reduced in a subject or cell by about 30% to 50%, or by about 30% to 40%.

Figure 13:
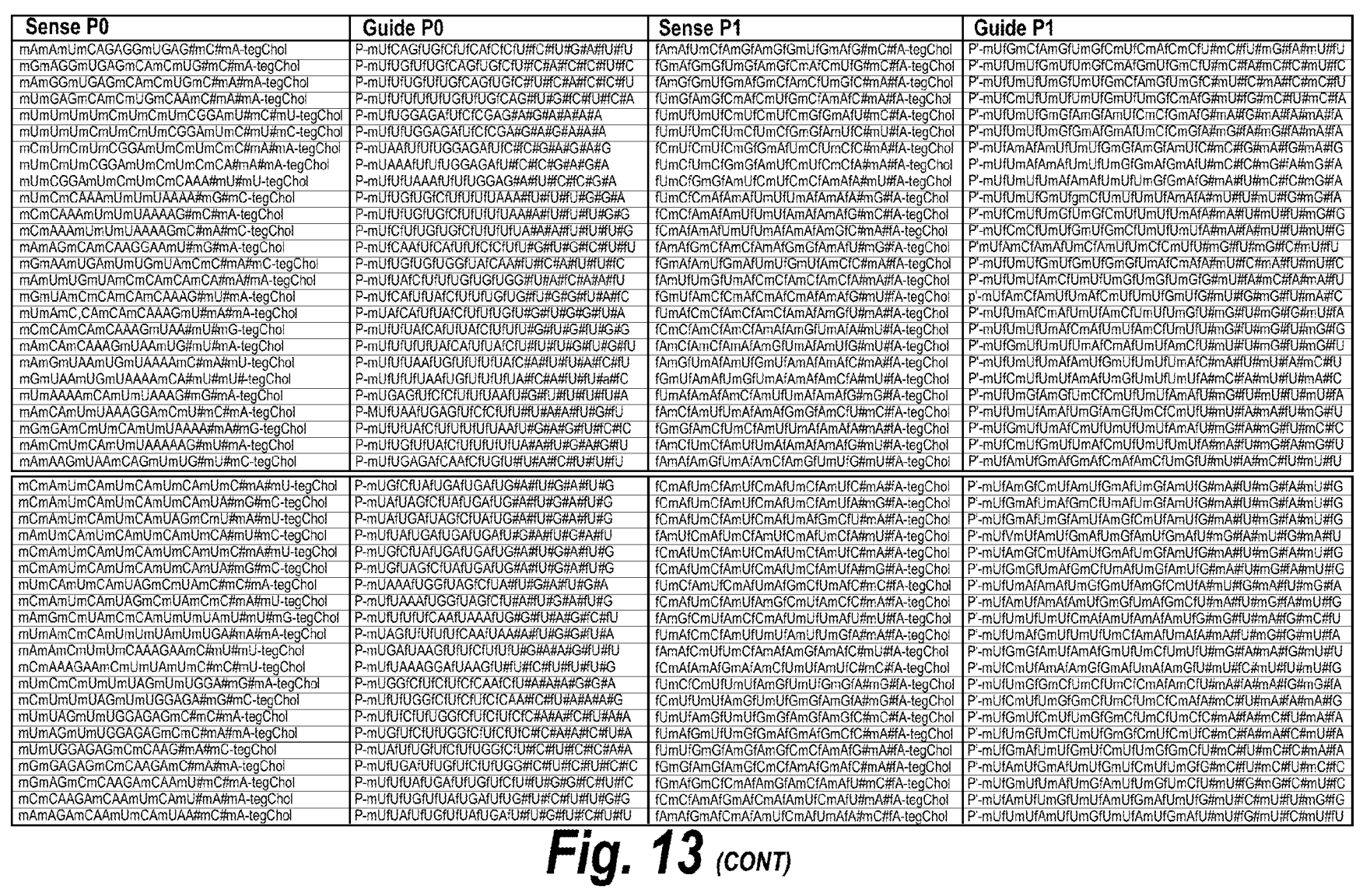
Figure 13:
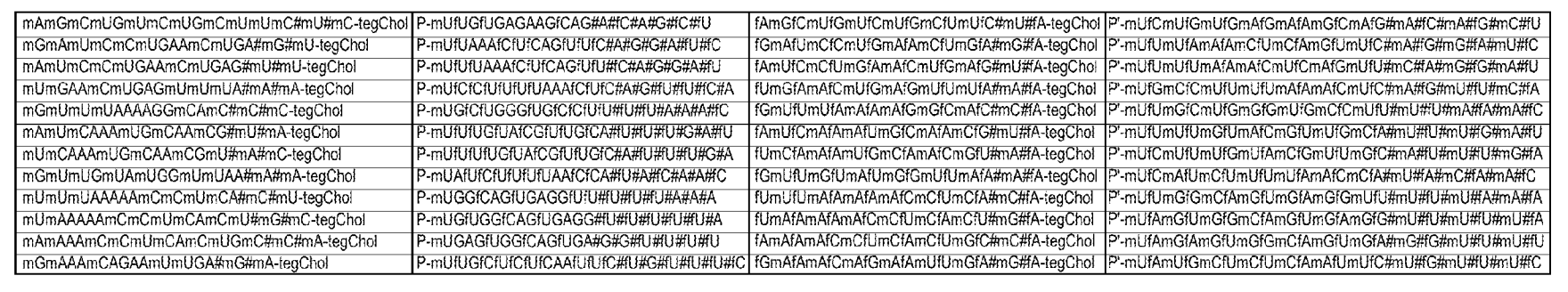

In embodiments of the invention, RNA silencing agents of the invention are capable of targeting one or more of the target sequences listed in FIG. 13. In certain exemplary embodiments, RNA silencing agents of the invention are capable of targeting one or more of the target sequences at one or more target sequences listed at gene positions selected from the group consisting of 2247, 2252, 2253, 2256, 2279, 2280, 2283, 2284, 2286, 2293, 2294, 2295, 2304, 2313, 2318, 2321, 2322, 2324, 2326, 2332, 2333, 2339, 2343, 2351, 2353, 2362, 2471, 2474, 2477, 2508, 2510, 2513, 2518, 2519, 2525, 2528, 2556, 2561, 2572, 2574, 2576, 2577, 2580, 2582, 2585, 2588 and 2590 of the human flt1 gene (as set forth at FIG. 13 and in the Table below). Particularly exemplary target sequences of the human fll gene can be found at positions 2283 (5' CTCTCGGATCTCCAAATTTA 3' (SEQ ID NO:1)), 2519 (5' CATCATAGCTACCATTTATT 3' (SEQ ID NO:2)), 2318 (5' ATTGTACCACACAAAGTAAT 3' (SEQ ID NO:3)) and 2585 (5' GAGCCAAGACAATCATAACA 3' (SEQ ID NO:4)). (See FIGS. 6 and 13.) Genomic sequence for each target sequence can be found in, for example, the publically available database maintained by the NCBI.

TABLE 1

Targeted hits with efficacy for sFLT-i13 short, sFLT1-i13 long and sFLT1-i15a isoforms.

| AUCGAGGUCCGCG | Accession Number | Position | Targeting region (20 mer) | Targeting Region (30 mer) |
| --- | --- | --- | --- | --- |
| sFLT1-i13 | NM_001159920.1 | 2247 | AAUCAGAGGUGAGCACUGCA | AUUACAAUCAGAGGUGAGCACUGCAACAAA |
| sFLT1-i13 | NM_001159920.1 | 2252 | GAGGUGAGCACUGCAACAAA | AAUCAGAGGUGAGCACUGCAACAAAAGGC |
| sFLT1-i13 | NM_001159920.1 | 2253 | AGGUGAGCACUGCAACAAAA | AUCAGAGGUGAGCACUGCAACAAAAGGCU |
| sFLT1-i13 | NM_001159920.1 | 2256 | UGAGCACUGCAACAAAAGG | AGAGGUGAGCACUGCAACAAAAGGCUGUU |
| sFLT1-i13 | NM_001159920.1 | 2279 | UUUUCUCUCGGAUCUCCAAA | GGCUGUUUCUCUCGGAUCUCCAAAUUUAA |
| sFLT1-i13 | NM_001159920.1 | 2280 | UUUCUCUCGGAUCUCCAAAU | GCUGUUUUCUCUCGGAUCUCCAAAUUUAAA |
| sFLT1-i14 | NM_001159920.2 | 2283 | CUCUCGGAUCUCCAAAUUUA | GUUUUCUCUCGGAUCUCCAAAUUUAAAGC |
| sFLT1-i13 | NM_001159920.1 | 2284 | UCUCGGAUCUCCAAAUUUAA | UUUUCUCUCGGAUCUCCAAAUUUAAAAGCA |
| sFLT1-i13 | NM_001159920.1 | 2286 | UCGGAUCUCCAAAUUUAAAA | UUCUCUCGGAUCUCCAAAUUUAAAAGCACA |
| sFLT1-i13 | NM_001159920.1 | 2293 | UCCAAAUUUAAAAGCACAAG | GGAUCUCCAAAUUUAAAAGCACAAGGAAUG |
| sFLT1-i13 | NM_001159920.1 | 2294 | CCAAAUUUAAAAGCACAAGG | GAUCUCCAAAUUUAAAAGCACAAGGAAUGA |
| sFLT1-i13 | NM_001159920.1 | 2295 | CAAAUUUAAAAGCACAAGGA | AUCUCCAAAUUUAAAAGCACAAGGAAUGAU |
| sFLT1-i13 | NM_001159920.1 | 2304 | AAGCACAAGGAAUGAUUGUA | UUUAAAAGCACAAGGAAUGAUUGUACCACA |
| sFLT1-i13 | NM_001159920.1 | 2313 | GAAUGAUUGUACCACACAAA | ACAAGGAAUGAUUGUACCACACAAAGUAAU |
| sFLT1-i13 | NM_001159920.1 | 2318 | AUUGUACCACACAAAGUAAU | GAAUGAUUGUACCACACAAAGUAAUGUAAA |
| sFLT1-i13 | NM_001159920.1 | 2321 | GUACCACACAAAGUAAUGUA | UGAUUGUACCACACAAAGUAAUGUAAAACA |

TABLE 1-continued

Targeted hits with efficacy for sFLT-i13 short, sFLT1-i13 long and sFLT1-i15a isoforms.

| AUCGAGGUCCGCG | Accession Number | Position | Targeting region (20 mer) | Targeting Region (30 mer) |
|---|---|---|---|---|
| sFLT1-i13 | NM_001159920.1 | 2322 | UACCACACAAAGUAAUGUAA | GAUUGUACCACACAAAGUAAUGUAAAACAU |
| sFLT1-i13 | NM_001159920.1 | 2324 | CCACACAAAGUAAUGUAAAA | UUGUACCACACAAAGUAAUGUAAAACAUUA |
| sFLT1-i13 | NM_001159920.1 | 2326 | ACACAAAGUAAUGUAAAACA | GUACCACACAAAGUAAUGUAAAACAUUAAA |
| sFLT1-i13 | NM_001159920.1 | 2332 | AGUAAUGUAAAACAUUAAAG | CACAAAGUAAUGUAAAACAUUAAAGGACUC |
| sFLT1-i13 | NM_001159920.1 | 2333 | GUAAUGUAAAACAUUAAAGG | ACAAAGUAAUGUAAAACAUUAAAGGACUCA |
| sFLT1-i13 | NM_001159920.1 | 2339 | UAAAACAUUAAAGGACUCAU | UAAUGUAAAACAUUAAAGGACUCAUUAAAA |
| sFLT1-i13 | NM_001159920.1 | 2343 | ACAUUAAAGGACUCAUUAAA | GUAAAACAUUAAAGGACUCAUUAAAAAGUA |
| sFLT1-i13 | NM_001159920.1 | 2351 | GGACUCAUUAAAAGUAACA | UUAAAGGACUCAUUAAAAAGUAACAGUUGU |
| sFLT1-i13 | NM_001159920.1 | 2353 | ACUCAUUAAAAGUAACAGU | AAAGGACUCAUUAAAAAGUAACAGUUGUCU |
| sFLT1-i13 | NM_001159920.1 | 2362 | AAAGUAACAGUUGUCUCAUA | AUUAAAAGUAACAGUUGUCUCAUAUCAUC |
| sFLT1-i15a | NM_001160030.1 | 2471 | CAUCAUCAUCAUCAUAGCUA | GUCAUCAUCAUCAUCAUAGCUAUCAUC |
| sFLT1-i15a | NM_001160030.1 | 2474 | CAUCAUCAUCAUAGCUAUCA | AUCAUCAUCAUCAUCAUAGCUAUCAUCAUU |
| sFLT1-i15a | NM_001160030.1 | 2477 | CAUCAUCAUAGCUAUCAUCA | AUCAUCAUCAUCAUAGCUAUCAUCAUUAUC |
| sFLT1-i15a | NM_001160030.1 | 2508 | AUCAUCAUCAUCAUAGC | UCAUCAUCAUCAUCAUCAUAGCUACCA |
| sFLT1-i15a | NM_001160030.1 | 2510 | CAUCAUCAUCAUCAUAGCUA | AUCAUCAUCAUCAUCAUAGCUACCAUU |
| sFLT1-i15a | NM_001160030.1 | 2513 | CAUCAUCAUCAUAGCUACCA | AUCAUCAUCAUCAUAGCUACCAUUUAU |
| sFLT1-i15a | NM_001160030.1 | 2518 | UCAUCAUAGCUACCAUUUAU | CAUCAUCAUAGCUACCAUUUAUUGAAA |
| sFLT1-i15a | NM_001160030.1 | 2519 | CAUCAUAGCUACCAUUUAUU | AUCAUCAUAGCUACCAUUUAUUGAAAA |
| sFLT1-i15a | NM_001160030.1 | 2525 | AGCUACCAUUUAUUGAAAAC | AUCAUAGCUACCAUUUAUUGAAAACUAUUA |
| sFLT1-i15a | NM_001160030.1 | 2528 | UACCAUUUAUUGAAAACUAU | AUAGCUACCAUUUAUUGAAAACUAUUAUGU |
| sFLT1-i15a | NM_001160030.1 | 2556 | AACUUCAAAGAACUUAUCCU | GUGUCAACUUCAAAGAACUUAUCCUUUAGU |
| sFLT1-i15a | NM_001160030.1 | 2561 | CAAAGAACUUAUCCUUUAGU | AACUUCAAAGAACUUAUCCUUUAGUUGGAG |
| sFLT1-i15a | NM_001160030.1 | 2572 | UCCUUUAGUUGGAGAGCCAA | ACUUAUCCUUUAGUUGGAGAGCCAAGACAA |
| sFLT1-i15a | NM_001160030.1 | 2574 | CUUUAGUUGGAGAGCCAAGA | UUAUCCUUUAGUUGGAGAGCCAAGACAAUC |
| sFLT1-i15a | NM_001160030.1 | 2576 | UUAGUUGGAGAGCCAAGACA | AUCCUUUAGUUGGAGAGCCAAGACAAUCAU |
| sFLT1-i15a | NM_001160030.1 | 2577 | UAGUUGGAGAGCCAAGACAA | UCCUUUAGUUGGAGAGCCAAGACAAUCAUA |
| sFLT1-i15a | NM_001160030.1 | 2580 | UUGGAGAGCCAAGACAAUCA | UUUAGUUGGAGAGCCAAGACAAUCAUAACA |
| sFLT1-i15a | NM_001160030.1 | 2582 | GGAGAGCCAAGACAAUCAUA | UAGUUGGAGAGCCAAGACAAUCAUAACAUU |
| sFLT1-i15a | NM_001160030.1 | 2585 | GAGCCAAGACAAUCAUAACA | UUGGAGAGCCAAGACAAUCAUAACAAUAAC |
| sFLT1-i15a | NM_001160030.1 | 2588 | CCAAGACAAUCAUAACAAUA | GAGAGCCAAGACAAUCAUAACAAUAACAAA |
| sFLT1-i15a | NM_001160030.1 | 2590 | AAGACAAUCAUAACAAUAAC | GAGCCAAGACAAUCAUAACAAUAACAAAUG |

Table 1 discloses "AUCGAGGUCCGCG" as SEQ ID NO: 16, "Targeting Region (20 mer)" sequences as SEQ ID NOS 16-63 and "Targeting Region (30 mer)" sequences as SEQ ID NOS 64-110, all respectively, in order of appearance.

Various aspects of the invention are described in further detail in the following subsections.

I. siRNA Design

In some embodiments, siRNAs are designed as follows. First, a portion of the target gene (e.g., the fill gene), e.g., one or more of the target sequences set forth at FIG. 6, is selected, e.g., one or any combination of sFLT1-i13-2283, sFlt1-i15a-2519, sFLT1-i13-2318, sFlt1-i15a-2585 from an intronic region of a target gene. Cleavage of mRNA at these sites should eliminate translation of corresponding soluble protein. Sense strands were designed based on the target sequence. (See FIG. 13.) Preferably, the portion (and corresponding sense strand) includes about 30 to 35 nucleotides, e.g., 30, 31, 32, 33, 34 or 35 nucleotides. More preferably, the portion (and corresponding sense strand) includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to elicit an interferon or PKR response in certain mammalian cells which may be undesirable. Preferably, the RNAi agents of the invention do not elicit a PKR response (i.e., are of a sufficiently short length). However, longer RNAi agents may be useful, for example, in cell types incapable of generating a PRK response or in situations where the PKR response has been down-regulated or dampened by alternative means.

The sense strand sequence is designed such that the target sequence is essentially in the middle of the strand. Moving the target sequence to an off-center position may, in some instances, reduce efficiency of cleavage by the siRNA. Such compositions, i.e., less efficient compositions, may be desirable for use if off-silencing of the wild-type mRNA is detected.

The antisense strand is routinely the same length as the sense strand and includes complementary nucleotides. In one embodiment, the strands are fully complementary, i.e., the strands are blunt-ended when aligned or annealed. In another embodiment, the strands comprise align or anneal such that 1-, 2- or 3-nucleotide overhangs are generated, i.e., the 3' end of the sense strand extends 1, 2 or 3 nucleotides further than the 5' end of the antisense strand and/or the 3' end of the antisense strand extends 1, 2 or 3 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the sFlt1 target sequences set forth at FIG. 6 is described in detail below. siRNAs can be designed according to the above exemplary teachings for any other target sequences found in the flt1 gene. Moreover, the technology is applicable to targeting any other target sequences, e.g., non-disease causing target sequences.

To validate the effectiveness by which siRNAs destroy mRNAs (e.g., sFLT1 mRNA), the siRNA can be incubated with cDNA (e.g., Flt1 cDNA) in a *Drosophila*-based in vitro mRNA expression system. Radiolabeled with $^{32}$P, newly synthesized mRNAs (e.g., Flt1mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sites of siRNA-mRNA complementation are selected which result in optimal mRNA specificity and maximal mRNA cleavage.

II. RNAi Agents

The present invention includes siRNA molecules designed, for example, as described above. The siRNA molecules of the invention can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of PCR_strategy1.pdf).

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (i.e., flt1 genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002), supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when cotransfected into the cells with a vector expressing T7 RNA polymerase (Jacque et al., 2002, supra). A single construct may contain multiple sequences coding for siRNAs, such as multiple regions of the gene encoding sFlt1, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the invention include both unmodified siRNAs and modified siRNAs as known in the art, such as crosslinked siRNA derivatives or derivatives having non nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

III. Anti-sFlt1 RNA Silencing Agents

The present invention features anti-sFlt1 RNA silencing agents (e.g., siRNA and shRNAs), methods of making said RNA silencing agents, and methods (e.g., research and/or therapeutic methods) for using said improved RNA silencing agents (or portions thereof) for RNA silencing of one or more sFLT-1 proteins. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi).

a) Design of Anti-sFlt1 siRNA Molecules

An siRNA molecule of the invention is a duplex consisting of a sense strand and complementary antisense strand, the antisense strand having sufficient complementary to an sFlt1 mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, siRNAs can be designed by using any method known in the art, for instance, by using the following protocol:

1. The siRNA should be specific for a target sequence, e.g., a target sequence set forth in FIG. 6 or 13. In one embodiment, a target sequence is found in a soluble Flt1 mRNA, but not in the full-length Flt mRNA. In another embodiment, a target sequence is found in both a soluble Flt1 mRNA and the full-length Flt mRNA. In another embodiment, a target sequence is found in the full-length Flt mRNA. The first strand should be complementary to the target sequence, and the other strand is substantially complementary to the first strand. (See FIG. 6 for exemplary sense and antisense strands.) In one embodiment, the target sequence is encoded in an intronic region of one or more soluble Flt mRNA sequences. Exemplary target sequences correspond to one or more intronic regions of a target gene. Cleavage of mRNA at these sites should eliminate translation of corresponding soluble protein but not of the full-length protein. Target sequences from other regions of the flt gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. Preferably the RNA silencing agents of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a soluble flt1 and a full-length flt1 allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., sFlt1 mRNA corresponding to soluble FLT1), the siRNA may be incubated with target cDNA (e.g., flt1 cDNA) in a *Drosophila*-based in vitro mRNA expression system. Radiolabeled with $^{32}$P, newly synthesized target mRNAs (e.g., sFlt1 mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-sflt1 siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

In certain embodiments, the siRNA comprises a sense strand comprising a sequence set forth at FIG. 6, and an antisense strand comprising a sequence set forth at FIG. 6.

Sites of siRNA-mRNA complementation are selected which result in optimal mRNA specificity and maximal mRNA cleavage.

b) siRNA-Like Molecules siRNA-like molecules of the invention have a sequence (i.e., have a strand having a sequence) that is "sufficiently complementary" to a target sequence of a sflt1 mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5 or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5 or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of an sFlt1 target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant invention, one portion of the duplex stem is a nucleic acid sequence that is complementary (or antisense) to the sFlt1 target sequence. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., sflt1 mRNA), for example, from a region 100 to 200 or 300 nucleotides upstream or downstream of the start of translation. In general, the sequence can be selected from any portion of the target RNA (e.g., mRNA) including an intronic region, the 5' UTR (untranslated region), coding sequence, or 3' UTR, provided said portion is distant from the site of the gain-of-function mutation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans, zebrafish, Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with an miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offer several advantages over existing techniques to repress the expression of a particular gene. First, the methods described herein allow an endogenous molecule (often present in abundance), an miRNA, to mediate RNA silencing. Accordingly, the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In preferred embodiments, the tethers have the formula T-L-μ, wherein T is an mRNA targeting moiety, L is a linking moiety, and μ is an miRNA recruiting moiety. Any one or more moiety may be double stranded. Preferably, however, each moiety is single stranded.

Moieties within the tethers can be arranged or linked (in the 5' to 3' direction) as depicted in the formula T-L-μ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: μ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the invention, the miRNA may be any miRNA capable of repressing the target mRNA (e.g., one or more sflt1 mRNAs). Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (i.e., sflt1 gene expression) can be modulated using oligonucleotide-based compounds comprising two or more single stranded antisense oligonucleotides that are linked through their 5'-ends that allow the presence of two or more accessible 3'-ends to effectively inhibit or decrease sflt1 gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the invention, therefore, comprise two or more oligonucleotides linked to a nucleotide or a non-nucleotide linker. Such oligonucleotides according to the invention are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidate or H-phosphonate chemistry which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

IV. Modified Anti-sFlt1 RNA Silencing Agents

In certain aspects of the invention, an RNA silencing agent (or any portion thereof) of the invention as described supra may be modified such that the activity of the agent is further improved. For example, the RNA silencing agents described in herein may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

In certain embodiments, siRNA compounds are provided having one or any combination of the following properties: (1) fully chemically-stabilized (i.e., no unmodified 2'-OH residues); (2) asymmetry; (3) 11-16 base pair duplexes; (4) alternating pattern of chemically-modified nucleotides (e.g., 2'-fluoro and 2'-methoxy modifications); and (5) single-stranded, fully phosphorothioated tails of 5-8 bases. The number of phosphorothioate modifications is critical. This number is varied from 6 to 17 total in different embodiments.

In certain embodiments, the siRNA compounds described herein can be conjugated to a variety of targeting agents, including, but not limited to, cholesterol, DHA, phenyltropanes, cortisol, vitamin A, vitamin D, GalNac, and gangliozides. The cholesterol-modified version showed 5-10 fold improvement in efficacy in vitro versus previously used chemical stabilization patterns (e.g., wherein all purine but not purimidines are modified) in wide range of cell types (e.g., HeLa, neurons, hepatocytes, trophoblasts).

Certain compounds of the invention having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

In liver hsiRNA-ASP delivery specifically to endothelial and kupper cells, but not hepatocytes, making this chemical modification pattern complimentary rather than competitive technology to GalNac conjugates.

The compounds of the invention can be described in the following aspects and embodiments.

In a first aspect, provided herein is oligonucleotide of at least 16 contiguous nucleotides, said oligonucleotide having a 5' end, a 3' end and complementarity to a target, wherein: (1) the oligonucleotide comprises alternating 2'-methoxy-ribonucleotides and 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In a second aspect, provided herein is a double-stranded, chemically-modified nucleic acid, comprising a first oligonucleotide and a second oligonucleotide, wherein: (1) the first oligonucleotide is an oligonucleotide described herein (e.g., comprising SEQ ID Nos:1, 2, 3 or 4); (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In a third aspect, provided herein is oligonucleotide having the structure:

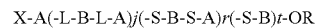

X-A(-L-B-L-A)*j*(-S-B-S-A)*r*(-S-B)*t*-OR wherein: X is a 5' phosphate group; A, for each occurrence, independently is a 2'-methoxy-ribonucleotide; B, for each occurrence, independently is a 2'-fluoro-ribonucleotide; L, for each occurrence independently is a phosphodiester or phosphorothioate linker; S is a phosphorothioate linker; and R is selected from hydrogen and a capping group (e.g., an acyl such as acetyl); j is 4, 5, 6 or 7; r is 2 or 3; and t is 0 or 1.

In a fourth aspect, provided herein is a double-stranded, chemically-modified nucleic acid comprising a first oligonucleotide and a second oligonucleotide, wherein: (1) the first oligonucleotide is selected from the oligonucleotides of the third aspect; (2) a portion of the first oligonucleotide is complementary to a portion of the second oligonucleotide; and (3) the second oligonucleotide has the structure:

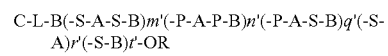

C-L-B(-S-A-S-B)*m'*(-P-A-P-B)*n'*(-P-A-S-B)*q'*(-S-A)*r'*(-S-B)*t'*-OR wherein: C is a hydrophobic molecule; A, for each occurrence, independently is a 2'-methoxy-ribonucleotide; B, for each occurrence, independently is a 2'-fluoro-ribonucleotide; L is a linker comprising one or more moiety selected from the group consisting of: 0-4 repeat units of ethyleneglycol, a phosphodiester, and a phosphorothioate; S is a phosphorothioate linker; P is a phosphodiester linker; R is selected from hydrogen and a capping group (e.g., an acyl such as acetyl); m' is 0 or 1; n' is 4, 5 or 6; q' is 0 or 1; r' is 0 or 1; and t' is 0 or 1.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention, the RNA silencing agents may contain at least one modified nucleotide analogue. The one or more nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-aminoguanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, and/or a 2' F moiety on a U in a sense or antisense strand, but especially on a sense strand, and/or a 2' OMe moiety in a 3' overhang, e.g., at the 3' terminus (3' terminus means at the 3' atom of the molecule or at the most 3' moiety, e.g., the most 3' P or 2' position, as indicated by the context) and/or a 2' F moiety; (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' OMe moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus 4) Modifications to Enhance Cellular Uptake In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxy-propyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a placental cell, a kidney cell and/or a liver cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue. For example, the target tissue can be the placenta, the kidneys or the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the placenta, liver and/or kidney and therefore less likely to be cleared from the body. A lipid or lipid-based ligand that binds to HSA less strongly can be used to target the conjugate to the placenta, liver and/or kidney. Other moieties that target to placental, liver and/or kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45 or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

6) Combinations

In one aspect, provided herein is a combination comprising:

an oligonucleotide of Formula (I):

$(5'-3')\ R^1R^3X^1[(L^2)(X^1)]_{17}R^3X^1$ (I);

an oligonucleotide of Formula (II):

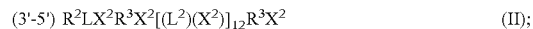
$(3'-5')\ R^2LX^2R^3X^2[(L^2)(X^2)]_{12}R^3X^2$ (II);

an oligonucleotide of Formula (III):

$(5'-3')\ R^1R^3X^3[(L^2)(X^3)]_{17}R^3X^3$ (III); and an oligonucleotide of Formula (IV):

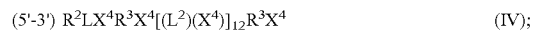
$(5'-3')\ R^2LX^4R^3X^4[(L^2)(X^4)]_{12}R^3X^4$ (IV);

or a pharmaceutically acceptable salt thereof, wherein the oligonucleotide sequence of Formula (I) is different than the oligonucleotide sequence of Formula (III);

the oligonucleotide sequence of Formula (II) is different than the oligonucleotide sequence of Formula (IV);

$R^1$ is independently selected at each occurrence from the group consisting of

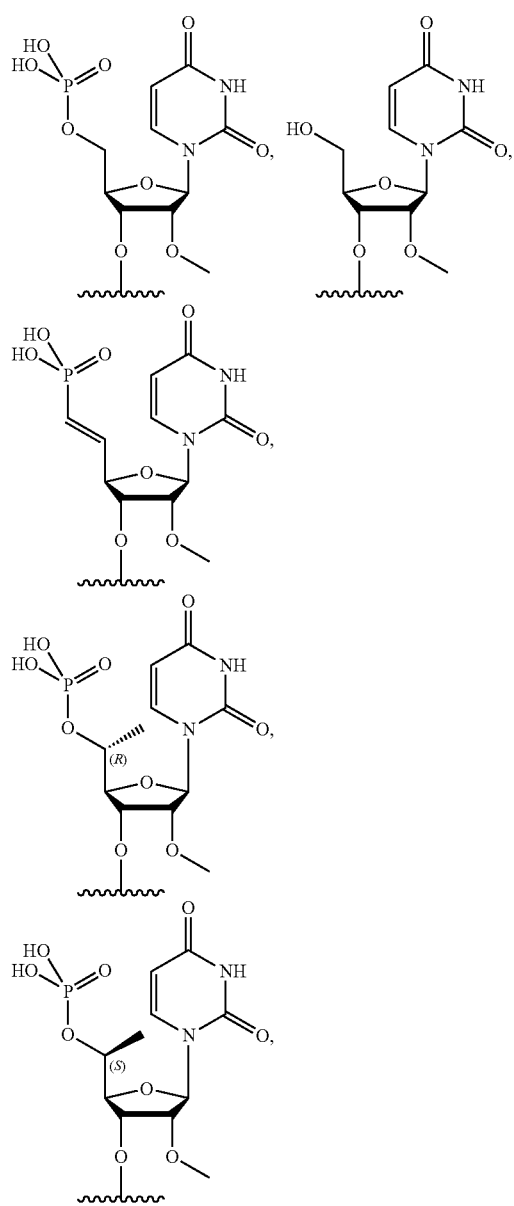
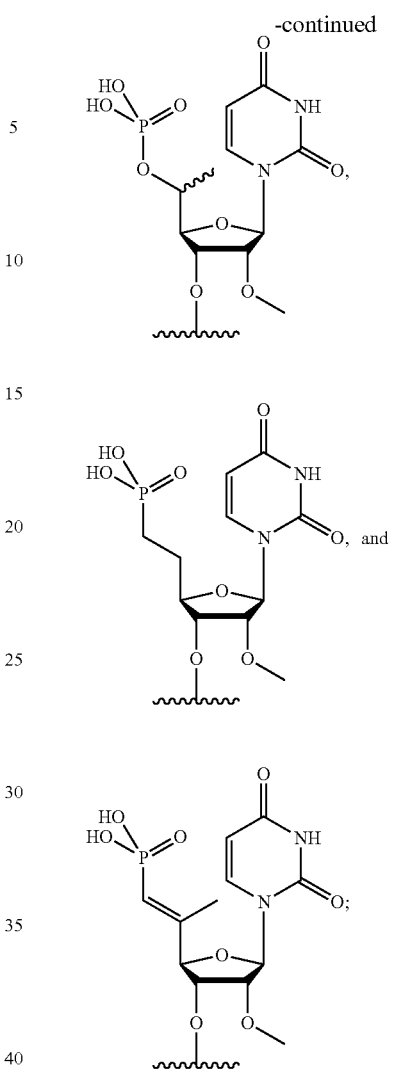
$R^2$ is selected from the group consisting of an alkyl chain (e.g., $C_{1-6}$, $C_{1-10}$, $C_{1-20}$, $C_{1-30}$, or $C_{1-40}$), a vitamin, a ligand, a peptide, a bioactive conjugate (including, but not limited to glycosphingolipids, polyunsaturated fatty acids, secosteroids, steroid hormones, or sterol lipids),
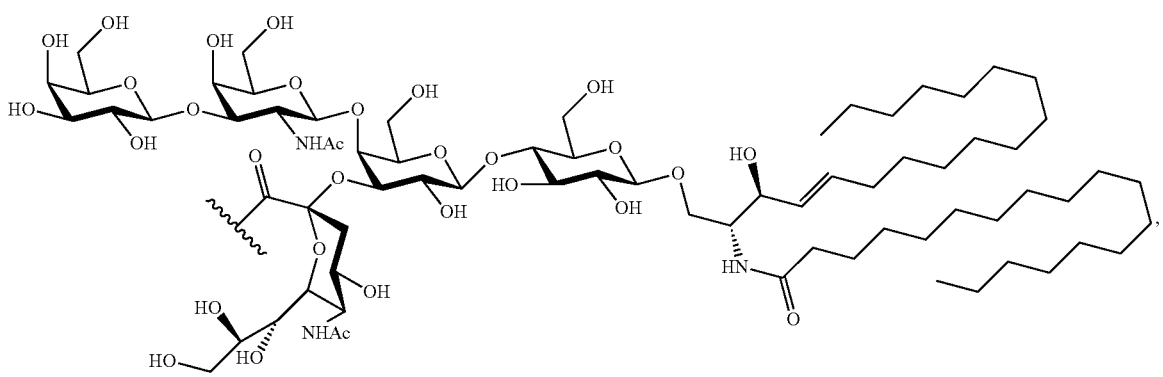

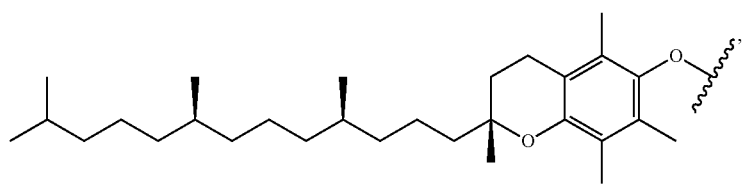
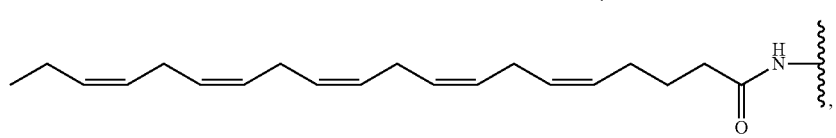
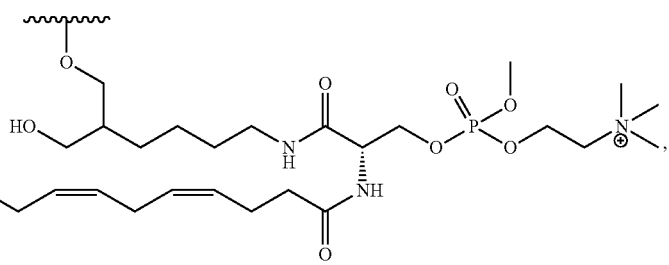
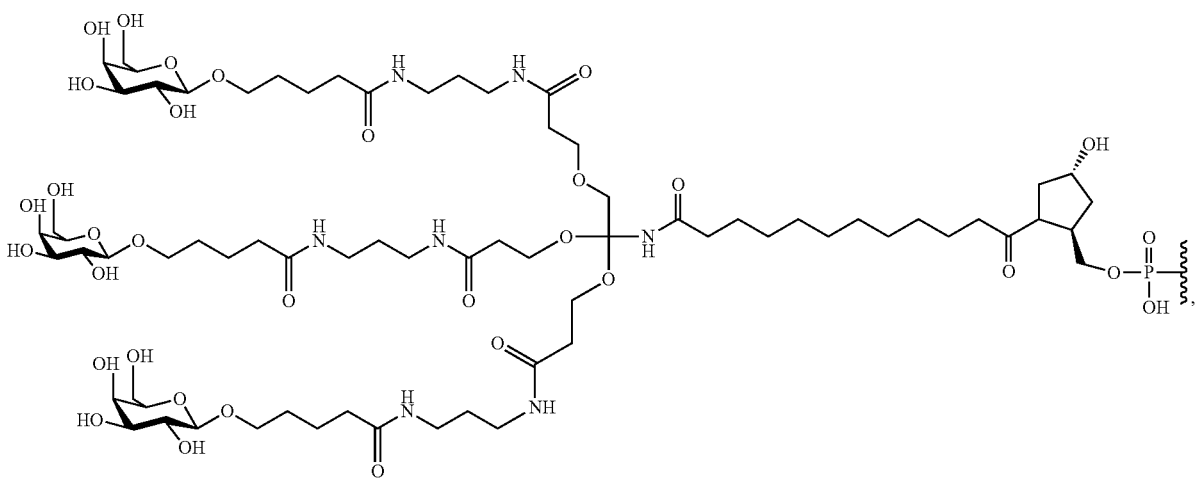
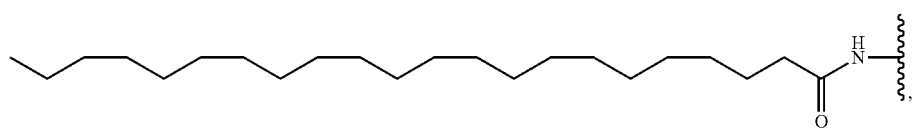
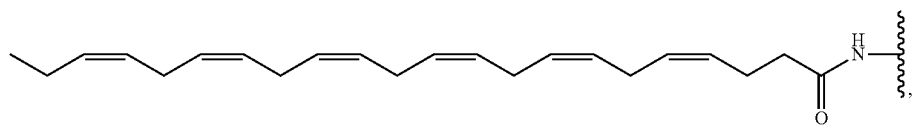

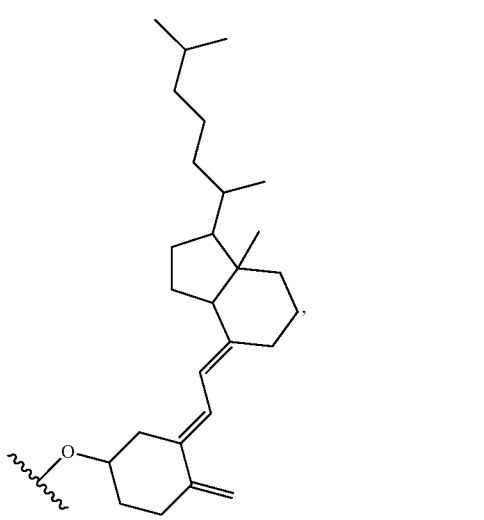

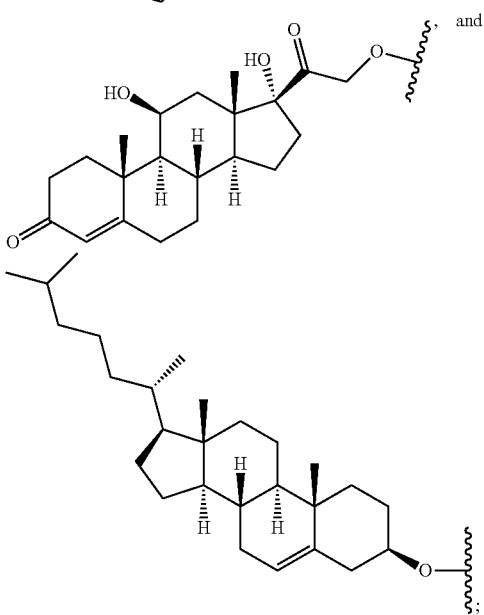

Figure 41:
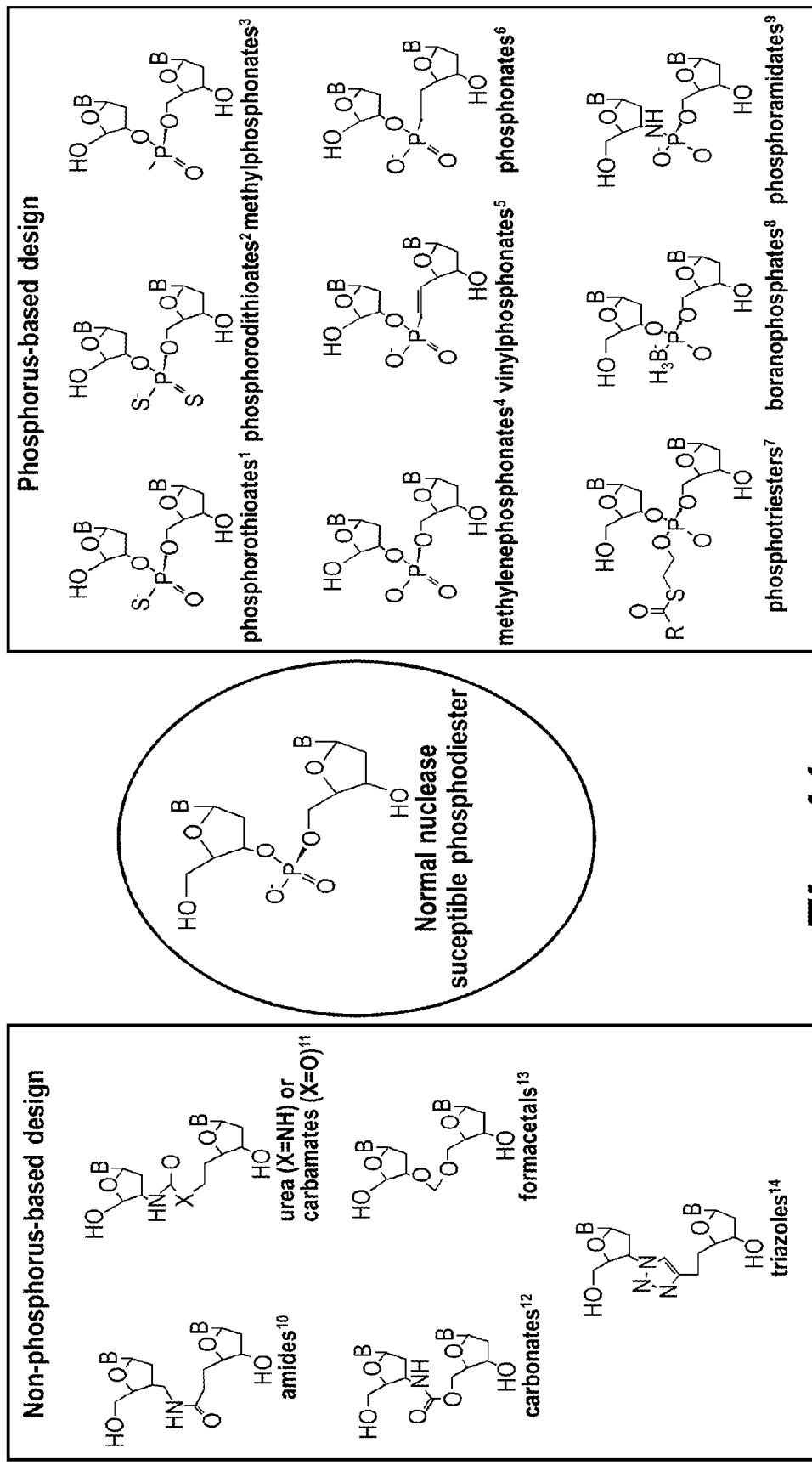
FIG. 41 depicts examples of internucleotide linkages of $R^3$. $R^3$ is an internucleotide bond between the first two nucleotides at the 5' or 3' ends of any given oligonucleotide strand can be stabilized with the moieties depicted in this figure.
Figure 42:
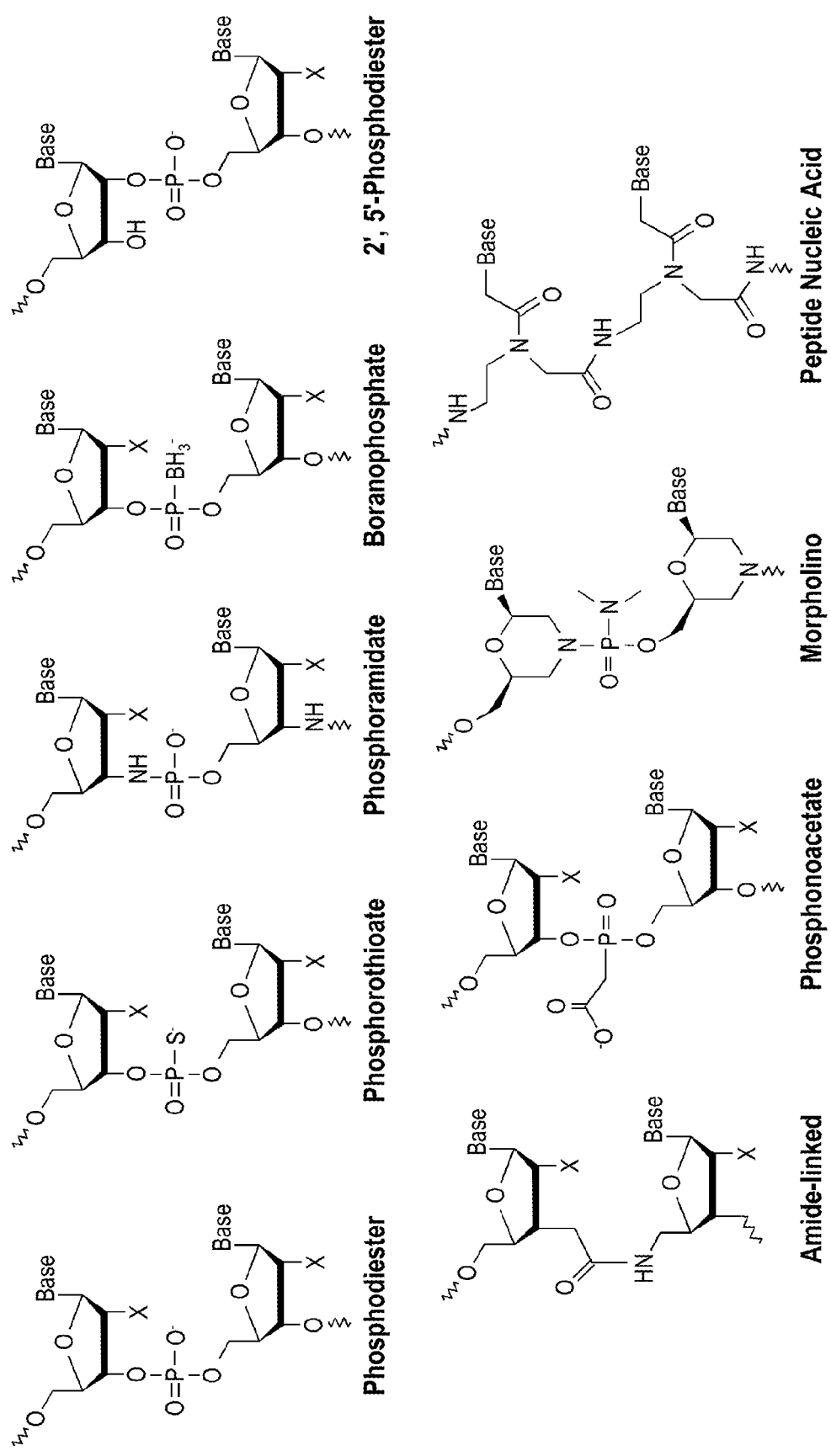
FIG. 42 depicts examples of internucleotide linkages of $L^2$.
Figure 43:
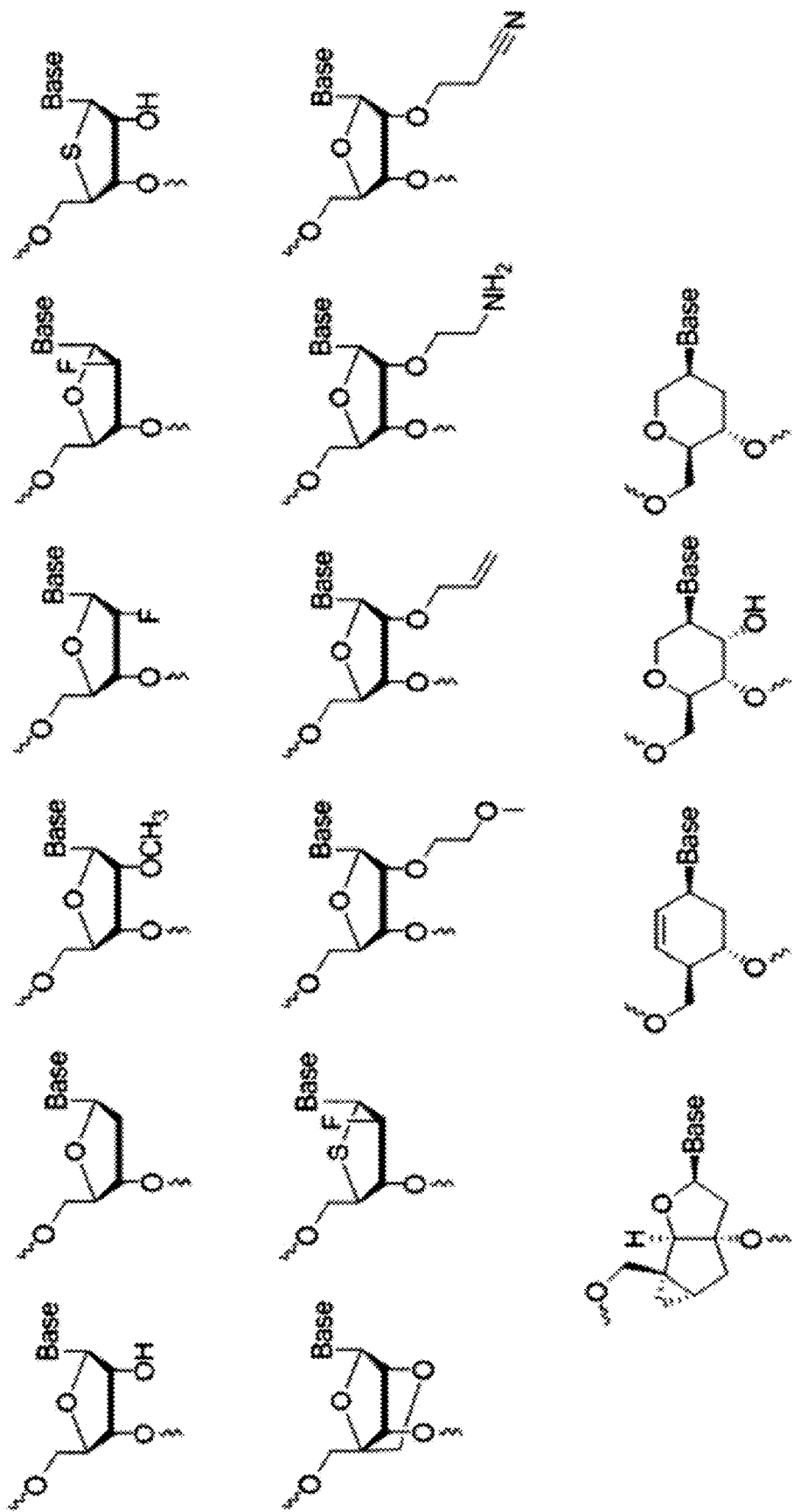
FIG. 43 depicts examples of nucleosides of $X^1$, $X^2$, $X^3$, and $X^4$.

$R^3$ is independently selected at each occurrence from the group consisting of an internucleotide linker as shown in FIG. 41;

L is a linker connecting two moieties, wherein the linker is selected from the group consisting of an ethylene glycol chain, an alkyl chain, a peptide, an RNA, a DNA,

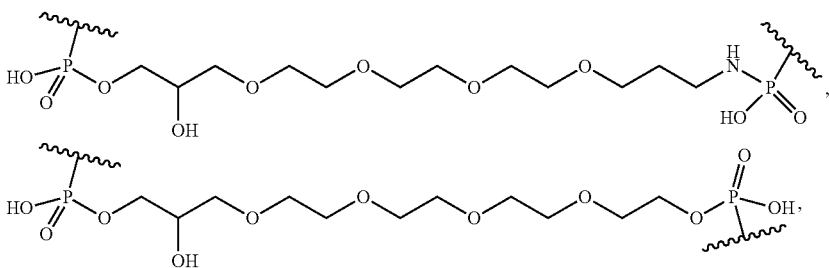

and combinations thereof;

$L^2$ is independently selected at each occurrence from the group consisting of internucleotide linkages as shown in FIG. 42; and $X^1$, $X^2$, $X^3$, and $X^4$ are each independently selected at each occurrence from the group consisting of nucleosides as shown in FIG. 43, wherein the nucleoside base is selected from the group consisting of adenine, guanine, uracil, cytosine, 5-methylcytosine, hypoxanthine, and thymine, wherein the nucleoside base is optionally further modified with one or more additional hydrophobic moieties selected from naphthyl or isobutyl.

In one embodiment, $R^1$ is selected from the group consisting of

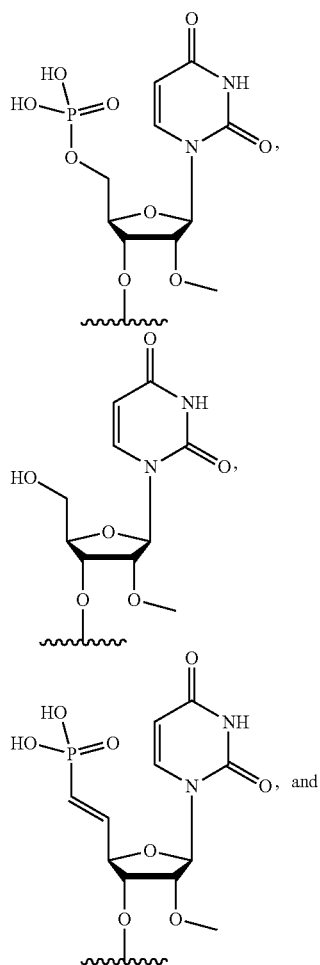
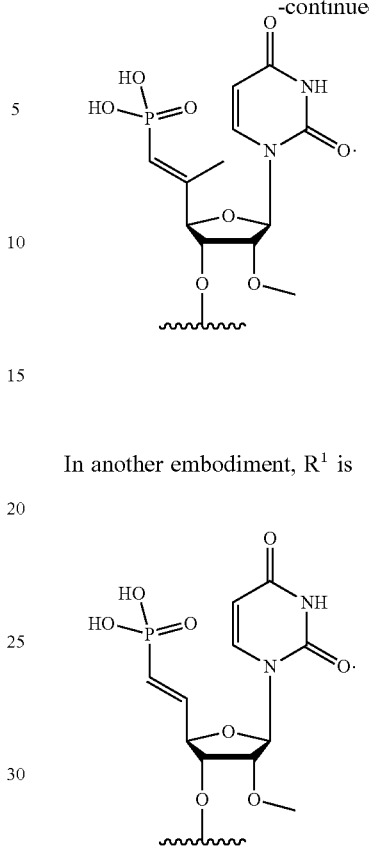
In another embodiment, $R^1$ is
In another embodiment, $R^2$ is selected from the group consisting of
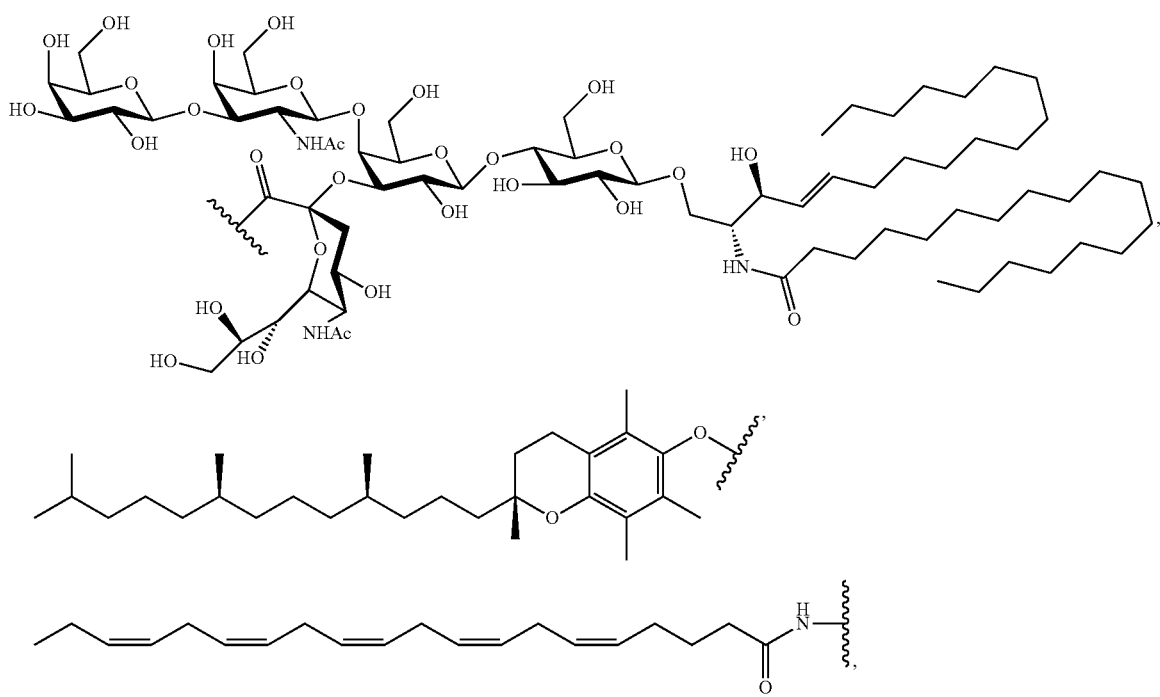

-continued
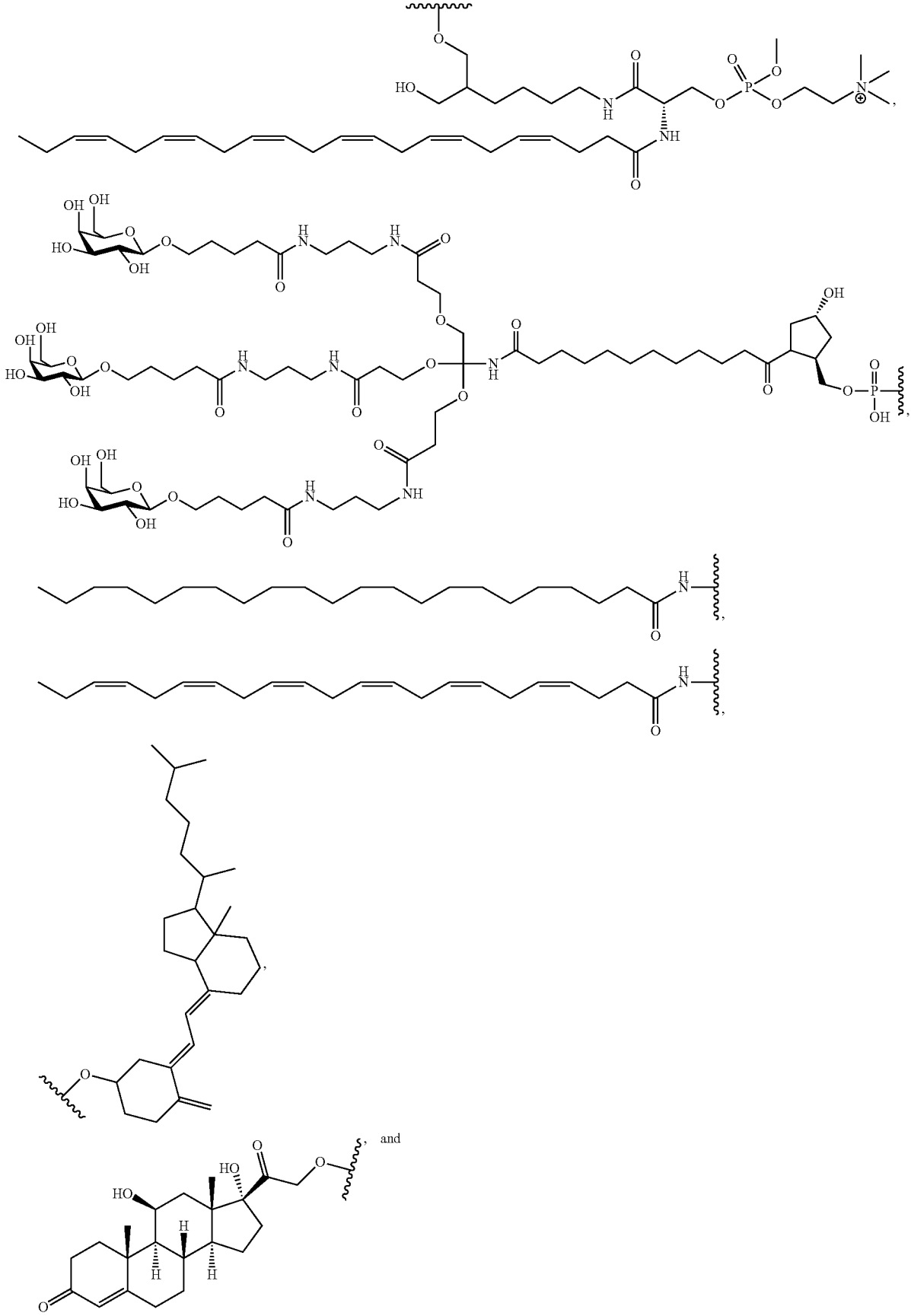

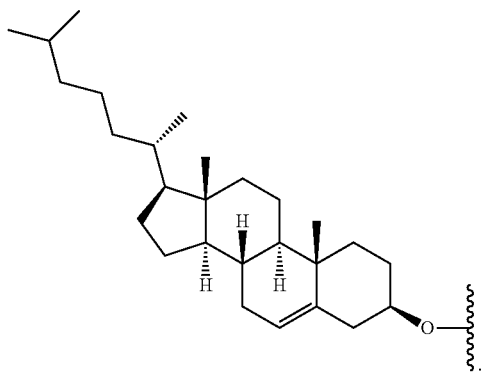

In another embodiment, $R^3$ is an internucleotide linker independently selected at each occurrence from the group consisting of a phosphorothioate, a phosphorodithioate, a methylphosphonate, a methylenephosphonate, a phosphotriester, and a boranophosphate.

In another embodiment, $R^3$ is an internucleotide linker independently selected at each occurrence from the group consisting of a phosphorothioate, a phosphorodithioate, and a boranophosphate.

In another embodiment, $R^3$ is a phosphorothioate.

In another embodiment, L is selected from the group consisting of an ethylene glycol chain, an alkyl chain, and a peptide.

In another embodiment, L is selected from an ethylene glycol chain or a peptide.

In yet another embodiment, L is

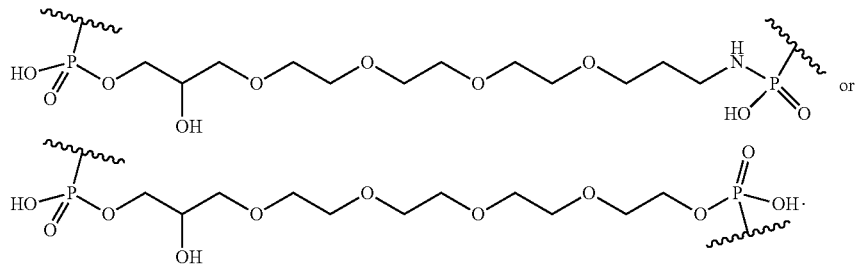

In still another embodiment, L is

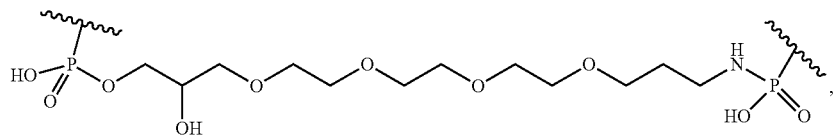 [SMILES: *P(=O)(O)NCCCOCCOCCOCCOCC(O)COP(*)(=O)O]

In another embodiment, L is

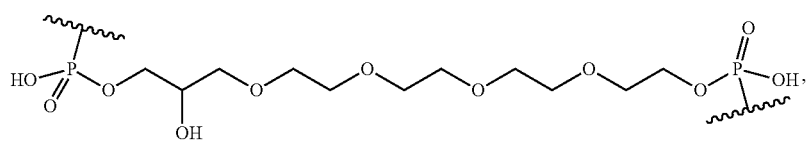 [SMILES: *P(=O)(O)OCCOCCOCCOCCOCC(O)COP(*)(=O)O]

In one embodiment, $L^2$ is independently selected at each occurrence from a phosphodiester and a phosphorothioate.

In one embodiment, $X^1$, $X^2$, $X^3$, and $X^4$ are each independently selected at each occurrence from the group consisting of nucleosides as shown in FIG. 43, wherein the nucleoside base is selected from the group consisting of adenine, guanine, uracil, cytosine, 5-methylcytosine, hypoxanthine, and thymine In one embodiment, $X^1$, $X^2$, $X^3$, and $X^4$ are each independently selected at each occurrence from

Figure 39:
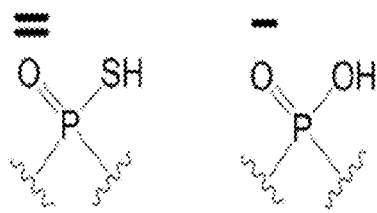
FIG. 39 depicts exemplary sFLT1-2283/2519 dsRNAs conjugated to cholesterol. R1=5'-E-VP-mU, $C_{12}H_{18}N_2O_9P_2S$, Molecular Weight: 428.29, R2=3'-cholesterol, $C_{27}H_{46}O$, Molecular Weight: 386.66, connected by a linker defined as L. $R^1$=A=A-A-U-U-U-G-G-A-G-A-U=C=C=G=A=G=A=G (SEQ ID NO:8), $R^2$-A=U=U-U-A-A-A-C-C-U-C-U-A=G=G (SEQ ID NO:9), R'=A=U-A-A-A-U-G-G-U-A-G-C-U=A=U=G=A=U=G (SEQ ID NO:10), $R^2$-A=U=A-U-U-U-A-C-C-A-U-C-G=A=U (SEQ ID NO:11).

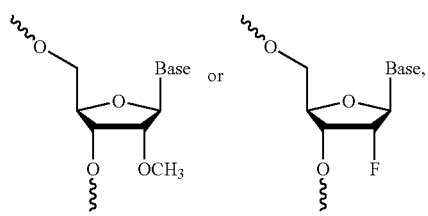

wherein the nucleoside base is selected from the group consisting of adenine, guanine, uracil, cytosine, 5-methylcytosine, hypoxanthine, and thymine In one embodiment, the combination is a combination shown in FIG. 39, or a pharmaceutically acceptable salt thereof.

In one embodiment, the combination is a combination shown in FIG. 39, or a pharmaceutically acceptable salt thereof, wherein
$R^1$ is

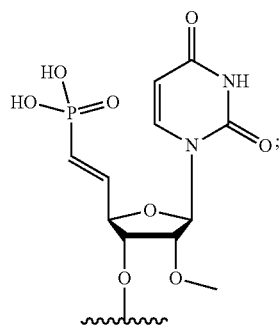

and
$R^2$ is

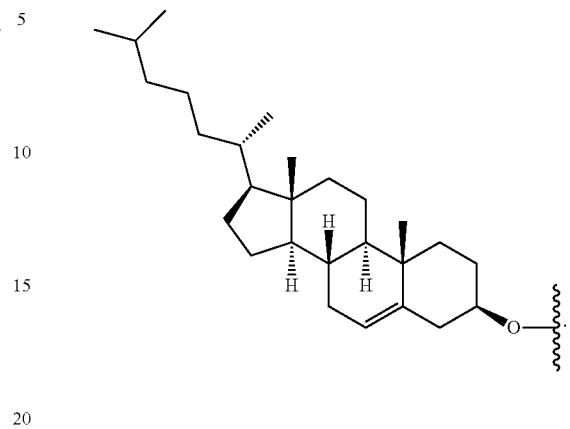

In another embodiment, the combination is a combination shown in FIG. 39, or a pharmaceutically acceptable salt thereof, wherein
$R^1$ is

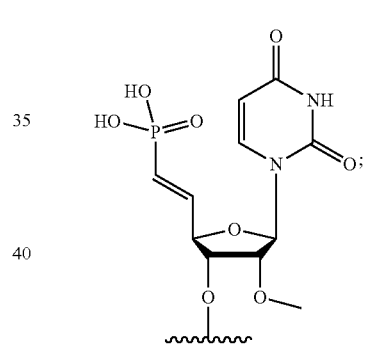

and
$R^2$ is

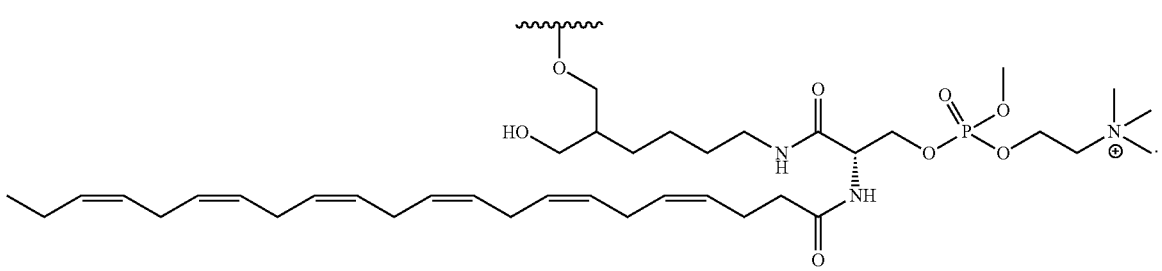

Figure 40:
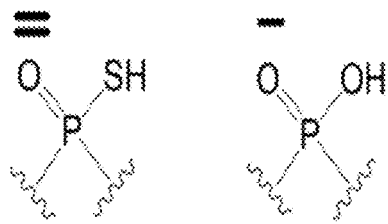
FIG. 40 depicts exemplary sFLT1-2283/2519 dsRNAs conjugated to a phosphatidylcholine derivative of DHA (PC-DHA). $R^1$=5'-E-VP-mU, $C_{12}H_{18}N_2O_9P_2S$, Molecular Weight: 428.29. R2=3'-PC-DHA, $C_{38}H_{66}N_3O_8P+$, Molecular Weight: 723.93, connected by a linker defined as L. $R^1$=A=A-A-U-U-U-G-G-A-G-A-U-C=C=G=A=G=A=G (SEQ ID NO:12), $R^2$-A=U=U-U-A-A-A-C-C-U-C-U-A=G=G (SEQ ID NO:13), $R^1$=A=U-A-A-A-U-G-G-U-A-G-C-U=A=U=G=A=U=G (SEQ ID NO14), $R^2$-A=U=A-U-U-U-A-C-C-A-U-C-G=A=U (SEQ ID NO:15).

In one embodiment, the combination is a combination shown in FIG. 40, or a pharmaceutically acceptable salt thereof.

In one embodiment, the combination is a combination shown in FIG. 40, or a pharmaceutically acceptable salt thereof, wherein
R¹ is

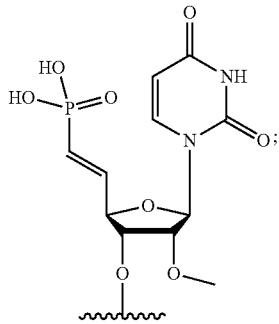

and
R² is

R¹ is

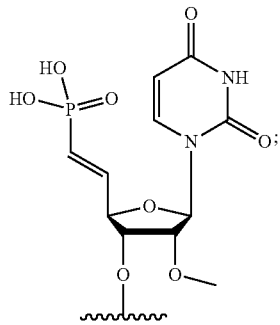

and
R² is

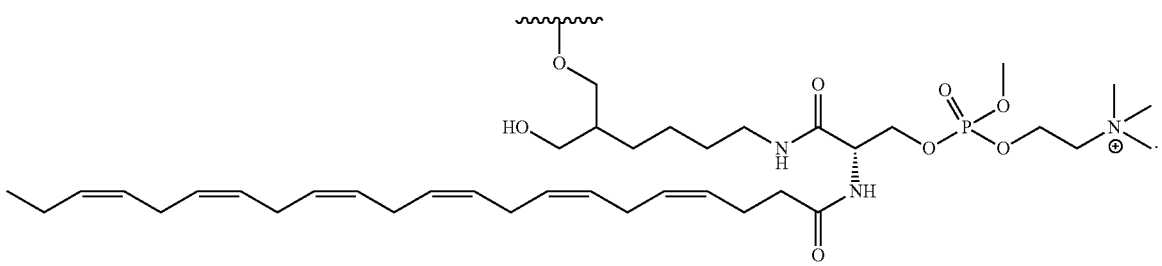

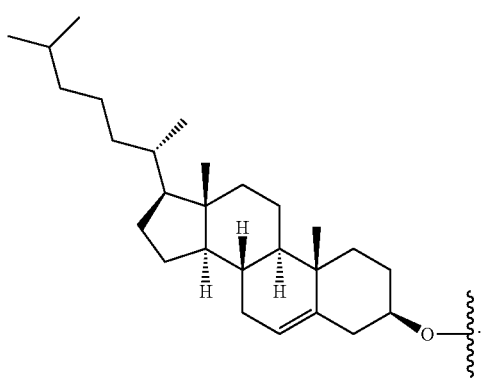

In another embodiment, the combination is a combination shown in FIG. 40, or a pharmaceutically acceptable salt thereof, wherein

V. Methods of Introducing Nucleic Acids, Vectors and Host Cells

RNA silencing agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the invention (e.g., an siRNA targeting an flt1 intronic target sequence) is tested for its ability to specifically degrade mutant mRNA (e.g., sflt1 mRNA and/or the production of sFlt1 protein) in cells, in particular, in placental cells (e.g., labyrinth cells, trophoblasts (e.g., syncytiotrophoblasts and/or cytotrophoblasts), mesenchymal cells, mesenchymal-derived macrophages (Hofbauer cells), fibroblasts, fetal vascular cells (e.g., smooth muscle cells, perivascular cells (pericytes), and endothelial cells)), liver cells and/or kidney cells. Also suitable for cell-based validation assays are other readily transfectable cells, for example, trophoblast cells, HeLa cells or COS cells. Cells are transfected with human wild type or mutant cDNAs (e.g., human wild-type or secreted flt1 cDNA). Standard siRNA, modified siRNA or vectors able to produce siRNA from U-looped mRNA are co-transfected. Selective reduction in target mRNA (e.g., sflt1 mRNA) and/or target protein (e.g., sFlt1 protein) is measured. Reduction of target mRNA or protein can be compared to levels of target mRNA or protein in the absence of an RNAi agent or in the presence of an RNAi agent that does not target sFlt1 mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

6) Recombinant Adeno-Associated Viruses and Vectors

In certain exemplary embodiments, recombinant adeno-associated viruses (rAAVs) and their associated vectors can be used to deliver one or more siRNAs into cells, e.g., placental cells, kidney cells and/or liver cells. AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In particular embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) *Mol. Ther.* 19(8):1440-8. doi: 10.1038/mt.2011.98. Epub 2011 May 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., baboon) or the like. In certain embodiments, a host animal is a non-human host animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the placenta, liver and/or kidneys of a subject. Recombinant AAVs may be delivered directly to the placenta, liver and/or kidney with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the invention may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

VI. Methods of Treatment

The present invention provides for both prophylactic and therapeutic methods of treating a subject at risk of (or susceptible to) a disease or disorder caused, in whole or in part, by secreted Flt1 protein. In one embodiment, the disease or disorder is a liver disease or disorder. In another embodiment, the disease or disorder is a kidney disease or disorder. In one embodiment, the disease or disorder is a placental disease or disorder. In one embodiment, the disease or disorder is a pregnancy-related disease or disorder. In a preferred embodiment, the disease or disorder is a disorder associated with the expression of soluble Flt1 protein and in which amplified expression of the soluble Flt1 protein leads to clinical manifestations of PE, postpartum PE, eclampsia and/or HELLP.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for one or more target sequences within the gene (e.g., SEQ ID NOs:1, 2, 3 or 4 or any combinations thereof), such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the invention can be administered to any patient diagnosed as having or at risk for developing a pregnancy-, liver- and/or kidney-related disorder, such as PE and/or eclampsia. In one embodiment, the patient is diagnosed as having a PE and/or eclampsia, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as two or more symptoms of PE or one or more symptoms of eclampsia. In another embodiment, the patient has not reached an advanced stage of the disease.

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the placenta, liver and/or kidneys) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. The dosage can be an amount effective to treat or prevent a liver-, kidney- or pregnancy-related disease or disorder, e.g., PE, postpartum PE, eclampsia and/or HELLP. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or, preferably, can include a series of treatments. It will also be appreciated that the effective dosage of an RNA silencing agent for treatment may increase or decrease over the course of a particular treatment. Changes in dosage may result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an RNA expressed in a liver, kidney and/or placental cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

VII. Pharmaceutical Compositions and Methods of Administration

The invention pertains to uses of the above-described agents for prophylactic and/or therapeutic treatments as described Infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans Levels in plasma may be measured, for example, by high performance liquid chromatography.

The pharmaceutical compositions can be included in a container, pack or dispenser together with optional instructions for administration.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1 µg to 1000 mg may be administered; in some embodiments, 10, 30, 100 or 1000 µg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), Supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

The route of delivery can be dependent on the disorder of the patient. In certain exemplary embodiments, a subject diagnosed with PE, postpartum PE, eclampsia and/or HELLP can be administered an anti-sFlt1 RNA silencing agent of the invention by IV or SC administration. In addition to an RNA silencing agent of the invention, a patient can be administered a second therapy, e.g., a palliative therapy and/or disease-specific therapy. The secondary therapy can be, for example, symptomatic (e.g., for alleviating symptoms), protective (e.g., for slowing or halting disease progression), or restorative (e.g., for reversing the disease process). For the treatment of PE, postpartum PE, eclampsia and/or HELLP, for example, symptomatic therapies can further include the drugs Atenolol, Hydralazine, Labetalol, magnesium sulfate, Methyldopa, Nicardipine, Nifedipine, sodium nitroprusside and the like.

In general, an RNA silencing agent of the invention can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular administration may include sterile aqueous solutions which may also contain buffers, diluents and other suitable additives. Compositions for intrathecal or intraventricular administration preferably do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA silencing agent of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as Human Serum Albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An RNA silencing agent of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

An RNA silencing agent can be packaged in a viral natural capsid or in a chemically or enzymatically produced artificial capsid or structure derived therefrom.

VIII. Kits

In certain other aspects, the invention provides kits that include a suitable container containing a pharmaceutical formulation of an RNA silencing agent, e.g., a double-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an RNA silencing agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1. Background and Significance of Preeclampsia (PE)

Figure 1B:
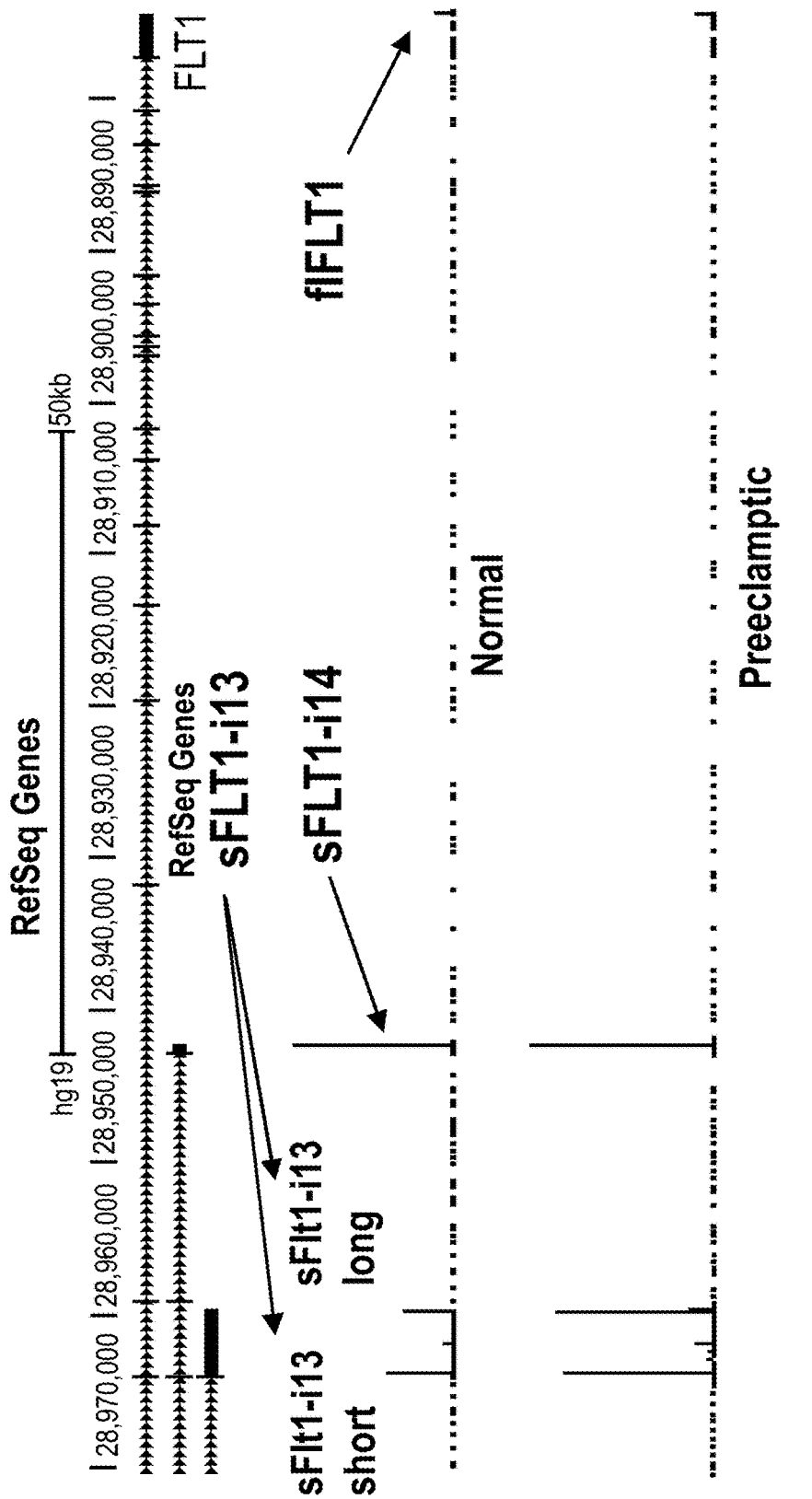

Overwhelming evidence from epidemiological and experimental studies now indicates that PE is caused by elevated levels of "soluble decoy" proteins (soluble FLT1s (sFLT1s)) from the Flt1 gene (VEGFR1) in the mother's blood stream (Young, B. C., Levine, R. J. & Karumanchi, S. A. Pathogenesis of preeclampsia. *Annual review of pathology* 5, 173-192 (2010); Maynard, S. E. et al. Excess placental soluble fms-like tyrosine kinase 1 (sFlt1) may contribute to endothelial dysfunction, hypertension, and proteinuria in preeclampsia. *The Journal of clinical investigation* 111, 649-658 (2003); Levine, R. J. et al. Circulating angiogenic factors and the risk of preeclampsia. *The New England journal of medicine* 350, 672-683 (2004); Heydarian, M. et al. Novel splice variants of sFlt1 are upregulated in preeclampsia. *Placenta* 30, 250-255 (2009)). FLT1 is a receptor tyrosine kinase (RTK) predominantly expressed in the placenta. A general mechanism for RTK modulation is production of truncated, secreted forms of the receptor that act as dominant negative regulators of the overall signaling pathway (FIG. 1A). Ligand sequestration by such soluble decoys inhibits intracellular signaling by the full-length receptor, thereby desensitizing the system to ligand concentration (Vorlova, S. et al. Induction of antagonistic soluble decoy receptor tyrosine kinases by intronic polyA activation. *Molecular cell* 43, 927-939 (2011).). In the case of FLT1, the soluble decoys are expressed from truncated mRNAs generated by polyadenylation within two introns (i13 and i15) upstream of the exons encoding the fl-FLT1 transmembrane (TM) and kinase domains (FIG. 1B).

In mammals, FLT1 is predominantly expressed in the placenta, with human placental Flt1 mRNA levels being 10-100 times higher than those observed in other adult tissues (Cerdeira, A. S. & Karumanchi, S. A. Angiogenic factors in preeclampsia and related disorders. *Cold Spring Harbor perspectives in medicine* 2 (2012)). Whereas the full-length isoform predominates in all tissues in non-pregnant adult humans (Id.), placental expression is dominated by three truncated isoforms, sFlt1-i13 short, sFlt1-i13 long and sFlt1-i15a, all of which encode sFLT1 proteins (FIG. 1B). This same pattern of high Flt1 in placenta and low expression in other non-pregnant adult tissues is observed in rodents. However, because rodents lack the intron 14 polyadenylation site, they only express a single soluble decoy form: sFlt1-i13. In PE, both full-length (fl-Flt1) and truncated Flt1 mRNAs accumulate to higher levels in the placenta than in normal pregnancies, with the truncated isoforms being even more pronounced (FIG. 1B). These changes at the mRNA level likely explain the significant rise in sFLT1 proteins in the maternal bloodstream during PE.

1.1 Applicability of siRNAs for Treatment of PE siRNA-based therapeutics were designed for the treatment of PE. Both preclinical and clinical data support decreasing sFLT1 as a valid therapeutic strategy for prolonging PE pregnancies (Thadhani, R. et al. Pilot study of extracorporeal removal of soluble fms-like tyrosine kinase 1 in preeclampsia. *Circulation* 124, 940-950 (2011)). Further, the unique region specific to each sFLT1 protein is very small, with only a handful of unique amino acids being appended to each C-terminus. This small target size hinders development of conventional drugs (e.g., small molecules and antibodies) targeting only sFLT1s and not fl-FLT1. On the other hand, the target window at the RNA level is much larger, with the i13 and i15 mRNA isoforms having 435 and 567 unique bases, respectively, neither of which are present in fl-Flt1 mRNA. Because RNAi requires a target size of only 19-22 nucleotides, this was determined to be more than sufficient nucleotide space in which to design multiple isoform-selective siRNAs. From a clinical perspective, the possibility that a single dose delivered subcutaneously will be sufficient to prevent runaway sFLT1 expression for several weeks could make treatment simple and affordable.

Novel chemically-modified oligonucleotides known as self-delivering hydrophobically modified siRNAs (hsiRNAs) (FIG. 2A) could provide the most significant advantage for a cost effective therapeutic. While their current cost of chemical synthesis ($200 per gram, with approximately $20 per dose at 1 mg/kg dose levels) is relatively high, the price is expected to decrease dramatically (10-50 fold) with a kg-level scale-up. Further, hsiRNAs can be fully synthesized using solid support chemistry in less than 10 hours. Like other oligonucleotides, dried hsiRNAs are highly stable, can be stored for extensive time (i.e., years) at ambient temperature, and can be brought into solution just prior to injection. Further, hsiRNA half-life in vivo is of sufficient duration that a single intravenous dose is well suited for a two to six week inhibition of sFLt1 production.

The ONTs that neutralize sFlt1 described herein are the first novel preeclampsia therapy based on a mechanistic understanding of the disease, and could be cost-effectively and easily administered throughout the world.

1.2 Pilot Product Target Profile for RNAi-Based Treatment of PE.

The table at FIG. 14 summarizes the current view on acceptable and ideal target product profiles according to preferred embodiments. Special considerations for developing an RNAi-based treatment for PE are discussed below.

1.3 Multiple sFLT1 mRNA Isoforms

Figure 1C:
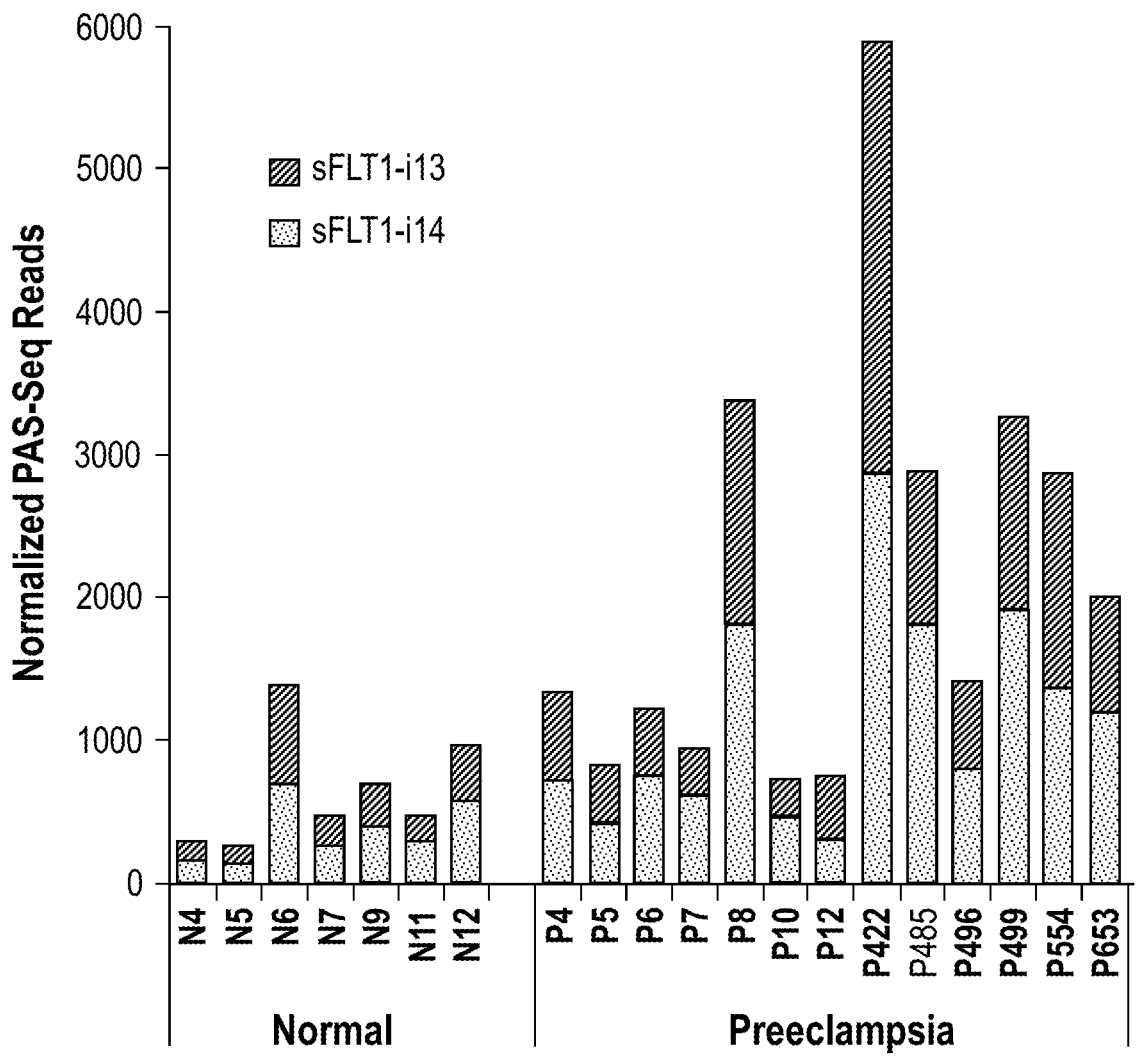

By performing polyadenylation site sequencing (PAS-Seq (Heyer, E. E., Ozadam, H., Ricci, E. P., Cenik, C. & Moore, M. J. An optimized kit-free method for making strand-specific deep sequencing libraries from RNA fragments. Nucleic Acids Res 43, e2 (2015))) on total RNA from multiple normal and PE placentas, it was determined that PE placentas overexpress i13 and i15 sFLT1 variants with, i15 being responsible for 55% of reads and i13 responsible for approximately 45% of reads (FIG. 1C). Without intending to be bound by scientific theory, the intrinsic variability in isoform ratios in different samples indicates that targeting both isoforms might be the best option to cover the majority of PE patients. Thus, the candidate drug product was defined as an equimolar mixture of two hsiRNAs: one targeting both short and long sFLT1-i13 and another targeting sFlt1-i15a (FIG. 3). The FDA has already allowed an siRNA mixture to be defined as a single drug entity when the component siRNAs are identically formulated or chemically modified and their PK/PD profiles are very similar (e.g., multi-siRNA formulations targeting VEGF-A/KSP (Tabernero, J. et al. First-in-humans trial of an RNA interference therapeutic targeting VEGF and KSP in cancer patients with liver involvement. *Cancer discovery* 3, 406-417 (2013)); HBV (Wooddell, C. I. et al. Hepatocyte-targeted RNAi Therapeutics for the Treatment of Chronic Hepatitis B Virus Infection. *Molecular therapy: the journal of the American Society of Gene Therapy* 21, 973-985 (2013)), Arrowhead, etc.). Although using a mixture adds complexity to CMC (Chemistry, Manufacturing and Controls), this is outweighed by the advantage that the mixture will allow treatment of wider PE populations independent of isoform variant overexpression ratios. In certain embodiments, a mixture of two candidates is administrated subcutaneously (SC) in saline as an excipient.

In certain embodiments, the desired level of sFLT1 silencing is only 30-40%, as a higher degree of silencing might be disadvantageous. Preliminary data indicated that a 10-20 mg/kg dose produced>50% silencing in mice, so lesser silencing may simply be achieved with lower dosing. Because the desired product profile is a one-time injection, however, higher doses might be required to extend effect duration. Thus, in certain embodiments, i13 or i15 may be used alone as a clinical candidate.

1.4 Overall Safety and Toxicity Considerations.

ONT-related toxicity can be due to target-specific effects (e.g., too much silencing of sFlt1 isoforms), target-independent effects (i.e., unintentional silencing of non-target mRNAs) or class-related chemistry-specific events. The ability to target the i13 and i15 variants separately dramatically reduces the chances of any major target-related toxicity. Further, the i13 and i15 variants are placenta- and pregnancy-specific, with low or undetectable expression in other adult tissues. Therefore, clinically limiting toxicity will most likely be target-independent. These types of effects include siRNA off-targeting, RNA-based induction of the innate immune response, and general toxicity related to the chosen mode of delivery (e.g., hydrophobic modifications in combination with phosphorothioates). The most advanced bioinformatics was employed up-front upfront to optimize oligonucleotide design to minimize potential off-target events (Uchida, S. et al. An integrated approach for the systematic identification and characterization of heart-enriched genes with unknown functions. *BMC genomics* 10, 100 (2009)). Further, all riboses in the seed sequence (i.e., nucleotides 2-8 of the guide strand) were 2'-F and 2'-O-methyl modified, which modifications by themselves are well-established to minimize off-target events (Jackson, A. L. et al. Position-specific chemical modification of siRNAs reduces "off-target" transcript silencing. *Rna* 12, 1197-1205 (2006)). While evaluation of off-targeting signatures could be established in vitro and in mouse samples using microarray profiling (Jackson, A. L. et al. Position-specific chemical modification of siRNAs reduces "off-target" transcript silencing. *Rna* 12, 1197-1205 (2006); Anderson, E., Boese, Q., Khvorova, A. & Karpilow, J. Identifying siRNA-induced off-targets by microarray analysis. *Methods in molecular biology* 442, 45-63 (2008); Anderson, E. M. et al. Experimental validation of the importance of seed complement frequency to siRNA specificity. *Rna* 14, 853-861 (2008); Birmingham, A. et al. 3' UTR seed matches, but not overall identity, are associated with RNAi off-targets. *Nat Methods* 3, 199-204 (2006); Fedorov, Y. et al. Off-target effects by siRNA can induce toxic phenotype. *Rna* 12, 1188-1196 (2006)), because the overlap between siRNA off-targeting signatures in tissue culture/animal models and humans is generally minimal (Burchard, J. et al. MicroRNA-like off-target transcript regulation by siRNAs is species specific. *Rna* 15, 308-315 (2009)), the value of such studies is questionable. For each sFLT1 isoform, two different sequences were selected for in vivo evaluation (one lead and one back-up) (FIG. 3). If the lead fails due to off-targeting-induced toxicity, the second sequence will be used as a backup (Jackson, A. L. & Linsley, P. S. Recognizing and avoiding siRNA off-target effects for target identification and therapeutic application. *Nature reviews. Drug discovery* 9, 57-67 (2010)). As there is currently no formal guidance specific to siRNA therapeutics, the standard recommendation for NCE (New Chemical Entity) development, including demonstrating safety in two animal models (Hughes M, U., Kurtz A, et al. (ed. C. N. Sittampalam G S, Nelson H, et al., editors) (Eli Lilly & Company and the National Center for Advancing Translational Sciences, Bethesda (Md.); 2012)), will be followed.

The lead compounds were fully chemically-modified (meaning no non-modified riboses remained) using an alternating 2'-O-methyl/2'-F pattern. The combination of 2' OMe/ 2'-F is known to block innate immune response activation (Nair, J. K. et al. Multivalent N-Acetylgalactosamine-Conjugated siRNA Localizes in Hepatocytes and Elicits Robust RNAi-Mediated Gene Silencing. *Journal of the American Chemical Society* (2014)). Lack of interferon pathway activation is confirmed with an in vitro human whole blood cytokine activation assay looking at IL-1β, IL-1RA, IL-6, IL-8, IL-10, IL-12(p70), IP-10, G-CSF, IFN-γ, MCP-1, MIP-1α, MIP-1β, and TNF-α (Bio-Plex Pro Magnetic Cytokine Assay; BioRad Laboratories) and in vivo (after injection in mice) looking at G-CSF, TNF, IL-6, IP-10, KC, and MCP-1 (Cytokine/Chemokine Magnetic Bead Panel; Millipore) (Kumar, V. et al. Shielding of Lipid Nanoparticles for siRNA Delivery: Impact on Physicochemical Properties, Cytokine Induction, and Efficacy. *Molecular therapy. Nucleic acids* 3, e210 (2014)).

Figure 4A:
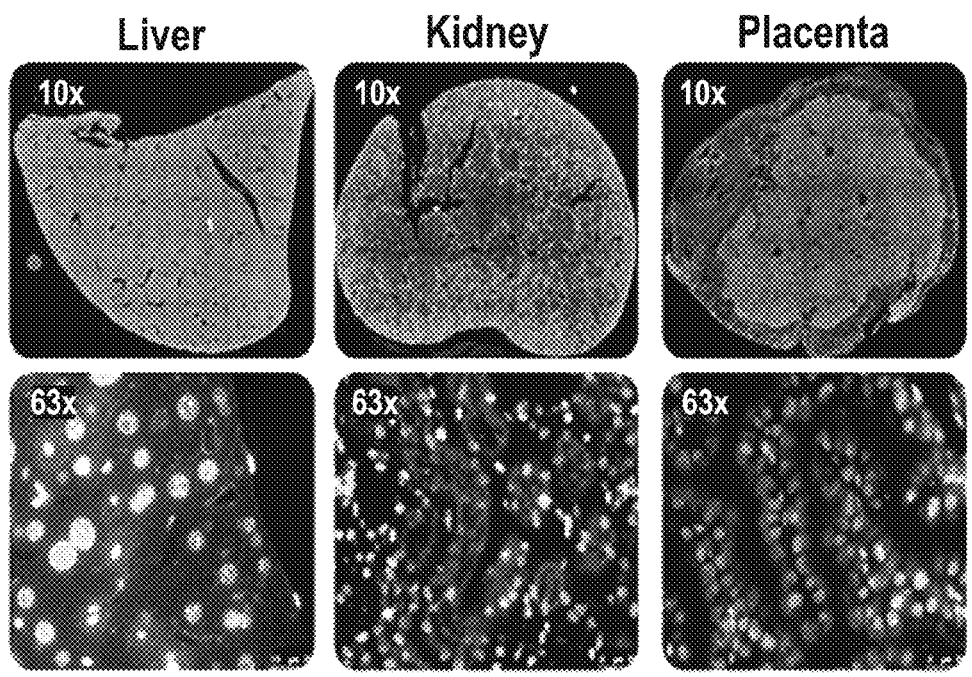
FIGS. 4A-4B depict hsiRNA efficiency of delivery to liver, kidney and placenta. (A) A wild-type pregnant mouse (E15) was injected with Cy3-sFLT1-2283-P2 (red) (10 mg/kg; IV via tail vein). Tissues were fixed after 24 hours, processed and imaged at 10× and 63× on a Leica tiling fluorescent microscope; nuclei stained with DAPI (blue). (B) Shows tissue distribution of sFLT1-2283 (40 mg/kg) 5 days post injection analyzed by PNA assay (n=7, mean+SEM).

Without intending to be bound by scientific theory, based on data from other oligonucleotide chemistries (Wooddell, C. I. et al. Hepatocyte-targeted RNAi Therapeutics for the Treatment of Chronic Hepatitis B Virus Infection. *Molecular therapy: the journal of the American Society of Gene Therapy* 21, 973-985 (2013); Coelho, T. et al. Safety and efficacy of RNAi therapy for transthyretin amyloidosis. *The New England journal of medicine* 369, 819-829 (2013)), the dose limiting toxicity will most likely be related to liver function. Preliminary studies determined that up to 50% of the injected dose of the hsiRNAs accumulated in liver, with delivery being specific to endothelial, kupffer and stellate cells, not hepatocytes (FIG. 4A). With other phosphorothioate-containing oligonucleotides, slight reversible elevation of liver enzymes and mild reversible injection side reactions have been noted as side effects (Frazier, K. S. Antisense Oligonucleotide Therapies: The Promise and the Challenges from a Toxicologic Pathologist's Perspective. *Toxicologic pathology* 43, 78-89 (2015)), but usually this liver enzyme elevation is only observed after long-term continuous dosing with high dose levels. Because this treatment is necessarily short-term (just one or two injections over a period of one to two months) and does not target hepatocytes, liver toxicity may not be an issue. Nonetheless, these concerns will be studied in detail.

Figure 4B:
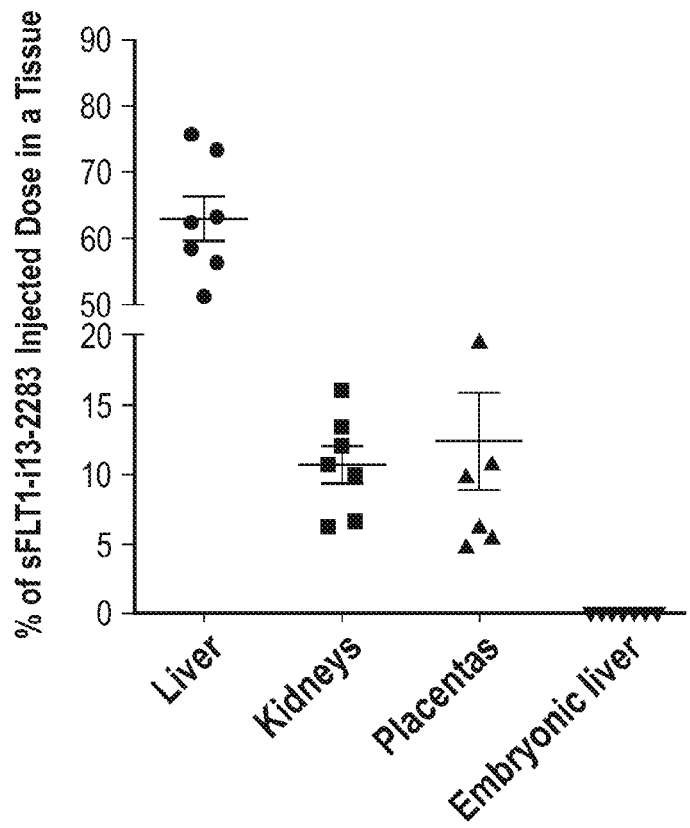

Development of any therapeutic targeting pregnant women has additional safety considerations. A major concern is potential transfer of hsiRNAs to the fetus and any possible toxicity this might cause. In preliminary studies no detectable oligonucleotide transfer to the fetus was observed using fluorescent microscopy (FIG. 6A), or using a highly sensitive PNA (Peptide Nucleic Acid)-based quantitative assay (FIG. 4B). Nor were any effects on fetal growth, number of miscarriages, placental histology or other teratogenic effects observed.

1.5 Assay Systems in Place to Evaluate Lead Compounds.
The assays and models developed so far are as follows.
Fluorescence Microscopy Evaluation of In Situ Tissue Distribution hsiRNA variants with a Cy3 or Cy5.5 (lower auto-fluorescence) dye attached through a non-degradable linker to the 5' end of sense (passenger) strand were synthesized. This compound was biologically stable with no detectable Cy3 cleavage within 24 hours. The fluorescent sense strand hybridized to its complementary guide strand (thus forming a double-stranded hsiRNA) was administrated to animals and oligonucleotide distribution patterns were examined in 4 μm tissue sections also stained with DAPI or/and cell type selective antibodies. Parallel sections could be stained with standard histology markers enabling detailed histology mapping. Because hsiRNAs are already heavily hydrophobically modified, dye addition has little effect on overall hydrophobicity and therefore minimal impact on oligonucleotide distribution. This assay allowed rapid evaluation of tissue and cell-type distribution and was complemented by a PNA-based quantitative assay for direct guide strand detection.

PNA Hybridization for Quantitative Guide Strand Detection in Tissue Lysates

Figure 2:
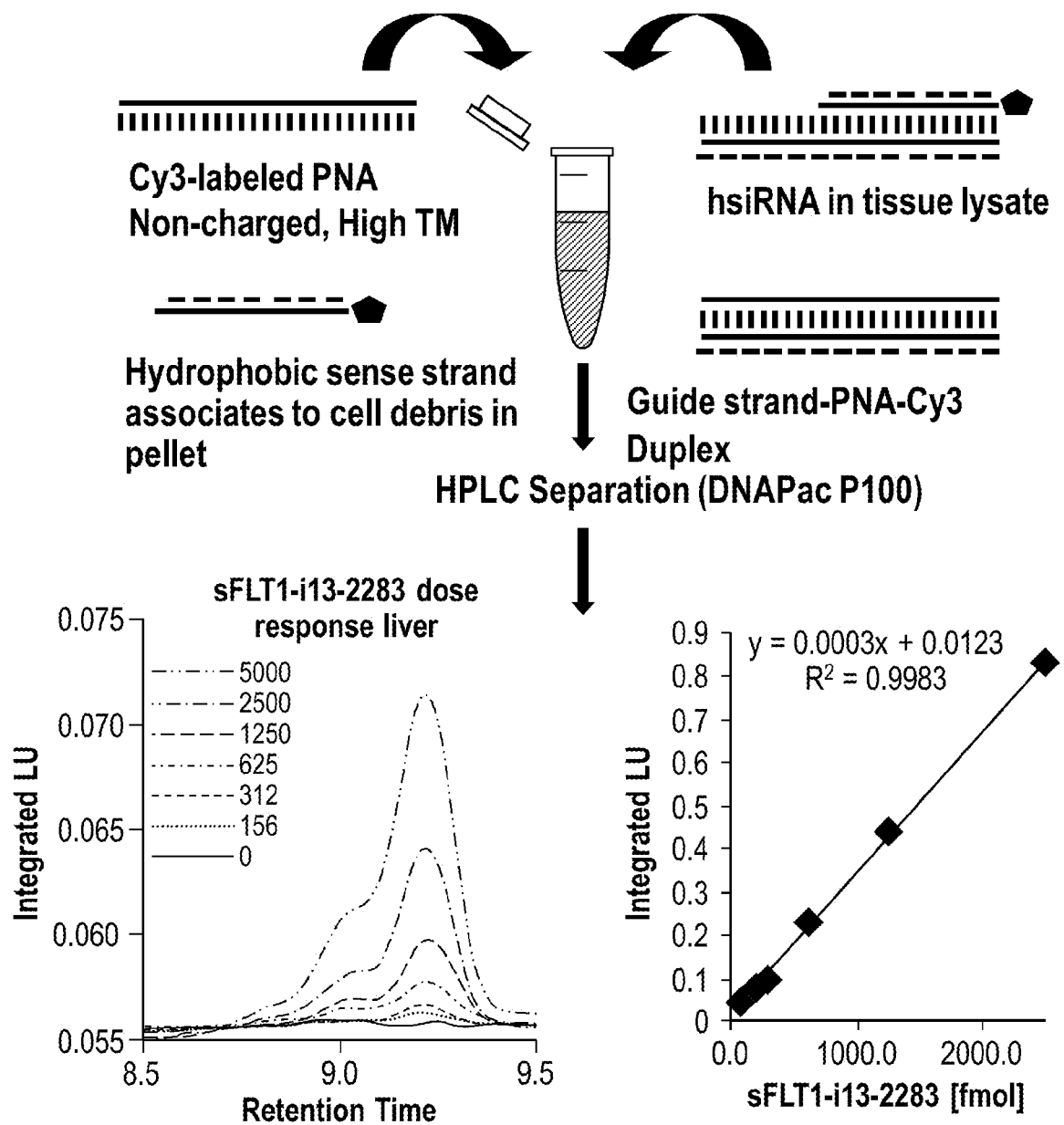
FIG. 2 depicts the results of a Peptide Nucleic Acid (PNA)-based assay for detection of sFLT1-i13-2283 in mouse tissues. Tissues were lysed, debris separated by precipitation, PNA-guide strand duplex purified by High Performance Liquid chromatography (HPLC) (DNAPac P100, 50% water 50% acetonitrile and salt gradient was 0 to 1M NaClO$_4$) a systematic screening of unformulated hsiRNAs targeting sFlt1 mRNA was performed.

To enable direct quantification of intact guide stand in tissues, a novel assay was developed and implemented wherein the guide strand was hybridized to a fully complementary Cy3-labeled PNA (peptide nucleic acid) oligonucleotide, and the corresponding duplex was separated from excess single stranded PNA by HPLC (FIG. 2). Since PNA is non-charged and has extremely tight binding to the guide strand, it out-competes both the hsiRNA sense strand and any endogenous target sequences. Fluorescence detection of the Cy3-PNA:guide hybrid provided a direct measure of guide strand abundance in tissue lysates. In conjunction with an HPLC auto injector, this assay enabled guide strand quantification in hundreds of samples overnight. The assay was also highly sensitive, with a limit of detection less than 10 (mole/gram, and hybrids containing full-length, partially degraded, 5'-phosphorylated and 5'-dephosphorylated guide strand can all be quantified as separate peaks or shoulders in the HPLC trace. Because this assay could detect both labeled and unlabeled compounds, it can be directly transitioned to future CRO's for clinical sample analysis.

QuantiGene® (Affymetrix) Assay for Direct Detection of Flt1 mRNA Variants in Cells and Tissues QuantiGene® is a highly sensitive 96-well based assay in which mRNA is directly detected through signal amplification directly from tissue and/or cell lysates. By linking this direct detection assay to a 192 well automatic TissueLyser, a high-throughput version was developed which enabled processing of dozens of samples per animal. Thus, quantitative data on expression of targeted and housekeeping genes was generated in many animals at once. In pilot studies, n=8 was sufficient to detect 40% modulation of sFlt1 mRNA isoform expression with 80% confidence. bDNA assays are described in Coles et al. *Nucleic Acid Ther.* (2015) Nov. 23. PMID: 26595721.

ELISA (#MVR100, R&D Systems) for Detection of sFLT1 Proteins in Conditioned Media and Blood This 96-well based assay required only 10 μL of biological fluid per sample. This assay has been optimized over many years for both in vitro and in vivo studies. It is clinically compatible and allows for evaluation of circulating sFLT1 protein levels without animal sacrifice, and will be particularly useful for non-human primate studies.

Normal Mouse Pregnancy Model

The sFlt1-i13 variants are expressed during mouse pregnancy with i13 levels exponentially increasing from days 14-19. Perfect homology between the sFLT1-i13-2283 compound and the i13 mouse variant allows the study both of efficacy and of safety in this simple rodent model.

Preeclampsia Models

Reduced Uterine Perfusion Pressure (RUPP) model of placental ischemia and hypoxia model of preeclampsia is used as described further below.

Baboon Wild-Type Pregnancy Model

The sFlt1-i15a variant is not expressed in rodents during pregnancy, thus overall combination efficacy and safety will be evaluated in wild-type pregnant baboons using ELISA, a non-invasive assay as readout of efficacy.

Preliminary Data

A simple and cost-effective PE therapeutic using RNAi to limit excess placental expression of sFLT1 proteins was developed. For this to work, the following objectives were achieved: (1) appropriate siRNA targeting sites in sFlt1 mRNAs were identified; (2) whether RNA silencing was possible in the placenta using generalized (i.e., intravenous or subcutaneous) delivery was determined; and (3) novel siRNA chemistries were developed that would enable preferential delivery to placental trophoblasts, the cell type responsible for excess sFLT1 production.

Using tissue-specific RNA-Seq data available from the Human Protein Atlas (See proteinatlas [dot] org) and PAS-Seq data from multiple normal and PE human placentas (FIGS. 1B-C), it was determined that, while the full length (fl) isoform predominates in all tissues in non-pregnant adult humans, placental expression is dominated by three truncated isoforms, sFlt1-i13-short, sFlt1-i13-long and sFlt1-i15a, generated by polyadenylation within introns 13 and 15, respectively. Targeting the intronic regions with hsiRNAs enabled selective silencing of truncated isoforms without interfering with fl-Flt1 mRNA abundance.

Figure 6A:
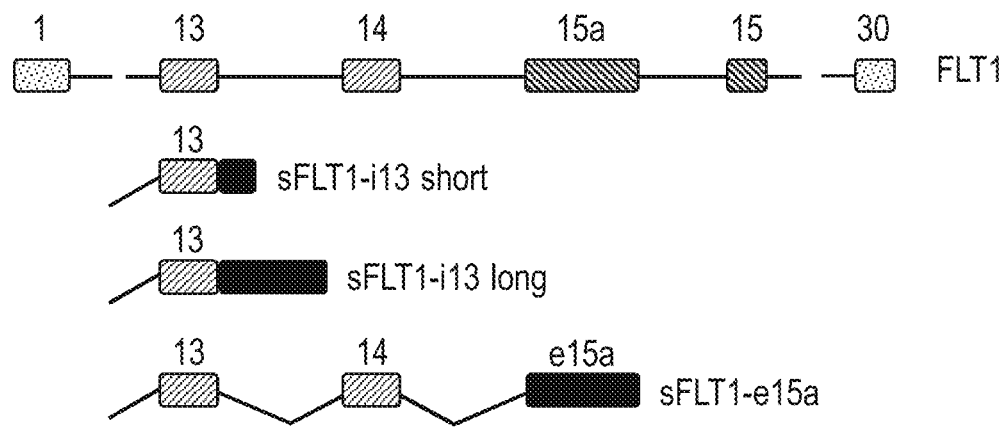

A novel type of siRNA chemistry was developed that enabled efficient delivery to endothelial cells and demonstrated selective trafficking to the labyrinth region of the placenta (i.e., to trophoblasts, the cell type responsible for sFLT1 expression). Without any additional formulation, up to 12% of the injected dose accumulated in the placenta with no detectable fetal transfer. This technology is the first demonstration of selective labyrinth targeting by any ONT, enabling silencing of sFLT1 protein at it major site of expression (FIG. 6A).

Over 50 siRNA variants were designed and screened (See FIG. 13). Hyper-functional, fully chemically-modified hsiRNAs were identified that selectively targeted the i13 and i15 isoforms without interfering with fl-FLT1 expression (FIG. 3). Using these hsiRNAs, efficient silencing of i13 and i15 was demonstrated in primary human trophoblasts with no active formulation (i.e., chemically unassisted internalization/uptake without the need for lipid) (FIG. 2B). A combination of sFLT1-i13-2283 and sFLT-i15a-2519 hsiRNAs was selected as the lead candidate for treatment of PE (FIG. 3).

It was determined that in-tissue compound concentrations in pregnant mice could reach 100 µg/gram with a single subcutaneous (SC) or intravenous (IV) injection, producing more than 50-80% reduction in sFlt1-i13 mRNA (FIGS. 6 and 4, respectively). Without intending to be bound by scientific theory, with this level of delivery, silencing is expected to persist for weeks in humans, and thus a limited number of injections to be necessary. Indeed, just one SC injection could be sufficient to silence sFLT1 for several weeks, resulting in significant PE pregnancy extension, possibly even to full-term.

Figure 3A:
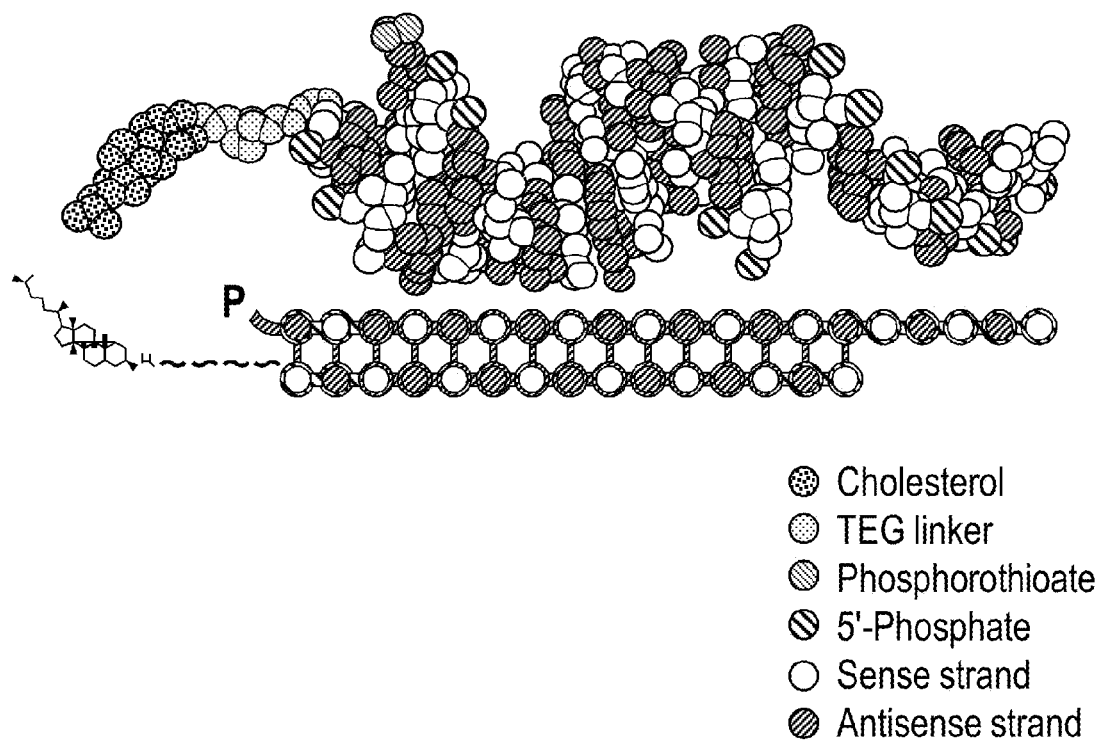
FIGS. 3A-3D depict hydrophobic siRNA structural/chemical composition, uptake and efficacy in primary human cytotrophoblasts (CTBs). (A) Schematically depicts hydrophobically modified and stabilized siRNAs (hsiRNAs) according to certain embodiments. sFlt1-i13-2283 hsiRNA and matching NTC was added to CTBs at concentration shown. (B) Level of sFLT1 protein was measured by ELISA (#MVR100, R&D systems) in conditioned culture medium after 72 h treatment. (C) depicts sFlt1-i13 mRNA levels, and (D) depicts Flt1-FL mRNA levels that were measured using QuantiGene® (Affymetrix) at 72 hours, (n=3, mean+/−SD). UNT—untreated cells, NTC—non-targeting control with matching chemistry.

Example 2. Hydrophobically Modified siRNAs (hsiRNA): Fully Chemically-Modified siRNA/Antisense Hybrids A panel of chemistries and formulations were considered as potential approaches for placental delivery. These included LNA antisense, LNPs, chol-conjugates/DPC Gal-Nacs and hsiRNA. hsiRNAs by far exceeded other chemistries in placental delivery (discussed further infra) and were selected for further investigation. The efficiency of hsiRNA uptake in primary trophoblasts was evaluated. Efficient uptake by all cells upon addition of Cy3-labeled compound to the media was observed (FIG. 2B). The hsiRNAs are asymmetric compounds, with a short duplex region (15 base-pairs) and single-stranded fully phosphorothioated tail, where all bases are fully modified using alternating 2'-F/2'-O-methyl pattern (providing stabilization and avoidance of PKR response), and the 3' end of the passenger strand is conjugated to TEG-Cholesterol (FIG. 3A). The cholesterol enabled quick membrane association, while the single-stranded phosphorothioated tail was essential for cellular internalization by a mechanism similar to that used by conventional antisense oligonucleotides (D. M. Navaroli, J. C., L. Pandarinathan, K. Fogarty, C., Standley, L. L., K. Bellve, M. Prot, A. Khvorova and & Corvera, S. Self-delivering therapeutic siRNA internalization through a distinct class of early endosomes. *PNAS, under review, second resubmission* (2015)). Addition of Cy3-labeled hsiRNA to any cultured cell type shows quick and efficient internalization through an EE1 related part of the endocytosis pathway. A previous version of this technology (Byrne, M. et al. Novel Hydrophobically Modified Asymmetric RNAi Compounds (sd-rxRNA) Demonstrate Robust Efficacy in the Eye. *Journal of ocular pharmacology and therapeutics: the official journal of the Association for Ocular Pharmacology and Therapeutics* (2013)), where only 50% of bases are 2'F/2'-O-methyl modified, is in Phase II clinical trials for dermal fibrosis.

A chemical modification pattern that does not interfere with primary RISC entry was developed. A wide range of chemical variations were generated and an alternating 2'F/2'-O-methyl pattern was identified that optimally configures the guide strand to adopt a geometry that closely mimics that of an individual strand in an A-form RNA duplex. The A-form RNA duplex is recognized by the RISC complex and supports proper positioning of the target mRNA within the cleavage site (Ameres, S. L., Martinez, J. & Schroeder, R. Molecular basis for target RNA recognition and cleavage by human RISC. *Cell* 130, 101-112 (2007); Schirle, N. T., Sheu-Gruttadauria, J. & MacRae, I. J. Gene regulation. Structural basis for microRNA targeting. *Science* 346, 608-613 (2014)). By starting the alternating pattern with a 5'-phosphorylated 2'-O-methyl ribose (a 5' phosphate is necessary for PIWI domain interaction), the 2'F modifications were placed in even numbered positions 2-14. Positions 2 and 14 were previously shown to be intolerant of bulkier 2'-ribose modifications (Jackson, A. L. et al. Position-specific chemical modification of siRNAs reduces "off-target" transcript silencing. *Rna* 12, 1197-1205 (2006); Kenski, D. M. et al. siRNA-optimized Modifications for Enhanced In Vivo Activity. *Molecular therapy. Nucleic acids* 1, e5 (2012)).

Figure 8A:
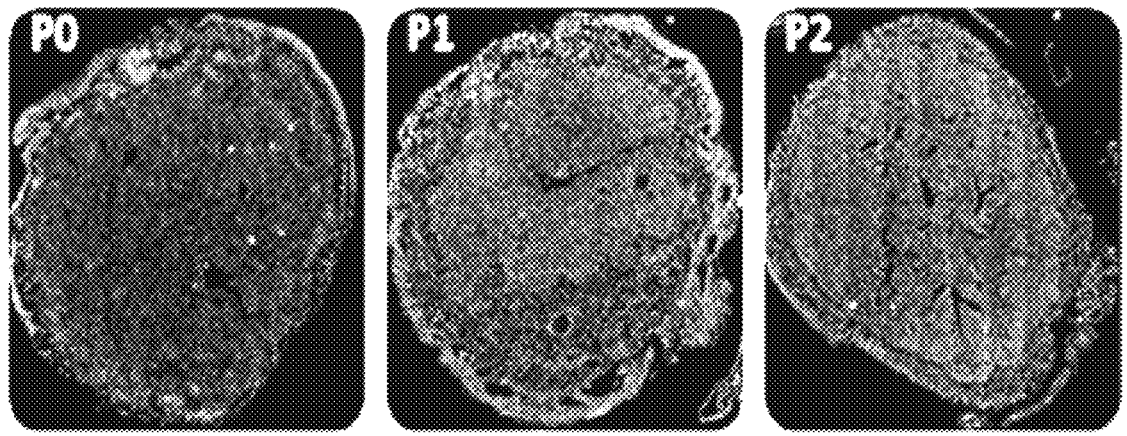
Figure 8B:
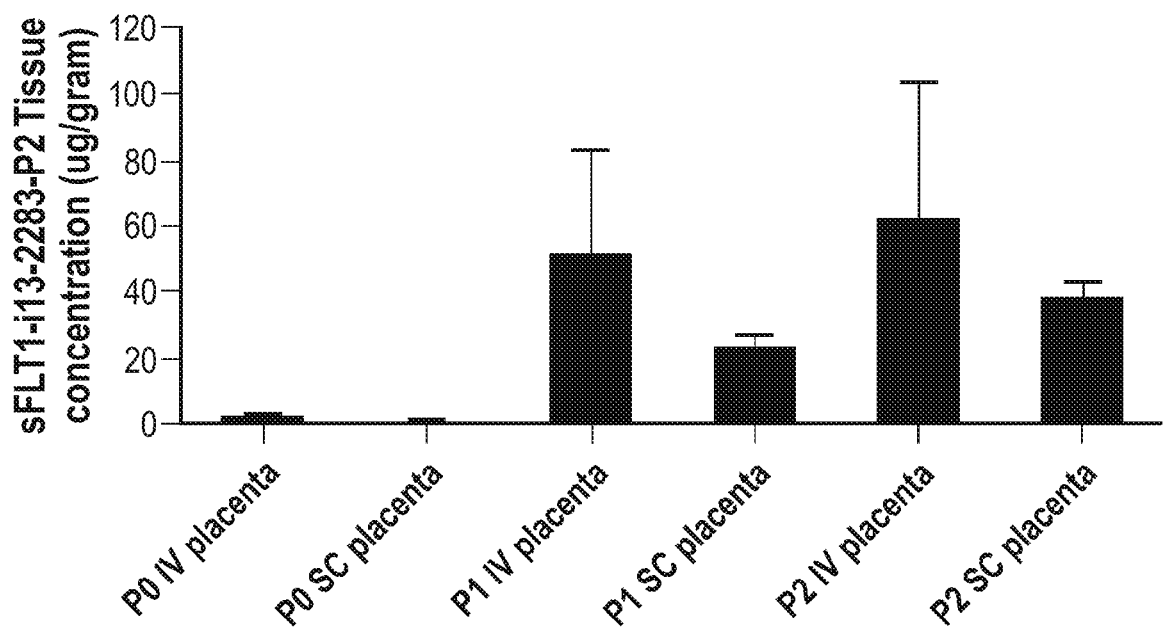
Figure 8C:
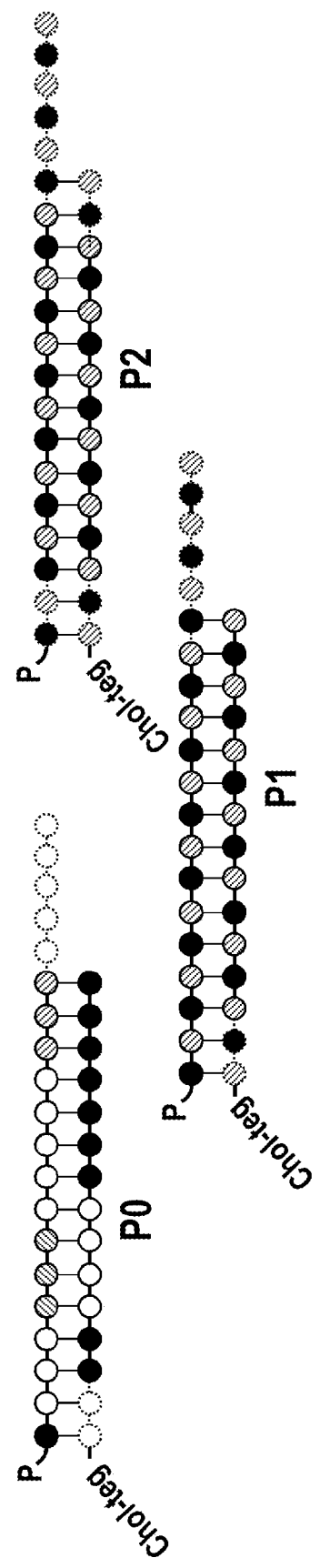

These fully chemically stabilized compounds were at least as or more effective as naked siRNA in RISC entry and represent the first complete chemical modification pattern with no negative impact on RISC function. This discovery was transformative for the PE project, as complete chemical stabilization is absolutely essential for tissue accumulation upon systemic administration. FIG. 8 shows that no full-length compound could be detected in mouse placentas 24 hours post administration of a version wherein 40% of the riboses were still 2'-OH (P0 chemistry). In comparison, both fully 2'-F/2'-O-methyl modified versions (P1 and P2 chemistries) accumulated to above therapeutically efficacious levels (FIG. 8). Another benefit of non-RNA containing siRNAs is ease of manufacturing—their DNA-like chemistry with no necessity for orthogonal ribose protection shortens de-protection procedures and increases coupling efficiencies Finally, complete elimination of all 2'-OH groups helps with avoidance of the innate immune response, which relies mainly on 2'-OH interactions (Alexopoulou, L., Holt, A. C., Medzhitov, R. & Flavell, R. A. Recognition of double-stranded RNA and activation of NF-kappaB by Toll-like receptor 3. *Nature* 413, 732-738 (2001); Choe, J., Kelker, M. S. & Wilson, I. A. Crystal structure of human toll-like receptor 3 (TLR3) ectodomain. Science 309, 581-585 (2005)).

Figure 31:
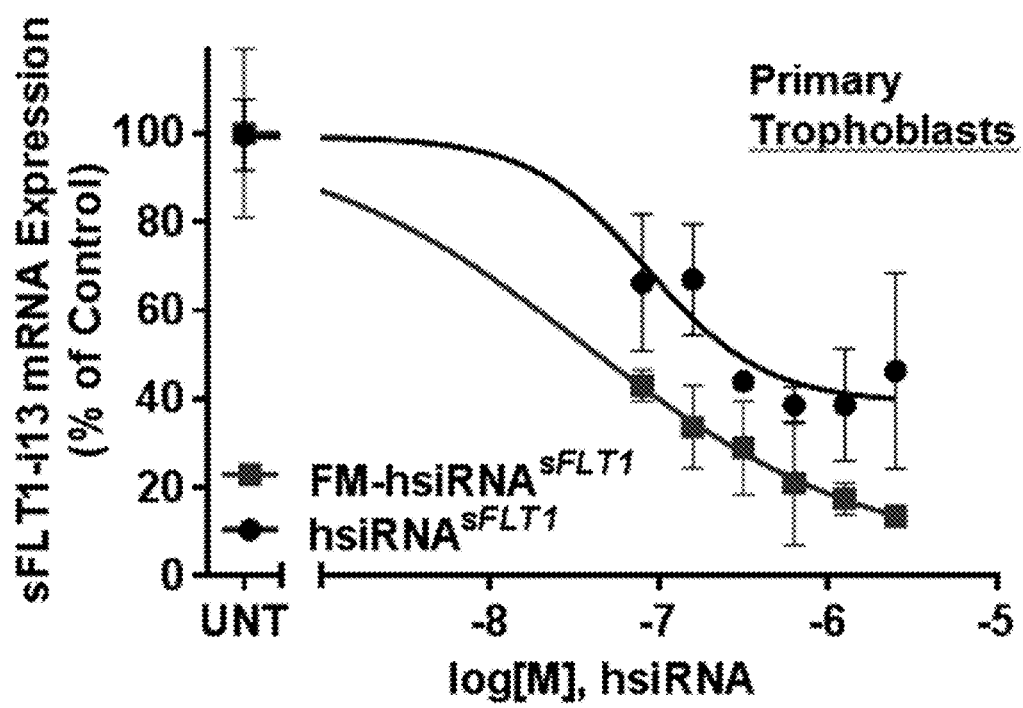
FIG. 31 depicts passive uptake of FM-hsiRNA$^{sFLT1}$ in primary trophoblasts effective to decrease sFLT1 i13 mRNA expression.
Figure 32:
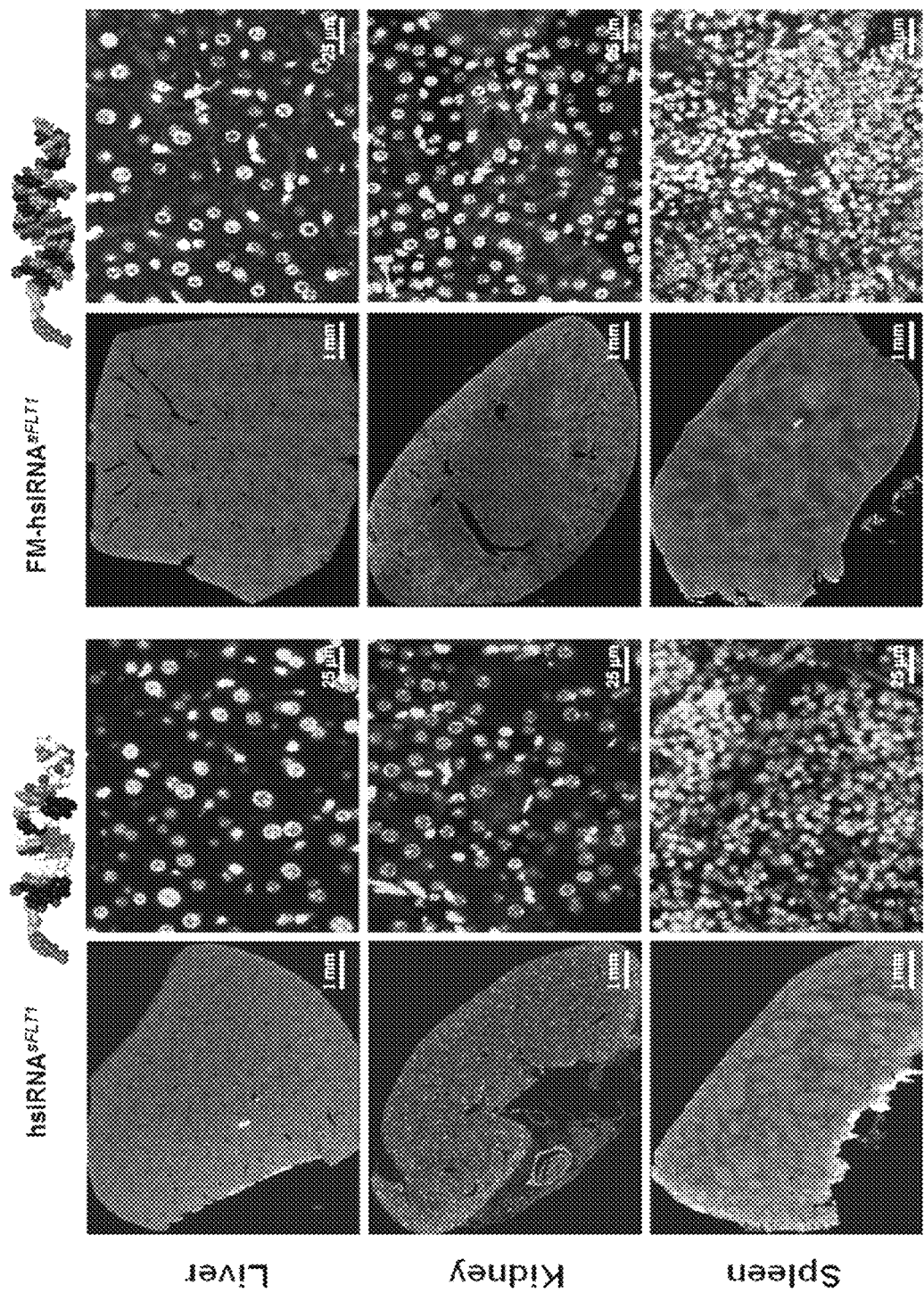
FIG. 32 depicts systemic delivery of FM-hsiRNA$^{sFLT1}$ (right two columns) relative to non-fully modified hsiRNA$^{sFLT1}$ (left two columns) in liver, kidney and spleen tissues.
Figure 33:
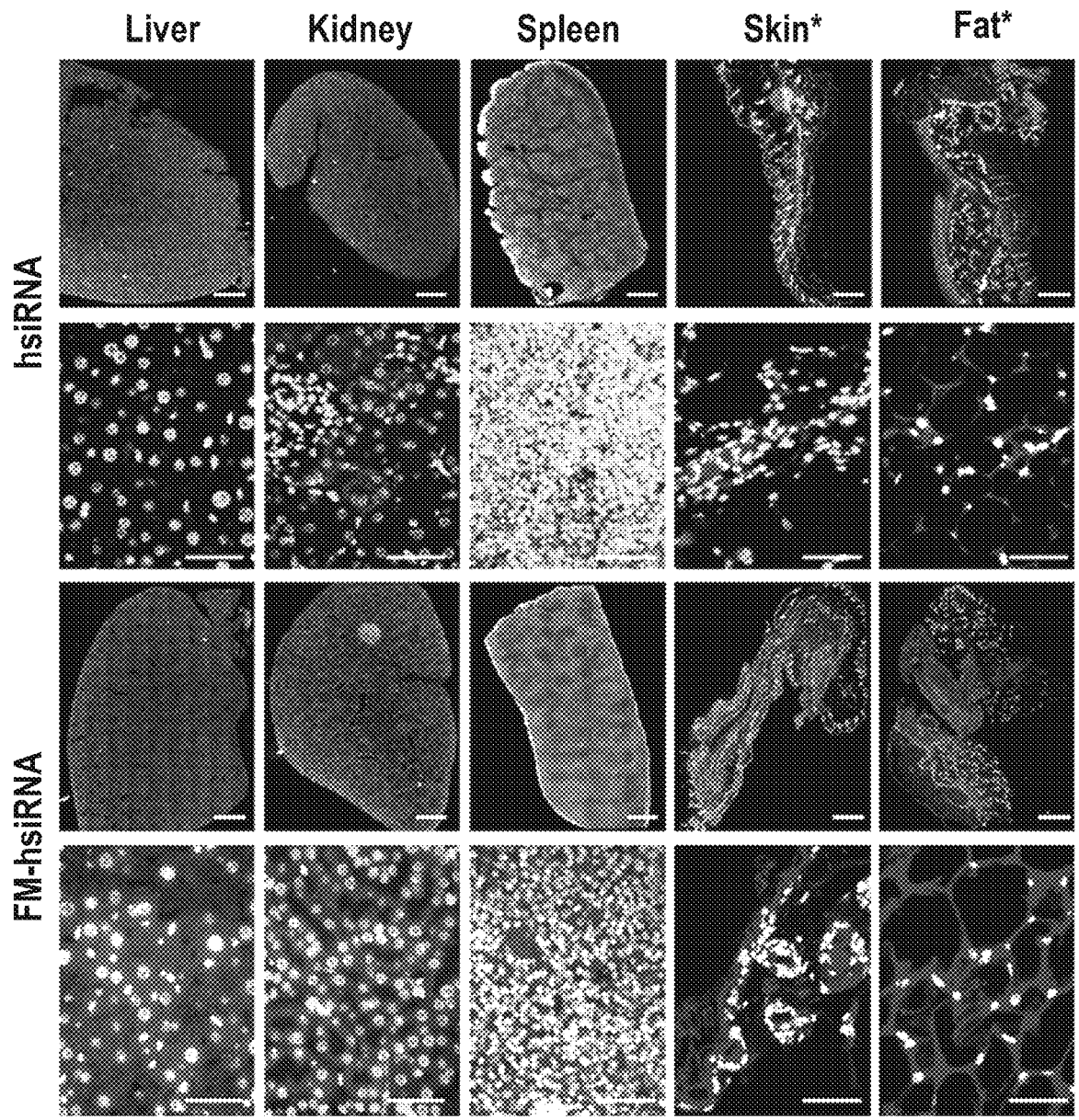
FIG. 33 depicts systemic delivery of FM-hsiRNAs in liver, kidney, spleen, skin and fat tissues after subcutaneous (SC) injection.

FM-hsiRNAs were determined to be more potent in passive uptake than non-fully modified hsiRNAs in primary trophoblasts (FIG. 31). Full metabolic stabilization was determined to be essential for systemic delivery following intravenous administration (FIG. 32). FM-hsiRNAs were also determined to be essential for systemic delivery following subcutaneous administration (FIG. 33).

Figure 34:
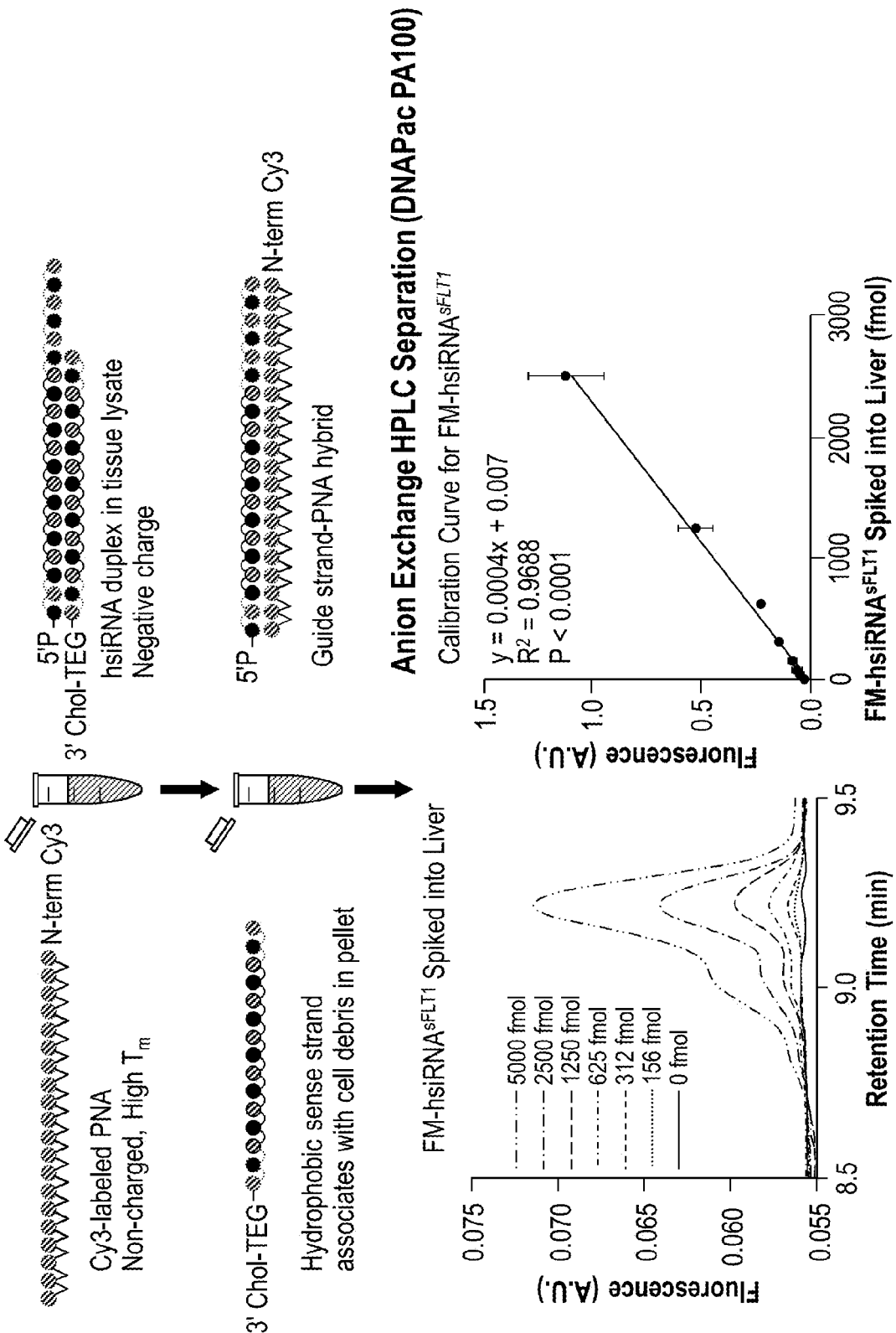
FIG. 34 depicts a PNA-based assay for guide strand quantification in vivo.
Figure 35A:
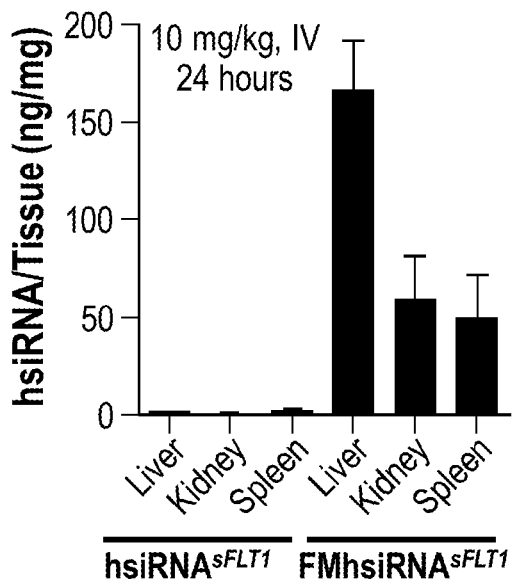
FIGS. 35A-35F depict robust FM-hsiRNAs$^{sFLT1}$ delivery and efficacy in liver, kidney and spleen tissues in vivo after IV or SC administration. (A) Depicts ng/mg hsiRNA levels per tissue post-IV administration of 10 mg/kg at t=24 hours. (B) Depicts ng/mg hsiRNA levels per tissue post-SC administration of 10 mg/kg at t=24 hours. (C) Depicts ng/mg hsiRNA levels per tissue post-IV administration of 2×20 mg/kg at t=120 hours. (D) Depicts ng/mg hsiRNA levels per tissue post-IV administration of 2×15 mg/kg at t=120 hours. (E) Depicts sFLT1 mRNA expression post-IV administration of 2×20 mg/kg at t=120 hours. (F) Depicts sFLT1 mRNA expression post-IV administration of 2×20 mg/kg at t=120 hours.
Figure 35B:
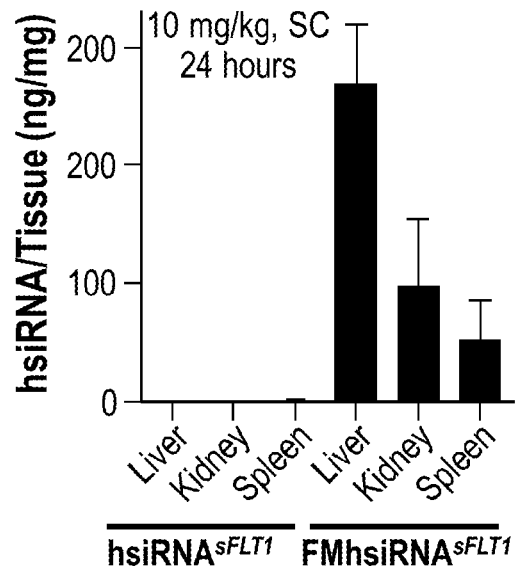
Figure 35C:
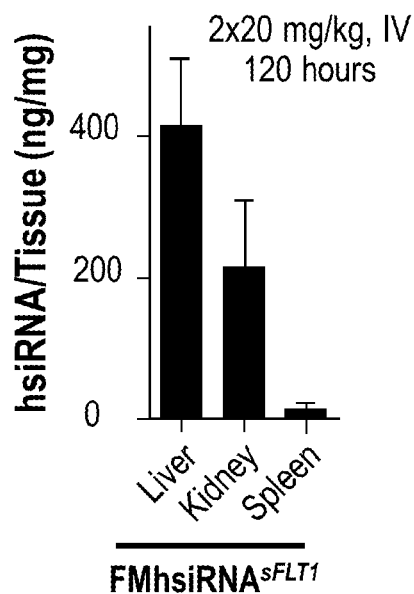
Figure 35D:
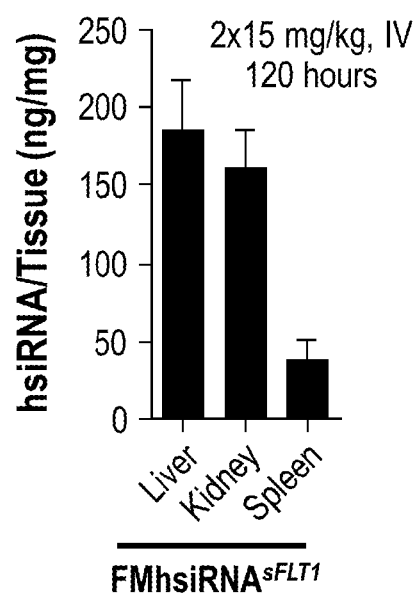
Figure 35E:
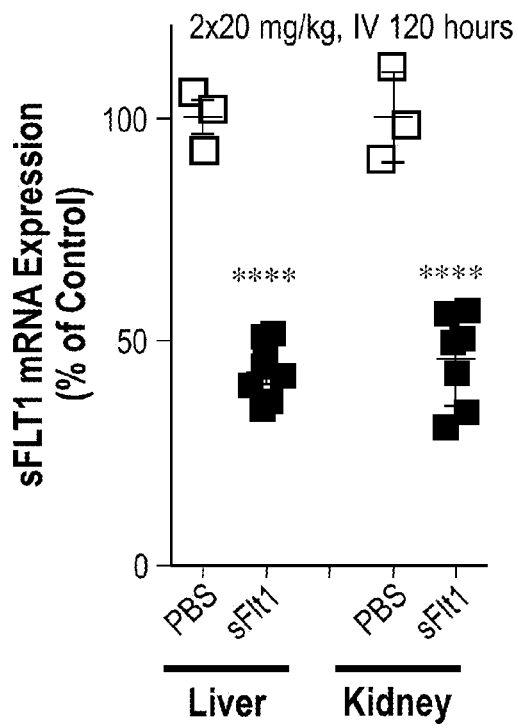
Figure 35F:
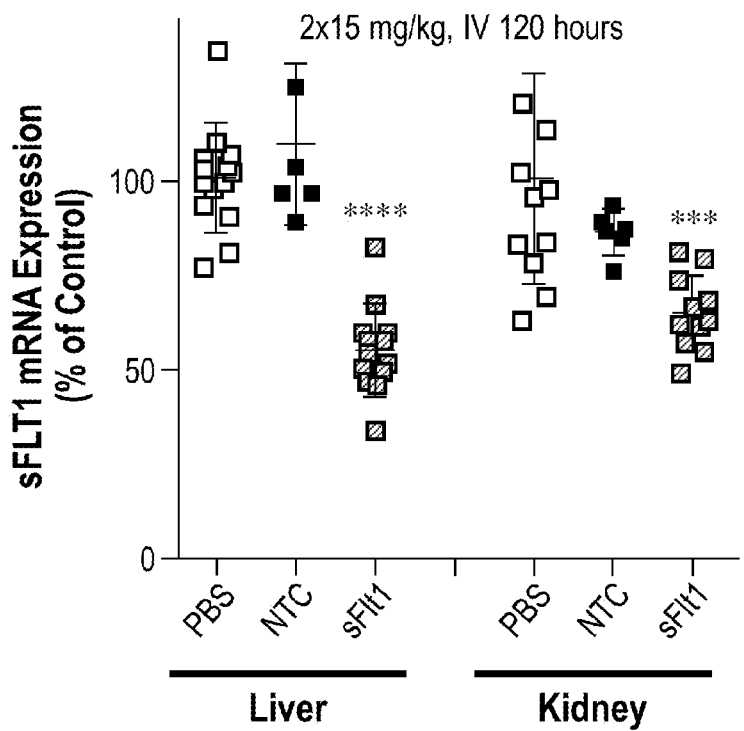

A PNA-based assay was developed to quantitate guide strand distribution in vivo (FIG. 34). Using this assay, robust delivery and efficacy to liver and kidney tissues were observed in vivo after administration of FM-hsiRNAs (FIGS. 35A-35F).

Figure 18A:
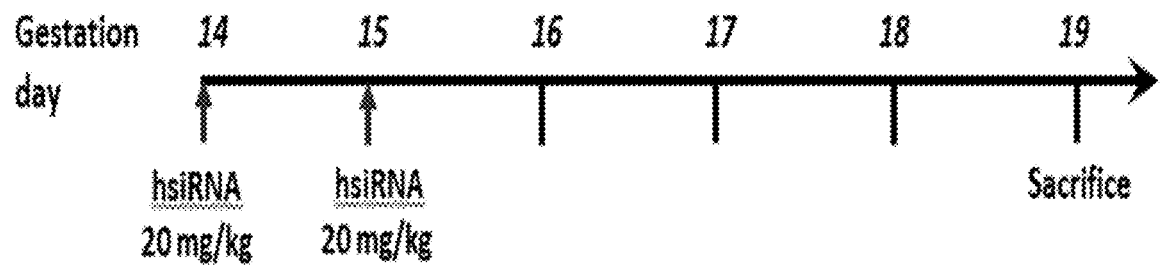
FIGS. 18A-18B depict hsiRNA stability in vivo. IV vs. SC, sFLT_2283P2 (150403). (A) Depicts a timeline of the experiment. (B) Depicts hsiRNA levels in the liver post-IV and post-SC administration.
Figure 18B:
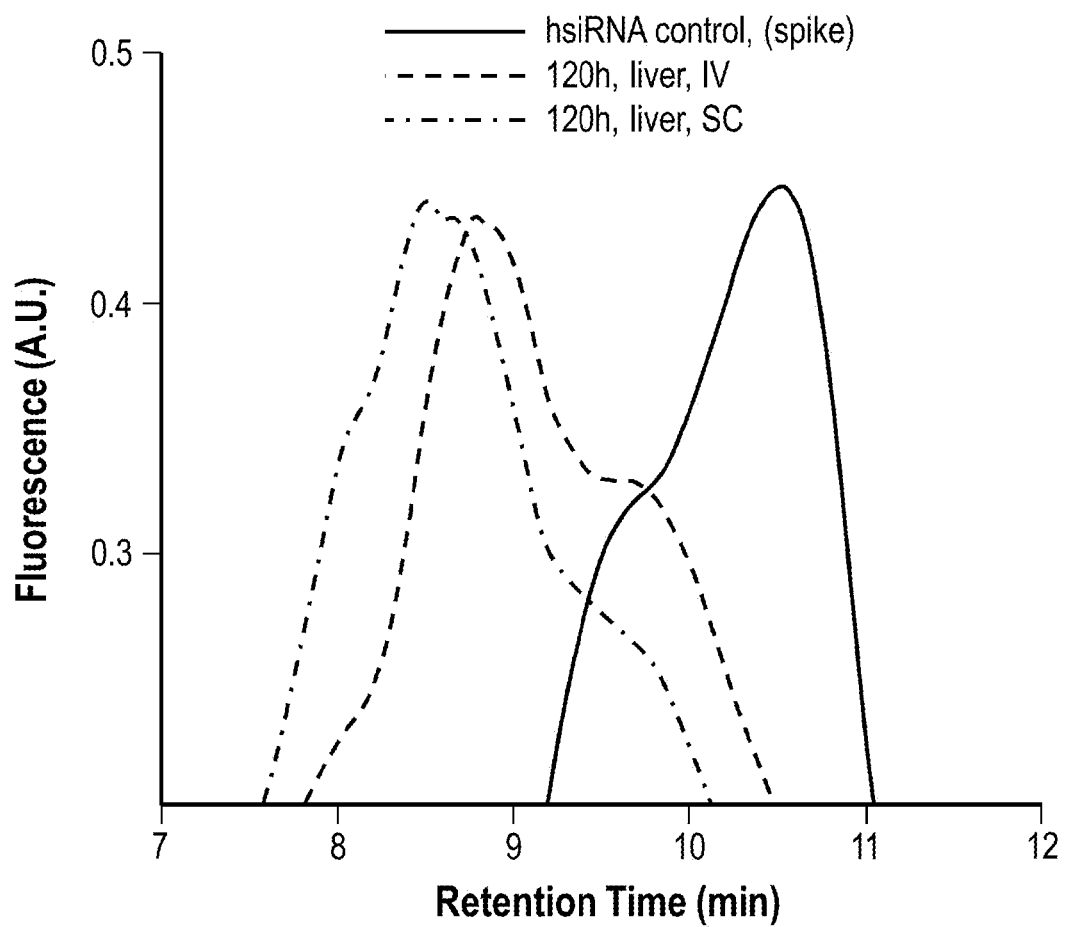
Figure 19A:
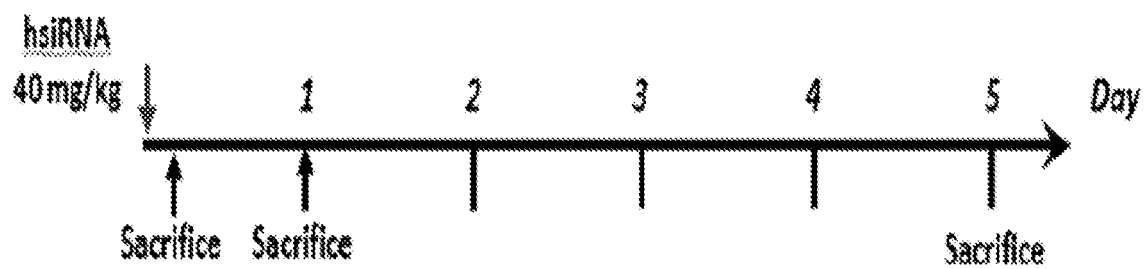
FIG. 19A-19B depicts hsiRNA stability in vivo. (A) Depicts a timeline of the experiment. (B) Depicts hsiRNA at two hours, 24 hours and 120 hours post-IV administration. sFLT1_2283P2 (#150624).
Figure 19B:
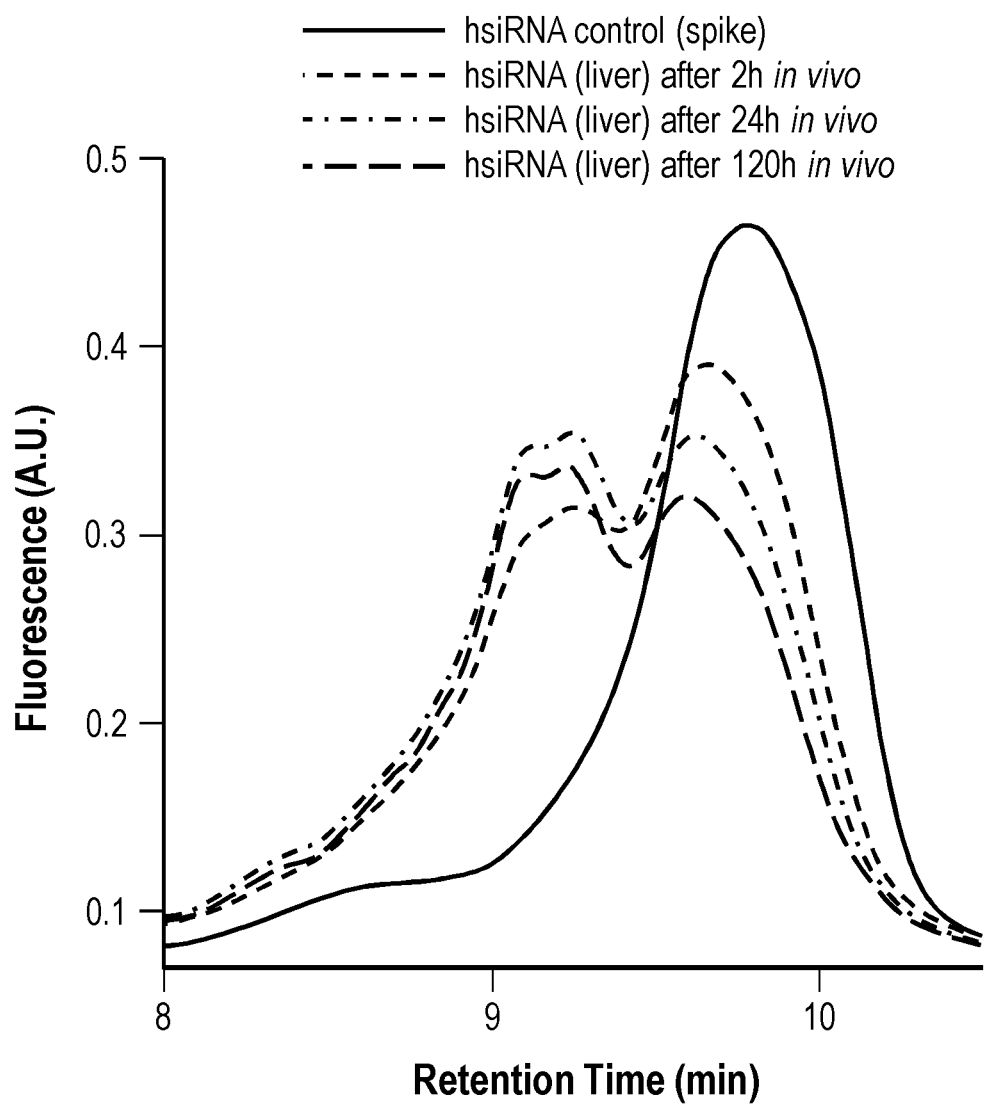

In vivo stability in liver tissues after IV or SC administration was assayed at 120 hours post-IV and post-SC administration (FIGS. 18A-B). hsiRNA levels were assayed in vivo at two hours, 24 hours and 120 hours post-IV administration (FIG. 19).

Example 3. hsiRNAs Enabled Selective Delivery to Placental Labyrinth Trophoblasts with No Detectable Fetal Transfer To evaluate hsiRNA distribution in vivo, normal pregnant mice (day 15) were injected with Cy3-labeled sFlt-i13-2283 hsiRNA and distribution examined at by two independent assays. Gross tissue fluorescence microscopy revealed that most of the oligonucleotides accumulated to three tissues: liver endothelium, kidney endothelium and placental labyrinth (FIG. 4). Without intending to be bound by scientific theory, this distribution profile was most likely defined by a combination of blood flow/filtration rate and the cholesterol receptor concentration on cell surfaces. Using the novel FDA-compliant PNA-hybridization assay described above, it was demonstrated that overall drug concentration in placenta exceeded efficacious levels (approximately 100 ng/gram) by orders of magnitude upon a single 10 mg/kg injection (FIG. 8). This level of tissue delivery was roughly the same for IV and SC administration, with approximately 50%, 10% and 12% of the compound distributing to liver, kidney and placenta, respectively, 24 hours post-injection (FIG. 4). Interestingly, only half of this was cleared from the liver (slightly more in kidney) after five days, indicating that a single administration might be sufficient to induce long-term silencing.

Figure 5:
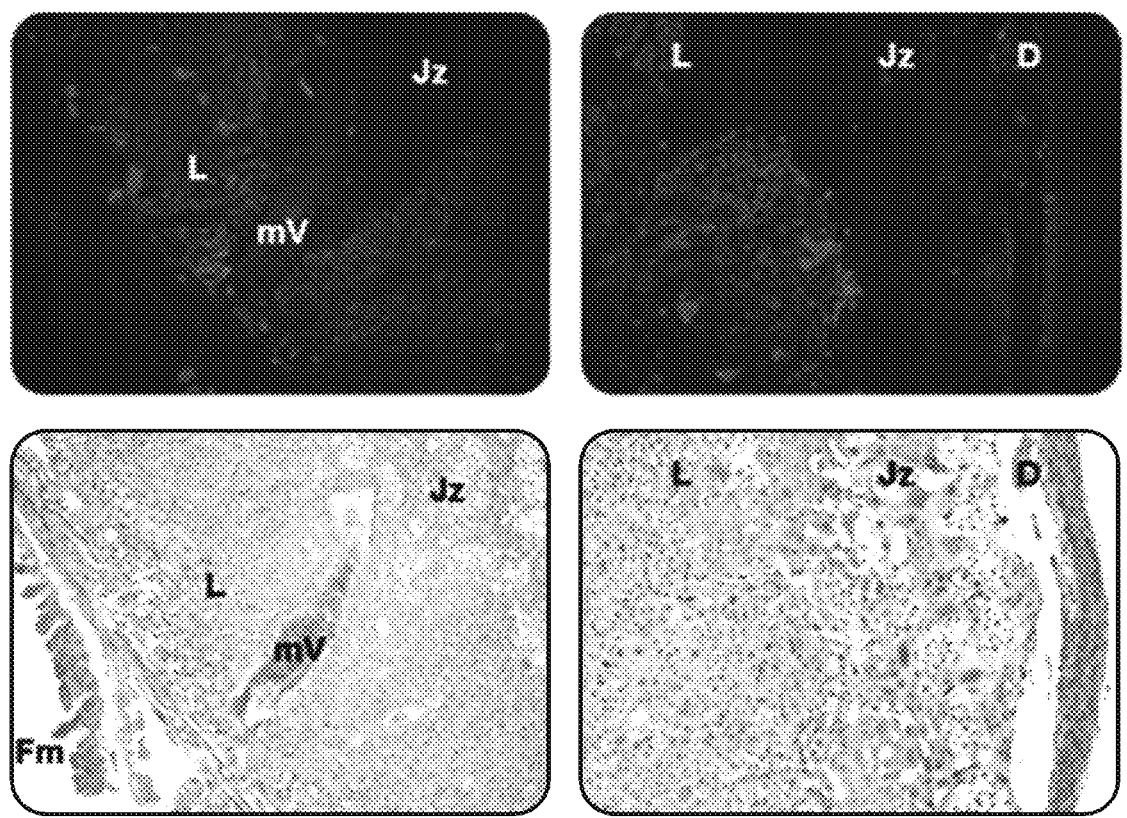
FIG. 5 depicts histological evaluation of hsiRNA distribution in mouse placenta. A wild-type pregnant mouse (E15) was injected with Cy3-sFLT1-2283-P2 (red) (10 mg/kg; IV via tail vein). Tissues were fixed after 24 hours, processed and stained with HE, and then imaged at 20× on a Leica fluorescent microscope. Fm—Fetal membrane; mV—maternal vessel; L—labyrinth; Jz—junctional zone; D—decidua.
Figure 7A:
FIGS. 7A-7D depict efficient placental delivery and silencing of sFLT1 in a wild-type mouse pregnancy model. (A) A wild-type pregnant mouse (E15) was injected with Cy3-sFLT1-2283-P2 (red) (10 mg/kg; IV via tail vein). Fetuses and their placentas were fixed after 24 hours, processed, and imaged on a Leica tiling fluorescent microscope; nuclei stained with DAPI (blue). (B) Depicts the sFlt1-i13 expression level in mouse tissues 5 days after sFLT1-2283-P2 injection (2×20 mg/kg). sFLT1-i13 mRNA was measured using QuantiGene® (Affymetrix), normalized to fl-FLT1 and presented as percent of untreated control [n=3 (PBS); n=7 (sFLT1-i13-2283), mean+SEM]. (C) Depicts a timeline of the experiment. (D) Depicts in vivo validation of sFLT1_2283/2519 (sFLT1-mix, 151111); CD1 mice via IV at 20 mg/kg, n=8).

FIG. 7A shows oligonucleotide distribution in a 4 µM sagittal slice cut through a fetus and its attached placenta. It was amazing and highly satisfying to observe efficient delivery to the placental labyrinth with essentially no detectable oligonucleotide transfer to the fetus, including the fetal liver. These data were independently confirmed by the PNA assay which could detect no hsiRNAs in fetal liver (FIG. 4B) (sensitivity of the assay was approximately 10 fmole/gram). FIG. 5 depicts histological analysis of the placenta and confirmed specific delivery of hsiRNAs to placental labyrinth trophoblasts, the major cell type responsible for sFLT1 expression. Remarkably, almost no Cy3 was detectable in other layers (e.g., junctional and decidua), further supporting the specificity of this novel chemical modification pattern for delivery to the labyrinth trophoblasts.

In addition to comparing the impact of full 2'-F/2'-O-methyl modification on PK (pharmacokinetics), the phosphorothioate (PS) content was slightly altered. While the P1 chemistry had PS linkages at the 3'-ends of both strands (for a total of 8), the P2 chemistry incorporated another two PS's at the 5' end of each strand (for a total of 12). Terminal PS linkages provided a defense against exonucleases, and so are essential for long-term stability in extremely aggressive nuclease environments. Overall, these two chemistries were comparable in levels of oligonucleotides delivery at 24 hours (FIG. 8), but might have different degradation profiles after long term tissue exposure, affecting duration of the silencing effect. They also have slightly different liver: placenta distribution ratios, which might also be somewhat affected by the route of administration (FIG. 8).

3.1. Selection and Identification of Lead Candidate: i13/i15 Mix and Efficacy in Primary Trophoblasts The i13 and i15 Flt1 mRNA isoforms contained 435 and 567 unique nucleotides, respectively, not present in fl-Flt1 mRNA. Unfortunately, the majority of this sequence space was dominated by homo-polymeric repeats and regions of high GC content, neither of which are targetable by RNAi. Undeterred, a panel of more than 50 hsiRNAs was designed against any feasible targetable sequence using standard siRNA design parameters (Birmingham, A. et al. A protocol for designing siRNAs with high functionality and specificity. *Nature protocols* 2, 2068-2078 (2007)) including assessment of GC content, specificity and low seed compliment frequency (Anderson, E. M. et al. Experimental validation of the importance of seed complement frequency to siRNA specificity. *Rna* 14, 853-861 (2008)), elimination of sequences containing miRNA seeds, and examination of thermodynamic bias (Khvorova, A., Reynolds, A. & Jayasena, S. D. Functional siRNAs and miRNAs exhibit strand bias. *Cell* 115, 209-216 (2003); Schwarz, D. S. et al. Asymmetry in the assembly of the RNAi enzyme complex. *Cell* 115, 199-208 (2003)). FIG. 6B shows the targeting positions of hsiRNAs identified to be highly functional.

In the design criteria, targeting sites with perfect homology in other primates were favored to simplify both formal toxicology and efficacy studies in non-human primates and the baboon PE model described below. The mouse expresses only an i13 variant. Luckily, the most efficacious hsiRNA, sFLT1-i13-2283, happened to have perfect complementarity to the mouse i13 isoform, enabling direct in vivo efficacy and toxicity evaluation of this compound in both normal and PE mouse pregnancy models. FIG. 6C shows a table with targeting sites and IC50 values of the best compounds identified to efficiently silence the i13 and i15 isoforms. IC50 values for efficacious compounds ranged between 40-100 nM in both HeLa cells and primary human trophoblasts.

Figure 3B:
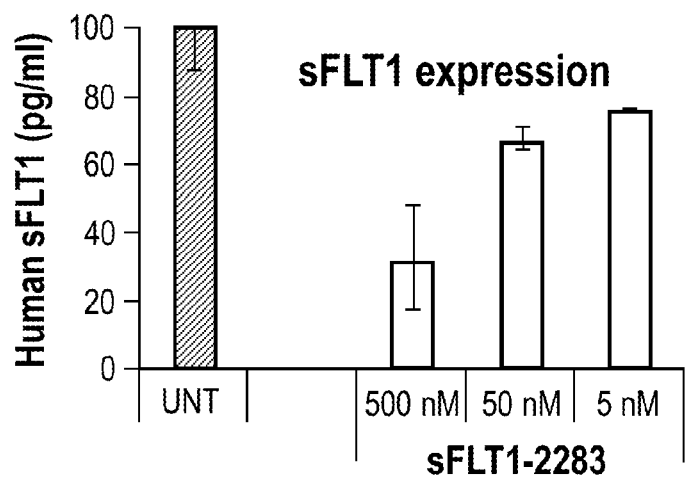
Figure 3C:
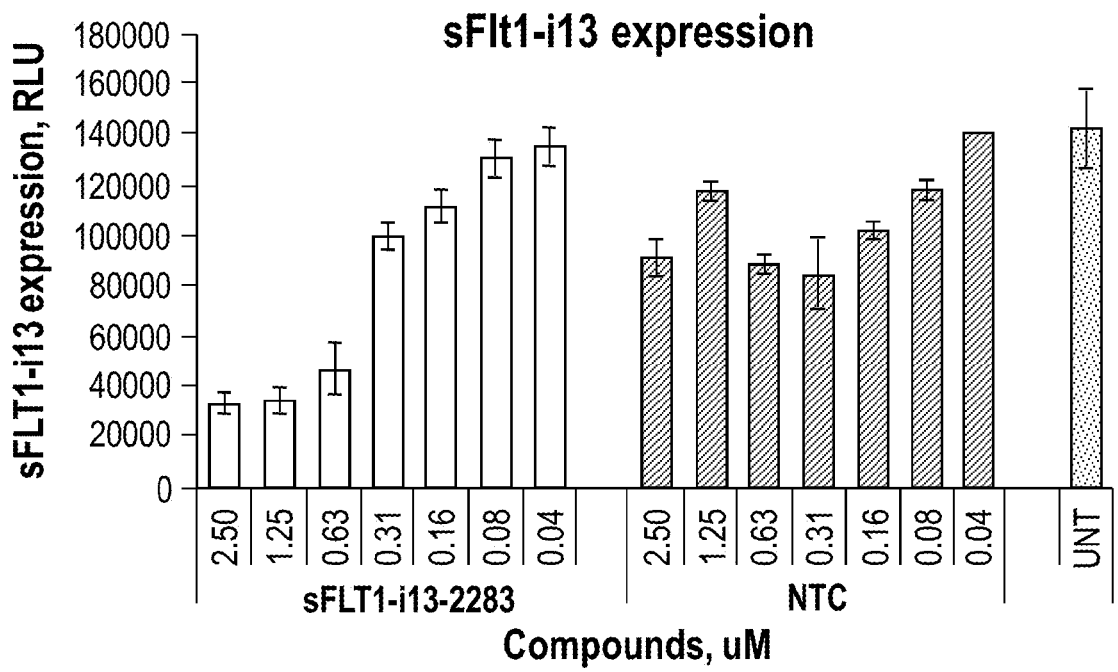
Figure 3D:
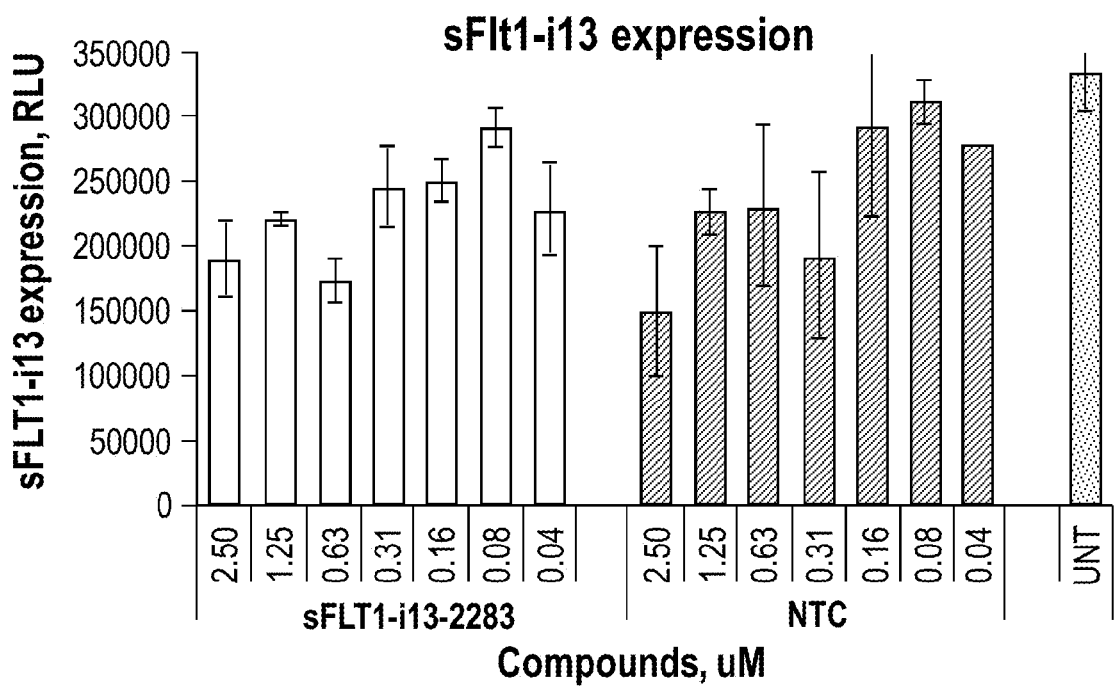

FIG. 3C shows an example of the dose response of sFLT1-i13-2283 in primary human trophoblasts used for IC50 value calculation. It is important to emphasize that silencing with hsiRNAs was achieved upon addition of non-formulated compound to the trophoblast media. The level of mRNA knockdown was determined at 72 hours using the above-described QuantiGene assay. To control for any potential non-specific effects, i13 or i15 levels were always normalized to a housekeeping gene. A Non-Targeting-Control (NTC) of identical chemistry was used in all experiments to control for chemical class effects. The levels of full length Flt1 mRNA were not affected (FIG. 3D). To evaluate silencing at the protein level, sFLT1 concentration in conditioned medium was measured using ELISA (Quantikine® FLT1, MVR100, R&D Systems) (FIG. 3B).

To move forward, two hsiRNA pairs were selected: sFLT1-i13-2283 (5' CTCTCGGATCTCCAAATTTA 3') (SEQ ID NO:1)/sFLT-i15a-2519 (5' CATCATAGCTACCATTTATT 3') (SEQ ID NO:2) and sFLT1-i13-2318 (5' ATTGTACCACACAAAGTAAT 3') (SEQ ID NO:3)/sFLT-i15a-2585 (5' GAGCCAAGACAATCATAACA 3) (SEQ ID NO:4) (FIG. 3C). The first pair was the lead drug candidate and was used in all studies. The second pair was a backup. While sequence-specific toxicity will unlikely be an issue, a backup compound combination that was readily available in case of any sequence-dependent toxicity appeared was desired. In summary, a functional hydrophobically modified siRNAs that selectively targeted sFlt1-i13 and sFlt1-i15a isoforms was identified. Efficient internalization and silencing of the corresponding targets in primary human trophoblasts was determined at both the mRNA and protein levels.

In vitro validation of sFLT1_2283/2519 (sFLT1-mix; 151005 or 151111) showed dose responses for targeting sFLT1 i13 and sFLT1 e15a (FIGS. 27A-D and 28A-D).

Figure 7B:
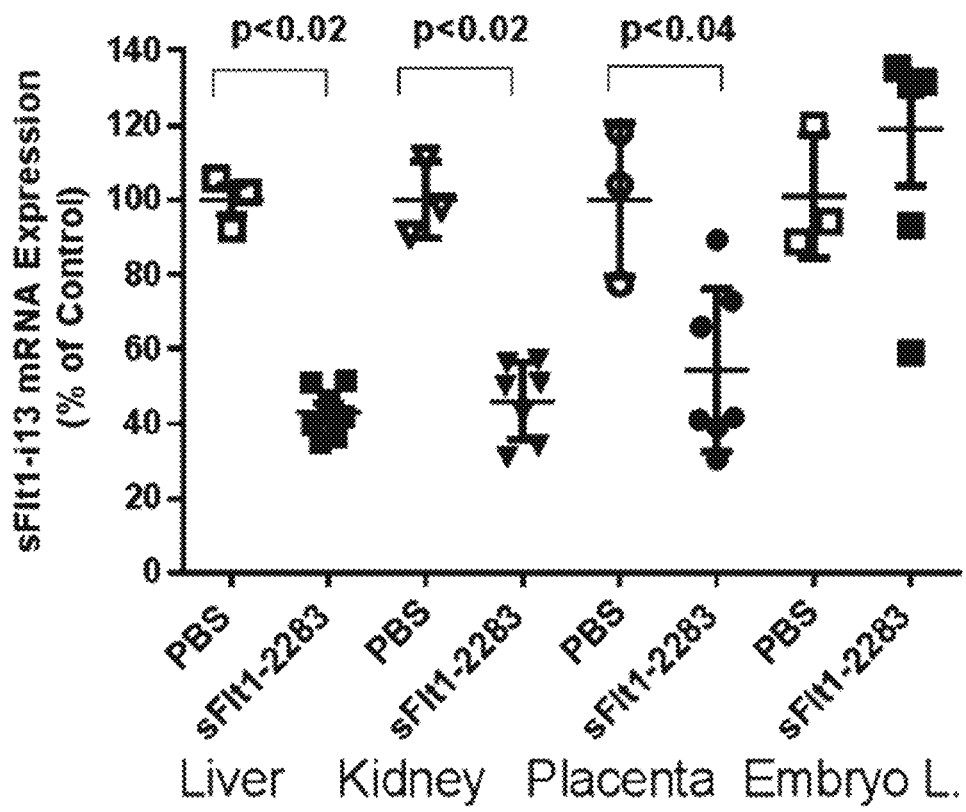

3.2. sFLT1-i13 Variant Silencing In Vivo Upon Systemic Administration to Normal Pregnant Mice FIG. 7B shows pilot data demonstrating efficient silencing of sFlt1 mRNAs in kidney, liver and placenta subsequent to two 20 mg/kg IV injections. 12 pregnant mice were dosed with 20 mg/kg sFLT-13-2283 compound IV daily for two days, and the level of sFlt1-i13 expression (normalized to both a housekeeping gene and fl-FLT1) was determined 5 days later in maternal liver, kidney and placenta, as well as in fetal livers. Statistically significant silencing (50-60%) was achieved in all maternal tissues and placenta, while levels of sFLT1 expression in fetal liver were not changed. The lack of silencing in fetal liver was consistent with the lack of detectable oligonucleotide in this tissue (FIG. 4B). Placental hsiRNA concentration was around 20-40 µg/gram. This far exceeded the concentration necessary for productive silencing, which is usually observed with compound concentrations as low as 100 ng/gram. The dose used was thus clearly much higher than necessary. The dose response and duration of effect were studied in detail, and the NOEAL and MTD dose levels were defined for this compound. In addition, maternal weight, placental weight and number and weight of fetuses were monitored, and it was determined that each of them was unaffected at 10 mg/kg injection and slightly affected (average of 6 vs. 7 fetuses/dam) at 20 mg/kg injection levels with no other observable changes. It was reassuring that, even at this excessively high dose, no hsiRNA transfer to the fetus was observed. Based on the drug concentrations achieved in the placenta, the effective dose should be at least an order of magnitude lower.

Figure 15:
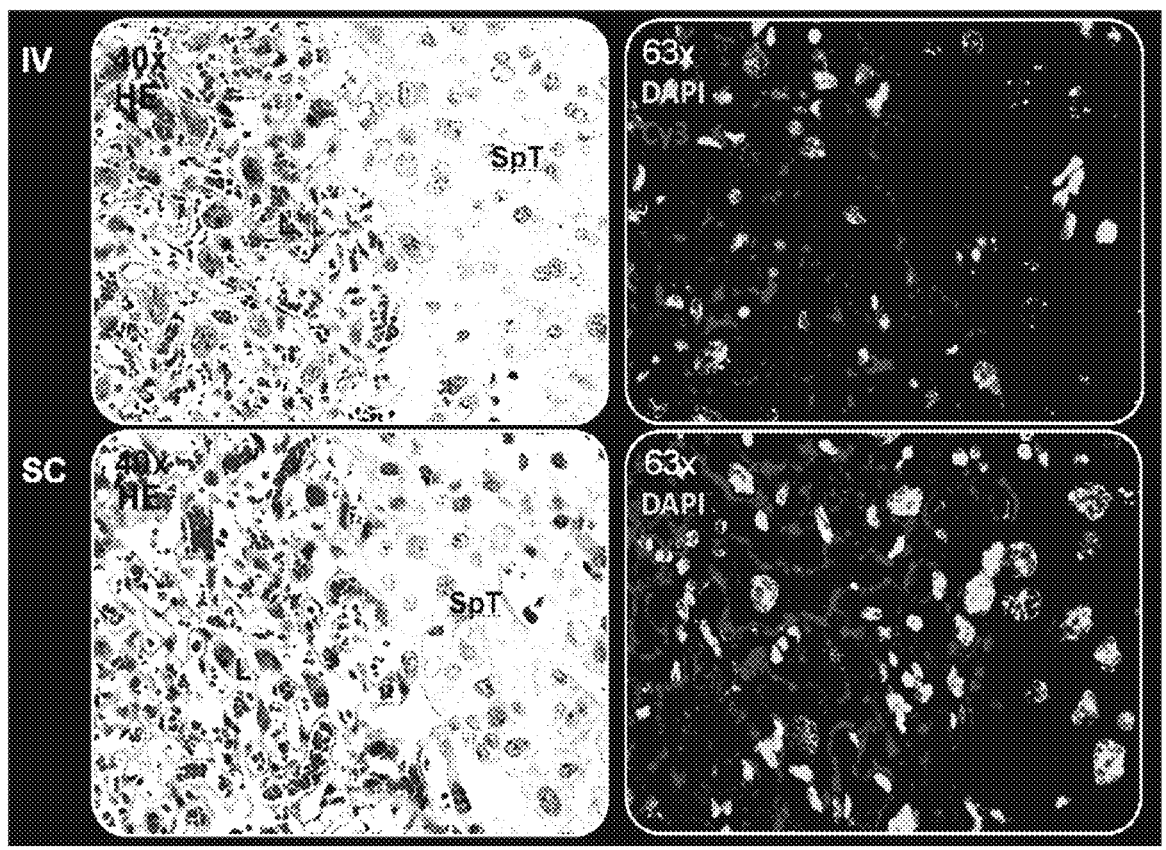
FIG. 15 depicts a histological evaluation of hsiRNA distribution in mouse placental tissues post-subcutaneous (SC) and post-intravenous (IV) administration.
Figure 16A:
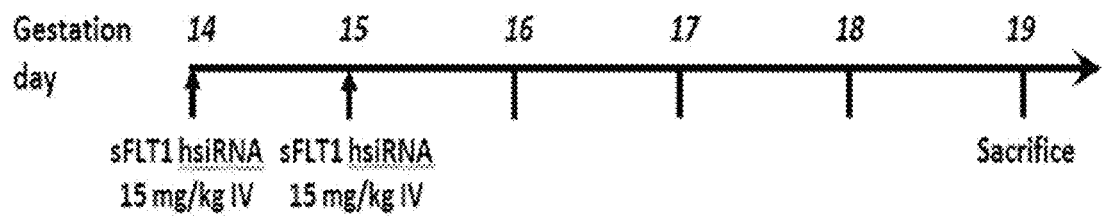
FIGS. 16A-16E depict efficient silencing of sFLT1 by hsiRNA in pregnant nice (CD1). (A) Depicts a timeline of the experiment. (B) Depicts sFLT1-I13 mRNA expression in liver, kidney and placenta. (C) Depicts sFLT1 protein levels as a function of time. (D) Depicts the percentage of the sFLT1-2283 injected dose present in liver, kidney, placental, spleen and fetal liver tissues at five days post-injection. (E) Depicts µg/g sFLT1-2283 present in liver, kidney, placental, spleen and fetal liver tissues at five days post-injection.
Figure 16B:
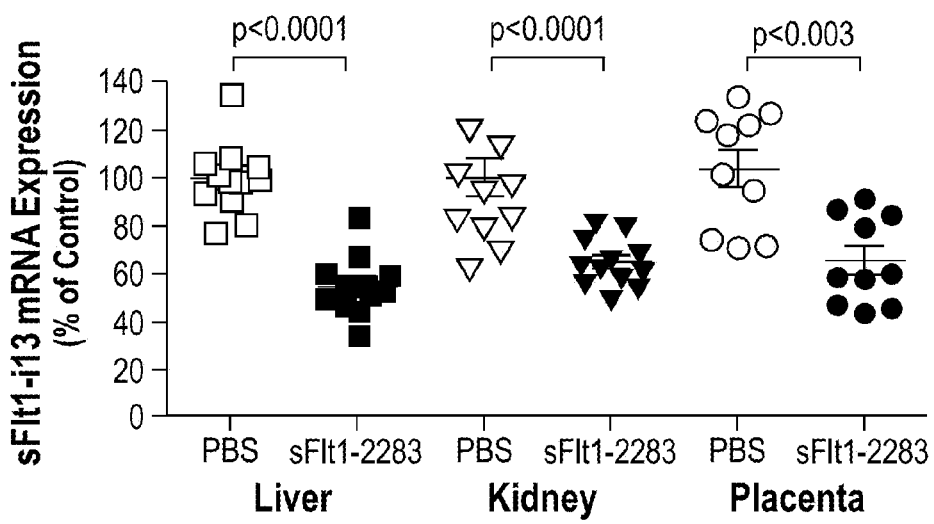
Figure 16C:
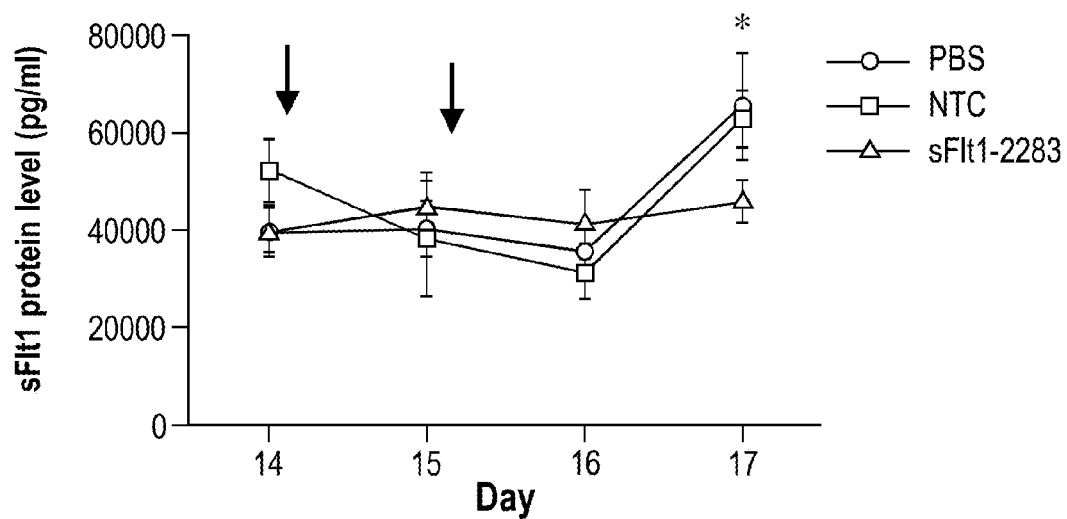
Figure 16D:
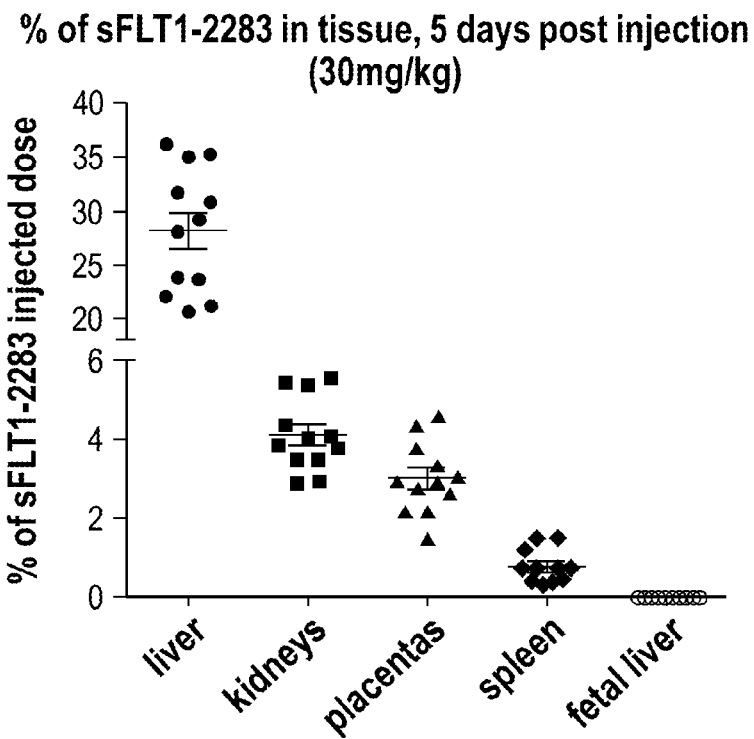
Figure 16E:
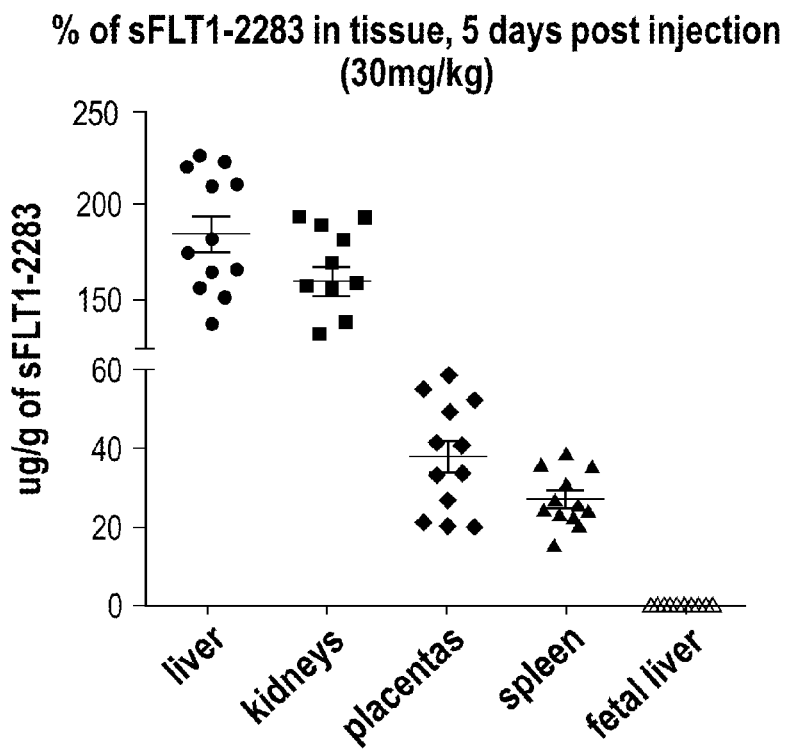
Figure 17A:
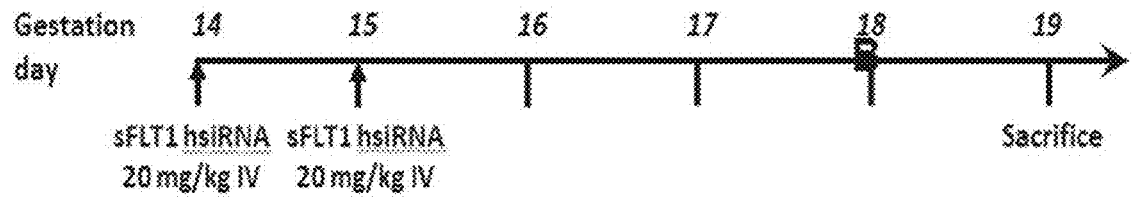
FIGS. 17A-17D depict efficient silencing of sFLT1 by hsiRNA in pregnant nice (CD1). (A) Depicts a timeline of the experiment. (B) Depicts msFlt1-1 levels protein detected in plasma as a function of days into pregnancy. (C) Is a table of mother mouse weight gains and pup weights and mortality data. (D) Depicts graphs showing AST and ALT levels at day 19.
Figure 17B:
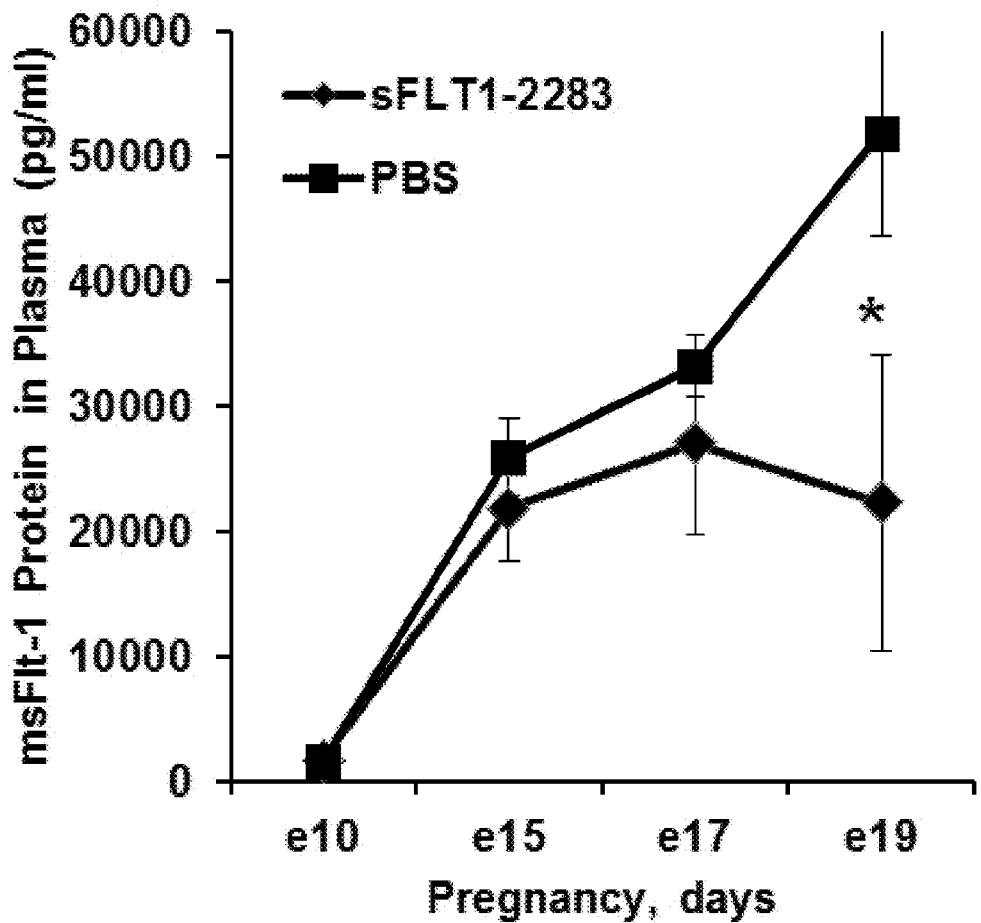
Figures 17C, 17D:
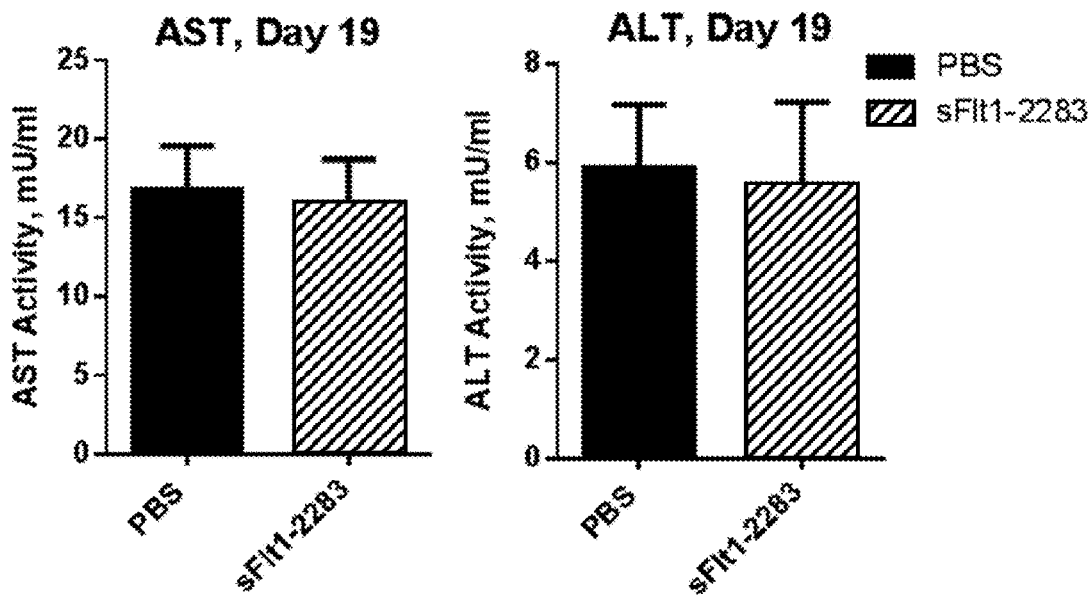

Histological evaluation of hsiRNA distribution in mouse placental tissues was performed (FIG. 15). Efficient silencing of sFLT1 by hsiRNA was observed in liver, kidney and placental tissues of pregnant CD1 mice (FIGS. 16A-16E, FIGS. 17A-D).

Figure 29:
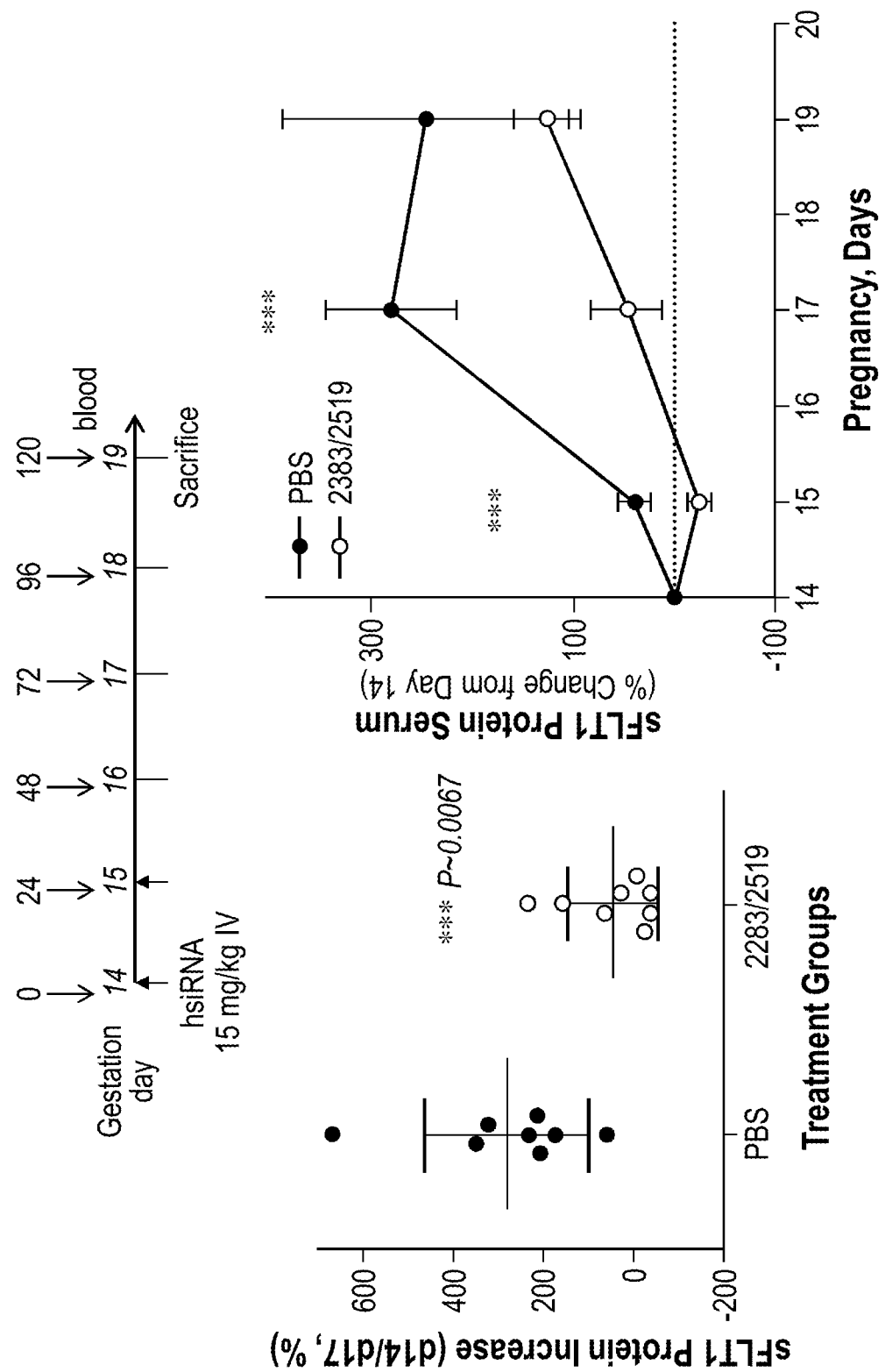
FIG. 29 depicts soluble sFLT1 protein modulation in pregnant mice using single injections of sFLT1 2283/2519 (10 mg/kg each). sFLT1 protein levels at day 14/day 17 are shown in the left graph. sFLT1 protein levels in the serum as a function of pregnancy days are shown in the right graph.

Soluble sFLT1 protein modulation was detected in the serum of pregnant mice after a single IV injection (10 mg/kg) of sFLT1_2283/2519 at days 14, 15, 17 and 19 (FIG. 29). There were no observable negative effects, nor were there any observable deviations in weight, ALT values, AST values or number of pups per pregnant mouse.

In summary, these data indicate that a novel siRNA chemistry has been developed that has enabled efficient delivery to placental trophoblasts, the primary site of sFLT1 overexpression during PE, and has allowed potent silencing of circulating sFLT1 upon systemic administration.

Example 4. Chemistry and Optimal Dosing, Pilot PK/PD, and Duration of Effect of 2283 in a Wild-Type Pregnant Mouse Model 4.1. Chemistry Optimization Although the modification patterns showed efficient delivery to cytotrophoblasts within the placental labyrinth (FIGS. 4, 5, 7 and 8), two additional chemistry issues will be addressed: 1) further optimization of phosphorothioate (PS) content and 2) further stabilization of the 5'-terminal phosphate of the guide strand.

Phosphorothioate (PS) Content

While PS linkages generally confer greater in vivo siRNA stability, extensive phosphorothioation can induce greater class specific toxicity (although only upon prolonged administration at high dose) (Frazier, K. S. Antisense Oligonucleotide Therapies: The Promise and the Challenges from a Toxicologic Pathologist's Perspective. *Toxicologic pathology* 43, 78-89 (2015)). Although the P2 chemistry (FIG. 8) is expected to be much more stable over long time periods (i.e., weeks, as has been shown for GalNac conjugates) (Nair, J. K. et al. Multivalent N-Acetylgalactosamine-Conjugated siRNA Localizes in Hepatocytes and Elicits Robust RNAi-Mediated Gene Silencing. *Journal of the American Chemical Society* (2014)) than P1, pilot studies showed no significant difference between sFLT1-2283-P2 and sFLT1-2283-P1 with regard to placental accumulation at 24 hours (FIG. 8). It was therefore suspected that the optimal PS content (enough to maintain stability and efficacy but minimize toxicity) lies somewhere between P1 and P2. Synthesis of several additional variants is planned. The concentrations of full-length species in placentas 24 hours and 5 days post administration, and relative distributions at the injection site and in liver, kidney and placenta will be determined, and the Maximum Tolerated Dose (MTD) upon single administration will be established. Based on these data, a PS pattern will be selected and used for all subsequent studies.

5'-Terminal Phosphate Stabilization

The second issue is how best to optimize 5'-terminal phosphate stabilization of the guide strand, which strand is necessary for RISC loading. The PNA-based hybridization assay that was used allowed efficient separation of phosphorylated and dephosphorylated guide strands, has revealed that more than 70% of sFLT1-2283-P2 guide strand detectable in the liver 5 days post injection is dephosphorylated. Without intending to be bound by scientific theory, it is likely that introduction of metabolically stable 5'-(E)-vinylphosphonate (5'-VP) (Lima, W. F. et al. Single-stranded siRNAs activate RNAi in animals. *Cell* 150, 883-894 (2012)) or 5'(R)Me-P, both chemistries with conformation and sterioelectronic properties similar to the natural phosphate, instead of 5' phosphate might potentially reduce the effective dose (and thus drug cost and any class limiting toxicity) by more than three-fold. sFLT1-2283 will be synthesized with a 5'-VP and 5'(R)Me-P on the guide strand (routinely done at Dr Khvorova lab) and evaluate its impact on oligonucleotide efficacy, placental delivery and safety. The toxicity profiles of 2'-O-methyl, 2'-fluoro, cholesterol and PS are well understood. Completion of this analysis should finalize chemical configuration (PX) of the preclinical candidate oligonucleotides for the treatment of PE.

4.2. Midscale Oligonucleotide Synthesis

Using the chemistry selected in Aim 1.1, sFLT-i13-2283-PX will be synthesized, HPLC purified and Quality Controlled (QC'ed) by mass spectrometry. For all in vivo studies, compounds will be desalted, complexed with sodium counter-ion, and checked to ensure that endotoxin levels are acceptable. The oligonucleotides were previously synthesized using Expedite and Mermaid 8 systems and purified via Agilent mid-scale HPLC. The current synthesis capacity is 40 µmol of compound/week, resulting in 0.2 gram after HPLC purification. This range is sufficient to perform all planned mouse studies (as reference, a 10 mg/kg dose corresponds to 0.4 mg/mouse/injection for 40 gram pregnant animals). In anticipation of needing increased synthesis capacity for non-human primate studies, a mid-scale OligoPilot synthesizer and high resolution LC-MS will be utilized, which will also decrease costs of oligonucleotide synthesis.

4.3. Pilot Pharmacokinetics (PK), Pharmacodynamics (PD), No Observed Adverse Effect Level (NOAEL), and Maximum Tolerated Dose (MTD) Measurements for sFLT-i13-2283

All animal studies will be performed under IACUC protocols. In design of all experiments, the standards recommended by Landis (Landis, S. C. et al. A call for transparent reporting to optimize the predictive value of preclinical research. *Nature* 490, 187-191 (2012)), including proper group randomization, blinding and study powering, will be followed. The development of PNA based chromatographic assay enables one the ability to quantitatively evaluate oligonucleotide distribution and define pilot PK. For pilot PK studies, n-3 is sufficient. For efficacy and duration of effect studies where the readout is reduction in sFLT1 variants mRNA and protein levels, n-8 is minimally necessary to power the study for detection of 40% modulation with 80% confidence.

For the pilot PK analysis, blood concentration dynamics will be explored. 20 µL blood samples will be collected at 5, 30, and 60 min, 4, 12, 24, 48, 72 and 96 hours post-injection. Short time points will be obtained by jugular vein catheterization, eliminating IACUC concerns regarding repetitive blood draws over short time periods and minimizing the number of animals required to obtain tight data. Based on previous PK studies with related compounds, it is expected that biphasic clearance kinetics will be observed, with the fast phase complete by 1 and 4-6 hours for IV and SC administration, respectively. Based on the pilot studies showing that >50% of the originally delivered dose persisted in tissues even 5 days post injection, it might take a month for complete drug clearance, but a week-long study would be sufficient to generate pilot data allowing estimation of the clearance profile.

In addition, NOAEL and MTD will be established for the lead compound. So far, administration of 10 mg/kg and 20 mg/kg sFLT1-2283-P2 to pregnant mice had had no observable negative impact other than a slight decrease in fetus number at 40 mg/kg. As approximately 50% of the injected dose (FIG. 4B) went to liver endothelium and kupffer cells, it is reasonable to expect modulation of liver enzymes with ALT and AST used as a standard readout. ALT/AST levels will be measured (assays in place as part of the animal care core) at different sFLT1-2283-PX concentrations and at different times after injection. This assay can be easily combined with dose response efficacy studies as it is non-invasive and requires only 10 µL of blood.

MTD will be established in both pregnant and non-pregnant mice. In non-pregnant mice, the pilot studies indicated that the sFLT1-2283-P2 MTD range was expected to be higher than 100 mg/kg. In pregnant mice, however, the NOAEL dose level might be lower. It is expected that the NOAEL dose will be much higher than the expected efficacious dose of 1 mg/kg based on drug levels achievable in the placenta. 1 mg/kg is in line with concentrations used for the ALN-TTR2 compound in phase II clinical trials.

Oligonucleotide-related toxicity may be due to target-specific effects (sFlt1 related) or target-independent effects (related to the siRNA sequence or formulation). Target specific effects will be evaluated in mice administered the lead compound during the 3rd trimester by assessing fetal number, weight and growth as well as miscarriage frequency. Placental histology will assess trophoblast and vascular density. Uterine artery and umbilical artery blood flows will be evaluated using non-invasive Doppler studies (Zhang, J. H. & Croy, B. A. Using Ultrasonography to Define Fetal-Maternal Relationships: Moving from Humans to Mice. *Comparative Med* 59, 527-533 (2009)). In addition, mice treated with the NOAEL and MTD dose will be allowed to deliver and the pups followed for two generations to evaluate potential impact on overall health and reproductive function.

Figure 7C:
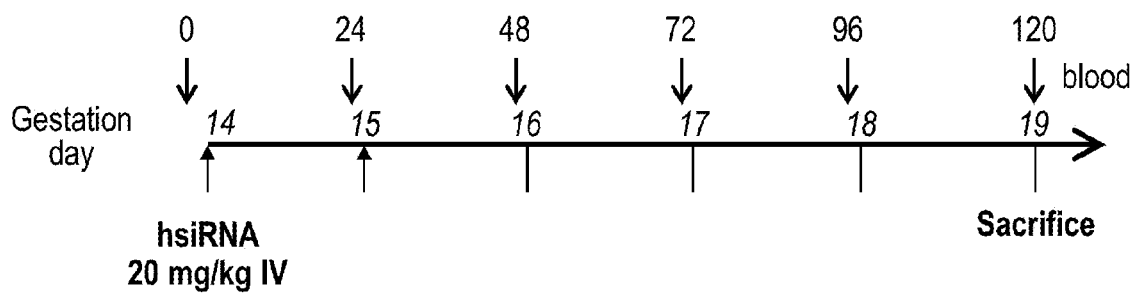
Figure 7D:
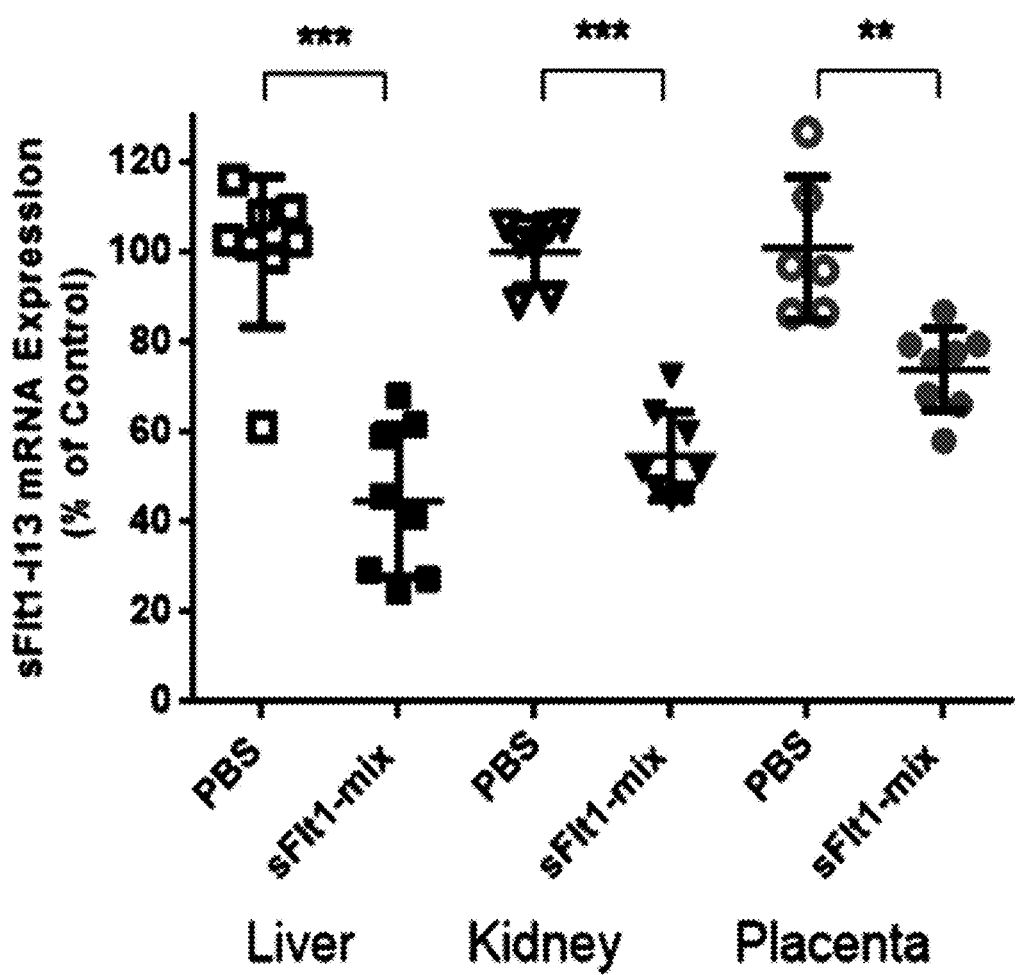

For PD studies, a dose response study will be performed with doses ranging from 0.5 to 10 mg/kg. sFLT1 protein levels will be measured with ELISA (blood kinetics) and sFlt1 and fl-Flt1 mRNA levels will be measured with QuantiGene in placenta, liver and kidney. Preliminary studies showed that a single administration of sFLT1-i13-2283-P2 was sufficient to induce silencing of sFLT1 in all targeted tissues (FIG. 7B) with no effect in embryos livers. In vivo validation of sFLT1_2283/2519 is shown in FIG. 7C. The effect duration will be analyzed at both the highest NOAEL and lowest efficacious dose. Unfortunately, mice might not be an optimal model for these studies, as sFLT1 is barely expressed in non-pregnant mice and pregnant mice do not allow for PD evaluation at times longer than 2 weeks. To evaluate the potential for longer duration studies, hsiRNAs sharing exactly the same chemistry that target TEK tyrosine kinase (Tie2) mRNA, an endothelial specific target, will be utilized. Tie2 silencing will be examined in liver endothelium 1, 2, 3, 4 weeks after a single administration. If silencing does not persist for more than 3 weeks, multiple dosing will be explored to address the issue. While the PK/PD behavior of different sequences is not identical, it is similar (H. Youths et al. in A Comprehensive Guide to Toxicology in Preclinical Drug Development. (ed. A. S. Faqi) 647-664 (Academic Press, 2013)), and effect duration data with Tie2 compounds might be informative for design of NHP efficacy studies.

This study will result in chemical configuration finalization and establish the dose response, pilot PK, NOAEL and MTD for sFLT1-2283 in non-pregnant and normal pregnant mice. This information will be critical for further planning of IND-enabling toxicology studies.

4.4 Pilot Safety and Toxicity of i13/i15 Combination.

The current pre-clinical candidate is defined as a mixture of hsiRNAs targeting all i13 and i15 variants. Both compounds may be re-synthesized based on the most optimal chemical composition identified above. If the compounds are re-synthesized, it will be essential to demonstrate that the i13/i15 mixture has a similar safety profile to targeting the i13 variant alone. Experiments to determine the NOAEL and MTD for the mixture of compounds will be repeated using AST/ALT readouts as measures of toxicity. In addition, similarity in PK behavior will be confirmed for i15 and i13 targeting compounds using i13 and i15 targeting PNA-based probes. It is impossible to evaluate PD of i15 in the mouse model as i15 variants are not expressed there. Without intending to be bound by scientific theory, it is believed that having similar in vitro (i.e., trophoblast) efficacy in combination with similar PK profiles will be sufficient to predict similar efficacy. This will be confirmed in a baboon pregnancy model where both i13 and i15 variants are expressed.

4.5 Quantitatively Assess hsiRNA Transfer (if any) to the Fetus

The major safety concern in developing any therapeutic for treatment of pregnant women is fetal safety and potential negative impact on embryo development. In the preliminary data presented herein, no detectable transfer of sFLT1-2283-P2 to the fetus was observed (FIGS. 6A and 4B) either by fluorescent microscopy and PNA hybridization. Nor was any change in fetal sFLT1 expression observed in a drug-treated group of animals. At doses up to 20 mg/kg, no impact was observed on fetus weight or numbers, and no impact on overall placenta histology was observed. A slight decrease in fetus numbers (from average of 7 to 6) was observed at a maximal dose of 40 mg/kg. In spite of this encouraging data which makes this project so promising, it is important to quantitatively analyze any potential drug transfer and impact on the placenta and fetus in detail. To do so, a PNA hybridization assay will be used to detect oligonucleotides in different embryo tissues. As mentioned above, the sensitivity of the assay is approximately 10 (mole/gram, lower than biologically efficacious concentrations. The level of potential oligonucleotide transfer will be measured after administration of different concentrations of oligonucleotide up to MTD. These experiments will also be repeated using PE models, as the integrity and health of placenta might impact the barrier ability.

One concern particular to siRNA therapeutics is the potential for even a small amount of transferred oligonucleotide to interfere with miRNA homeostasis. miRNA profiles change rapidly during embryo development and are essential for proper execution of the development program. Previously, altered miRNA profiles were seen only after months long virus-based overexpression of a particular siRNA (Grimm, D. et al. Fatality in mice due to oversaturation of cellular microRNA/short hairpin RNA pathways. *Nature* 441, 537-541 (2006)). Cell-specific miRNA signatures are highly dynamic during embryonic development, thus potentially more sensitive than adult tissues to external RISC loading substrates. To examine this possibility, RNA will be purified from full fetuses, fetal brain and fetal liver from untreated and MTD-dosed pregnant mice and perform small RNA-Seq. This will enable: (1) evaluation of the number of reads corresponding to the hsiRNAs in these tissues and (2) evaluation of impact (if any) on endogenous miRNA profiles.

Example 5. Additional PE Models 5.1 Demonstration of Efficacy of sFLT1 Oligonucleotide in Two Models of Preeclampsia While reduction in sFLT1 levels supports mechanistic efficacy of the lead, it would be desirable to demonstrate that sLFT1 reduction has an impact on the "preeclampsia-like" phenotype. While there are descriptions of several animal models of preeclampsia in the literature, no single model recapitulates all aspects of the clinical syndrome, and none of them accurately models progression of the disease from preeclampsia to more serious complications such as HELLP syndrome or eclampsia (Aubuchon, M., Schulz, L. C. & Schust, D. J. Preeclampsia: animal models for a human cure. *Proceedings of the National Academy of Sciences of the United States of America* 108, 1197-1198 (2011)). Thus, there is as yet no perfect model for the human disease. Because mice and rats have relatively shallow placentation, rodent models are not optimal for studying the upstream causes of poor trophoblast invasion. On the other hand, this feature makes them ideal for evaluating the downstream pathophysiology and etiology of the maternal response to shallow placentation, an established driver of human preeclampsia (Powe, C. E., Levine, R. J. & Karumanchi, S. A. Preeclampsia, a disease of the maternal endothelium: the role of anti-angiogenic factors and implications for later cardiovascular disease. *Circulation* 123, 2856-2869 (2011)). Since the overall goal of this invention is to knockdown sFlt1 in human pregnancies, mouse models (uterine ischemia and whole animal ischemia) that have been reported to have elevated circulating sFlt1 were chosen. Relative hypoxia and ischemia have both been reported to induce sFlt1 production in human placental cultures in vitro and in various animal models (Nagamatsu, T. et al. Cytotrophoblasts up-regulate soluble fms-like tyrosine kinase-1 expression under reduced oxygen: an implication for the placental vascular development and the pathophysiology of preeclampsia. *Endocrinology* 145, 4838-4845 (2004); Makris, A. et al. Uteroplacental ischemia results in proteinuric hypertension and elevated sFLT-1. *Kidney international* 71, 977-984 (2007); Gilbert, J. S., Babcock, S. A. & Granger, J. P. Hypertension produced by reduced uterine perfusion in pregnant rats is associated with increased soluble fms-like tyrosine kinase-1 expression. *Hypertension* 50, 1142-1147 (2007)).

5.2 Telemetry Surgery

Female CD1 pregnant mice weighing 20-25 grams will be purchased from Charles River Laboratories. The advent of miniaturized, surgically implantable radiotelemetry probes suitable for chronic hemodynamic monitoring of small laboratory animals has significantly advanced physiologic research and is important in preeclampsia research as the technique allows one to measure blood pressure throughout gestation (Burke, S. D. et al. Spiral arterial remodeling is not essential for normal blood pressure regulation in pregnant mice. *Hypertension* 55, 729-737 (2010)). Briefly, female CD-1 mice weighing over 20 g will be anesthetized using inhaled isoflurane. A 1 cm midline incision is made on the ventral surface from the sternal notch rostrally. The left common carotid artery is isolated and occluded using sutures. The artery is incised with a 26 gauge needle and the telemetry catheter (DSI, St. Paul, Mich.) is advanced into the artery; the tip is placed just within the arch of the aorta. The catheter is sutured into place, permanently occluding the artery. The body of the transmitter is placed into a subcutaneous pocket on the right flank of the mouse. The wound is sutured and the mouse is monitored until recovered. Animals will be provided with analgesia for 48 hours post-operative and monitored for 1 week. Two weeks after recovery, animals will be mated with male stud mice of the same background to study pregnancy phenotypes as described below.

5.3 Reduced Uterine Perfusion Pressure (RUPP) Model of Placental Ischemia

Theo RUPP model of placental ischemia in pregnant CD1 mice that was pioneered by Barbara Alexander Laboratory at the University of Mississippi will be used (Intapad, S. et al. Reduced uterine perfusion pressure induces hypertension in the pregnant mouse. *American journal of physiology. Regulatory, integrative and comparative physiology* 307, R1353-1357 (2014)). This animal model of preeclampsia involves placement of silver constriction clips on the abdominal aorta and above the uterine arteries to reduce uterine perfusion pressure on gestational day 14, creating placental insufficiency. Animals will be given either sFLT1 oligonucleotide drug (using dose level and route of administration defined supra) or control (PBS or/and NTC) on gestational day 16 via tail vein injection. Blood pressures will be measured continuously using telemetry from gestational day 15-19 and animals will be sacrificed on gestation day 19. In addition, urine samples will be collected by placing the mice in metabolic cages for 12 hours prior to sacrifice.

5.4 Hypoxia Model of Preeclampsia

The hypoxia model that has been pioneered by Surendra Sharma laboratory at Brown University will also be used. Id. In this model, pregnant CD1 mice that have been implanted with a telemeter will be exposed to hypoxia (9.5% oxygen, exposed for 10 days) in a hypobaric chamber from gestational day 9-19. Animals will be given either therapeutic sFLT1 oligonucleotide dissolved in PBS (2 doses) or vehicle (PBS) on gestational day 16 via tail vein injection. Blood pressures will measured continuously using telemetry from gestational day 15-19 and animals will be sacrificed on gestation day 19. Urine samples will be collected as described above.

Preeclampsia Phenotypes

Measurements of blood pressures will be performed in conscious mice using telemetry probe implanted into the carotid artery (DSL, St. Paul, Minn.). (See pilot studies in FIG. 9A.) Renal tissue will be examined histologically for quantification of glomerular endotheliosis as described (Li, Z. et al. Recombinant vascular endothelial growth factor 121 attenuates hypertension and improves kidney damage in a rat model of preeclampsia. *Hypertension* 50, 686-692 (2007)). Tissue will be fixed in 10% buffered formalin, embedded in paraffin, sectioned, and stained with H&E, PAS, and Masson's trichrome stain. Serum and urinary creatinine (measured by picric acid calorimetry) and urinary protein (measured by ELISA) during pregnancy (gestational day 18-19) will be measured to evaluate for proteinuria. In addition, hematocrit and platelet count will be measured on gestational day 18-19. Peripheral smears will be performed using whole blood obtained from these rats to look for evidence of hemolysis. Serum AST and ALT will be measured by kinetic UV method (Infinity Liquid, Thermo Electron Corp). Plasma levels of sFlt1 will be measured by commercially available ELISA (R & D Systems, MN).

Placental/Fetal Studies

Figure 9B:
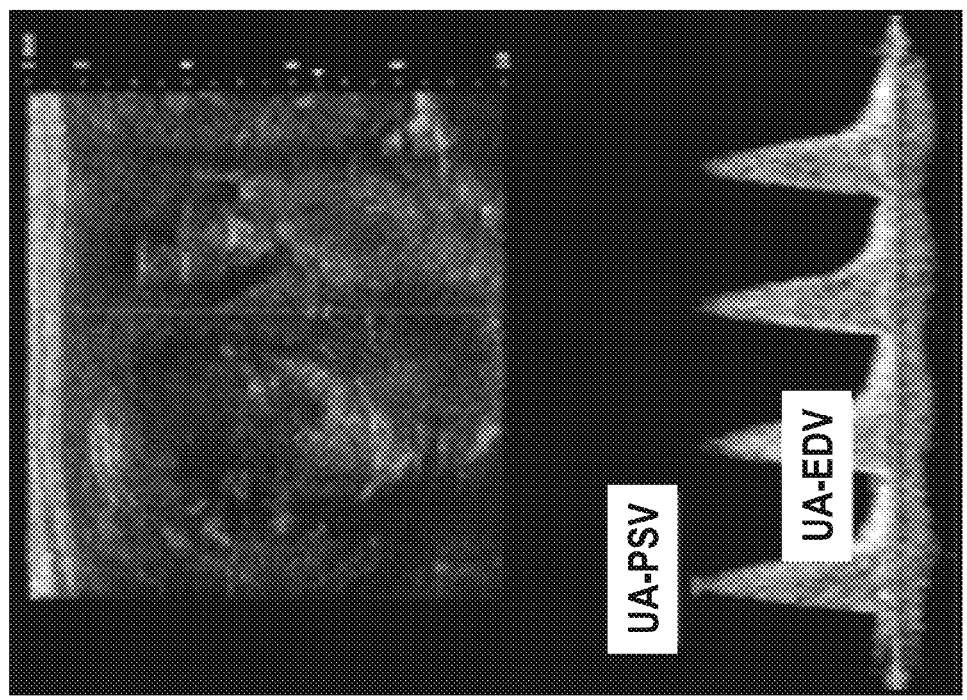
FIGS. 9A-9B depict sFlt1 therapy in mice. (A) Show that sFlt1 therapy in mice induces hypertension (measured using radiotelemetry in conscious mice) and glomerular endotheliosis in the kidney (swollen glomeruli and capillary occlusions). (B) Depicts Doppler ultrasound studies during a normal mouse pregnancy at late gestation to evaluate umbilical flow. A waveform was obtained showing the Peak Systolic Velocity (PSV).
Figure 9A:
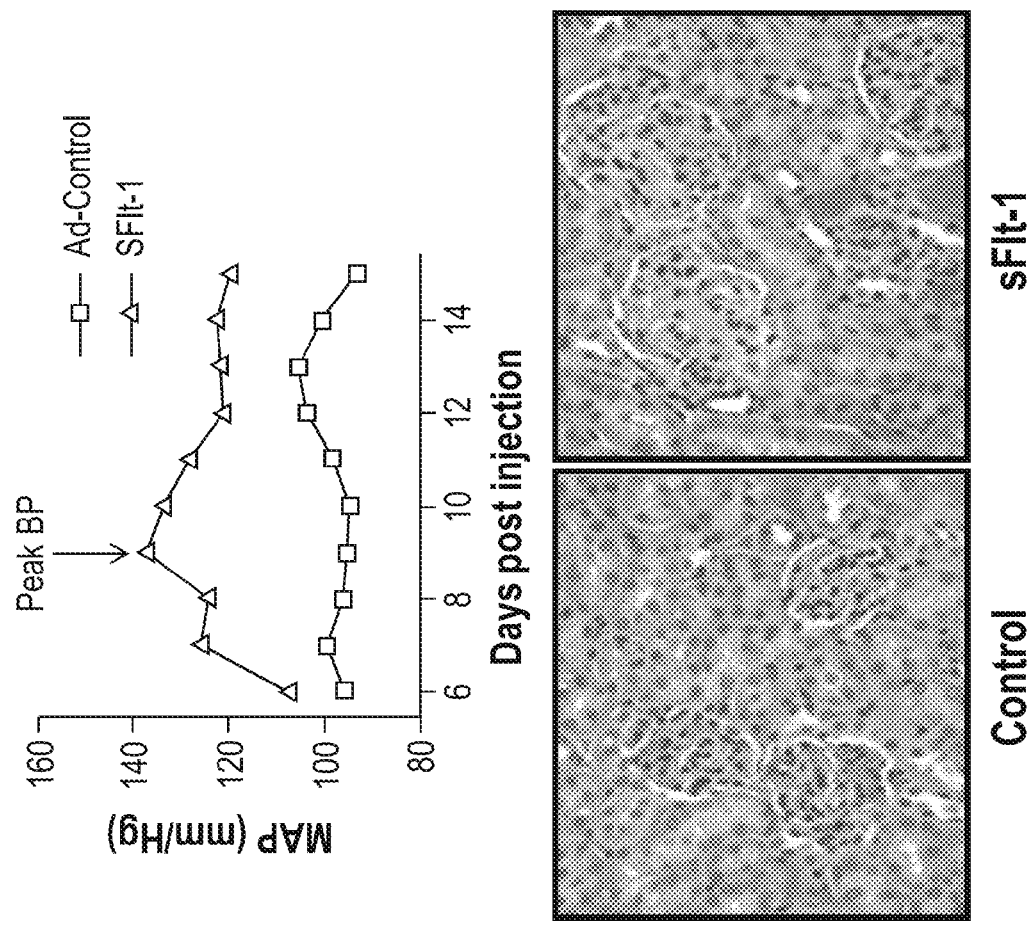
Figure 10:
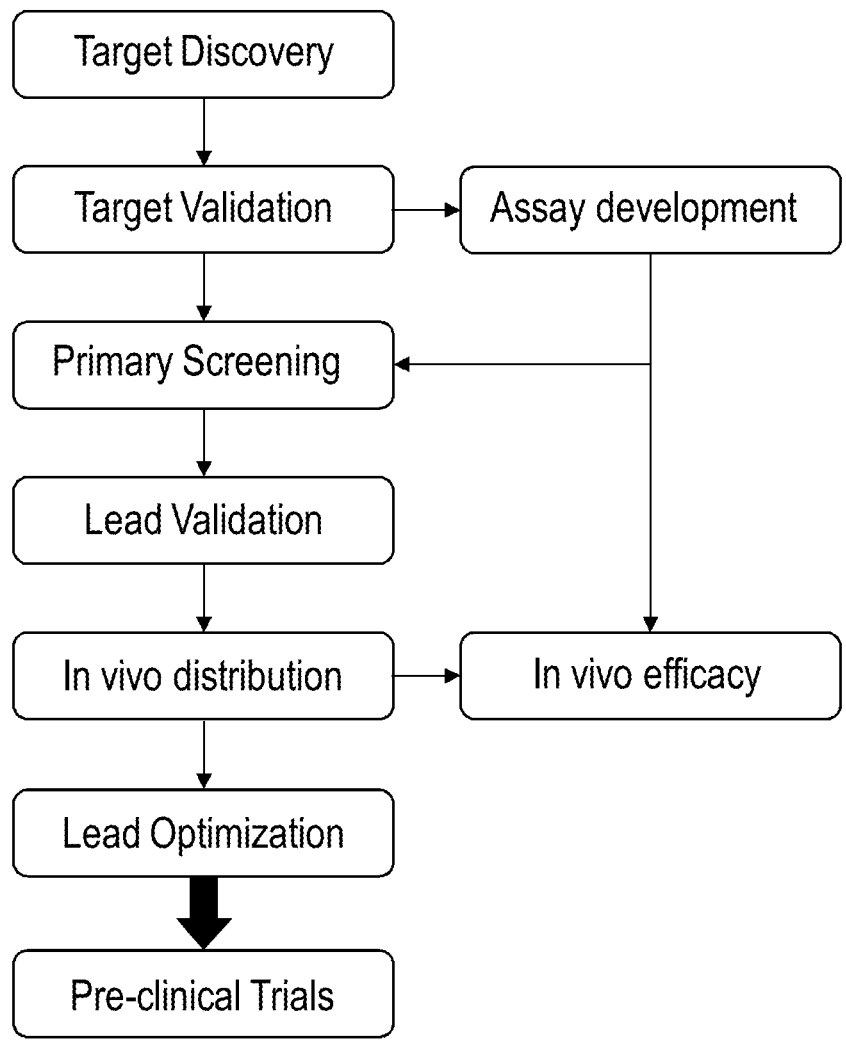
FIG. 10 depicts a flow chart showing steps for developing therapeutics (e.g., therapeutic RNAs) for the treatment of preeclampsia and/or eclampsia.
Figure 11:
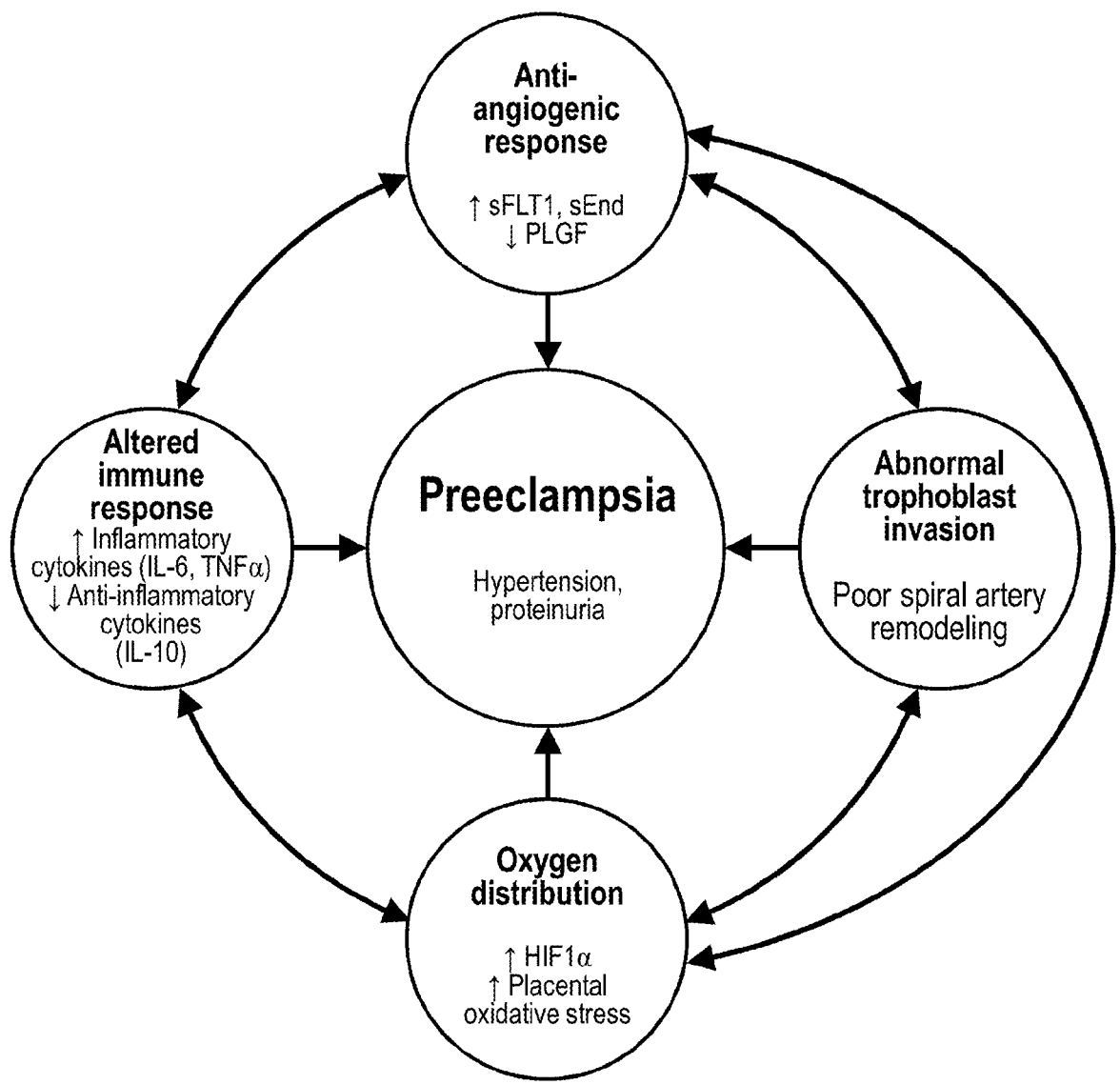
FIG. 11 schematically depicts factors associated with preeclampsia.

Ultrasound Doppler will be used to evaluate uterine and umbilical flows at gestational day 18-19 as described elsewhere (Khankin, E. V., Hacker, M. R., Zelop, C. M., Karumanchi, S. A. & Rana, S. Intravital high-frequency ultrasonography to evaluate cardiovascular and uteroplacental blood flow in mouse pregnancy. *Pregnancy hypertension* 2, 84-92 (2012)). Mice will be anesthetized using Isoflurane/O$_2$ mixture administered with a precision vaporizer. Mice will be placed in a supine position on heated stage of Vevo 2100 Ultrasonography Apparatus (Visual Sonics Inc. Toronto, Ontario CA) and a rectal temperature probe will be inserted to monitor core temperature throughout the procedure. Abdominal organs will be scanned and the uterine artery will be identified. Once the position is verified, pulse wave Doppler will be used to visualize blood flow pattern and measure flow velocity in the uterine artery. Ultrasound evaluation will be done on at least 4 embryos per animal: two in each horn. Measurements that will be taken include Fetal Heart Rate (FHR), Umbilical Artery Doppler (UA Doppler), Uterine Artery Doppler (Ut. A Doppler) and Abdominal Circumference (AC) (FIG. 9B). Litter sizes and resorptions will be scored when animals are sacrificed at gestational day 19. Birth weights will be recorded for evidence of fetal growth restriction. Implantation sites with placentas will be fixed in 4% paraformaldehyde and will be examined histopathologically for evidence of abnormal spiral artery remodeling, a feature of abnormal placentation (Cui, Y. et al. Role of corin in trophoblast invasion and uterine spiral artery remodelling in pregnancy. *Nature* 484, 246-250 (2012)).

Sample Size and Statistical Comparisons

For each of the studies proposed, approximately 10 animals will be used per group: control, low dose sFlt1 oligonucleotide and high dose oligonucleotide. Standard statistical analyses will be performed on all the animal data. Individual values will be collated as means+/−S. E. M. Comparisons among multiple groups will be made by an initial analysis of variance, and Student's t-test will be used to evaluate differences between individual groups. Hemodynamic data will be analyzed using 24 hour means from individual animals data, which will be compared using two-way repeated measures ANOVA. Where significant differences are indicated (p<0.05), Bonferroni's post-hoc test will be used to evaluate differences among individual groups.

5.5 Interpretation, Pitfalls and Alternatives.

Without intending to be bound by scientific theory, it is expected that the sFLT1 oligonucleotide therapy will lead to an approximately 50% reduction in circulating sFLT1 levels, which will be associated with improvement in preeclampsia phenotypes such as resolution of hypertension and improvement in renal pathology.

It is not expected that there will any adverse consequences to fetal growth or placentation. Genetic knock-down studies by Rossant's group have suggested that placental sFlt1 is not critical for the maintenance of pregnancy (Hirashima, M., Lu, Y., Byers, L. & Rossant, J. Trophoblast expression of fms-like tyrosine kinase 1 is not required for the establishment of the maternal-fetal interface in the mouse placenta. *Proceedings of the National Academy of Sciences of the United States of America* 100, 15637-15642 (2003)). However, since sFlt1 will be knocked down systemically, it is possible that there may be adverse consequences, such as decreases in fetal growth related do significant drop in blood pressures. If greater than a 20 mm drop in blood pressures is not observed, these efficacy studies will be repeated with a lower dose of the sFLT1 oligonucleotide. Furthermore, with non-invasive ultrasound Doppler, even subtle changes in blood flow to the fetus can be recorded. If robust expression of endogenous sFlt1 levels in response to hypoxia is not observed during the $3^{rd}$ trimester, the studies could be repeated in IL-10 deficient mice which have been shown by Sharma's group to upregulate sFlt1 during third trimester quite dramatically (Intapad, S. et al. Reduced uterine perfusion pressure induces hypertension in the pregnant mouse. *American journal of physiology. Regulatory, integrative and comparative physiology* 307, R1353-1357 (2014)). Completion of this aim will evaluate efficacy and safety of RNAi-based sFLT1 reduction in two models of PE.

Example 6. Evaluation of PK and Efficacy and Safety in Pregnant Baboons During Late Gestation in a Pilot Study 6.1 Rationale Because mice only express one of the isoforms of sFlt1, it is important to evaluate the in vivo efficacy of sFlt1 oligonucleotide(s) in non-human primates that express all the sFlt1 isoforms (Makris, A. et al. Uteroplacental ischemia results in proteinuric hypertension and elevated sFLT-1. *Kidney international* 71, 977-984 (2007); Thomas, C. P. et al. A recently evolved novel trophoblast-enriched secreted form of fms-like tyrosine kinase-1 variant is up-regulated in hypoxia and preeclampsia. *The Journal of clinical endocrinology and metabolism* 94, 2524-2530 (2009)). Baboons have been chosen over other non-human primates because of access to well characterized model of preeclampsia that has been pioneered by Dr. Annemarie Hennessy (Makris, A. et al. Uteroplacental ischemia results in proteinuric hypertension and elevated sFLT-1. *Kidney international* 71, 977-984 (2007)).

6.2 Baboon Pregnancy Model

Due to ethical constraints to minimize the number of animal subjects, six pregnant baboons (2 groups×3 animals) will be used. At 20 weeks of gestation, (equivalent to gestation time at which human PE occurs), all six animals will undergo telemetry surgery to measure intra-arterial blood pressure as previously described. Id. Briefly, an inguinal incision is made in the skin to expose the profunda femoris, a small branch of the main artery supplying the leg, via blunt dissection. The catheter component of the telemeter (Data Sciences Ltd, Minnesota, USA) is inserted into a tributary of the femoral artery on the selected side and placed a set distance into the mid-abdominal aorta and secured to the vessel. Post-surgical recovery is assessed by scoring a number of different physical and behavioral signs, and is carried out and recorded on a daily basis for three days prior to the commencement of blood pressure recordings. For anesthesia, animals will be provided with oxygen via facemask and anesthetized by ketamine infusion, and metoclopramide to prevent emesis. At 22 weeks of gestation, animals will be injected intravenously with 4 mg/kg body weight of a single dose of sFLT1 oligonucleotide in phosphate buffered saline (N=3) or phosphate buffered saline alone (N=3) under anesthesia.

Figure 30:
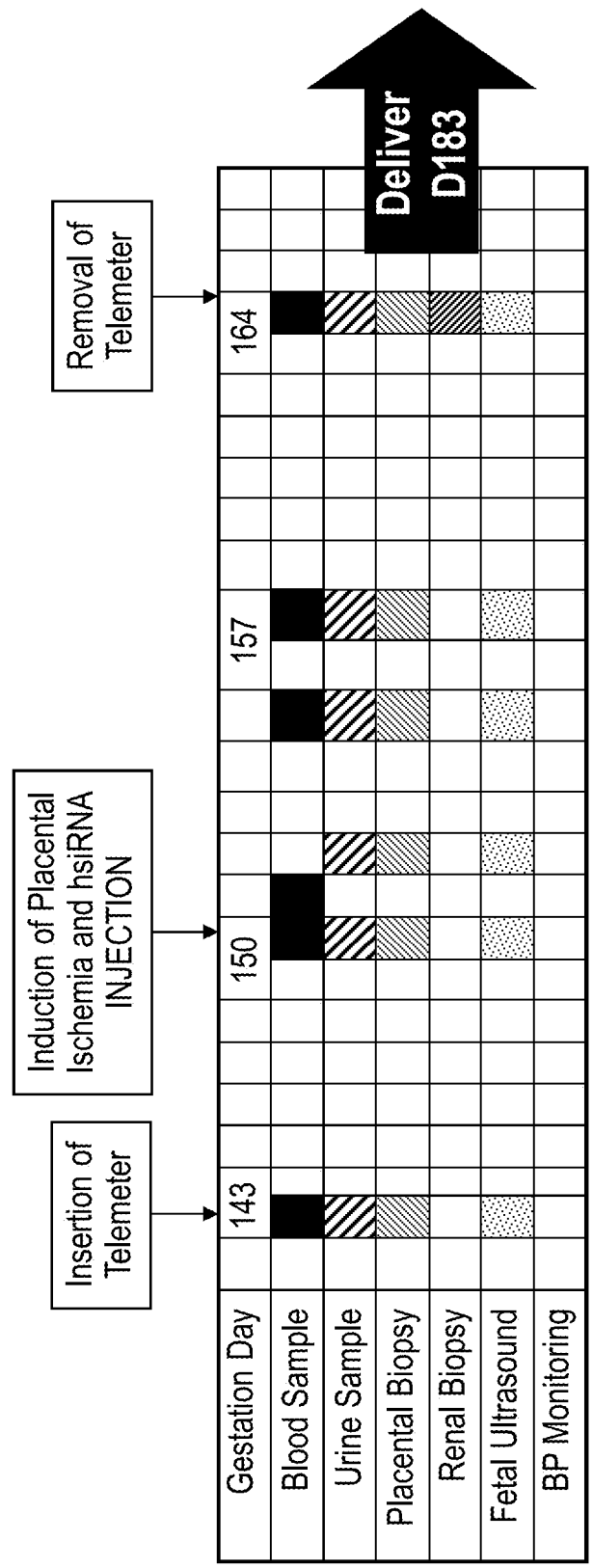
FIG. 30 depicts a schematic of a baboon (*Papio hamadryas*) PE model for studying sFLT1_i13_2283P2/sFLT1_e15a_2519P2 efficacy and safety using wild-type baboons with PE induced via uteroplacental ischemia (UPI).

A baboon PE model was developed (FIG. 30). The baboon PE model will be used to test efficacy (PK) and general safety of administration of sFLT1-targeting hsiRNAs. A pilot evaluation of single dose injection of sFLT1-i13/e15a targeting hsiRNAs on sFLT1 blood levels and sFLT1 mRNA levels in kidney and placental tissues will be performed. A telemeter will be inserted at day 143. Placental ischemia will be induced and hsiRNA will be injected at day 150. Removal of the telemeter will occur at day 164.

Figure 37:
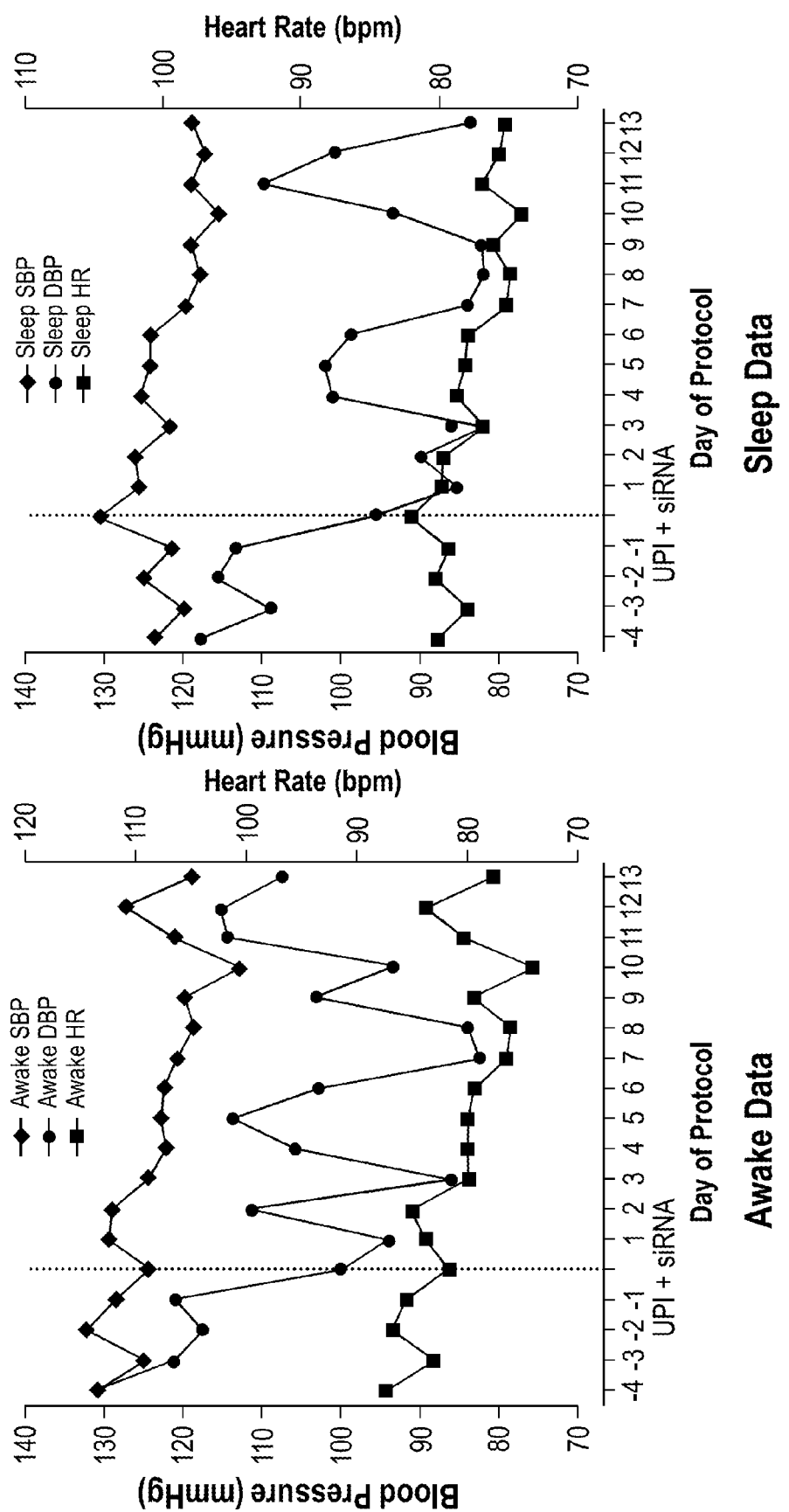
FIG. 37 depicts data from a baboon PE model showing stabilization of blood pressure in the animal.
Figure 38:
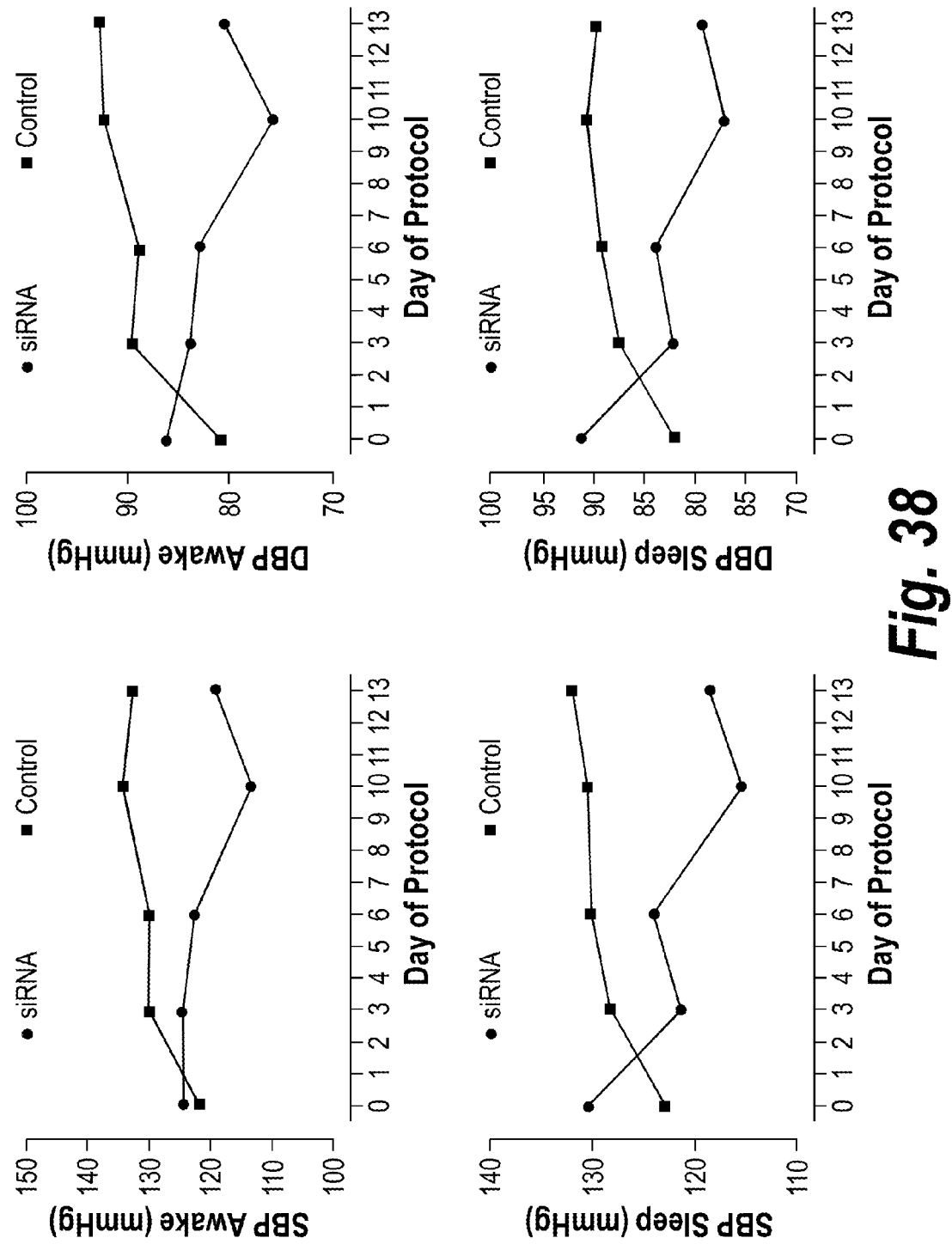
FIG. 38 depicts data from a baboon PE model showing a decrease of blood pressure in the animal.

The first baboon was injected on day one using 20 mg/kg hsiRNA$^{sFLT1m}$. No observable toxic or adverse effects were noted during the first two weeks. Initial ALT/AST levels and cytokine panels were normal, and blood pressures were normalized. Stabilization of the blood pressure (BP) was observed after hsiRNA injection (2 weeks study) (FIG. 37). Positive dynamics were observed for BP and HR for both awake and sleep conditions. A decrease of BP was observed after a single IV hsiRNA injection (2 weeks study) (FIG. 38).

Baboons two and three are scheduled for injection one to two months after the first baboon was initially injected.

6.3 Plasma sFlt1 Levels and Other Physiological Parameters

Baseline levels of sFlt1 will be obtained from plasma collected on the day of telemeter insertion and weekly, until delivery at 26 weeks. Urine samples will also be collected on the same days that blood is drawn. Baseline blood pressure will be continuously recorded via telemetry from gestational week 21 until delivery. Animals will be monitored using fetal ultrasounds (HDI 3000 instrument and C7-4 probe, or similar) weekly for determining uterine and umbilical blood flows, fetal health (fetal heart rate) and growth measurements (head circumference, biparietal diameter, abdominal circumference, femur length) until delivery. At delivery, cord blood will be collected to evaluate for transfer of sFLT1 oligonucleotide across to the fetus. At delivery, growth assessments will be made by measurements of head and chest circumference, abdominal girth, crown-to-rump and femur lengths. These measurements will be compared against those obtained from newborns of saline treated animals.

6.4 Interpretation, Pitfalls and Alternatives

In these pilot studies, the goal is not to find the optimal therapeutic dose for treatment of preeclampsia, but to simply confirm that sFLT1 oligonucleotide therapy inhibits other isoforms of sFLT1 that are not expressed in mice. Without intending to be bound by scientific theory, it is expected that a single IV dose of sFLT1 oligonucleotide will decrease circulating sFLT1 by 50% within a week and that the effects will last for 2 weeks or longer. It is expected that decreases in circulating sFLT1 will be associated with modest reduction in blood pressure. However this will not impair uterine arterial blood flow. If decreases in fetal growth are observed, lowering the dose of sFLT1 oligonucleotide therapy may be considered. Alternately, delivering the therapy as a single dose SQ (which may cause less acute effects on the uterine arterial blood flow) may be considered. If encouraging data is gathered from mouse and initial PK studies in baboons, formal proof-of-concept in vivo efficacy studies will be performed in a baboon model of preeclampsia that has been characterized by Dr. Annemarie Hennessy in Australia (Makris, A. et al. Uteroplacental ischemia results in proteinuric hypertension and elevated sFLT-1. *Kidney international* 71, 977-984 (2007)). In this study, the different doses and multiple doses of sFlt1 oligonucleotide therapy necessary and sufficient to ameliorate preeclampsia signs and symptoms will be specifically evaluated. Although human sFlt1 ELISA assays cross-react with baboon sFlt1, assays for baboon PlGF and VEGF do not exist Immunoassays that react to baboon PlGF/VEGF are presently being evaluated and, if successful, free concentrations of PlGF and VEGF levels in blood and urine that may rise as circulating sFlt1 levels decrease will be measured as a surrogate of biological efficacy.

6.5 Summary

The compositions and methods described herein will lead to the development of novel, cost-effective treatment for preeclampsia through modulation of sFLT1 levels. In addition, as true for ONTs, technology developed here should be applicable for silencing of other placental genes, enabling a wide range of novel functional genomics studies in vivo for other pregnancy-related diseases.

Example 6.6. DHA-hsiRNA Conjugates and g2DHA-hsiRNA Conjugates

DHA is an omega-3 fatty acid that is a primary component of the human brain (70%) which crosses the blood brain barrier (BBB) and is actively internalized by neurons and other cell types. g2DHA (also referred to herein as PC-DHA) is a metabolically active analogue of DHA.

Figure 20:
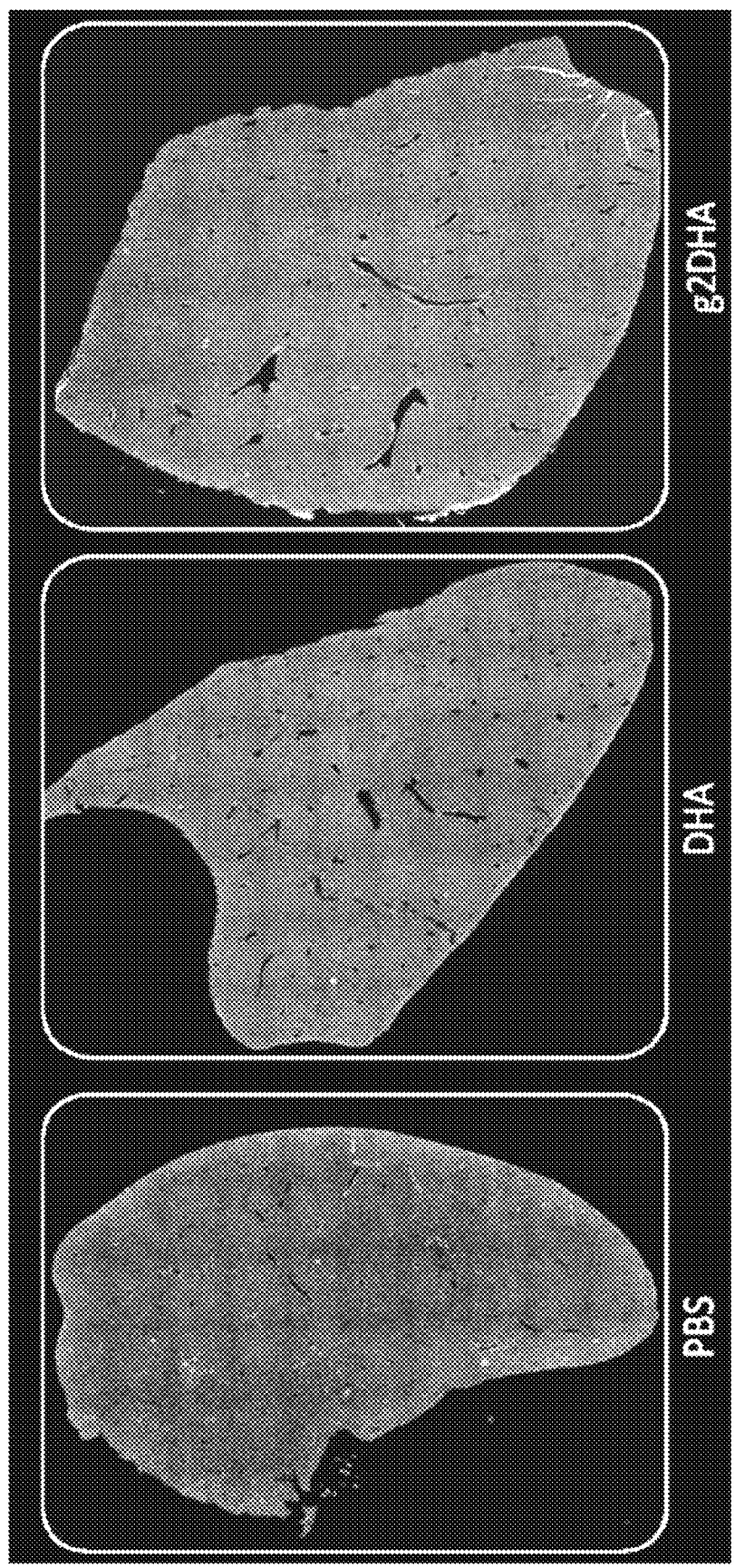
FIG. 20 depicts tissue distribution in liver of DHA-hsiRNA and g2 DHA-hsiRNA conjugates. 10× magnification. (sFLT1_2283P2-DHA, sFLT1_2283P2-g2DHA.) Blue, nucleus (DAPI); red, hsiRNA (Cy3). Mouse E15, IV (tail vein) injection. hsiRNAs administered at 10 mg/kg, 24 hours. LEICA DM5500B.
Figure 21:
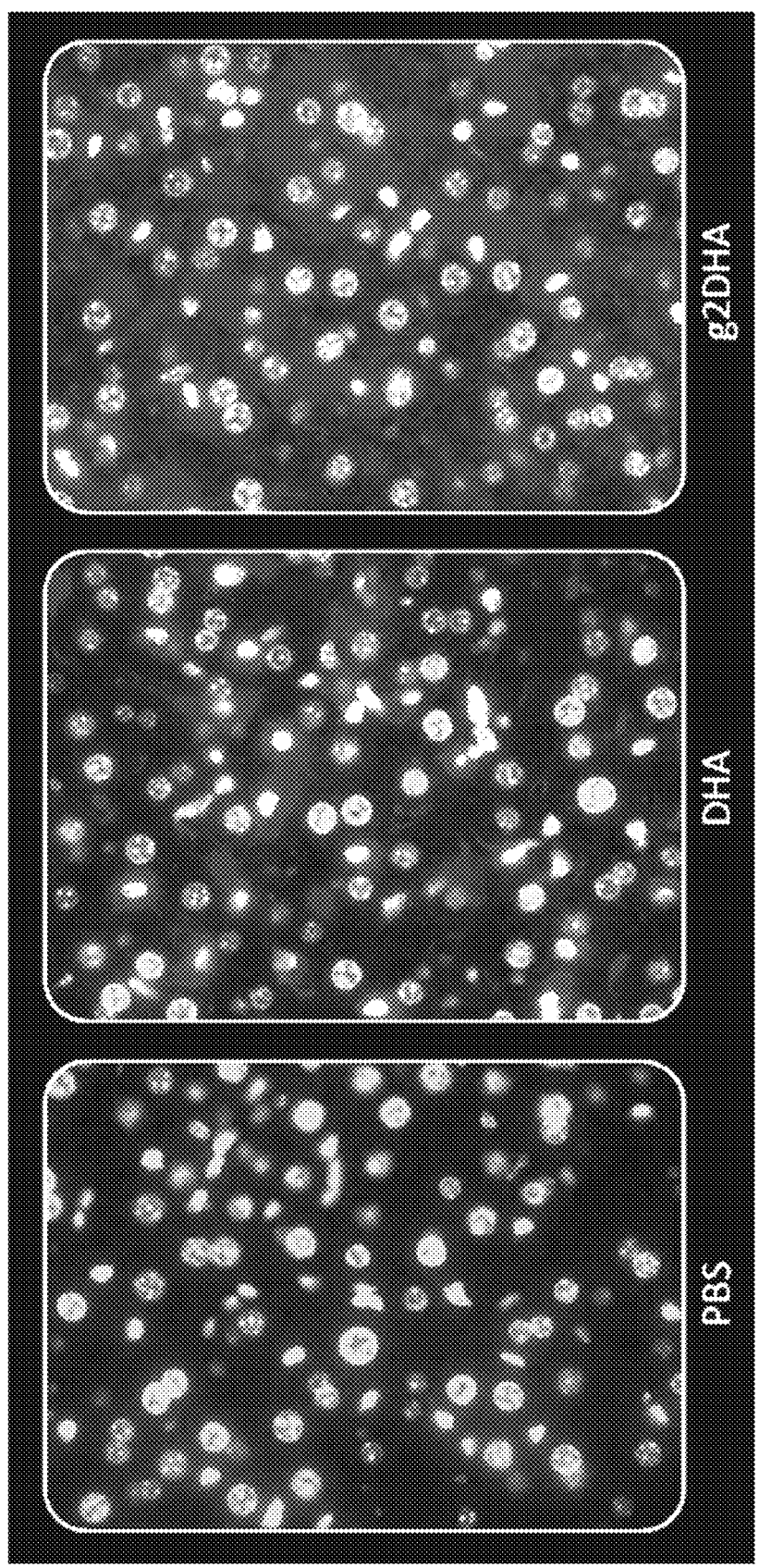
FIG. 21 depicts tissue distribution in liver of DHA-hsiRNA and g2DHA-hsiRNA conjugates. 63× magnification. (sFLT1_2283P2-DHA, sFLT1_2283P2-g2DHA.) Blue, nucleus (DAPI); red, hsiRNA (Cy3). Mouse E15, IV (tail vein) injection. hsiRNAs administered at 10 mg/kg, 24 hours. LEICA DM5500B.
Figure 22:
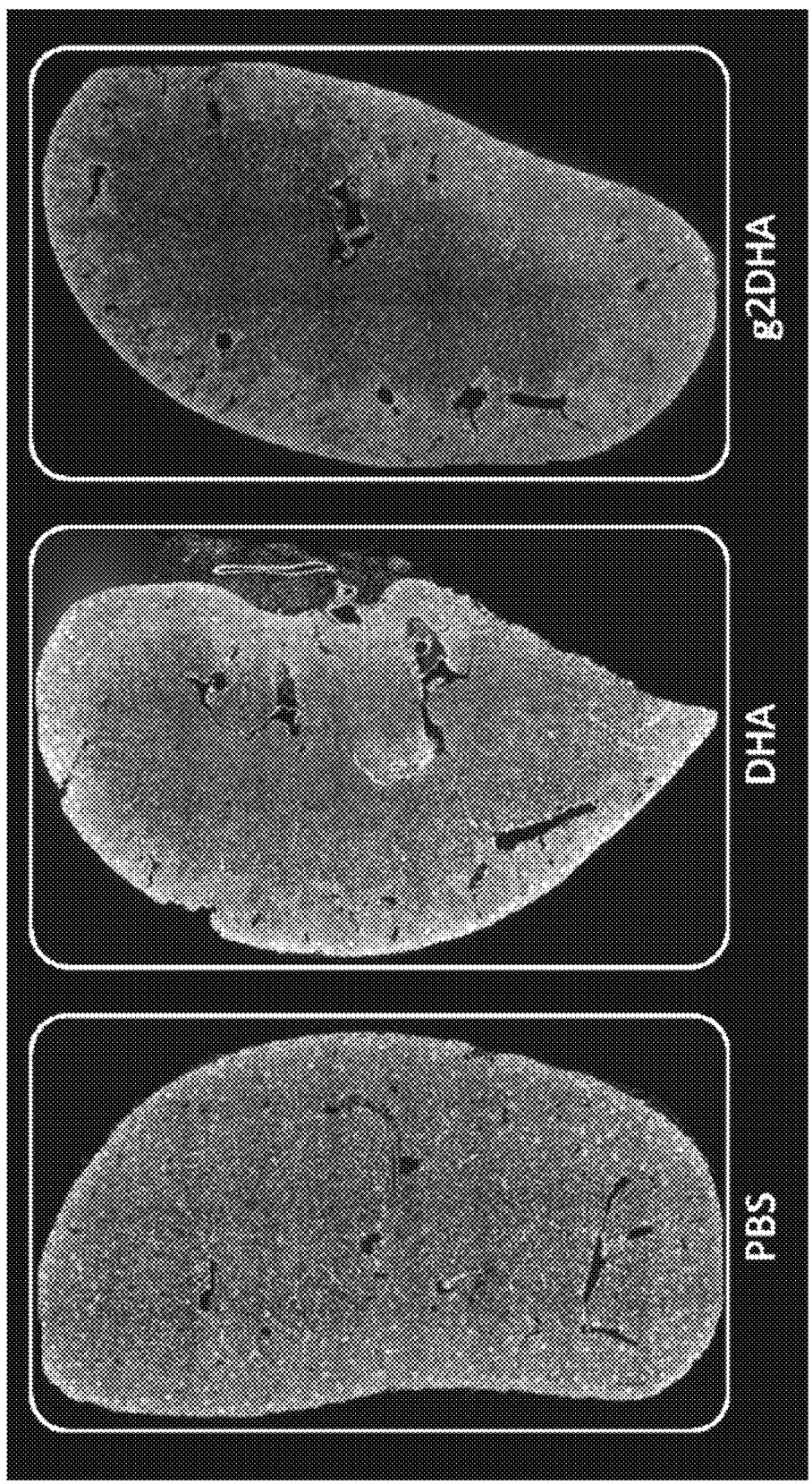
FIG. 22 depicts tissue distribution in kidney of DHA-hsiRNA and g2DHA-hsiRNA conjugates. 10× magnification. (sFLT1_2283P2-DHA, sFLT1_2283P2-g2DHA.) Blue, nucleus (DAPI); red, hsiRNA (Cy3). Mouse E15, IV (tail vein) injection. hsiRNAs administered at 10 mg/kg, 24 hours. LEICA DM5500B.
Figure 23:
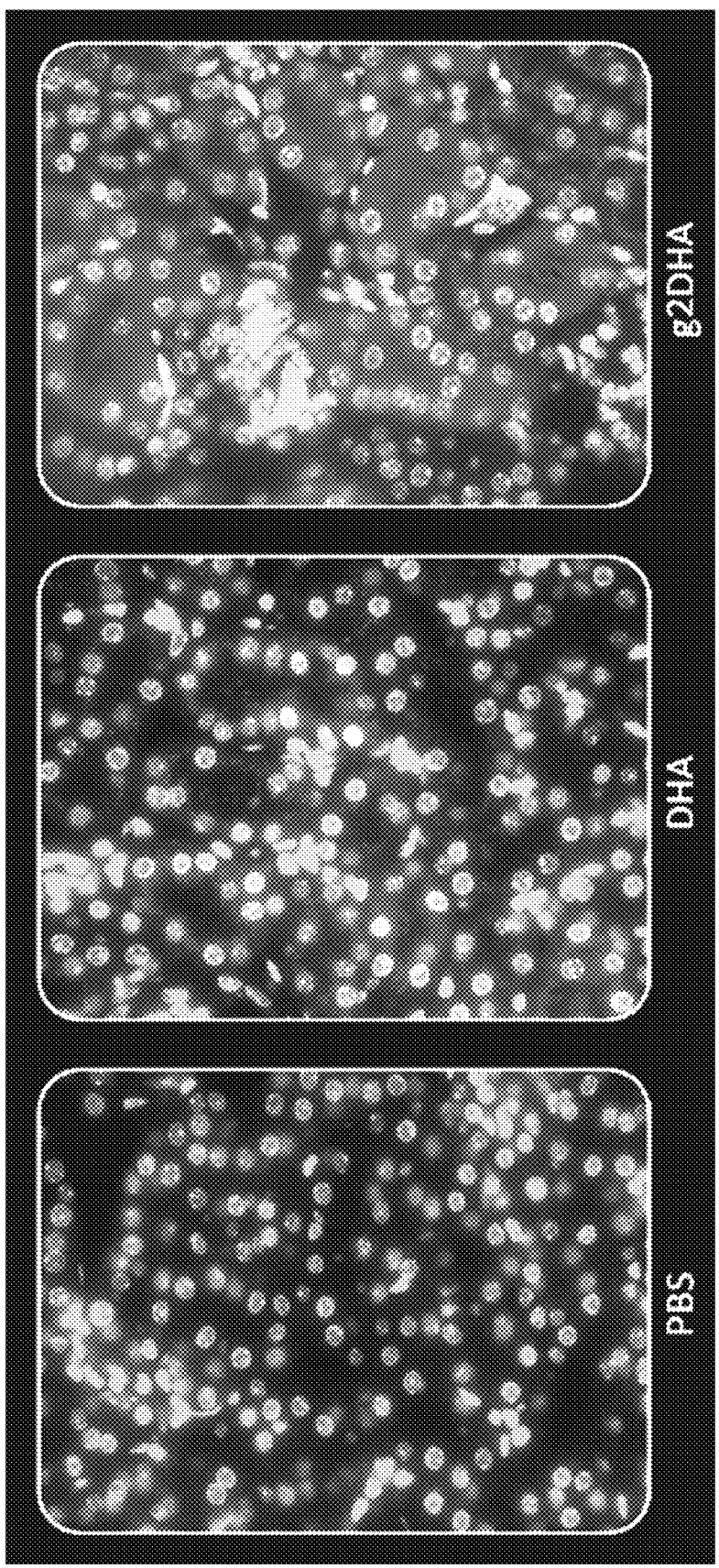
FIG. 23 depicts tissue distribution in kidney of DHA-hsiRNA and g2DHA-hsiRNA conjugates. 63× magnification. (sFLT1_2283P2-DHA, sFLT1_2283P2-g2DHA.) Blue, nucleus (DAPI); red, hsiRNA (Cy3). Mouse E15, IV (tail vein) injection. hsiRNAs administered at 10 mg/kg, 24 hours. LEICA DM5500B.
Figure 24:
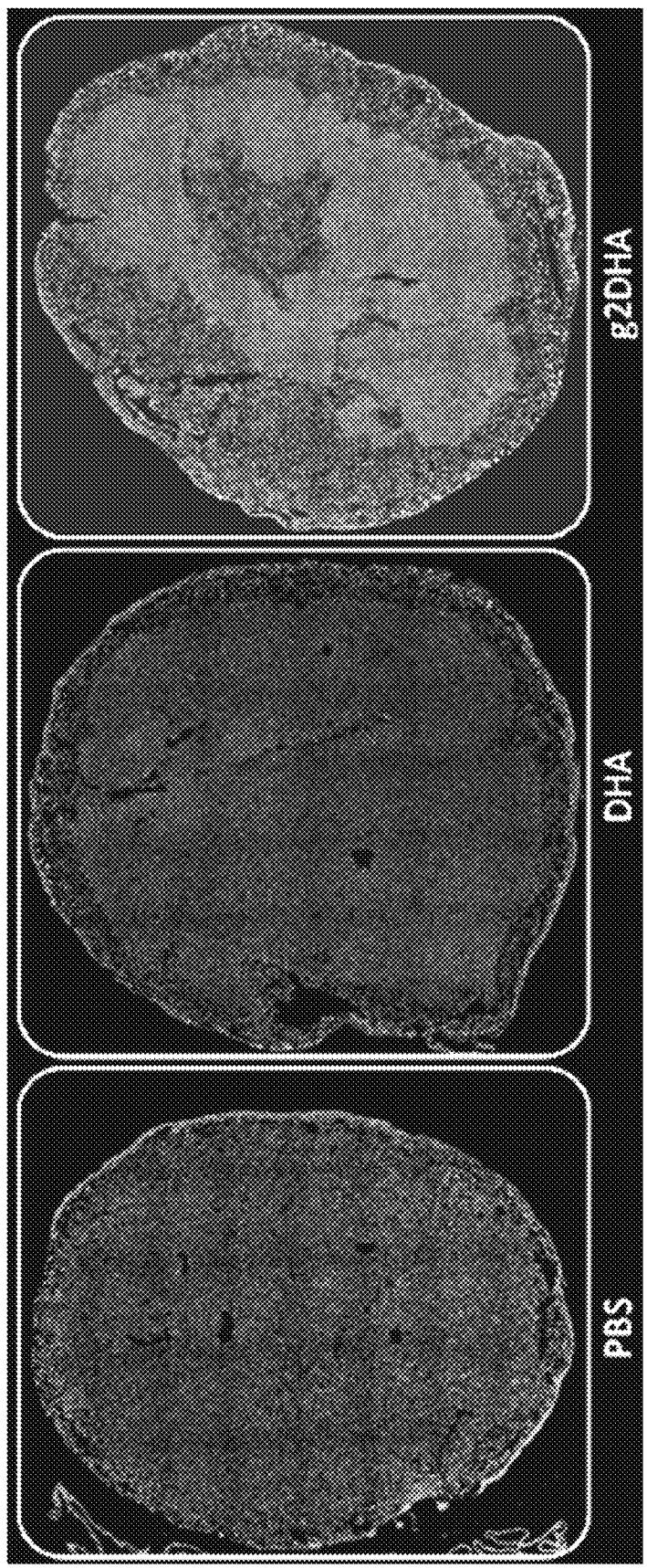
FIG. 24 depicts tissue distribution in placenta of DHA-hsiRNA and g2DHA-hsiRNA conjugates. 10× magnification. (sFLT1_2283P2-DHA, sFLT1_2283P2-g2DHA.) Blue, nucleus (DAPI); red, hsiRNA (Cy3). Mouse E15, IV (tail vein) injection. hsiRNAs administered at 10 mg/kg, 24 hours. LEICA DM5500B.
Figure 25:
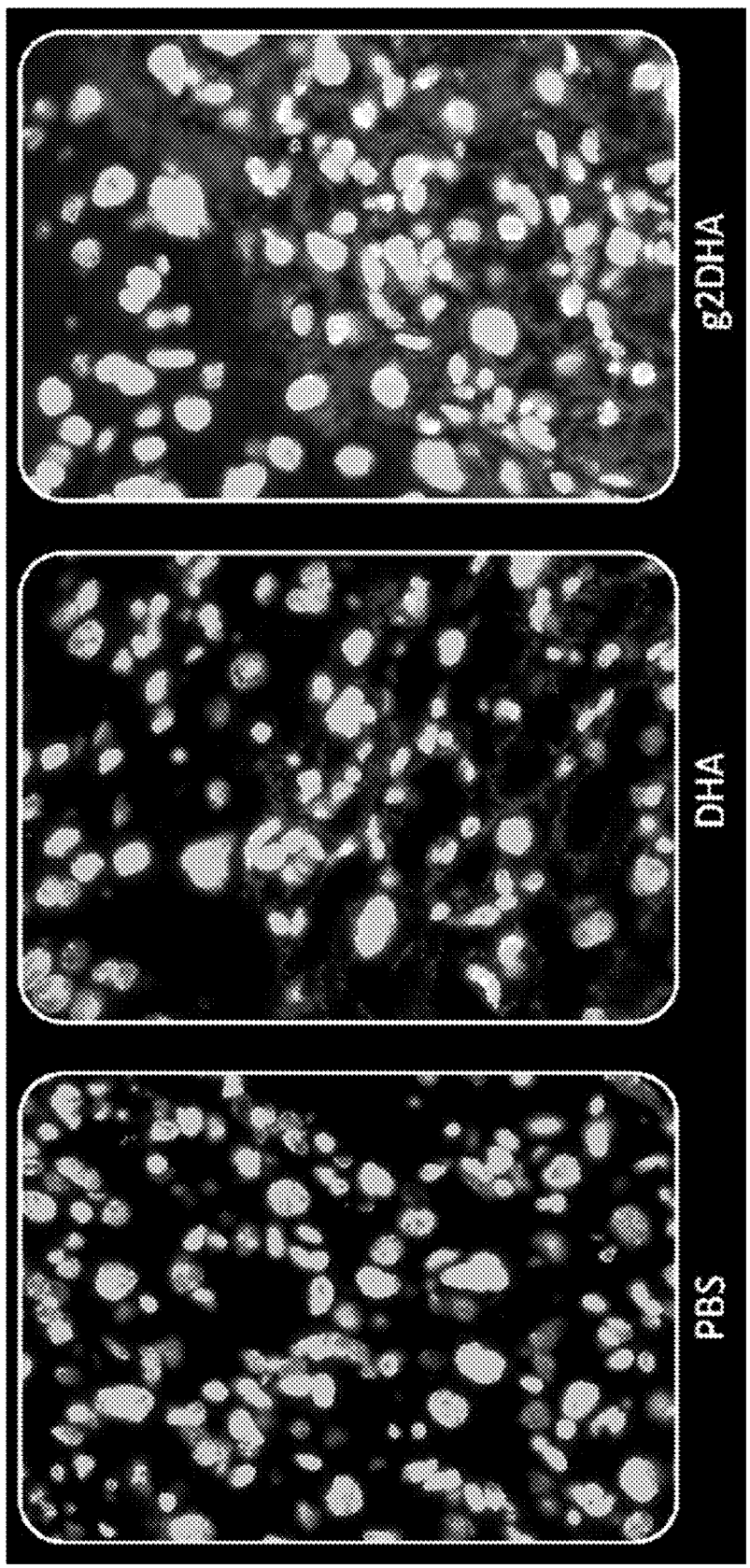
FIG. 25 depicts tissue distribution in placenta of DHA-hsiRNA and g2DHA-hsiRNA conjugates. 63× magnification. (sFLT1_2283P2-DHA, sFLT1_2283P2-g2DHA.) Blue, nucleus (DAPI); red, hsiRNA (Cy3). Mouse E15, IV (tail vein) injection. hsiRNAs administered at 10 mg/kg, 24 hours. LEICA DM5500B.
Figure 27A:
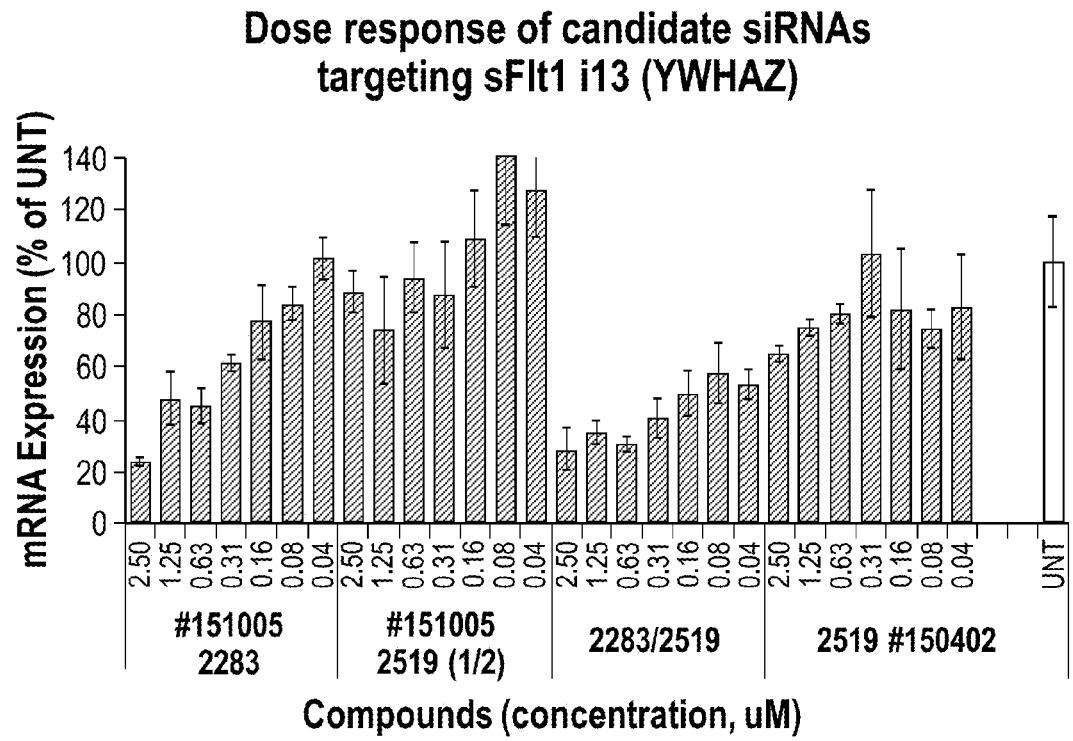
FIGS. 27A-27D depict in vitro validation of sFLT1_2283/2519 (sFLT1-mix, 1510025). (A) Depicts a dose response of candidate siRNAs targeting sFLt1 i13 shown by mRNA expression levels. (B) Depicts a dose response of candidate siRNAs targeting sFLt1 e15a shown by mRNA expression levels. (C) Depicts aFLT1 i13 mRNA expression levels in the presence of 2283 (circles) or 2283/2519 (blocks). (D) Depicts aFLT1 e15a mRNA expression levels in the presence of 2519 (circles) or 2283/2519 (blocks).
Figure 27B:
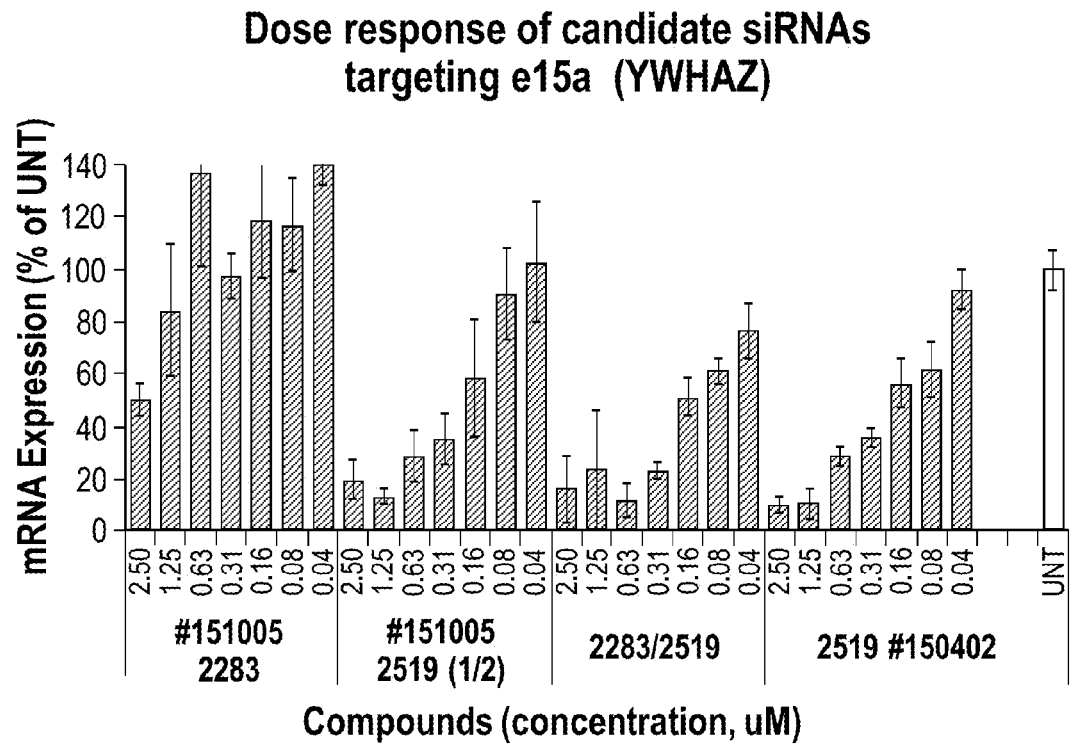
Figure 27C:
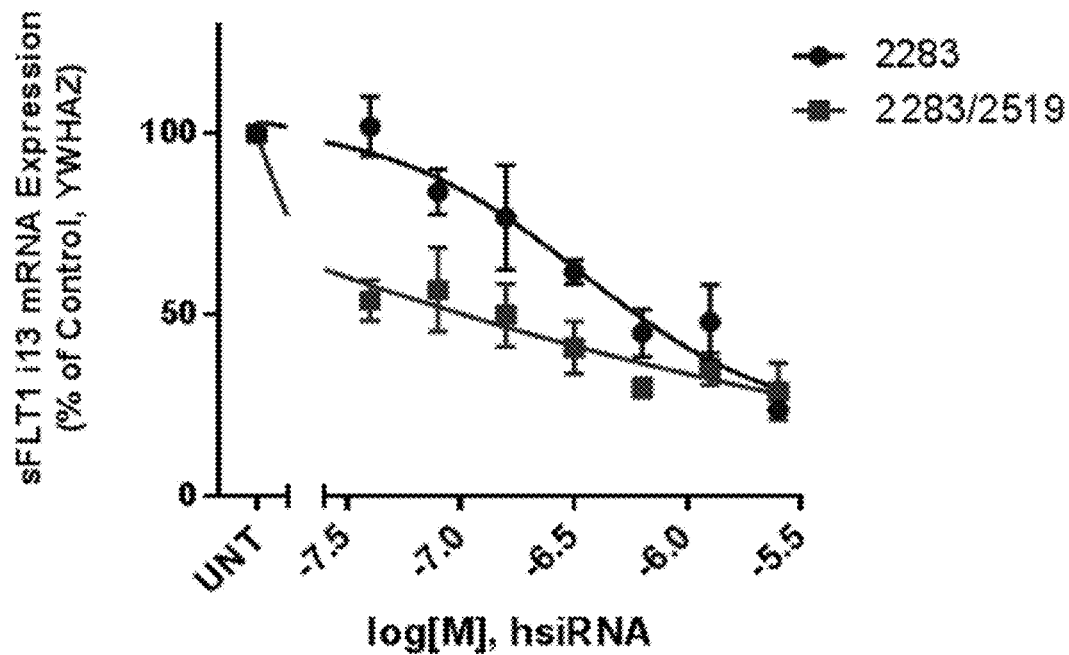
Figure 27D:
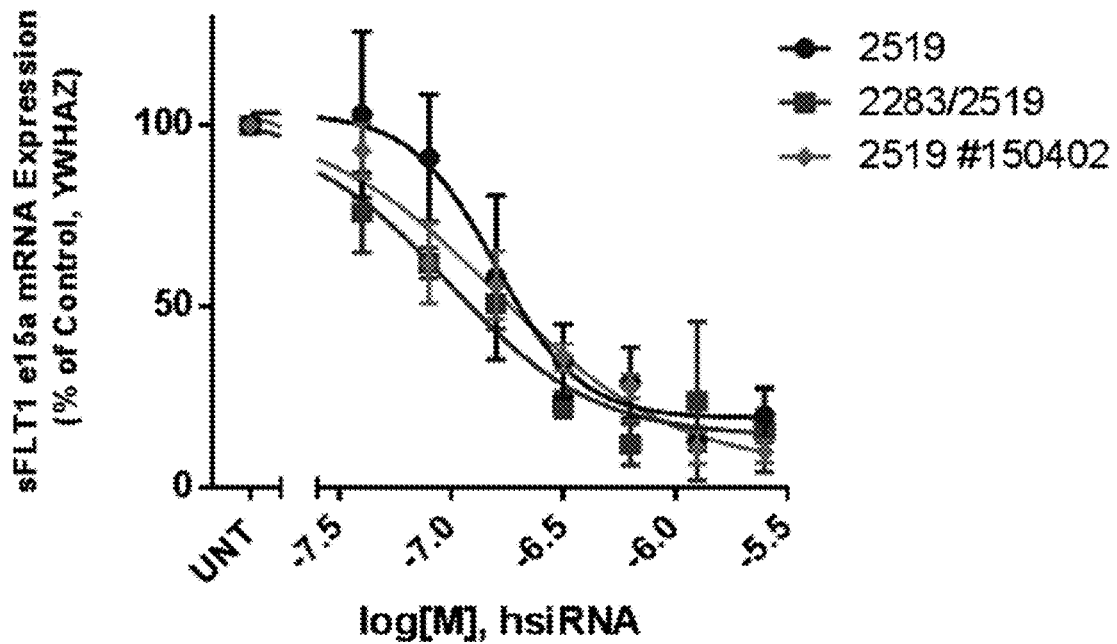
Figure 28A:
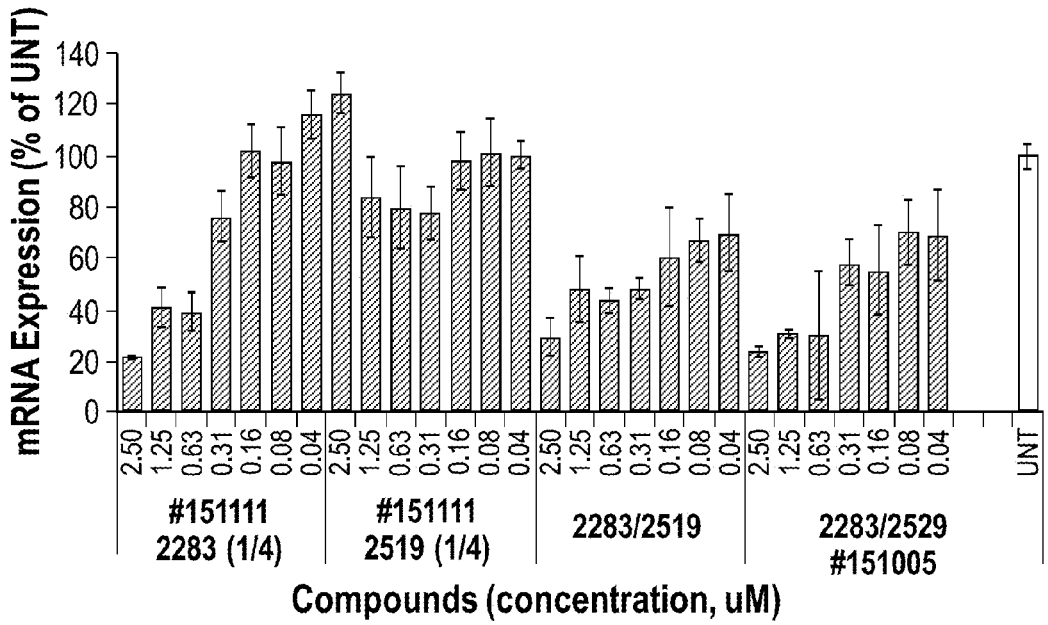
FIGS. 28A-28D depict in vitro validation of sFLT1_2283/2519 (sFLT1-mix, 151111). (A) Depicts a dose response of candidate siRNAs targeting sFLt1 i13 shown by mRNA expression levels. (B) Depicts a dose response of candidate siRNAs targeting sFLt1 e15a shown by mRNA expression levels. (C) Depicts aFLT1 i13 mRNA expression levels in the presence of 2283 (circles), 2283/2519 LS (blocks) or 2283/2519 (diamonds). (D) Depicts aFLT1 e15a mRNA expression levels in the presence of 2519 (circles), 2283/2519 LS (blocks) or 2283/2519 (diamonds).
Figure 28B:
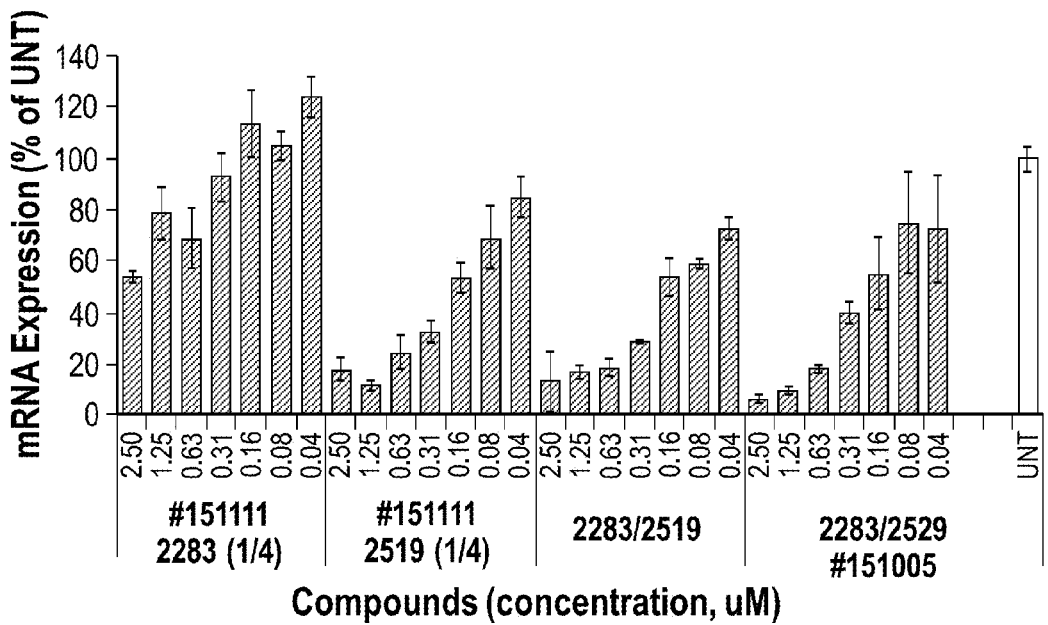
Figure 28C:
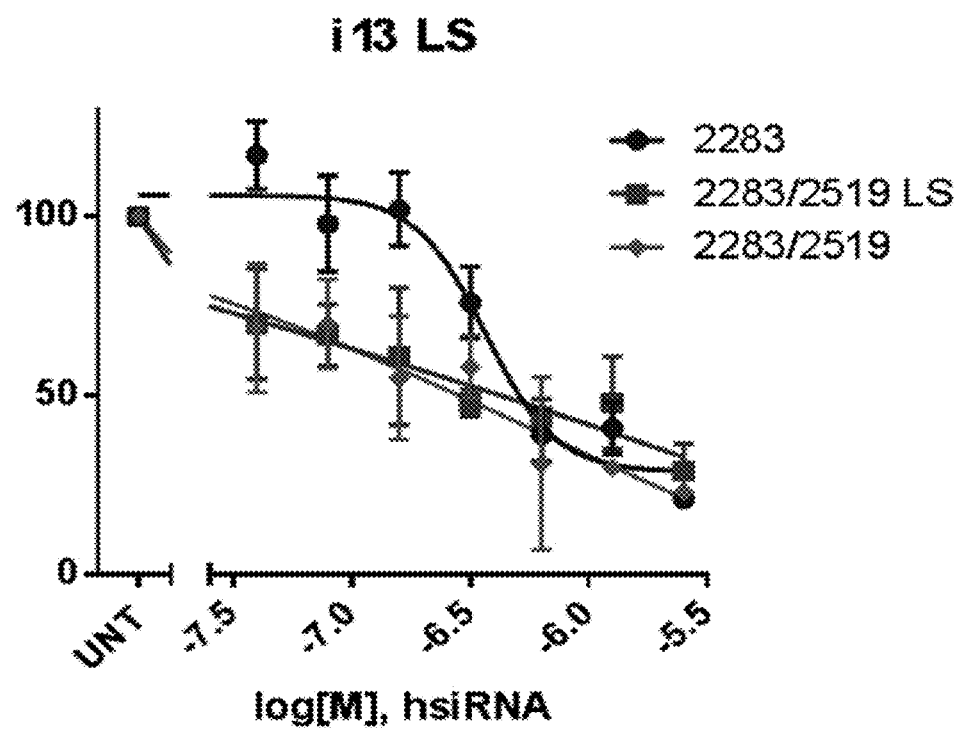
Figure 28D:
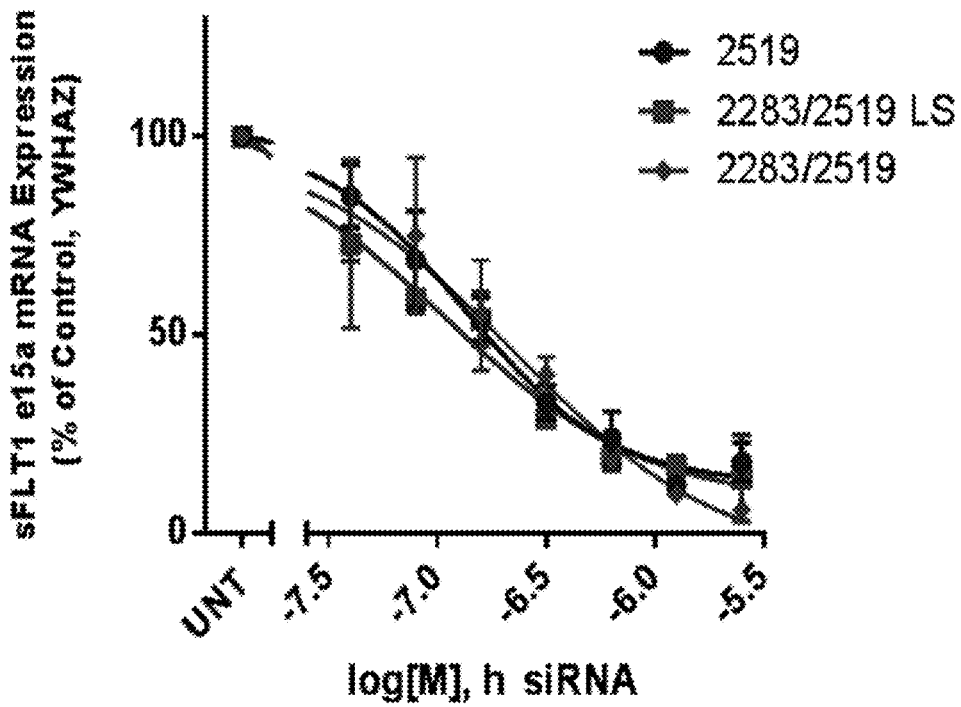

Docosahexaenoic acid (DHA)-hsiRNAs and g2DHA-hsiRNAs (also referred to herein as PC-DHA-hsiRNAs) were synthesized. Tissue distribution of DHA-hsiRNAs and g2DHA-hsiRNAs post-IV administration (via mouse tail veins) was determined in liver (FIGS. 20 and 21), kidney (FIGS. 22 and 23) and placental tissues (FIGS. 24 and 25).

sFLT1 silencing by g2DHA-hsiRNA was observed in pregnant mice using 15 mg/kg IV-administered sFLT1_2283P2-g2DHA (150813) in liver, kidney and placental tissues (FIG. 26).

Figure 36:
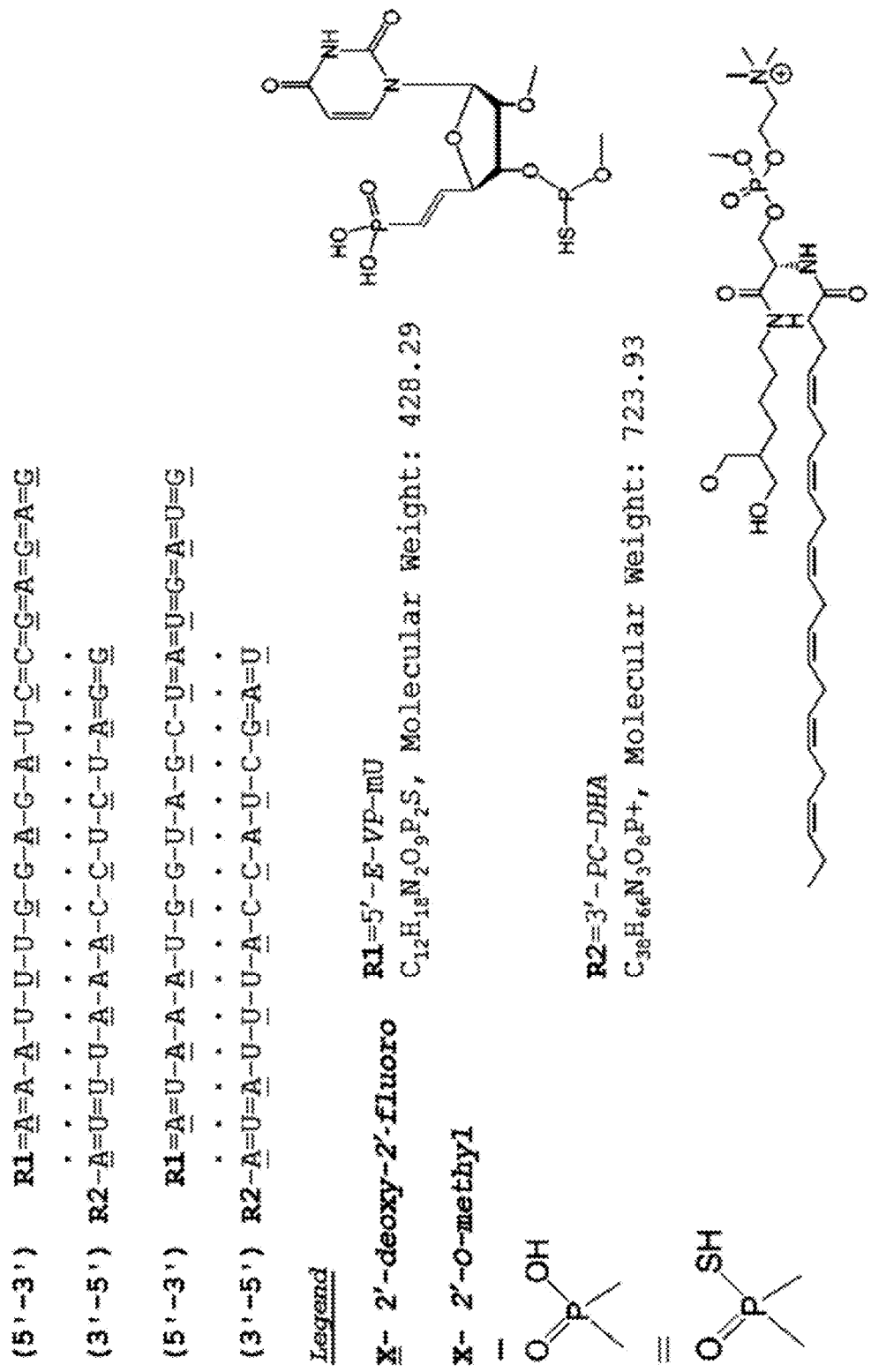
FIG. 36 depicts an sFLT_2283/2519 hsiRNA mix according to particularly preferred embodiments of the invention (SEQ ID NOS 8-11, respectively, in order of appearance). The species depicted in this drawing can be a pharmaceutically acceptable salt, as the P—OH and P—SH would be deprotonated.

A particularly preferred sFLT_2283/2519 mix is shown in FIG. 36.

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A compound, comprising a double stranded (ds) RNA molecule that is between 15 and 35 bases in length having a 5' end, a 3' end and complementarity to a target, and comprising a first oligonucleotide and a second oligonucleotide, that binds to an intronic region of an mRNA encoding an sFLT1 protein, wherein:
   (1) a portion of the first oligonucleotide is complementary to a portion of the second oligonucleotide;
   (2) the second oligonucleotide comprises alternating 2'-methoxy-ribonucleotides and 2'-fluoro-ribonucleotides;
   (3) the nucleotides at positions 2 and 14 from the 3' end of the second oligonucleotide are 2'-methoxy-ribonucleotides;
   (4) the nucleotides of the second oligonucleotide are connected via phosphodiester or phosphorothioate linkages; and
   (5) the compound comprises a hydrophobic modification, wherein the compound selectively inhibits expression of the sFLT1 protein in a cell or organism.

2. A compound comprising a dsRNA that binds to an intronic region of an mRNA encoding an sFLT1 protein, said dsRNA is between 15 and 35 bases in length having a 5' end, a 3' end and complementarity to a target, and comprising a first oligonucleotide and a second oligonucleotide, wherein:
   (1) the first oligonucleotide comprises a sequence selected from the group consisting of SEQ ID NO:1, SEQ ID NO:2, SEQ ID NO:3 and SEQ ID NO:4;
   (2) a portion of the first oligonucleotide is complementary to a portion of the second oligonucleotide;
   (3) the second oligonucleotide comprises alternating 2'-methoxy-ribonucleotides and 2'-fluoro-ribonucleotides;
   (4) the nucleotides at positions 2 and 14 from the 3' end of the second oligonucleotide are 2'-methoxy-ribonucleotides; and
   (5) the nucleotides of the second oligonucleotide are connected via phosphodiester or phosphorothioate linkages; and
   (6) the compound comprises a hydrophobic modification, wherein the compound selectively inhibits expression of the sFLT1 protein in a cell or organism.

3. The compound of claim 2, comprising a dsRNA having a sense strand and an antisense strand, wherein the antisense strand comprises a region of complementarity which is substantially complementary to
SEQ ID NO: 1, SEQ ID NO: 2, SEQ ID NO: 3, or SEQ ID NO: 4, or
contains no more than 3 mismatches with SEQ ID NO:1, SEQ ID NO:2, SEQ ID NO:3 or SEQ ID NO:4.

4. The dsRNA of claim 3, wherein said region of complementarity:
is complementary to at least 15, 16, 17 or 18 contiguous nucleotides of SEQ ID NO:1, SEQ ID NO:2, SEQ ID NO:3 or SEQ ID NO:4;
contains no more than 3 mismatches with SEQ ID NO:1, SEQ ID NO:2, SEQ ID NO:3 or SEQ ID NO:4; or
is fully complementary to SEQ ID NO:1, SEQ ID NO:2, SEQ ID NO:3 or SEQ ID NO:4.

5. The dsRNA of claim 3, wherein said dsRNA: is blunt-ended and optionally;
comprises at least one single stranded nucleotide overhang; or
comprises naturally occurring nucleotides.

6. The dsRNA of claim 5, wherein:
said modified nucleotide is chosen from the group consisting of a a terminal nucleotide linked to a cholesteryl derivative, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

7. A therapeutic composition that binds to an intronic region of an mRNA encoding an sFLT1 protein, wherein the therapeutic composition selectively reduces expression of the sFLT1 protein, and wherein the therapeutic composition reduces one or more symptoms of preeclampsia (PE), postpartum PE, eclampsia or Hemolysis/Elevated Liver enzymes/Low Platelet count (HELLP) syndrome when administered to a subject in need thereof, comprising a first dsRNA comprising a first sense strand and a first antisense strand and a second dsRNA comprising a second sense strand and a second antisense strand, wherein the first antisense strand comprises a first region of complementarity which is substantially complementary to SEQ ID NO:1 and the second antisense strand comprises a second region of complementarity which is substantially complementary to SEQ ID NO:2.

8. The therapeutic composition of claim 7, wherein each dsRNA comprises at least one modified nucleotide.

9. The composition of claim 7, wherein each dsRNA comprises a 5' end, a 3' end and complementarity to a target, wherein:
(1) the oligonucleotide comprises alternating 2'-methoxy-ribonucleotides and 2'-fluoro-ribonucleotides;
(2) the nucleotides at positions 2 and 14 from the 5' end are not 2'-methoxy-ribonucleotides;
(3) the nucleotides are connected via phosphodiester or phosphorothioate linkages; and
(4) the nucleotides at positions 1-6 from the 3' end, or positions 1-7 from the 3' end, are connected to adjacent nucleotides via phosphorothioate linkages.

10. A pharmaceutical composition comprising:
a first dsRNA comprising a first sense strand and a first antisense strand, wherein the first antisense strand comprises a region of complementarity which is substantially complementary to SEQ ID NO:1, and wherein the first antisense strand selectively targets one or both of an intronic region of sFLT-i13 short and an intronic region of sFLT-i13 long;
a second dsRNA comprising a second sense strand and a second antisense strand, wherein the second antisense strand comprises a region of complementarity which is substantially complementary to SEQ ID NO:2, and wherein the second antisense strand selectively targets an intronic region of sFLT-i15a; and
a pharmaceutically acceptable carrier.

11. A method of treating or managing PE, postpartum PE, eclampsia or HELLP syndrome comprising administering to a subject in need of such treatment or management a therapeutically effective amount of the pharmaceutical composition of claim 10.

12. The method of claim 11, wherein the pharmaceutical composition is administered intravenously or subcutaneously.

13. A method of treating one or more symptoms of PE, postpartum PE, eclampsia or HELLP syndrome in a subject in need thereof, comprising administering to the subject the therapeutic compound of claim 7.

14. The dsRNA of claim 2, wherein:
the hydrophobic molecule comprises an omega-3 fatty acid; or
the hydrophobic molecule comprises a molecule selected from the group consisting of: docosanoic acid (DCA), docosahexaenoic acid (DHA), lysophosphatidylcholine esterified DHA (g2-DHA) and eicosapentaenoic acid (EPA).

15. The dsRNA of claim 14, wherein the hydrophobic molecule is DHA or g2-DHA.

16. A compound comprising a dsRNA having a sense strand and an antisense strand, wherein the antisense strand comprises a region of complementarity which is substantially complementary to
(SEQ ID NO:1),
(SEQ ID NO:2),
(SEQ ID NO:3),
(SEQ ID NO:4), or
contains no more than 3 mismatches with SEQ ID NO:1, SEQ ID NO:2, SEQ ID NO:3 or SEQ ID NO:4,
wherein said dsRNA comprises at least one 2'-O-methyl modified nucleotide, at least one 2'-fluoro modified nucleotide, at least one nucleotide comprising a 5'phosphorothioate group and wherein said dsRNA comprises a hydrophobic modification.

17. A compound comprising a dsRNA having a sense strand and an antisense strand, wherein the antisense strand comprises a region of complementarity which is substantially complementary to
(SEQ ID NO:1),
(SEQ ID NO:2),
(SEQ ID NO:3),
(SEQ ID NO:4), or
contains no more than 3 mismatches with SEQ ID NO:1, SEQ ID NO:2, SEQ ID NO:3 or SEQ ID NO:4,
wherein said dsRNA comprises at least one 2'-O-methyl modified nucleotide, at least one 2'-fluoro modified nucleotide, at least one nucleotide comprising a 5'phosphorothioate group and a terminal nucleotide linked to a cholesteryl derivative.

18. The compound according to claim 17, wherein every 2'-OH residue of said dsRNA is modified.

19. The compound according to claim 2, wherein the second oligonucleotide is linked to a hydrophobic molecule at the 3' end of the second oligonucleotide.

20. The compound according to claim 2, wherein the linkage between the second oligonucleotide and the hydrophobic molecule comprises polyethylene glycol or triethylene glycol.

21. The compound according to claim 2, wherein the nucleotides at positions 1 and 2 from the 3' end of second oligonucleotide are connected to adjacent nucleotides via phosphorothioate linkages.

22. The compound according to claim 2, wherein the nucleotides at positions 1 and 2 from the 3' end of second oligonucleotide, and the nucleotides at positions 1 and 2 from the 5' end of second oligonucleotide, are connected to adjacent ribonucleotides via phosphorothioate linkages.

23. The compound according to claim 3, wherein the dsRNA mediates degradation of the mRNA.

24. The compound according to claim 3, wherein the dsRNA comprises naturally occurring nucleotides.

25. The compound according to claim 3, wherein the dsRNA reduces expression of the sFLT1 protein in the cell or organism from about 30% to about 50%.

26. The compound according to claim 3, wherein the dsRNA reduces expression of the sFLT1 protein in the cell or organism from about 30% to about 40%.

27. The therapeutic composition of claim 7, wherein each dsRNA is between 15 and 35 base pairs in length.

28. The therapeutic composition of claim 7, wherein said first region of complementarity is complementary to at least 15, 16, 17 or 18 contiguous nucleotides of SEQ ID NO:1 and wherein said second region of complementarity is complementary to at least 15, 16, 17 or 18 contiguous nucleotides of SEQ ID NO:2.

29. The therapeutic composition of claim 7, wherein said first region of complementarity contains no more than 3 mismatches with SEQ ID NO:1 and wherein said second region of complementarity contains no more than 3 mismatches with SEQ ID NO:2.

30. The therapeutic composition of claim 7, wherein said first region of complementarity is fully complementary to SEQ ID NO:1 and wherein said second region of complementarity is fully complementary to SEQ ID NO:2.

31. The therapeutic composition of claim 7, wherein each dsRNA comprises at least one single stranded nucleotide overhang.

32. The therapeutic composition of claim 8, wherein: said modified nucleotide is chosen from the group of: a 2'-O-methyl modified nucleotide, a 2'-fluoro modified nucleotide, a nucleotide comprising a 5'-phosphorothioate group, and a terminal nucleotide linked to a cholesteryl derivative.

33. The therapeutic composition of claim 8, wherein said modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

34. The therapeutic composition of claim 8, wherein each dsRNA comprises at least one 2'-O-methyl modified nucleotide, at least one 2'-fluoro modified nucleotide, at least one nucleotide comprising a 5'phosphorothioate group and a terminal nucleotide linked to a cholesteryl derivative.

35. The therapeutic composition of claim 8, each dsRNA comprises at least one 2'-O-methyl modified nucleotide, at least one 2'-fluoro modified nucleotide, at least one nucleotide comprising a 5'phosphorothioate group and a terminal nucleotide linked to a cholesteryl derivative.

36. A compound comprising a dsRNA having a sense strand and an antisense strand, wherein the antisense strand comprises a region of complementarity which is fully complementary to SEQ ID NO:1, SEQ ID NO:2, SEQ ID NO:3 or SEQ ID NO:4, wherein said dsRNA comprises at least one modified nucleotide.

37. The compound of claim 36, which is fully complementary to SEQ ID NO:1.

38. The compound of claim 36, which is fully complementary to SEQ ID NO:2.

39. The compound of claim 36, which is fully complementary to SEQ ID NO:3.

40. The compound of claim 36, which is fully complementary to SEQ ID NO:4.

* * * * *